United States Patent
Bibillo et al.

(10) Patent No.: US 12,163,164 B2
(45) Date of Patent: Dec. 10, 2024

(54) HYBRID REVERSE TRANSCRIPTASES

(71) Applicant: Bio-Rad Laboratories, Inc., Hercules, CA (US)

(72) Inventors: Arkadiusz Bibillo, Walnut Creek, CA (US); Pranav Patel, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 944 days.

(21) Appl. No.: 16/928,915

(22) Filed: Jul. 14, 2020

(65) Prior Publication Data

US 2021/0017504 A1    Jan. 21, 2021

Related U.S. Application Data

(60) Provisional application No. 62/874,308, filed on Jul. 15, 2019, provisional application No. 62/874,366, filed on Jul. 15, 2019, provisional application No. 62/874,388, filed on Jul. 15, 2019.

(51) Int. Cl.
| | |
|---|---|
| *C12N 9/12* | (2006.01) |
| *C12N 1/20* | (2006.01) |
| *C12R 1/01* | (2006.01) |
| *C40B 40/06* | (2006.01) |

(52) U.S. Cl.
CPC ........... *C12N 9/1276* (2013.01); *C12N 1/205* (2021.05); *C07K 2319/80* (2013.01); *C07K 2319/85* (2013.01); *C12R 2001/01* (2021.05); *C12Y 207/07049* (2013.01); *C40B 40/06* (2013.01)

(58) Field of Classification Search
CPC .............. C07K 14/195; C07K 2319/80; C07K 2319/85; C12N 1/205; C12N 9/1276; C12N 15/1096; C12R 2001/01; C12Y 207/07049; C40B 40/06; C12Q 2521/107
See application file for complete search history.

(56) References Cited

U.S. PATENT DOCUMENTS

| | | |
|---|---|---|
| 5,668,005 A | 9/1997 | Kotewicz et al. |
| 5,723,584 A | 3/1998 | Schatz |
| 6,627,424 B1 | 9/2003 | Wang |
| 7,153,672 B1 | 12/2006 | Eickbush et al. |

(Continued)

FOREIGN PATENT DOCUMENTS

| | | |
|---|---|---|
| EP | 1934372 B1 | 2/2013 |
| WO | 2010036352 A1 | 4/2010 |

(Continued)

OTHER PUBLICATIONS

Govindaraju et al. (Nucleic Acids Res, 2016, 44:3276) (Year: 2016).*

(Continued)

*Primary Examiner* — Jeremy C Flinders
(74) *Attorney, Agent, or Firm* — Withers Bergman LLP; Thomas C. Meyers

(57) ABSTRACT

Hybrid reverse transcriptases are provided that comprise a non-retroviral retrotransposon, or a fragment of the non-retroviral retrotransposon having reverse transcriptase activity, joined to a nucleic acid binding protein. Also provided are methods of using the hybrid reverse transcriptases to prepare a cDNA molecule library.

21 Claims, 28 Drawing Sheets
(23 of 28 Drawing Sheet(s) Filed in Color)
Specification includes a Sequence Listing.

(56) References Cited

U.S. PATENT DOCUMENTS

| | | | |
|---|---|---|---|
| 7,541,170 | B2 | 6/2009 | Wang et al. |
| 8,043,840 | B2 | 10/2011 | Reppas et al. |
| 8,741,618 | B2 | 6/2014 | Nikiforov |
| 8,828,700 | B2 | 9/2014 | Lee et al. |
| 9,156,010 | B2 | 10/2015 | Colston, Jr. et al. |
| 9,481,715 | B2 | 11/2016 | Vernet et al. |
| 9,547,003 | B2 | 1/2017 | Howarth |
| 9,580,743 | B2 | 2/2017 | Lee et al. |
| 10,073,087 | B2 | 9/2018 | Deng et al. |
| 2003/0198956 | A1 | 10/2003 | Makowski et al. |
| 2007/0059713 | A1 | 3/2007 | Lee et al. |
| 2011/0189659 | A1 | 8/2011 | Clark et al. |
| 2014/0323691 | A1 | 10/2014 | Tan et al. |
| 2015/0291664 | A1 | 10/2015 | Ng et al. |
| 2017/0146522 | A1 | 5/2017 | Howarth |
| 2017/0159032 | A1 | 6/2017 | Gong |
| 2018/0230462 | A1 | 8/2018 | Gong et al. |
| 2018/0244730 | A1 | 8/2018 | Howarth |
| 2018/0344871 | A1 | 12/2018 | Tsourkas et al. |
| 2019/0002509 | A1 | 1/2019 | Gremyachinskiy et al. |
| 2019/0119343 | A1 | 4/2019 | Chung et al. |
| 2021/0340562 | A1* | 11/2021 | Christensen ............. C12N 9/22 |

FOREIGN PATENT DOCUMENTS

| | | |
|---|---|---|
| WO | 2016154621 A1 | 9/2016 |
| WO | 2016183387 A1 | 11/2016 |
| WO | 2016193746 A1 | 12/2016 |
| WO | 2017070742 A1 | 5/2017 |
| WO | 2017112784 A1 | 6/2017 |
| WO | 2018053180 A2 | 3/2018 |
| WO | 2018089860 A1 | 5/2018 |
| WO | 2019222523 A2 | 11/2019 |

OTHER PUBLICATIONS

Chen et al. (Adv Drug Deliv Rev., 2013, 65(10): 1357-1369) (Year: 2013).*

Abe, H., et al. "Split Spy0128 as a Potent Scaffold for Protein Cross-Linking and Immobilization." Bioconjugate Chem., Jan. 27, 2013, 24(2), pp. 242-250.

Alam, M.K et al., "Synthetic Modular Antibody Construction Using the SpyTag/SpyCatcher Protein Ligase System," ChemBioChem, Nov. 16, 2017, 18(22), pp. 2217-2221.

Alam, M.K. et al., "Site-Specific Fluorescent Labeling of Antibodies and Diabodies Using SpyTag/SpyCatcher System for In Vivo Optical Imaging," Molecular Imaging and Biology, Jun. 12, 2018, URL: https://doi.org/10.1007/s11307-018-1222-y.

Beckett et al. "A minimal peptide substrate in biotin holoenzyme synthetase-catlyzed biotinylation," Protein Science, Jan. 8, 1999, vol. 8, pp. 921-929.

Bibillo and Eickbush "High Processivity of the Reverse Transcriptase from a Non-long Terminal Repeat Retrotransposon," Jul. 5, 2002, J. Biol. Chem., 277(38), pp. 34836-34845.

Bibillo and Eickbush "End-to-End Template Jumping by the Reverse Transcriptase Encoded by the R2 Retrotransposon," J. Biol. Chem. Jan. 28, 2004, 279(15), pp. 14945-14953.

Buldun, C.M., et al., "SnoopLigase catalyzes peptide-peptide locking and enables solid-phase conjugate isolation." J Am Chem Soc., Feb. 28, 2018 140(8), 3008-3018.

Burke et al. "The Domain Structure and Retrotransposition Mechanism of R2 Elements Are Conserved Throughout Arthropods," Mol. Biol. Evol., Apr. 1999, 16(4), pp. 502-511.

Das and Shuman "Mechanism of RNA 2',3'-cyclic phosphate end healing by T4 polynucleotide kinase-phosphatase," Nucleic Acids Research, Oct. 30, 2012, 41(1), pp. 355-365.

Debinski et al. "A Wide Range of Human Cancer Express Interleukin 4 (IL4) Receptors That Can Be Targeted with Chimeric Toxin Composed of IL4 and Pseudomonas Exotoxin," J. Biol. Chem., Jul. 5, 1993, 268(19), pp. 14065-14070.

Fairhead, M and Howarth, M. "Site-specific biotinylation of purified proteins using BirA," Methods Mol Biol., Jul. 1, 2015, vol. 1266, pp. 171-184. doi: 10.1007/978-1-4939-2272-7_12.

Fierer, J.O., et al. "SpyLigase peptide-peptide ligation polymerizes affibodies to enhance magnetic cancer cell capture," Proc. Natl. Acad. Sci., Mar. 17, 2014, vol. 111, pp. E1176-E1181.

Head et al. "Library construction for next-generation sequencing: Overviews and challenges," Biotechniques, Mar. 6, 2015, 56(2): 61-passim. doi:10.2144/000114133.

Heck et al., "Enzyme-catalyzed protein crosslinking," Appl Microbiol Biotechnol, Nov. 25, 2012, 97:461-475; DOI 10.1007/s00253-012-4569-z.

Kalichuk et al. "The archaeal "7 kDa DNA-binding" proteins: extended characterization of an old gifted family," Sci. Rep. Nov. 17, 2016, 6, 37274; doi: 10.1038/srep37274, 10 pp.

Keeble, A.H., et al. "Evolving Accelerated Amidation by SpyTag/SpyCatcher to Analyze Membrane Dynamics," Angew. Chem. Int. Ed., Dec. 5, 2017, vol. 56:16521-16525.

Kerr et al. "Insights into ssDNA recognition by the OB fold from a structural and thermodynamic study of Sulfolobus SSB protein," The EMBO Journal, Apr. 14, 2003, 22(11), pp. 2561-2570.

Kojima, KK & Kanehisa, M "Systematic Survey for Novel Types of Prokaryotic Retroelements Based on Gene Neighborhood and Protein Architecture," Mol. Biol. Evol. Apr. 7, 2008, vol. 25, No. 7, pp. 1395-1404.

Li et al., "Structural Analysis and Optimization of the Covalent Association between SpyCatcher and a Peptide Tag," J. Mol. Biol., Jan. 23, 2014, vol. 426(2), pp. 309-317.

Lodish H, Berk A, Zipursky SL, et al. "Section 9.3 Mobile DNA," Molecular Cell Biology. 4th edition. New York: W. H. Freeman; 2000, 18 pp, Available from: https://www.ncbi.nlm.nih.gov/books/NBK21495/.

Simon D. et al. "A diversity of uncharacterized reverse transcriptases in bacteria" Nucleic Acids Res., Nov. 12, 2008, vol. 36No. 22, pp. 7219-7229.

Sun and Huang "Sulfolobus chromatin proteins modulate strand displacement by DNA polymerase B1," Nucleic Acids Research, Jul. 1, 2013, 41(17):, pp. 8182-8195.

Walker-Daniels (2012) "Current PCR Methods," Mater. Methods 2(119). DOI/dx.doi.org/10.13070/mm.en.2.119; Date last modified: Oct. 22, 2020; original version: Apr. 19, 2012, 12 pp.

Wang and Shuman "Domain Structure and Mutational Analysis of T4 Polynucleotide Kinase," J. Biol. Chem., Jul. 20, 2001, 279(29), pp. 26868-26874.

Nguyen, G.K.T., et al. "Butelase 1 is an Asx-specific ligase enabling peptide macrocyclization and synthesis," Nat Chem Biol, Jul. 20, 2014, vol. 2014, 10, pp. 732-738.

Reddington, S.C., et al., "Secrets of a covalent interaction for biomaterials and biotechnology: SpyTag and SpyCatcher." Current Opinion in Chemical Biology, Oct. 30, 2015, vol. 29, pp. 94-99.

Schmohl, L., Schwarzer, D., "Sortase-mediated ligations for the site-specific modification of proteins." Current Opinion in Chemical Biology, Oct. 6, 2014, 22, pp. 122-128.

Siegmund et al., "Spontaneous Isopeptide Bond Formation as a Powerful Tool for Engineering Site-Specific Antibody-Drug Conjugates," Scientific Reports, Dec. 16, 2016, 6, 39291, pp. 1-9.

Tan et al., "Kinetic Controlled Tag-Catcher Interactions for Directed Covalent Protein Assembly." PloS ONE, Oct. 26, 2016, 11(10), e0165074.

Toplak, A., et al., "Peptiligase, an Enzyme for Efficient Chemoenzymatic Peptide Synthesis and Cyclization in Water," Adv. Synth. Catal., May 24, 2016, 358:32140-32147.

Veggiani, G. et al., "Programmable polyproteams built using twin peptide superglues," Proc Natl Acad Sci USA, Feb. 2, 2016, vol. 113, No. 5, pp. 1202-1207.

Yumura, K. et al., "Use of SpyTag/SpyCatcher to construct bispecific antibodies that target two epitopes of a single antigen," J. Biochem., Jun. 16, 2017, 162(3), pp. 203-210.

Zakeri, B. et al., "Peptide tag forming a rapid covalent bond to a protein, through engineering a bacterial adhesin," Proc. Natl. Acad. Sci., Feb. 24, 2012, vol. 109, No. 12, pp. E690-E697.

* cited by examiner

HYBRID REVERSE TRANSCRIPTASES

This application claims the benefit of U.S. Provisional Application 62/874,308 filed on Jul. 15, 2019; U.S. Provisional Application 62/874,366 filed on Jul. 15, 2019; and U.S. Provisional Application 62/874,388 filed on Jul. 15, 2019 which are hereby incorporated by reference in their entirety.

The Sequence Listing for this application has been submitted electronically in ASCII format and is hereby incorporated by reference in its entirety. The ASCII copy was created on Jul. 1, 2024 is named "BIOR-073-US01_Sequence_Listing-3.txt", and is 572 KB in size.

BACKGROUND

A common technique used to study gene expression in living cells is to produce complementary deoxyribonucleic acid (cDNA) from a ribonucleic acid (RNA) molecule. This technique provides a means to study RNA from living cells that avoids the direct analysis of inherently unstable RNA. As a first step in cDNA synthesis, the RNA molecules from an organism are isolated from an extract of cells or tissues of the organism. After the messenger RNA (mRNA) is isolated, a RNA or DNA oligonucleotide sequence (i.e., a primer) is annealed to the isolated mRNA molecules and enzymes with reverse transcriptase activity are used to produce cDNA copies of the template RNA sequence. Reverse transcription of mRNA is used in many forms of gene expression analyses. For example, mRNA is reverse transcribed into cDNA for subsequent analysis by primer extension or polymerase chain reaction.

Many reverse transcriptases of retroviral origin are used commercially. Retroviral-derived reverse transcriptases have a RNA-directed DNA polymerase activity, a DNA-directed DNA polymerase activity, and an RNAse H activity. The RNAse H activity degrades RNA in an RNA: DNA duplex. Although retroviral-derived reverse transcriptases have been developed in which the RNAse H activity is absent, the enzymes have other properties that limit their utility. For example, retroviral-derived reverse transcriptases require a primer that can anneal to the RNA template, have low processivity (i.e., the enzyme dissociates from the RNA template before reaching the 5' end), and the enzyme cannot transcribe through a region of the RNA template having secondary structure. Thus, retroviral-derived reverse transcriptases cannot transcribe long sequences of mRNA and have limited utility in such applications as single cell transcriptomics.

Protein Ligation

Several technologies enable covalent conjugation of polypeptides at specific pre-determined sites. One example is the sortase system (Schmohl et al., 2014), whereby a short peptide (the sorting motif) is genetically fused to the C-terminus of one polypeptide and two glycine residues are genetically fused to the N-terminus of a second peptide (or vice versa). In the presence of the sortase enzyme, the two modified polypeptides are fused together. Other enzymatic protein ligase systems are butelase (Nguyen et al., 2014) or peptiligase (Toplak et al., 2016).

Another example is the in-frame addition of nucleotides encoding one or more cysteines to the C- or N-termini of polypeptides. When such free cysteine containing polypeptides are mixed under oxidizing conditions, they will form disulfide bridges. Such systems, however, suffer from the synthesis of many side-products and from instability of the disulfide bridge under reducing conditions.

Another example is the Spy Tag/SpyCatcher (Reddington et al., 2015) system. Here, the concept of spontaneous isopeptide formation in naturally occurring proteins has been used to covalently attach one polypeptide to another. A domain from the *Streptococcus pyogenes* protein FbaB, which contains such isopeptide bond is split into two parts. One part, the SpyTag (SEQ ID NO: 6), is a 13 amino acid peptide that contains part (e.g., an aspartic acid) of the autocatalytic center. The other part, the SpyCatcher (SEQ ID NO: 9), is a 116 amino acid protein domain containing the other part (e.g., a lysine) of the center, promoted by a nearby glutamate or aspartate. Mixing those two polypeptides restores the autocatalytic center and leads to formation of the isopeptide bond, thereby covalently linking the SpyTag to the SpyCatcher (Zakeri et al., 2012). Further engineering has led to a shorter version of SpyCatcher with only 84 amino acids (SpyCatcher Short; SEQ ID NO: 11) as well as an optimized version, SpyTag002 (SEQ ID NO: 7) and SpyCatcher002 (SEQ ID NO: 10) with accelerated reaction (Li et al., 2014 and Keeble et al., 2017); both of which are hereby incorporated by reference in their entirety. A further modification of the system was the invention of SpyLigase (Fierer et al., 2014), which was achieved by splitting the FbaB domain into three parts: the SpyTag, the K-tag (SEQ ID NO: 13) and the SpyLigase. SpyLigase is a fragment of the FbaB domain comprising a glutamic acid residue that induces or catalyzes the formation of the isopeptide bond between the aspartate and lysine residues in SpyTag and K-tag, respectively.

Applications of such systems includes stabilization of proteins by circularization, vaccine generation, multimerization of proteins by integrating streptavidin/biotin with SpyTag/SpyCatcher (Reddington et al., 2015), affibody and Fab multimerization (Fierer et al., 2014), generation of antibodies from modules (Alam et al., 2017) as well as creation of antibody-drug conjugates (Siegmund et al., 2016), and generation of bispecific antibodies (Yumura et al., 2017). A similar system using the adhesin RrgA from *Streptococcus pneumoniae* was developed and termed SnoopTag/SnoopCatcher (Veggiani et al., 2016), with a later development of a SnoopLigase system (Buldun et al., 2018). The SnoopTag/SnoopCatcher technologies are hereby incorporated by reference in their entirety. Another system using *Streptococcus pyogenes* pilin subunit Spy0128 has also been developed and is called Isopeptag/Split Spy0128 (Abe et al., 2013). Yet another system derived from the *Streptococcus dysgalactiae* fibronectin-binding protein has also been developed and is called SdyTag/SdyCatcherDANG short (Tan et al., 2016). The Isopeptag/Split Spy0128 and SdyTag/SdyCatcherDANG short technologies are hereby incorporated by reference in their entirety.

Biotinylation

Biotinylation is a method used to covalently attach biotin to biomolecules such as proteins and nucleic acids. Biotin has a small size that is unlikely to interfere with the function of the biomolecule. Biotin also binds tightly to streptavidin, resulting in a biotin-streptavidin complex that is resistant to extremes of heat, pH and proteolysis. The strong affinity between biotin and streptavidin is widely used in biotechnology, for example, to purify biomolecules via attachment to a solid support.

Proteins can be biotinylated chemically or enzymatically. Chemical biotinylation uses coupling chemistry to non-specifically attach biotin to the protein of interest, which can result in loss of protein activity. Unlike chemical biotinylation, enzymatic biotinylation allows biotin to be attached to one amino acid residue in the protein, which is less likely to have an impact on the protein activity. Beckett et al. (1999) developed a method to enzymatically biotinylate proteins by recombinantly fusing a 15 amino acid peptide (called AviTag or acceptor peptide) to a protein of interest. The acceptor peptide serves as a substrate for *E. coli* biotin holoenzyme synthetase or biotin ligase. When the protein fused to the acceptor peptide is incubated with biotin ligase in the presence of biotin and ATP, the biotin ligase catalyzes biotinylation of a lysine group in the acceptor peptide.

SUMMARY

The invention relates to hybrid reverse transcriptases having improved properties that overcome current limitations in the field and, among other things, result in increased processivity. Hybrid reverse transcriptases of the invention comprise a protein having reverse transcriptase activity and a protein that binds to a nucleic acid template (i.e., a nucleic acid binding protein). The proteins are covalently joined to each other via recombinant methods or via protein ligation, or are non-covalently joined to a biotin-binding protein. A preferred protein having reverse transcriptase activity transcribes RNA with a primer that is not complementary to the 3' end of the template RNA, can jump from the 5' end of the template RNA to a second template (an "acceptor-adaptor") to continue transcription, and can transcribe through a region of the RNA template having secondary structure. The nucleic acid binding protein enhances the ability of the hybrid reverse transcriptase to bind to the template RNA and can therefore improve the processivity of the enzyme. Thus, these properties of the hybrid reverse transcriptases allow the enzymes to bind to and transcribe mRNA sequences (e.g., long mRNA sequences) for subsequent amplification and sequence analysis.

In an embodiment, a hybrid reverse transcriptase comprises a non-retroviral retrotransposon, or a fragment of the non-retroviral retrotransposon having reverse transcriptase activity, recombinantly joined to a nucleic acid binding protein or a fragment of the nucleic acid binding protein. The nucleic acid binding protein can be a single stranded deoxyribonucleic acid (ssDNA) binding protein, a double stranded deoxyribonucleic acid (dsDNA) binding protein, a nucleic acid tag binding protein or fragments thereof.

The non-retroviral retrotransposon, or the fragment of the non-retroviral retrotransposon, is joined either directly or via a linker to the nucleic acid binding protein or a fragment of the nucleic acid binding protein. The nucleic acid binding protein can be, for example, Sso7d, a fragment of Sso7d, Cren7, a fragment of Cren7, *Sulfolobus* SSB, a fragment of *Sulfolobus* SSB, or an anti-nucleic acid tag antibody (e.g., an anti-Digoxigenin antibody).

In some embodiments, two or more nucleic acid binding proteins, or fragments of two or more nucleic acid binding proteins, are joined to the N-terminus or C-terminus of the non-retroviral retrotransposon or the fragment of the non-retroviral retrotransposon. The two or more nucleic acid binding proteins, or fragments of two or more nucleic acid binding proteins, can be in sequential or random order.

In some embodiments, the non-retroviral retrotransposon, or the fragment of the non-retroviral retrotransposon, is covalently joined to the nucleic acid binding protein, or the fragment of the nucleic acid binding protein.

In certain embodiments, the hybrid reverse transcriptase is a multimeric enzyme comprising two or more non-retroviral retrotransposons, or two or more fragments of the non-retroviral retrotransposon having reverse transcriptase activity joined with or without a linker. In some embodiments, the two or more non-retroviral retrotransposons, or the two or more fragments of the non-retroviral retrotransposon, are covalently joined.

In some embodiments, the non-retroviral retrotransposon, or the fragment of the non-retroviral retrotransposon, is an R2 reverse transcriptase or a fragment of the R2 reverse transcriptase (e.g., a recombinant R2 enzyme minus an N-terminal DNA binding domain), respectively. Some embodiments of the R2 reverse transcriptase comprise domains from two or more arthropods.

In certain embodiments, the linker lacks a secondary structure. Exemplary linkers include, but are not limited to, VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), VGTGGGSGGGTGGGSA (SEQ ID NO: 107), $(GGGS)_n$ (SEQ ID NO: 108), $(GGS)_n$, $(GGGGS)_n$ (SEQ ID NO: 109), and $(EAAAK)_n$ (SEQ ID NO: 110) where n is 1, 2, 3, 4, or 5.

In some embodiments, the hybrid reverse transcriptase comprises a purification tag at an N-terminus or a C-terminus.

In certain embodiments, the hybrid reverse transcriptase comprises a non-retroviral retrotransposon having at least 75% sequence identity to SEQ ID NO: 1 joined to a nucleic acid binding protein or a fragment of the nucleic acid binding protein. In some embodiments, the hybrid reverse transcriptase comprises a fragment of a non-retroviral retrotransposon having at least 75% sequence identity to SEQ ID NO: 2 joined to a nucleic acid binding protein or a fragment of the nucleic acid binding protein.

In some embodiments, the hybrid reverse transcriptase comprises SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100 or a sequence with at least 75% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100.

In an embodiment, a hybrid reverse transcriptase comprises a non-retroviral retrotransposon, or a fragment of the non-retroviral retrotransposon having reverse transcriptase activity, in either case comprising a first binding motif and a nucleic acid binding protein, or a fragment of the nucleic acid binding protein, in either case comprising a second binding motif. The first binding motif is covalently joined to the second binding motif via protein ligation.

In some embodiments, the binding motif is located at a C terminus or an N-terminus of the non-retroviral retrotransposon, the fragment of the non-retroviral retrotransposon, the nucleic acid binding protein, or the fragment of the nucleic acid binding protein. In certain embodiments, the binding motif is joined to the non-retroviral retrotransposon, the fragment of the non-retroviral retrotransposon, the nucleic acid binding protein, or the fragment of the nucleic acid binding protein via a linker.

In some embodiments, the hybrid reverse transcriptase is a multimeric enzyme comprising a first non-retroviral retrotransposon, or a first fragment of the non-retroviral retrotransposon having reverse transcriptase activity, in either case comprising a first binding motif and a second non-retroviral retrotransposon, or a second fragment of the non-retroviral retrotransposon having reverse transcriptase activity, in either case comprising a second binding motif. The first binding motif is covalently joined to the second binding motif via protein ligation.

In some embodiments, the first binding motif comprises SEQ ID NO: 48, 49, or 50 or a sequence with at least 60% identity to 48, 49, or 50 and the second binding motif comprises SEQ ID NO: 51, 52, 53, 54, or 55 or a sequence with at least 60% identity to 51, 52, 53, 54, or 55; or the first binding motif comprises SEQ ID NO: 51, 52, 53, 54, or 55 or a sequence with at least 60% identity to 51, 52, 53, 54, or 55 and the second binding motif comprises SEQ ID NO: 48, 49, or 50 or a sequence with at least 60% identity to 48, 49, or 50. In certain embodiments, the first binding motif comprises SEQ ID NO: 56, 57, or 58 or a sequence with at least 60% identity to 56, 57, or 58 and the second binding motif comprises SEQ ID NO: 59, 60, or 61 or a sequence with at least 60% identity to 59, 60, or 61; or the first binding motif comprises SEQ ID NO: 59, 60, or 61 or a sequence with at least 60% identity to 59, 60, or 61 and the second binding motif comprises SEQ ID NO: 56, 57, or 58 or a sequence with at least 60% identity to 56, 57, or 58.

In certain embodiments, the first binding motif comprises a sortase A or B recognition domain comprising the amino acid sequence: LPTGAA (SEQ ID NO: 62), LPTGGG (SEQ ID NO: 63), LPKTGG (SEQ ID NO: 64), LPETG (SEQ ID NO: 65), LPXTG (SEQ ID NO: 66) or LPXTG(X)$_n$ (SEQ ID NO: 67), where X is any amino acid, and n is 0, 1, 2, 3, 4, 5, 7, 8, 9, 10, in the range of 0-5 or 0-10, or any integer up to 100, or NPXITX2 (SEQ ID NO: 68), where X1 is glutamine or lysine; X2 is asparagine or glycine; N is asparagine; P is proline and T is threonine, and the second binding motif comprises a sortase A or B bridging domain comprising: Gly, (Gly)$_2$, (Gly)$_3$, (Gly)$_4$, or (Gly)$_x$, where x is an integer of 1-20.

In some embodiments, the hybrid reverse transcriptase comprises a non-retroviral retrotransposon having at least 75% sequence identity to SEQ ID NO: 1 joined via protein ligation to a nucleic acid binding protein or a fragment of the nucleic acid binding protein. In some embodiments, the hybrid reverse transcriptase comprises a fragment of a non-retroviral retrotransposon having at least 75% sequence identity to SEQ ID NO: 2 joined via protein ligation to a nucleic acid binding protein or a fragment of the nucleic acid binding protein.

In an embodiment, a hybrid reverse transcriptase comprises a non-retroviral retrotransposon, or a fragment of the non-retroviral retrotransposon having reverse transcriptase activity, in either case comprising a biotinylated first acceptor peptide and a nucleic acid binding protein, or a fragment of the nucleic acid binding protein, comprising a biotinylated second acceptor peptide. The biotinylated first and second acceptor peptides are joined to a biotin-binding protein via non-covalent interactions. The nucleic acid binding protein can be a single stranded deoxyribonucleic acid (ssDNA) binding protein or a double stranded deoxyribonucleic acid (dsDNA) binding protein. For example, the nucleic acid binding protein can be Sso7d, a fragment of Sso7d, Cren7, a fragment of Cren7, Sulfolobus SSB, or a fragment of Sulfolobus SSB.

In certain embodiments, the acceptor peptide is located at a C terminus or an N-terminus of the non-retroviral retrotransposon, the fragment of the non-retroviral retrotransposon, the nucleic acid binding protein, or the fragment of the nucleic acid binding protein. In some embodiments, the acceptor peptide is joined to the non-retroviral retrotransposon, the fragment of the non-retroviral retrotransposon, the nucleic acid binding protein, or the fragment of the nucleic acid binding protein via a linker.

In some embodiments, the hybrid reverse transcriptase comprises a first non-retroviral retrotransposon, or a first fragment of the non-retroviral retrotransposon having reverse transcriptase activity, comprising a biotinylated first acceptor peptide and a second non-retroviral retrotransposon, or a second fragment of the non-retroviral retrotransposon having reverse transcriptase activity, comprising a biotinylated second acceptor peptide. The biotinylated first and second acceptor peptides are non-covalently joined to a biotin-binding protein via non-covalent interactions.

In some embodiments, the first and second acceptor peptides comprise SEQ ID NO: 85, 86, 87, 88, or 89.

In certain embodiments, the hybrid reverse transcriptase comprises a non-retroviral retrotransposon having at least 75% sequence identity to SEQ ID NO: 1 and a nucleic acid binding protein, or a fragment of the nucleic acid binding protein, non-covalently joined to a biotin-binding protein. In some embodiments, the hybrid reverse transcriptase comprises a fragment of a non-retroviral retrotransposon having at least 75% sequence identity to SEQ ID NO: 2 and a nucleic acid binding protein, or a fragment of the nucleic acid binding protein, non-covalently joined to a biotin-binding protein.

In some embodiments, the biotin-binding protein is streptavidin, traptavidin, or neutravidin.

In some embodiments, the hybrid reverse transcriptase comprises a purification tag at an N-terminus or a C-terminus of the non-retroviral retrotransposon, the fragment of the non-retroviral retrotransposon, the nucleic acid binding protein, and/or the fragment of the nucleic acid binding protein.

Nucleic acid constructs comprising a polynucleotide sequence encoding the periplasmic fusion proteins are also provided.

Also provided are a pair of nucleic acid constructs comprising a first nucleic acid construct comprising a polynucleotide sequence encoding a non-retroviral retrotransposon, or a fragment of the non-retroviral retrotransposon having reverse transcriptase activity, fused to a first binding motif, and a second nucleic acid construct comprising a polynucleotide sequence encoding a nucleic acid binding protein, or a fragment of the nucleic acid binding protein, fused to a second binding motif. Also provided are a pair of nucleic acid constructs comprising a first nucleic acid construct comprising a polynucleotide sequence encoding a first non-retroviral retrotransposon, or a first fragment of the non-retroviral retrotransposon having reverse transcriptase activity, fused to a first binding motif, and a second nucleic acid construct comprising a polynucleotide sequence encoding a second non-retroviral retrotransposon, or a second fragment of the non-retroviral retrotransposon having reverse transcriptase activity fused to a second binding motif. For both pairs of nucleic acid constructs, the first binding motif and the second binding motif form a covalent bond via protein ligation when brought into contact with one another either spontaneously or with the help of an enzyme.

Also provided are a pair of nucleic acid constructs comprising a first nucleic acid construct comprising a polynucleotide sequence encoding a non-retroviral retrotransposon, or a fragment of the non-retroviral retrotransposon having reverse transcriptase activity fused to a first acceptor peptide, and a second nucleic acid construct comprising a polynucleotide sequence encoding a nucleic acid binding protein, or a fragment of the nucleic acid binding protein, fused to a second acceptor peptide. Also provided are a pair of nucleic acid constructs comprising a first nucleic acid construct comprising a polynucleotide sequence encoding a first non-retroviral retrotransposon, or a first fragment of the non-retroviral retrotransposon having reverse transcriptase activity fused to a first acceptor peptide, and a second nucleic acid construct comprising a polynucleotide sequence encoding a second non-retroviral retrotransposon, or a second fragment of the non-retroviral retrotransposon having reverse transcriptase activity fused to a second acceptor peptide. For both pairs of nucleic acid constructs, the first acceptor peptide and the second acceptor peptide are biotinylated in the presence of biotin ligase and non-covalently bind to a biotin-binding protein when brought into contact with one another.

The invention contemplates vectors comprising nucleic acid constructs disclosed herein and host cells comprising the nucleic acid constructs and/or the vectors.

Methods in which the hybrid reverse transcriptase comprises a dsDNA binding protein are also provided for producing a complementary deoxyribonucleic acid (cDNA) molecule or a cDNA library. In an exemplary method, a template RNA molecule and free nucleotides, are contacted with: a primer that is complementary to the template RNA molecule; an acceptor-adapter; and a hybrid reverse transcriptase comprising a dsDNA binding protein or a fragment of a dsDNA binding protein. The next step of the method comprises allowing the hybrid reverse transcriptase to transcribe the template RNA molecule under conditions effective to produce a cDNA molecule complementary to the RNA molecule and, optionally, to the acceptor-adapter, wherein the hybrid reverse transcriptase jumps to a 3'-end of the acceptor-adapter upon reaching a 5' end of the RNA molecule.

In some embodiments, a method of preparing a cDNA molecule library comprises fragmenting a template RNA molecule to produce RNA fragments. In the next step, a 2', 3'-cyclic phosphate and a 3'-phosphate are removed from the RNA fragments, thereby generating dephosphorylated RNA fragments. A poly-A tail is then added to the dephosphorylated RNA fragments to form poly-A tailed RNA fragments. In the next step, a primer-adapter comprising an oligo-T sequence; an acceptor-adapter; free nucleotides; and a hybrid reverse transcriptase comprising a dsDNA binding protein, or a fragment of a dsDNA binding protein, are added to the poly-A tailed RNA fragments. The hybrid reverse transcriptase is then allowed to transcribe the poly-A tailed RNA fragments under conditions effective to produce a cDNA molecule library, wherein the hybrid reverse transcriptase jumps to a 3'-end of the acceptor-adapter upon reaching a 5' end of the poly-A tailed RNA fragments. In this method, the dephosphorylation and poly (A) addition steps can be combined into one step.

In some embodiments, a method of preparing a cDNA molecule library comprises annealing a primer adapter comprising a poly (T) tail to a template RNA molecule comprising a poly (A) tail, thereby generating an annealed RNA molecule. Next, free nucleotides, the annealed RNA molecule, an acceptor-adapter, and a hybrid reverse transcriptase comprising a a dsDNA binding protein, or a fragment of a dsDNA binding protein, are mixed. The hybrid reverse transcriptase is then allowed to transcribe the annealed RNA molecule at a temperature from about 12° C. to about 42° C. to produce a cDNA molecule library, wherein the hybrid reverse transcriptase jumps to a 3'-end of the acceptor-adapter upon reaching a 5' end of the annealed RNA molecule. The template RNA molecule can be a messenger RNA molecule.

In some embodiments, a method of preparing a cDNA molecule library comprises annealing one or more random primer adapters to template RNA molecules comprising a poly (A) tail, thereby generating annealed RNA molecules. Next, free nucleotides, the annealed RNA molecules, one or more acceptor-adapters, and a hybrid reverse transcriptase comprising a dsDNA binding protein, or a fragment of a dsDNA binding protein, are mixed. The hybrid reverse transcriptase is then allowed to transcribe the annealed RNA molecule without thermal cycling to produce a cDNA molecule library, wherein the hybrid reverse transcriptase jumps to a 3'-end of the acceptor-adapter upon reaching a 5' end of the annealed RNA molecules. In this method, all the steps can be performed in a single reaction vessel. The template RNA molecules can comprise messenger RNAs, ribosomal RNAs, transfer RNAs (tRNAs), micro RNAs, and/or long non-coding RNAs.

Methods in which the hybrid reverse transcriptase comprises a ssDNA binding protein are also provided for producing a complementary deoxyribonucleic acid (cDNA) molecule or a cDNA library. In some embodiments, a method of preparing a cDNA molecule comprises contacting a template RNA molecule and free nucleotides with: a primer that is not complementary to the template RNA molecule, an acceptor-adapter, and a hybrid reverse transcriptase comprising a ssDNA binding protein or a fragment of a ssDNA binding protein. The hybrid reverse transcriptase is then allowed to transcribe the template RNA molecule under conditions effective for producing a cDNA molecule complementary to the RNA molecule and, optionally, to the acceptor-adapter, wherein the hybrid reverse transcriptase jumps to a 3'-end of the acceptor-adapter upon reaching a 5' end of the RNA molecule. The primer can be ssDNA or ssRNA. In some embodiments in which the hybrid reverse transcriptase is a fusion protein, the ssDNA binding protein is an anti-Digoxigenin antibody and the primer comprises a Digoxigenin tag.

In some embodiments, a method of preparing a cDNA molecule library comprises fragmenting a template RNA molecule to produce RNA fragments. The RNA fragments and free nucleotides are then contacted with: a primer-adapter that is not complementary to the RNA fragments, an acceptor-adapter, and a hybrid reverse transcriptase comprising a ssDNA binding protein or a fragment of a ssDNA binding protein. In the next step of the method, the hybrid reverse transcriptase is allowed to transcribe the RNA fragments under conditions effective to produce a cDNA molecule library, wherein the hybrid reverse transcriptase jumps to a 3'-end of the acceptor-adapter upon reaching a 5' end of the RNA fragments. All the steps of the method can be combined into one step. Any or all of the steps can be performed in a partition.

In some embodiments, a method of preparing a cDNA molecule library comprises providing a partition comprising: a cell comprising template RNA molecules, nucleotides, a primer adapter that is not complementary to the RNA molecules, an acceptor-adapter, an endonuclease, and a hybrid reverse transcriptase comprising a ssDNA binding protein or a fragment of a ssDNA binding protein. In the partition, template RNA molecules are then released from the cell, the template RNA molecules are fragmented to form RNA fragments, and the hybrid reverse transcriptase is allowed to transcribe the RNA fragments under conditions effective to produce a cDNA molecule library, wherein the hybrid reverse transcriptase jumps to a 3'-end of the acceptor-adapter upon reaching a 5' end of the dephosphorylated RNA fragments.

The method may further comprise removing one or more non-annealed primer adapter after the last step. The one or more non-annealed primer-adapter can be removed with an immobilized poly A oligo.

In some embodiments, the jumping of the hybrid reverse transcriptase to the 3'-end of the acceptor-adapter is independent of sequence identity between the template RNA molecule(s) and the acceptor-adapter. The cDNA molecule or cDNA library can be prepared in about 2 hours or less.

In certain embodiments, the method further comprises amplifying the cDNA molecule(s) by polymerase chain reaction to form one or more amplicons. The amplifying can be performed at a temperature sufficient to inactivate the reverse transcriptase. In some embodiments, producing and amplifying the cDNA molecule(s) is performed in the same reaction vessel.

In some embodiments, the method further comprises adding a label to the template RNA molecule(s) to generate a labeled cDNA molecule(s). In certain embodiments, the method further comprises sequencing the labeled cDNA molecule(s).

In certain embodiments, the acceptor-adapter, the primer adapter, or both the acceptor-adapter and primer adapter can comprise a nucleotide analogue that stops the reverse transcription by the hybrid reverse transcriptase. In some embodiments, the nucleotide analogue can be at the 5' end of the acceptor-adapter or at the 5' end of the primer adapter. In some embodiments, the acceptor-adapter comprises a 3'-dideoxynucleotide.

In some embodiments, the hybrid reverse transcriptase comprises at least one improved property including, but not limited to, higher processivity, longer shelf life, higher strand displacement, higher end-to-end template jumping, and higher affinity as compared to a non-retroviral retrotransposon, or a fragment of the non-retroviral retrotransposon, that is not joined to a nucleic acid binding protein. In certain embodiments, the processivity of the hybrid reverse transcriptase is about 20 or more nucleotides.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIGS. 1A and 1B (and subsequent figures), "ANABP" refers to nucleic acid binding protein minus fragments that do not affect the function of the nucleic acid binding protein.

DETAILED DESCRIPTION

The invention provides hybrid reverse transcriptases that comprise a non-retroviral retrotransposon, or a fragment of the non-retroviral retrotransposon having reverse transcriptase activity, is covalently joined (i.e., via recombinant methods or via protein ligation) to a nucleic acid binding protein, or a fragment of the nucleic acid binding protein. The invention also provides hybrid reverse transcriptases that comprise a biotinylated non-retroviral retrotransposon, or a fragment of the biotinylated non-retroviral retrotransposon having reverse transcriptase activity, and a biotinylated nucleic acid binding protein, or a fragment of the biotinylated nucleic acid binding protein, non-covalently joined to a biotin-binding protein. The invention comprises nucleic acid constructs encoding the hybrid reverse transcriptases and vectors comprising the nucleic acid constructs. The hybrid reverse transcriptases can jump from a 5' end of a first nucleic acid template to a 3' end of a second nucleic acid template (an "acceptor-adapter"). Hybrid reverse transcriptases comprising a single-stranded nucleic acid binding protein, or a fragment of the single-stranded nucleic acid binding protein, can be used with primers that are not complementary to a template RNA. Hybrid reverse transcriptases comprising a ssDNA binding protein, or a fragment of the ssDNA binding protein can also be used with template RNA that is phosphorylated and does not have a poly (A) tail.

The hybrid reverse transcriptases may have the following improved properties: higher processivity (i.e., does not dissociate from the RNA template before reaching the 5' end), higher strand displacement, higher end-to-end template jumping, higher affinity, and longer shelf life as compared to a non-retroviral retrotransposon, or a fragment of the non-retroviral retrotransposon, that is not joined to a nucleic acid binding protein. The hybrid reverse transcriptases are suitable for use in methods to generate cDNA libraries from total-RNA, messenger RNA (mRNA), micro RNA (miRNA), ribosomal RNAs, transfer RNAs (tRNAs), long non-coding RNA, cell free-RNA or from a single cell. The hybrid reverse transcriptases are also suitable for use in nucleic acid amplification methods (e.g., PCR, quantitative PCR (qPCR), reverse transcription PCR (RT-PCR), or digital droplet PCR (ddPCR)), and sequencing methods. Methods to generate a cDNA library can be performed in a partition (e.g., a droplet in an emulsion) or in a single reaction vessel.

Hybrid Reverse Transcriptases

Figure 1A:
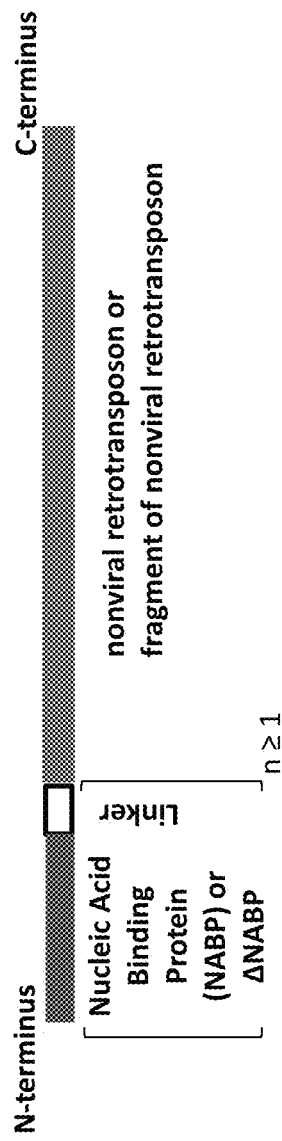
FIGS. 1A and 1B illustrates hybrid reverse transcriptase constructs according to embodiments. In the embodiments, one or more nucleic acid binding proteins or one or more fragments of nucleic acid binding protein is recombinantly joined via an optional linker to an N-terminus (FIG. 1A) or a C-terminus (FIG. 1B) of a nonviral retrotransposon or fragment of the nonviral retrotransposon.
Figure 1B:
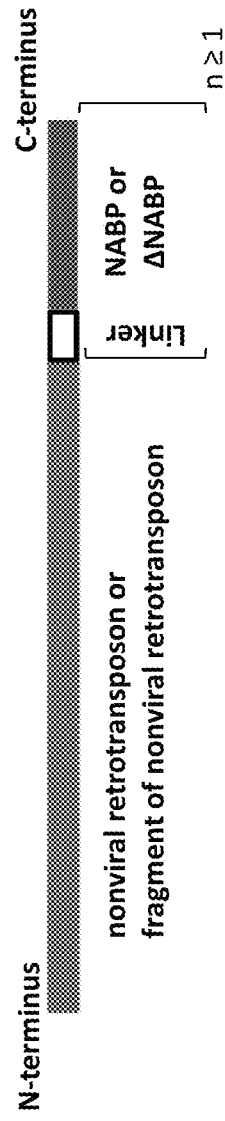

In an embodiment, a hybrid reverse transcriptase comprises a non-retroviral retrotransposon, or a fragment of the non-retroviral retrotransposon having reverse transcriptase activity, joined to a nucleic acid binding protein or a fragment of the nucleic acid binding protein (FIGS. 1A and 1B). In some embodiments, the hybrid reverse transcriptase is a fusion protein. As used herein, a "fusion protein" refers to a protein comprising two or more polypeptides attached by covalent bonding. The two or more polypeptides are encoded by separate genes that are joined so that they are transcribed and translated as a single unit (i.e., in a single open reading frame), producing a single polypeptide that has functional properties derived from each of the original polypeptides. Fusion of the nucleic acid binding protein, or a fragment of the nucleic acid binding protein, to a non-retroviral retrotransposon, or a fragment of the non-retroviral retrotransposon, may enhance the ability of the enzyme to bind and reverse transcribe the nucleic acid.

As used herein, "non-retroviral retrotransposon" refers to naturally occurring proteins encoded by non-retroviral retrotransposons and polypeptide fragments of non-retroviral retrotransposons having reverse transcriptase activity, as well as proteins or polypeptides derived therefrom having one or more amino acid substitutions that either enhance the reverse transcriptase activity thereof or have no deleterious effect thereon. A class of non-retroviral retrotransposon is R2 proteins or polypeptides. Thus, as used herein, "R2 protein or R2 enzyme or polypeptide or a functional fragment thereof" refers to naturally occurring proteins encoded by R2 elements and polypeptide fragments thereof which possess reverse transcriptase activity, as well as proteins or polypeptides derived therefrom which contain one or more amino acid substitutions that either enhance the reverse transcriptase activity thereof or have no deleterious effect thereon.

In some embodiments, the non-retroviral retrotransposon, or the fragment of the non-retroviral retrotransposon is a non-long terminal repeat (LTR) retrotransposon derived from the R2 element of the silkmoth, *Bombyx mori*. In an embodiment, the non-retroviral retrotransposon comprises at least 60%, 65%, 70%, 75%, 80%, 85%, 90%, 91%, 92%, 93%, 94%, 95%, 96%, 97%, 98%, or 99% sequence identity to SEQ ID NO: 1 (i.e., wild type R2 enzyme derived from *Bombyx mori*).

The R2 element of many arthropods have three functional domains: an N-terminal DNA binding domain, a central reverse transcriptase domain, and a C-terminal endonuclease domain (Burke et al., "The Domain Structure and Retrotransposition Mechanism of R2 Elements Are Conserved Throughout Arthropods," *Mol. Biol. Evol.* 16 (4): 502-511 (1999)). In certain embodiments, the fragment derived from the R2 element of the silkmoth is lacking an N-terminal DNA binding domain. In some embodiments, the fragment derived from the R2 element of the silkmoth has at least 60%, 65%, 70%, 75%, 80%, 85%, 90%, 91%, 92%, 93%, 94%, 95%, 96%, 97%, 98%, or 99% sequence identity to SEQ ID NO: 2.

Proteins derived from the R2 element of other arthropods than the silkmoth can also be used in embodiments of the hybrid reverse transcriptase and include, but are not limited to, R2 elements from *Drosophila* spp. (fruit fly), *Forficula auricularia* (earwig), *Popillia japonica* (Japanese beetle), *Nasonia vitripennis* (jewel wasp), *Tenebrio molitor* (mealworm), *Collembola* spp. (springtails), *Isopoda* spp. (pillbugs), and *Limulus polyphemus* (horseshoe crab). Any of the proteins listed in Table 1, including homologs, variants, or fragments thereof of the proteins, can also be used in the hybrid reverse transcriptase. The proteins listed in Table 1 are from the same phylogenetic tree as silkmoth and have at least 27% identity to silkmoth. In some embodiments, the hybrid reverse transcriptase comprises R2 element domains from two or more arthropods. For example, the N-terminal binding domain from any of the proteins listed in Table 1 can be combined with the central reverse transcriptase domain and the C-terminal endonuclease domain of the silk worm.

TABLE 1

| GenBank Number | Description |
| --- | --- |
| KRX33447.1 | retrovirus-related Pol polyprotein from type-2 retrotransposable element R2DM, partial [*Trichinella murrelli*] |
| KRX36111.1 | retrovirus-related Pol polyprotein from type-2 retrotransposable element R2DM [*Trichinella murrelli*] |
| KRZ48391.1 | Retrovirus-related Pol polyprotein from type-1 retrotransposable element [*Trichinella nativa*] |
| KRZ66264.1 | Retrovirus-related Pol polyprotein from type-2 retrotransposable element R2DM [*Trichinella papuae*] |
| BAC82594.1 | reverse transcriptase [*Danio rerio*] |
| AAC34903.1 | reverse transcriptase, partial [*Anurida maritima*] |
| AAC34904.1 | reverse transcriptase, partial [*Limulus polyphemus*] |
| AFO19998.1 | R2 protein [*Lepidurus couesii*] |
| KMQ90176.1 | Reverse transcriptase [*Lasius niger*] |
| ACJ71597.1 | reverse transcriptase [*Rhynchosciara americana*] |
| AIL01110.1 | Reverse transcriptase [*Bacillus rossius*] |
| KMQ88340.1 | reverse transcriptase [*Lasius niger*] |
| AFM44926.1 | R2 protein [*Eyprepocnemis plorans*] |
| AAB94032.1 | reverse transcripta [*Drosophila mercatorum*] |
| KRY44798.1 | Retrovirus-related Pol polyprotein from type-2 retrotransposable element R2DM [*Trichinella britovi*] |
| CAX83712.1 | endonuclease-reverse transcriptase [*Schistosoma japonicum*] |
| PIS84891.1 | reverse transcriptase [*Fasciola hepatica*] |
| BAX24491.1 | reverse transcriptase [*Beryx splendens*] |
| ACV95454.1 | reverse transcriptase/endonuclease [*Adineta vaga*] |
| PAA70689.1 | hypothetical protein BOX15_Mlig021084g2 [*Macrostomum lignano*] |

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region or the entire designated sequence if a region is not specified), when compared and aligned for maximum correspondence over a comparison window.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, about 10 to about 300, about 10 to about 150 in which a sequence may be compared to a reference sequence of the same number of contiguous positions after the two sequences are optimally aligned. The comparison window can also be the entire length of either the reference or the test sequence.

Percent sequence identity and sequence similarity can be determined using the BLAST 2.0 algorithm, which is described in Altschul et al. (*J. Mol. Biol.* 215:403-10, 1990). Software for performing BLAST 2.0 analyses is publicly available through the National Center for Biotechnology Information (Worldwide Website: ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The nucleic acid binding protein portion of the hybrid reverse transcriptase binds to nucleic acid in a nucleotide sequence-independent manner, (i.e., binding does not exhibit a preference for a particular sequence). In certain embodiments, the nucleic acid binding protein is a double-stranded DNA (dsDNA) binding protein (i.e., the dsDNA binding protein preferentially binds dsDNA over single-stranded DNA (ssDNA)), or a ssDNA binding protein. In some embodiments, a dsDNA binding protein is Sso7d (SEQ ID NO: 3) or Cren7 (SEQ ID NO: 4) or homologs, variants, or fragments thereof. Any of the dsDNA binding proteins listed in TABLES 2 and 3, including homologs, variants, or fragments thereof, can also be used in the hybrid reverse transcriptases.

TABLE 2

| UniProt Number | Description |
| --- | --- |
| P13123 | Sac7d [*Sulfolobus acidocaldarius*] |
| P13125 | Sac7e [*Sulfolobus acidocaldarius*] |
| A4YEA2 | Mse7 [*Metallosphaera sedula*] |
| F4FYY6 | Mcu7 [*Metallosphaera cuprina*] |
| F4B9I1 | Aho7a [*Acidianus hospitalis*] |
| F4B9I5 | Aho7b [*Acidianus hospitalis*] |
| F4B8X5 | Aho7c [*Acidianus hospitalis*] |
| Q96X56 | Sto7 [*Sulfurisphaera tokodaii*] |
| O59632 | Ssh7b [*Saccharolobus shibatae*] |
| D2PHL8 | Sis7a [*Sulfolobus islandicus*] |
| F0NJT3 | Sis7b [*Sulfolobus islandicus*] |
| P61990 | Ssh7a [*S. shibatea*] |
| P39476 | Sso7d [*Saccharolobus Solfataricus*] |

TABLE 3

| GenBank Number | Description |
| --- | --- |
| ARM76599.1 | chorismate-binding protein [*Acidianus manzaensis*] |
| WP_110270921.1 | chorismate-binding protein [*Acidianus brierleyi*] |
| WP_011822047.1 | chorismate-binding protein [*Hyperthermus butylicus*] |
| WP_058370641.1 | chorismate-binding protein [*Pyrodictium occultum*] |
| WP_109160791.1 | chorismate-binding protein [*Desulfurococcaceae archaeon*] |
| AFH42781.1 | chromatin protein Cren7 [*Fervidicoccus fontis* Kam940] |
| WP_014027454.1 | chorismate-binding protein [*Pyrolobus fumarii*] |

In some embodiments, a ssDNA binding protein is *Sulfolobus* SSB (SEQ ID NO: 5), or homologs, variants, or fragments thereof. In some embodiments, the ssDNA binding protein is anti-nucleic acid tag antibody (e.g., anti-Digoxigenin antibody). Any of the ssDNA binding proteins listed in TABLE 4, including homologs, variants, or fragments thereof, can also be used in the hybrid reverse transcriptases.

TABLE 4

| GenBank Number | Description |
| --- | --- |
| WP_013561922.1 | single-stranded DNA-binding protein [*Desulfurococcus mucosus*] |
| PVU72461.1 | single-stranded DNA-binding protein [*Sulfolobales archaeon* SCGC AB-777_J03]) |
| WP_013561922.1 | single-stranded DNA-binding protein [*Thermoplasma* sp. Kam2015] |
| RLG83789.1 | single-stranded DNA-binding protein [*Thermoprotei archaeon*] |
| ALU11621.1 | single-stranded DNA-binding protein [*Ignicoccus islandicus* DSM 13165] |
| WP_012718085.1 | single-stranded DNA-binding protein [*Sulfolobus islandicus*] |
| WP_010978480.1 | single-stranded DNA-binding protein [*Sulfurisphaera tokodaii*] |
| WP_012020631.1 | single-stranded DNA-binding protein [*Metallosphaera sedula*] |
| EWG07842.1 | single-stranded DNA-binding protein [*Candidatus Aramenus sulfurataquae*] |
| RLG38958.1 | single-stranded DNA-binding protein [*Candidatus Korarchaeota archaeon*] |
| WP_011821997.1 | single-stranded DNA-binding protein [*Hyperthermus butylicus*] |
| BAN90306.1 | ssDNA-binding protein [*Aeropyrum camini* SY1 = JCM 12091] |
| WP_131159968.1 | single-stranded DNA-binding protein [*Aeropyrum pernix*] |
| BAA80315.2 | single-stranded DNA binding protein [*Aeropyrum pernix* K1] |
| TDA40126.1 | single-stranded DNA-binding protein [*Candidatus Verstraetearchaeota archaeon*] |
| RLI67762.1 | hypothetical protein DRO63_04010 [*Candidatus Heimdallarchaeota archaeon*] |
| OLD91798.1 | hypothetical protein AUG86_00240 [*Euryarchaeota archaeon* 13_1_20CM_4_64_14] |
| WP_010901557.1 | single-stranded DNA-binding protein [*Thermoplasma acidophilum*] |
| PUA31887.1 | hypothetical protein B9J98_05180 [*Aigarchaeota archaeon* NZ13_MG1] |
| RLG96403.1 | hypothetical protein DRO27_02395 [*Candidatus Bathyarchaeota archaeon*] |
| WP_054838323.1 | single-stranded DNA-binding protein [*Sulfolobus metallicus*] |
| PMP92383.1 | single-stranded DNA-binding protein [*Caldisphaera* sp.] |
| EQB65396.1 | hypothetical protein AMDU3_IPLC00002G0033 [*Thermoplasmatales archaeon* I-plasma] |
| WP_055409701.1 | single-stranded DNA-binding protein [*Pyrodictium delaneyi*] |

TABLE 4-continued

| GenBank Number | Description |
| --- | --- |
| WP_100692737 | single-stranded DNA-binding protein SSB1 [*Escherichia coli*] |
| WP_003898320 | single-stranded DNA-binding protein [*Mycolicibacterium smegmatis*] |

In some embodiments, one or more nucleic acid binding proteins, or one or more fragments of a nucleic acid binding protein, is joined to the non-retroviral retrotransposon, or the fragment of the non-retroviral retrotransposon (FIGS. 1A and 1B). The nucleic acid binding proteins or fragments thereof can be identical or non-identical and can be joined in sequential or random order to the N-terminus (FIG. 1A) or the C-terminus (FIG. 1B) of the non-retroviral retrotransposon, or the fragment of the non-retroviral retrotransposon.

In some embodiments, the hybrid reverse transcriptase comprises at least one linker between the non-retroviral retrotransposon, or the fragment of the non-retroviral retrotransposon, and the nucleic acid binding protein, or a fragment of the nucleic acid binding protein. As used herein, a "linker" refers to a peptide or polypeptide containing one or more amino acid residues (e.g., 1, 2, 3, 4, 5, 10 or more amino acid residues) joined by a peptide bond(s). Such linkers can provide rotational freedom that allows each component of the hybrid reverse transcriptase to interact with its intended target without hindrance. These linkers can be mixtures of glycine and serine, such as -(GGS)$_n$-, -(GGGS)$_n$-(SEQ IN NO: 108), -(GGGGS)$_n$-(SEQ ID NO: 109), and -(EAAAK)$_n$-(SEQ ID NO: 110) where n is 1, 2, 3, 4, or 5 where n is any integer. Other suitable peptide/polypeptide linker sequences optionally include naturally occurring or non-naturally occurring peptides or polypeptides. Optionally, the peptide or polypeptide linker sequences are flexible peptides or polypeptides. Exemplary flexible peptides/polypeptides include, but are not limited to, the amino acid sequences Gly-Ser, Gly-Ser-Gly-Ser (SEQ ID NO: 118), Ala-Ser, Gly-Gly-Gly-Ser (SEQ ID NO: 108), Gly$_4$-Ser (SEQ ID NO: 109), (Gly$_4$-Ser) 2, (Gly$_4$-Ser) 3, (Gly$_4$-Ser)$_4$, (Gly$_4$-Ser)$_2$-Gly-Ala-Gly-Ser-Gly$_4$-Ser (SEQ ID NO 119), Gly-(Gly$_4$-Ser)$_2$ (SEQ ID NO: 120), Gly$_4$-Ser-Gly (SEQ ID NO: 121), Gly-Ser-Gly$_2$ (SEQ ID NO: 122), and Gly-Ser-Gly$_2$-Ser (SEQ ID NO: 123). Exemplary peptides/polypeptides include, but are not limited to, VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), and VGTGGGSGGGTGGGSA (SEQ ID NO: 107). In some embodiments, a sequence of 1 to 50 amino acid residues can be used as a linker.

In some embodiments, a hybrid reverse transcriptase comprises two or more non-retroviral retrotransposons, or two or more fragments of the non-retroviral retrotransposon having reverse transcriptase activity, joined by an optional linker. In some embodiments, the hybrid reverse transcriptase comprises two or more fragments of R2 enzyme joined by an optional linker.

Hybrid reverse transcriptase constructs according to embodiments are listed in TABLE 5 along with their respective SEQ ID NO. In TABLE 5, ORF refers to Original Reading Frame. "WT R2 enzyme" refers to wild type R2 enzyme (SEQ ID NO: 1). "ΔR2 enzyme" refers to R2 enzyme minus the N-terminal DNA binding domain (SEQ ID NO: 2). "ΔSSB" refers to SSB minus C-terminal fragments (SEQ ID NO: 46).

TABLE 5

| SEQ ID NO: | N-terminal ORF | Linker ORF | C-terminal ORF |
| --- | --- | --- | --- |
| 6 and 7 | Sso7d | Linker | WT R2 enzyme and ΔR2 enzyme |
| 8 and 9 | Sso7d-Sso7d | Linker | WT R2 enzyme and ΔR2 enzyme |
| 10 and 11 | Cren7 | Linker | WT R2 enzyme and ΔR2 enzyme |
| 12 and 13 | Cren7-Cren7 | Linker | WT R2 enzyme and ΔR2 enzyme |
| 14 and 15 | SSB | Linker | WT R2 enzyme and ΔR2 enzyme |
| 16 and 17 | SSB-SSB | Linker | WT R2 enzyme and ΔR2 enzyme |
| 18 and 19 | WT R2 enzyme and ΔR2 enzyme | Linker | Sso7d |
| 20 and 21 | WT R2 enzyme and ΔR2 enzyme | Linker | Sso7d-Sso7d |
| 22 and 23 | WT R2 enzyme and ΔR2 enzyme | Linker | Cren7 |
| 24 and 25 | WT R2 enzyme and ΔR2 enzyme | Linker | Cren7-Cren7 |
| 26 and 27 | WT R2 enzyme and ΔR2 enzyme | Linker | Cren7-Cren7-Cren7 |
| 28 and 29 | WT R2 enzyme and ΔR2 enzyme | Linker | Sso7d-Cren7 |
| 30 and 31 | WT R2 enzyme and ΔR2 enzyme | Linker | Sso7d-Cren7-Cren7 |
| 32 and 33 | WT R2 enzyme and ΔR2 enzyme | Linker | Cren7-Sso7d |
| 34 and 35 | WT R2 enzyme and ΔR2 enzyme | Linker | SSB |
| 36 and 37 | WT R2 enzyme and ΔR2 enzyme | Linker | SSB-SSB |
| 38 and 39 | WT R2 enzyme and ΔR2 enzyme | Linker | SSB-SSB-SSB |
| 40 and 41 | WT R2 enzyme and ΔR2 enzyme | Linker | SSB-Cren7 |
| 42 and 43 | WT R2 enzyme and ΔR2 enzyme | Linker | SSB-Cren7-Cren7 |
| 44 and 45 | WT R2 enzyme and ΔR2 enzyme | Linker | WT R2 enzyme and ΔR2 enzyme |
| 98 and 47 | WT R2 enzyme and ΔR2 enzyme | Linker | ΔSSB-ΔSSB |
| 99 and 100 | ΔSSB-ΔSSB | Linker | WT R2 enzyme and ΔR2 enzyme |

Accordingly, in some embodiments, the hybrid reverse transcriptase comprises a sequence with at least 75% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100. In some embodiments, the hybrid reverse transcriptase comprises SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO:

27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100.

Hybrid Reverse Transcriptases Formed Via Protein Ligation

The term "binding motif" refers to a protein sequence that is attached to a first polypeptide (e.g., a non-retroviral retrotransposon or a fragment of the non-retroviral retrotransposon having reverse transcriptase activity) and a second polypeptide (e.g., a nucleic acid binding protein/fragment of the nucleic acid binding protein or a second non-retroviral retrotransposon/fragment of the non-retroviral retrotransposon). The binding motifs facilitate the formation of a covalent bond between the first and second polypeptides. Non-limiting examples of binding motifs include SpyTag sequences (including SpyTag002), SpyCatcher sequences (including SpyCatcher short and SpyCatcher002), SnoopTag sequences (including SnoopTagJr), SnoopCatcher sequences, Isopeptag sequences, Split Spy0128 sequences, K-tag sequences, SdyTag sequences, SdyCatcherDANG short sequences, DogTag sequences, and sortase sequences (including sortase recognition domain and sortase bridging domain). The binding motifs may be fused to an N-terminus or a C-terminus of the polypeptide. One or more linker sequences (e.g., a glycine/serine rich linker) may flank the binding motifs to enhance accessibility for reaction or to enhance flexibility of the fused polypeptides.

The term "protein ligation" as used herein refers to site-specific covalent bond formation, either spontaneously or with the help of an enzyme, between a first binding motif and a second binding motif when the first and second binding motifs are brought into contact with one another. Non-limiting examples of the protein ligation systems include the Spy Tag/SpyCatcher system, Spy Tag with the shorter version of SpyCatcher (i.e., SpyCatcher short), SpyTag002 and SpyCatcher002 with accelerated reaction, the SpyTag/K-tag/SpyLigase system, the Isopeptag/Split Spy0128 system, the SnoopTag/SnoopCatcher system, the SdyTag/SdyCatcher system, the SnoopTagJr/DogTag/SnoopLigase system, and the sortase system.

Protein ligation occurs between mutually reactive or cognate pairs of binding motifs. For example, if the first binding motif is SpyTag (SEQ ID NO: 48), then the second binding motif can be SpyCatcher (SEQ ID NO: 51), SpyCatcher002 (SEQ ID NO: 52), or SpyCatcher short (SEQ ID NO: 53), but cannot be SnoopCatcher (SEQ ID NO: 59) or SdyCatcherDANG short (SEQ ID NO: 60) because the SpyTag/SpyCatcher system is orthogonal to the SnoopTag/SnoopCatcher system. As used herein, "orthogonal" refers to mutually unreactive or noncognate binding pairs. Protein ligation can also occur between the following combinations of binding motifs: between SpyTag or SpyTag002 (SEQ ID NO: 49) and SpyCatcher, SpyCatcher short, or SpyCatcher002 (SEQ ID NO: 52); between SnoopTag (SEQ ID NO: 56) and SnoopCatcher (SEQ ID NO: 59); between Isopeptag (SEQ ID NO: 50) and Split Spy0128 (SEQ ID NO: 54); between SdyTag (SEQ ID NO: 57) and SdyCatcherDANG short (SEQ ID NO: 60), between SpyTag and K-Tag (SEQ ID NO: 55); and between SnoopTagJr (SEQ ID NO: 58) and DogTag (SEQ ID NO: 61).

The sortase system uses sortase enzymes and sortase recognition and bridging domains. In embodiments of the hybrid reverse transcriptase, the sortase recognition and bridging domains are considered binding motifs. Sortases are transpeptidases produced by Gram-positive bacteria to anchor cell surface proteins covalently to the cell wall. The *Staphylococcus aureus* sortase A (SrtA) cleaves a short C-terminal recognition motif (LPXTG (SEQ ID NO: 66) (referred to herein as a sortase recognition domain). The sortase recognition domain is a sortase A recognition domain or a sortase B recognition domain. The sortase A recognition domain comprises or consists of the amino acid sequence: LPTGAA (SEQ ID NO: 62), LPTGGG (SEQ ID NO: 63), LPKTGG (SEQ ID NO: 64), LPETG (SEQ ID NO: 65), LPXTG (SEQ ID NO: 66) or LPXTG(X)$_n$ (SEQ ID NO: 67), where X is any amino acid, and n is 0, 1, 2, 3, 4, 5, 7, 8, 9, 10, in the range of 0-5 or 0-10, or any integer up to 100. The sortase B recognition domain comprises the amino acid sequence NPX1TX2 (SEQ ID NO: 68), where X1 is glutamine or lysine; X2 is asparagine or glycine; N is asparagine; P is proline and T is threonine.

The sortase A and B bridging domains comprise one or more glycine residues at the N-terminus of a peptide. In certain embodiments, the one or more glycine residues may optionally be: Gly, (Gly)$_2$, (Gly)$_3$, (Gly)$_4$, or (Gly) x, where x is an integer of 1-20.

Components of the mutually reactive binding motif pair or cognate binding motif pair can be interchanged between the non-retroviral retrotransposon, or the fragment of the non-retroviral retrotransposon, and the nucleic acid binding protein, or a fragment of the nucleic acid binding protein (e.g., one embodiment provides a non-retroviral retrotransposon, or a fragment of the non-retroviral retrotransposon, comprising SpyTag and a nucleic acid binding protein, or a fragment of the nucleic acid binding protein, comprising SpyCatcher, SpyCatcher short, or SpyCatcher002. An alternative embodiment provides a nucleic acid binding protein, or a fragment of the nucleic acid binding protein, comprising SpyTag and a non-retroviral retrotransposon, or a fragment of the non-retroviral retrotransposon, comprising SpyCatcher, SpyCatcher short, or SpyCatcher002). Exemplary first and second binding motifs for the hybrid reverse transcriptase embodiments are provided in Table 5.

TABLE 6

| First Binding Motif | Second Binding Motif |
|---|---|
| SEQ ID NO: 48, 49, or 50 or a sequence with at least 60% sequence identity to SEQ ID NO: 48, 49, or 50. | SEQ ID NO: 51, 52, 53, 54, or 55 or a sequence with at least 60% sequence identity to SEQ ID NO: 51, 52, 53, 54, or 55. |
| SEQ ID NO: 51, 52, 53, 54, or 55 or a sequence with at least 60% sequence identity to SEQ ID NO: 51, 52, 53, 54, or 55. | SEQ ID NO: 48, 49, or 50 or a sequence with at least 60% sequence identity to SEQ ID NO: 48, 49, or 50. |
| SEQ ID NO: 56, 57, or 58 or a sequence with at least 60% sequence identity to SEQ ID NO: 56, 57, or 58. | SEQ ID NO: 59, 60, or 61 or a sequence with at least 60% sequence identity to SEQ ID NO: 59, 60, or 61. |
| SEQ ID NO: 59, 60, or 61 or a sequence with at least 60% sequence identity to SEQ ID NO: 59, 60, or 61. | SEQ ID NO: 56, 57, or 58 or a sequence with at least 60% sequence identity to SEQ ID NO: 56, 57, or 58. |
| SEQ ID NO: 62, 63, 64, 65, 66, 67, or 68. | Gly, (Gly)$_2$, (Gly)$_3$, (Gly)$_4$, or (Gly)$_x$, where x is an integer of 1-20 |
| Gly, (Gly)$_2$, (Gly)$_3$, (Gly)$_4$, or (Gly)$_x$, where x is an integer of 1-20 | SEQ ID NO: 62, 63, 64, 65, 66, 67, or 68. |

In some embodiments, the binding motif is joined to the N- or C-terminus of the non-retroviral retrotransposon, the fragment of the non-retroviral retrotransposon, the nucleic acid binding protein, or a fragment of the nucleic acid binding protein, via an optional linker as indicated in Table 7. In Table 7, ORF refers to Original Reading Frame. "WT R2 enzyme" refers to wild type R2 enzyme (SEQ ID NO: 1). "ΔR2 enzyme" refers to R2 enzyme minus the N-terminal DNA binding domain (SEQ ID NO: 2). "ΔNucleic Acid Binding Protein" refers to nucleic acid binding protein minus a fragment(s).

TABLE 7

| N-terminal ORF | Linker ORF | C-terminal ORF |
|---|---|---|
| WT R2 enzyme or ΔR2 enzyme | Linker | First or Second Binding Motif |
| Nucleic Acid Binding Protein (Sso7d, Cren7, or SSB) or ΔNucleic Acid Binding Protein | Linker | First or Second Binding Motif |
| First or Second Binding Motif | Linker | WT R2 enzyme or ΔR2 enzyme |
| First or Second Binding Motif | Linker | Nucleic Acid Binding Protein (Sso7d, Cren7, or SSB) or ΔNucleic Acid Binding Protein |

Hybrid RTs Formed Via Non-Covalent Process with AviTag

The term "acceptor peptide" refers to an amino acid sequence that is attached to a first polypeptide (e.g., a non-retroviral retrotransposon or a fragment of the non-retroviral retrotransposon having reverse transcriptase activity) and a second polypeptide (e.g., a nucleic acid binding protein or a second non-retroviral retrotransposon/fragment of the non-retroviral retrotransposon). The acceptor peptide is a substrate for enzymatic biotinylation. As used herein, "enzymatic biotinylation" refers to the enzyme-catalyzed attachment of biotin to a lysine group in the acceptor peptide. The acceptor peptide can be biotinylated in vitro or in vivo by, for example, E. coli biotin ligase (the BirA protein) in the presence of biotin and ATP (Beckett et al., 1999). Non-limiting examples of acceptor peptides include, but are not limited to AviTag (SEQ ID NO: 85; GLNDIFEAQKIEWHE), BioTag (SEQ ID NO: 86; ALNDIFEAQKIEWHA), Biotin ligase recognition peptide (SEQ ID NO: 87; MAGGLNDIFEAQKIEWHEDTGGS), BirA Substrate Peptide (SEQ ID NO: 88; LHHILDAQKMVWNHR) and LX§ IFEAQKIEWR (SEQ ID NO: 89), where X=any amino acid and § =any amino acid but not L, V, I, W, F or Y (Fairfield et al., 2015). Beckett et al. (1999) and Fairfield et al. (2015) are hereby incorporated by reference in their entirety.

The acceptor peptide may be fused to the N- or C-terminus of the non-retroviral retrotransposon, the fragment of the non-retroviral retrotransposon, or the nucleic acid binding protein via an optional linker as indicated in Table 8.

TABLE 8

| N-terminal ORF | Linker ORF | C-terminal ORF |
|---|---|---|
| WT R2 enzyme or ΔR2 enzyme | Linker | Acceptor Peptide |
| Nucleic Acid Binding Protein (Sso7d, Cren7, or SSB) or ΔNucleic Acid Binding Protein | Linker | Acceptor Peptide |
| Acceptor Peptide | Linker | WT R2 enzyme or ΔR2 enzyme |
| Acceptor Peptide | Linker | Nucleic Acid Binding Protein (Sso7d, Cren7, or SSB) or ΔNucleic Acid Binding Protein |

As used herein, the term "non-covalent interactions" refers to interactions between molecules that do not involve the sharing of electrons. Examples of non-covalent interactions can include hydrogen bonding, electrostatic interactions, pi stacking, van der Waals interactions, and dipole-dipole interactions.

As used herein, the term "biotin-binding protein" refers to a protein that can specifically bind to biotin with high binding affinity. The biotin-binding protein can be streptavidin, traptavidin, or neutravidin or any protein that can bind to biotin with a binding affinity similar to streptavidin. In some embodiments, the dissociation constant of the biotin-binding protein is about 10-14 to about 10-15 mol/L.

In certain embodiments, a purification tag is attached to the N-terminus, the C-terminus, or to both the N- and C-termini of the hybrid reverse transcriptase. Exemplary purification tags include, but are not limited to, polyhistidine or His-tag and FLAG-tag (i.e., amino acid sequence DYKDDDDK (SEQ ID NO: 124) where D is aspartic acid, Y is tyrosine, and K is lysine).

In certain embodiments, the hybrid reverse transcriptase comprises at least one improved property as compared to a reverse transcriptase that does not comprise a nucleic acid binding domain (i.e., a non-retroviral retrotransposon, or a fragment of the non-retroviral retrotransposon having reverse transcriptase activity that is not joined to a nucleic acid binding protein). In some embodiments, the improved property is higher processivity, higher strand displacement, higher affinity, higher end-to-end template jumping, longer shelf life, and/or higher expression yield (i.e., higher milligrams fusion recovered per milligrams of E. coli cells). As used herein, "processivity" refers to the ability of a nucleic acid modifying enzyme to remain attached to the template or substrate and perform multiple modification reactions. Typically processivity refers to the ability to modify relatively long tracts of nucleic acid. In some embodiments, the processivity of the hybrid reverse transcriptase is about 20, 30, 40, 50 or more nucleotides.

As used herein, "strand displacement" is the ability of the fusion enzyme to displace a complementary strand of RNA or DNA during transcription, resulting in the ability of the enzyme to generate long cDNA products. As used herein, "affinity" is the ability of the fusion enzyme to bind and stay bound to the RNA template during transcription and; thus, is also related to the ability of the enzyme to modify relatively long tracts of nucleic acid. Since processivity, strand displacement, and affinity are related to the ability of the enzyme to transcribe long tracts of nucleic acid, they can be determined by, for example, using qPCR to quantify the amount or yield of cDNA products for specific templates. Exemplary templates that can be used are an External RNA Controls Consortium (ERCC) standard mix of 90 different RNA templates with known concentrations, lengths, and secondary structure (or GC content). Highly processive and strand displacing enzymes with high affinity will generate exact cDNA copies of the RNA templates with the original ratio of long to short RNA templates or high to low secondary structure. Low processive and strand displacing enzymes with low affinity will predominantly copy short RNA templates having low amounts of secondary structure. The ratio of amount of long to short transcripts and/or high to low secondary structure-containing transcripts can be measured with qPCR using appropriate primers for the RNA templates.

As used herein, "end-to-end template jumping" refers to the fusion enzyme jumping from a 3' end of a primer-adapter to the 3' end of the RNA template or from the 5' end of the RNA template to a 3' end of an acceptor-adapter. In some embodiments, end-to-end template jumping is measured by allowing the fusion enzyme to transcribe a short synthetic RNA template with an annealed DNA primer in the presence of a DNA acceptor-adapter and then determining a jumping efficiency. Jumping efficiency is the ratio (or percent) of fully reverse transcribed RNA template to jumping product (i.e., cDNA including sequences of RNA template and acceptor-adapter).

As used herein, a "primer" refers to a polynucleotide sequence that serves as a point of initiation of nucleic acid synthesis. The primer may optionally hybridize (i.e., is complementary) to a sequence on a target nucleic acid. Primers can be of a variety of lengths and are often less than 50 nucleotides in length, for example 12-30 nucleotides, in length. In some embodiments, a primer may comprise one or more random primer(s). In some embodiments, the primer is a "primer-adapter". As used herein, a primer-adapter refers to a primer comprising an adapter sequence in which the 5' tail sequence does not hybridize to the template nucleic acid. In some embodiments, the primer-adapter comprises a digoxigenin-tag (DIG-tag) label (i.e., digoxigenin is incorporated in the primer-adapter during synthesis).

As used herein, the term "acceptor-adapter" refers to a single-stranded nucleic acid to which a hybrid reverse transcriptase can jump from a 5' end of a template nucleic acid in the absence of sequence identity between the accepter-adapter and the template nucleic acid. In some embodiments, an acceptor-adapter may be modified. In some embodiments, an acceptor-adapter may be modified at the 3' end, for example to protect it from being mistaken as an RNA primer. In some embodiments, the modification of the acceptor-adapter comprises a dideoxy 3' end. In some embodiments, the 3' end of the acceptor-adapter is blocked by the addition of, for example, a C3 spacer, a phosphate, an amine group ($NH_2$), or any other chemical modification that inhibits formation of a subsequent phosphodiester bond between the 3' end of the acceptor-adapter and another nucleotide. In certain embodiments, a 5' end of the accepter-adapter comprises a nucleotide analogue that stops the reverse transcription.

As used herein, "shelf life" refers to the ability of the fusion enzyme to retain reverse transcriptase activity over a given period of time and at a given condition. In some embodiments, the fusion enzyme has a shelf life in solution at room temperature, −20° C., or 37° C. for at least 1 day (5 days, 10 days, 15 days, 20 days, 25 days, one month, 2 months, or 3 months). Shelf life can be determined by, for example, using qPCR and three or more reference RNA templates (e.g., ERCC RNAs, known synthetic RNAs, or Universal Human Reference RNAs) at known concentrations to quantify the amount of primer extension products and to determine when the fusion enzyme has lost 50% reverse transcriptase activity (i.e., when the amount of primer extension products has decreased by 50%). Thus, for example, if the fusion enzyme has lost 40% reverse transcriptase activity at 4 days in solution at room temperature and has lost 50% reverse transcriptase activity at 5 days in solution at room temperature, then the fusion enzyme has a shelf life of 5 days in solution at room temperature.

Nucleic Acid Constructs

Also provided are the following nucleic acid constructs:
1. Nucleic acid constructs that encode for a hybrid reverse transcriptase, without or with a linker between the non-retroviral retrotransposon, or the fragment of the non-retroviral retrotransposon having reverse transcriptase activity, and the nucleic acid binding protein(s) or fragment(s) of the nucleic acid binding protein;
2. Nucleic acid constructs that encode for a non-retroviral retrotransposon, or a fragment of the non-retroviral retrotransposon having reverse transcriptase activity, and a nucleic acid binding protein, or a fragment of the nucleic acid binding protein, fused to a binding motif; and
3. Nucleic acid constructs that encode for a non-retroviral retrotransposon, a fragment of the non-retroviral retrotransposon having reverse transcriptase activity, and a nucleic acid binding protein, or a fragment of the nucleic acid binding protein, fused to an acceptor peptide.

Such nucleic acids can be present in an expression vector in an appropriate prokaryotic host cell.

In an embodiment, a pair of nucleic acid constructs comprises:
a) a first nucleic acid construct comprising a polynucleotide sequence encoding a non-retroviral retrotransposon, or a fragment of the non-retroviral retrotransposon having reverse transcriptase activity, fused to a first binding motif; and
b) a second nucleic acid construct comprising a polynucleotide sequence encoding a nucleic acid binding protein, or a fragment of the nucleic acid binding protein, fused to a second binding motif,
wherein the first binding motif and the second binding motif form a covalent bond via protein ligation when brought into contact with one another either spontaneously or with the help of an enzyme.

In some embodiments, a pair of nucleic acid constructs comprises:
a) a first nucleic acid construct comprising a polynucleotide sequence encoding a first non-retroviral retrotransposon, or a first fragment of the non-retroviral retrotransposon having reverse transcriptase activity, fused to a first binding motif; and
b) a second nucleic acid construct comprising a polynucleotide sequence encoding a second non-retroviral retrotransposon, or a second fragment of the non-retroviral retrotransposon having reverse transcriptase activity, fused to a second binding motif,
wherein the first binding motif and the second binding motif form a covalent bond via protein ligation when brought into contact with one another either spontaneously or with the help of an enzyme.

In an embodiment, a pair of nucleic acid constructs comprises:
a) a first nucleic acid construct comprising a polynucleotide sequence encoding a non-retroviral retrotransposon, or a fragment of the non-retroviral retrotransposon having reverse transcriptase activity, fused to a first acceptor peptide; and
b) a second nucleic acid construct comprising a polynucleotide sequence encoding a nucleic acid binding protein, or a fragment of the nucleic acid binding protein, fused to a second acceptor peptide,
wherein the first and second acceptor peptides are biotinylated in the presence of biotin, a biotin ligase, and adenosine triphosphate (ATP) to form biotinylated first and second acceptor peptides; and
wherein the biotinylated first and second acceptor peptides bind to a biotin-binding protein via non-covalent interactions when brought into contact with one another.

In some embodiments, a pair of nucleic acid constructs comprises:
  a) a first nucleic acid construct comprising a polynucleotide sequence encoding a first non-retroviral retrotransposon, or a first fragment of the non-retroviral retrotransposon having reverse transcriptase activity, fused to a first acceptor peptide; and
  b) a second nucleic acid construct comprising a polynucleotide sequence encoding a second non-retroviral retrotransposon, or a second fragment of the non-retroviral retrotransposon having reverse transcriptase activity, fused to a second acceptor peptide,
  wherein the first and second acceptor peptides are biotinylated in the presence of biotin, a biotin ligase, and adenosine triphosphate (ATP) to form biotinylated first and second acceptor peptides; and
  wherein the biotinylated first and second acceptor peptides bind to a biotin-binding protein via non-covalent interactions when brought into contact with one another.

The nucleic acid constructs are typically introduced into various vectors. The vectors described herein generally comprise transcriptional or translational control sequences required for expressing the fusion proteins. Suitable transcription or translational control sequences include, but are not limited to, replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes, the expression vector typically comprises ori sequences directing autonomous replication of the vector within the prokaryotic cells. Preferred prokaryotic ori is capable of directing vector replication in bacterial cells. Non-limiting examples of this class of ori include pMB1, pUC, as well as other *E. coli* origins.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase.

The choice of promoters will largely depend on the host cells in which the vector is introduced. For prokaryotic cells, a variety of robust promoters are known in the art. Preferred promoters are lac promoter, Trc promoter, T7 promoter and pBAD promoter.

In constructing the subject vectors, the termination sequences associated with the protein coding sequence can also be inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various yeast transcriptional termination sequences or mammalian polyadenylation sequences that are known in the art and are widely available. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, zeocin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In one embodiment, the expression vector is a shuttle vector, capable of replicating in at least two unrelated host systems. In order to facilitate such replication, the vector generally contains at least two origins of replication, one effective in each host system. Typically, shuttle vectors are capable of replicating in a eukaryotic host system and a prokaryotic host system. This enables detection of protein expression in the eukaryotic host (the expression cell type) and amplification of the vector in the prokaryotic host (the amplification cell type). Preferably, one origin of replication is derived from SV40 or 2u and one is derived from pUC, although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized.

The vectors encompassed by the invention can be obtained using recombinant cloning methods (e.g., PCR, restriction endonuclease digestion and ligation methods) and/or by chemical synthesis. Sequence data provided herein or sequence data in the public or proprietary databases can be used to obtain a desired vector by any synthetic means available in the art. Additionally, by using restriction and ligation techniques, appropriate sequences can be excised from various DNA sources and integrated in operative relationship with the exogenous sequences to be expressed in accordance with embodiments.

Methods of Producing Hybrid Reverse Transcriptases

The invention also provides methods for producing the disclosed hybrid reverse transcriptases. Methods of producing the hybrid reverse transcriptase include, but are not limited to, chemical methods, recombinant methods, and protein ligation methods in which polypeptides are covalently linked. Biotinylated acceptor peptides and a biotin-binding protein can also be used to join polypeptides via non-covalent interactions.

Chemical methods of joining polypeptides are described, for example, in Bioconjugate Techniques, Hermanson, Ed., Academic Press (1996). These chemical methods include, for example, derivitization for the purpose of linking the polypeptides to each other, either directly or through a linking compound, by methods that are well known in the art of protein chemistry. For example, a heterobifunctional-coupling reagent can be used to form an intermolecular disulfide bond between the polypeptides. Other types of coupling reagents that can be used to join polypeptides are described, for example, in U.S. Pat. No. 4,545,985. Alternatively, an intermolecular disulfide bond may be formed between cysteines in each polypeptide, which occur naturally or are inserted by genetic engineering. The means of linking the polypeptides may also use thioether linkages between heterobifunctional crosslinking reagents or specific low pH cleavable crosslinkers or specific protease cleavable linkers or other cleavable or noncleavable chemical linkages.

In some embodiments, nonclassical amino acids or chemical amino acid analogs can be introduced as a substitution or addition into one or all of the polypeptide sequences to be joined. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

Production of Hybrid Reverse Transcriptases Using Recombinant Techniques

In an embodiment, a hybrid reverse transcriptase is produced by recombinant expression of a nucleic acid encoding the protein. Such a protein can be made by fusing the appropriate nucleic acid sequences encoding the desired amino acid sequences to each other in the proper coding frame and then expressing the product in an appropriate expression system.

Nucleic acids encoding the hybrid reverse transcriptases can be obtained using routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-1999). Such nucleic acids may also be obtained through in vitro amplification methods such as those described in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&&EN* 36-47; *The Journal Of NIH Research* (1991) 3:81-94; Kwoh et al. (1989) *Proc. Natl. Acad. Sci.* USA 86:1173; Guatelli et al. (1990) *Proc. Natl. Acad. Sci.* USA 87, 1874; Lomeli et al. (1989) *J. Clin. Chem.*, 35:1826; Landegren et al., (1988) *Science* 241:1077-1080; Van Brunt (1990) *Biotechnology* 8:291-294; Wu and Wallace (1989) *Gene* 4:560; and Barringer et al. (1990) *Gene* 89:117.

Modifications can additionally be made to the hybrid reverse transcriptases without diminishing their biological activity. Some modifications may be made to facilitate the cloning, expression, or incorporation of a domain into a fusion protein. Such modifications include, for example, the addition of codons at either terminus of the polynucleotide. For example, a codon that encodes an initiation site can be added to the amino terminus (e.g., a methionine added at the amino terminus). Additional amino acids (e.g., poly His) can also be placed on either terminus to create conveniently located restriction sites or termination codons or purification sequences.

Expression systems for producing the polypeptides are described by, for example, *Gene Expression Systems*, Fernandex and Hoeffler, Eds. Academic Press, 1999; Sambrook and Russell, supra; and Ausubel et al, supra. Typically, the polynucleotide that encodes the polypeptide is placed under the control of a promoter that is functional in the desired host cell. The promoter selected depends upon the cell in which the promoter is to be active. Other expression control sequences such as ribosome binding sites, transcription termination sites are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198:1056), the tryptophan (trp) promoter system (Goeddel et al., *Nucleic Acids Res.* (1980) 8:4057), the tac promoter (DeBoer, et al., *Proc. Natl. Acad. Sci.* U.S.A. (1983) 80:21-25); and the lambda-derived PL promoter and N-gene ribosome binding site (Shimatake et al., *Nature* (1981) 292:128). The particular promoter system is not critical; any available promoter that functions in prokaryotes and provides the desired level of activity can be used.

Standard bacterial expression vectors include plasmids such as pBR322-based plasmids, e.g., pBLUESCRIPT™, pSKF, pET23D, lambda-phage derived vectors, and fusion expression systems such as GST and LacZ. The vector containing a nucleic acid encoding the hybrid reverse transcriptase can be transformed into a cell using standard techniques, for example, by employing chemical methods (Green R, Rogers E J. Transformation of chemically competent *E. coli*. Methods Enzymol 2013; 529:329-36) or by electroporation.

Polypeptides can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells. Cells able to express the one or more markers are able to survive/grow/multiply under certain artificially imposed conditions, for example the addition of a toxin or antibiotic to the culture medium, because of the properties endowed by the polypeptide/gene or polypeptide component of the selection system incorporated therein (e.g., antibiotic resistance). Those cells that cannot express the one or more markers are not able to survive/grow/multiply in the artificially imposed conditions.

Any suitable selection system may be employed in the expression methods. Typically the selection system may be based on including in the vector one or more genes that provides resistance to a known antibiotic, for example a tetracycline, chloramphenicol, kanamycin or ampicillin resistance gene. Cells that grow in the presence of a relevant antibiotic can be selected as they express both the gene that gives resistance to the antibiotic and the desired protein.

In an embodiment, the method further comprises the step of culturing the transformed cell in a medium to thereby express the hybrid reverse transcriptase. Any suitable medium may be used to culture the transformed cell. The medium may be adapted for a specific selection system, for example the medium may comprise an antibiotic, to allow only those cells which have been successfully transformed to grow in the medium.

The hybrid reverse transcriptases can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2:800; Schoner et al., Bio/Technology (1985) 3:151).

Once expressed, the hybrid reverse transcriptases can be purified according to standard procedures of the art, including ammonium sulfate precipitation, affinity columns, column chromatography, gel electrophoresis, dialysis, ammonium sulphate, ethanol or PEG fractionation/precipitation, ion exchange membranes, expanded bed adsorption chromatography, or simulated moving bed chromatography. Substantially pure compositions of at least about 90 to 95% homogeneity are preferred, and 98 to 99% or more homogeneity are most preferred. Once purified, partially or to homogeneity as desired, the polypeptides may then be used (e.g., in disclosed methods to generate a cDNA molecule or cDNA library).

To facilitate purification of the polypeptides, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1N5-His are suitable for expression in mammalian cells). Additional expression vectors suitable for attaching a tag to the fusion proteins of the invention, and corresponding detection systems are commercially available (e.g., "FLAG" (Kodak, Rochester N.Y.)). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" in *Genetic Engineering: Principles and Methods*, J. K. Setlow, Ed., Plenum Press, N.Y.; commercially available from Qiagen (Santa Clarita, Calif.)).

After biological expression or purification, the hybrid reverse transcriptases may possess a conformation substantially different than the native conformations of the constituent polypeptides. In this case, it may be necessary or desirable to denature and reduce the polypeptide and then to cause the polypeptide to re-fold into the preferred conformation. A method of reducing and denaturing proteins and inducing re-folding is described, for example, in Debinski et al. (1993) *J. Biol. Chem.* 268:14065-14070.

In some embodiments, the method further comprises measuring the quantity of expression of the hybrid reverse transcriptase after purification.

Production of Hybrid Reverse Transcriptases Using Protein Ligation

Also provided are methods for producing the disclosed hybrid reverse transcriptases via protein ligation. To produce a hybrid reverse transcriptase, a binding motif is first recombinantly fused to the non-retroviral retrotransposon, or the fragment of the non-retroviral retrotransposon having reverse transcriptase activity, and the nucleic acid binding protein or the fragment of the nucleic acid binding protein. Any of the protein ligation systems described previously or otherwise known in the art can be used to design binding motifs that are fused to the non-retroviral retrotransposon, or the fragment of the non-retroviral retrotransposon, and the nucleic acid binding protein, or the fragment of the nucleic acid binding protein, to produce a hybrid reverse transcriptase.

In some embodiments, a first fusion protein is produced with a first binding motif N- or C-terminally fused to a non-retroviral retrotransposon, or a fragment of the non-retroviral retrotransposon having reverse transcriptase activity. A second fusion protein is also produced with a second binding motif N- or C-terminally fused to a nucleic acid binding protein or a fragment of the nucleic acid binding protein, depending on which ends of the fusion proteins are to be ligated.

In a dimeric embodiment of the hybrid reverse transcriptase, a first fusion protein is produced with a first binding motif N- or C-terminally fused to a first non-retroviral retrotransposon, or a first fragment of the non-retroviral retrotransposon having reverse transcriptase activity. A second fusion protein is also produced with a second binding motif N- or C-terminally fused to a second non-retroviral retrotransposon, or a second fragment of the non-retroviral retrotransposon having reverse transcriptase activity, depending on which ends of the fusion proteins are to be ligated.

Interchangeable binding motif cognate pairs are used in the first and second fusion proteins. For example, if the first binding motif SpyTag or SpyTag002 is fused to the C-terminus of the non-retroviral retrotransposon, or the fragment of the non-retroviral retrotransposon, then the second binding motif SpyCatcher, SpyCatcher short or SpyCatcher002 is fused to the N-terminus of the nucleic acid binding protein or the fragment of the nucleic acid binding protein. Alternatively, if SpyCatcher, SpyCatcher short or SpyCatcher002 is fused to the C-terminus of the non-retroviral retrotransposon, or the fragment of the non-retroviral retrotransposon, then SpyTag or SpyTag002 is fused to the N-terminus of the nucleic acid binding protein or the fragment of the nucleic acid binding protein. Other combinations of binding motif pairs include, but are not limited to: SnoopTag and SnoopCatcher, Isopeptag and Split Spy0128, SdyTag and SdyCatcherDANG short, SpyTag and K-Tag, SnoopTagJr and DogTag, and sortase recognition domain and sortase bridging domain (see Table 6).

In an embodiment, the first and second fusion proteins are produced by recombinant expression of nucleic acids encoding the fusion proteins. Such proteins can be made by fusing the appropriate nucleic acid sequences encoding the desired amino acid sequences to each other in the proper coding frame and then expressing the product in an appropriate expression system and by processes described previously. The expressed fusion proteins can then be purified by methods described previously.

Ligation

Figure 2A:
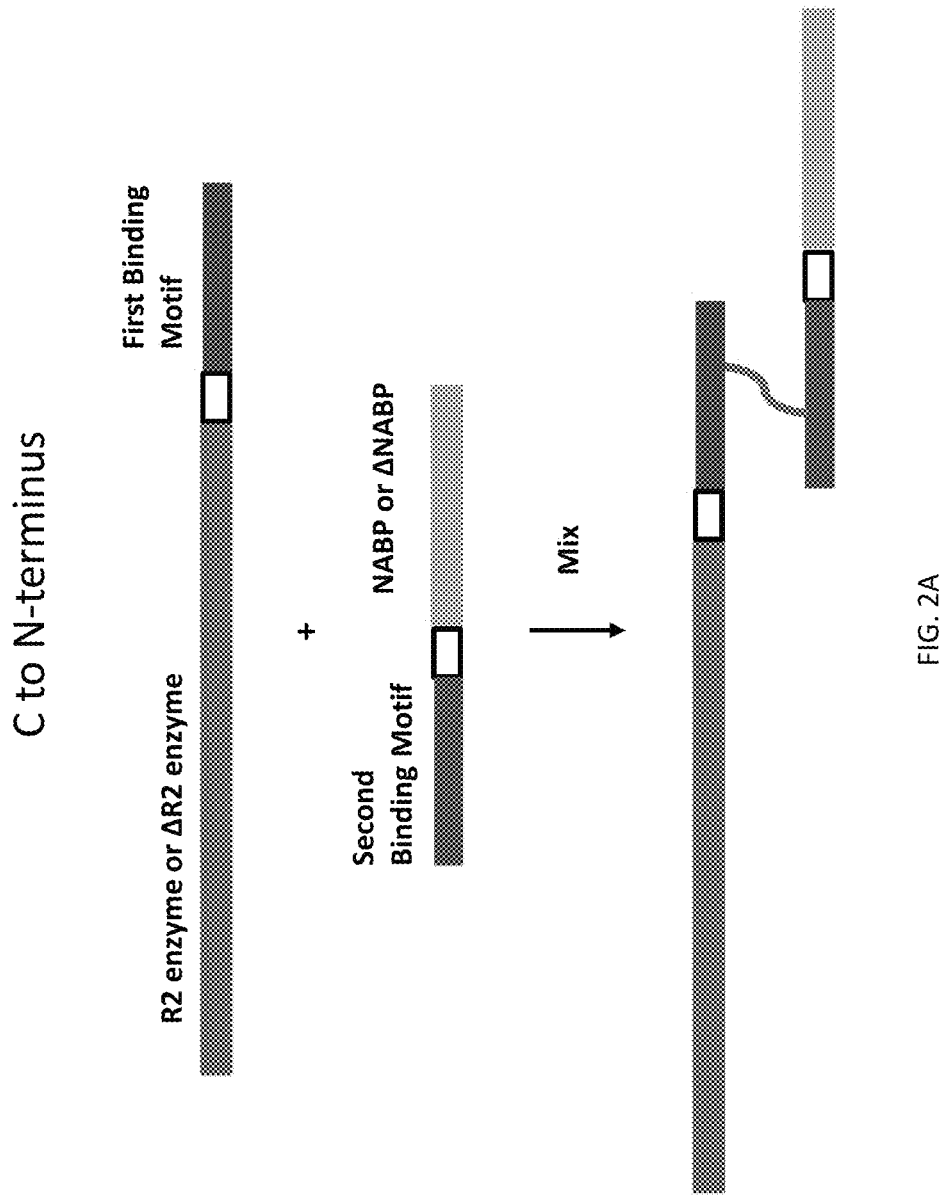
FIGS. 2A-4B illustrate methods of producing hybrid reverse transcriptases according to embodiments. In the embodiments, a nucleic acid binding protein, or a fragment of the nucleic acid binding protein, is joined via protein ligation to a nonviral retrotransposon or a fragment of the nonviral retrotransposon.
Figure 2B:
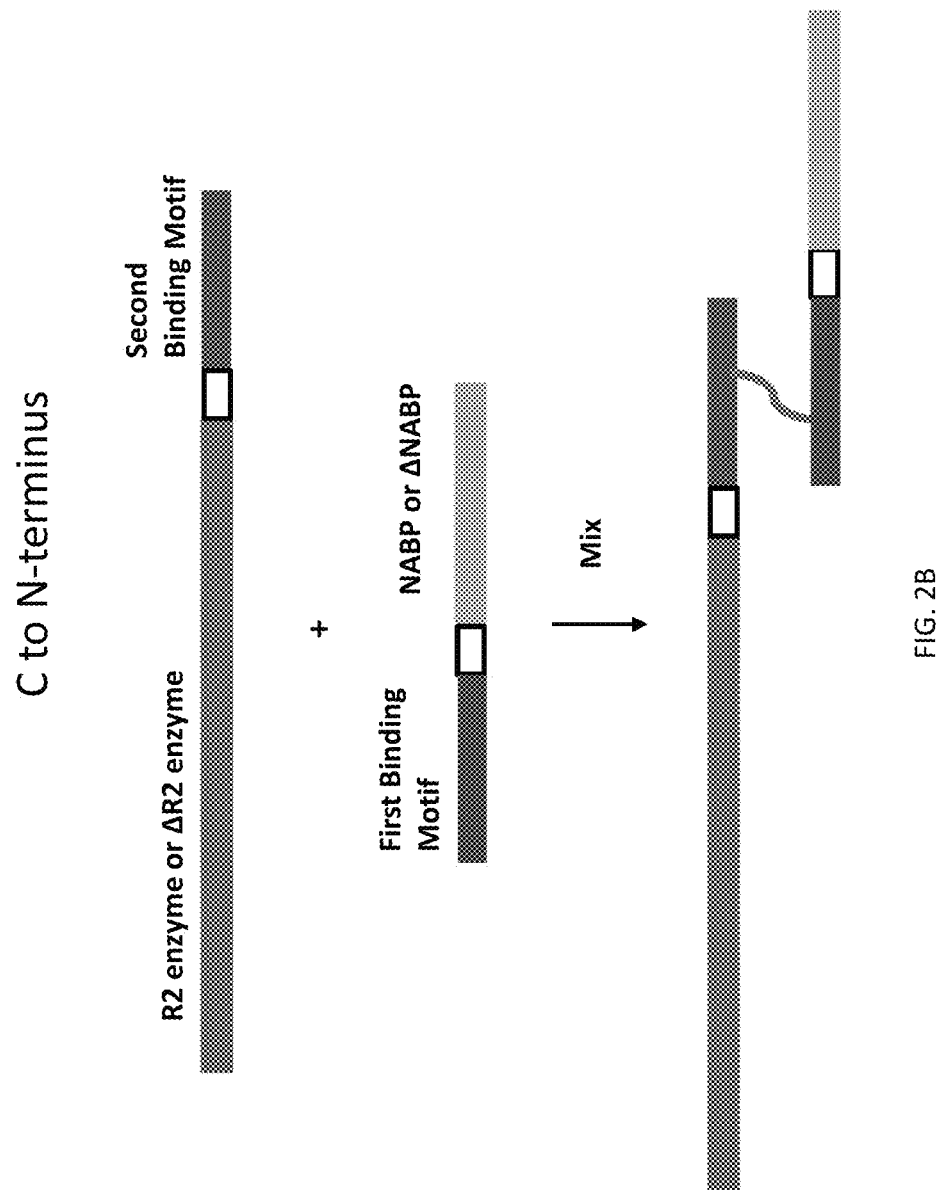
Figure 2C:
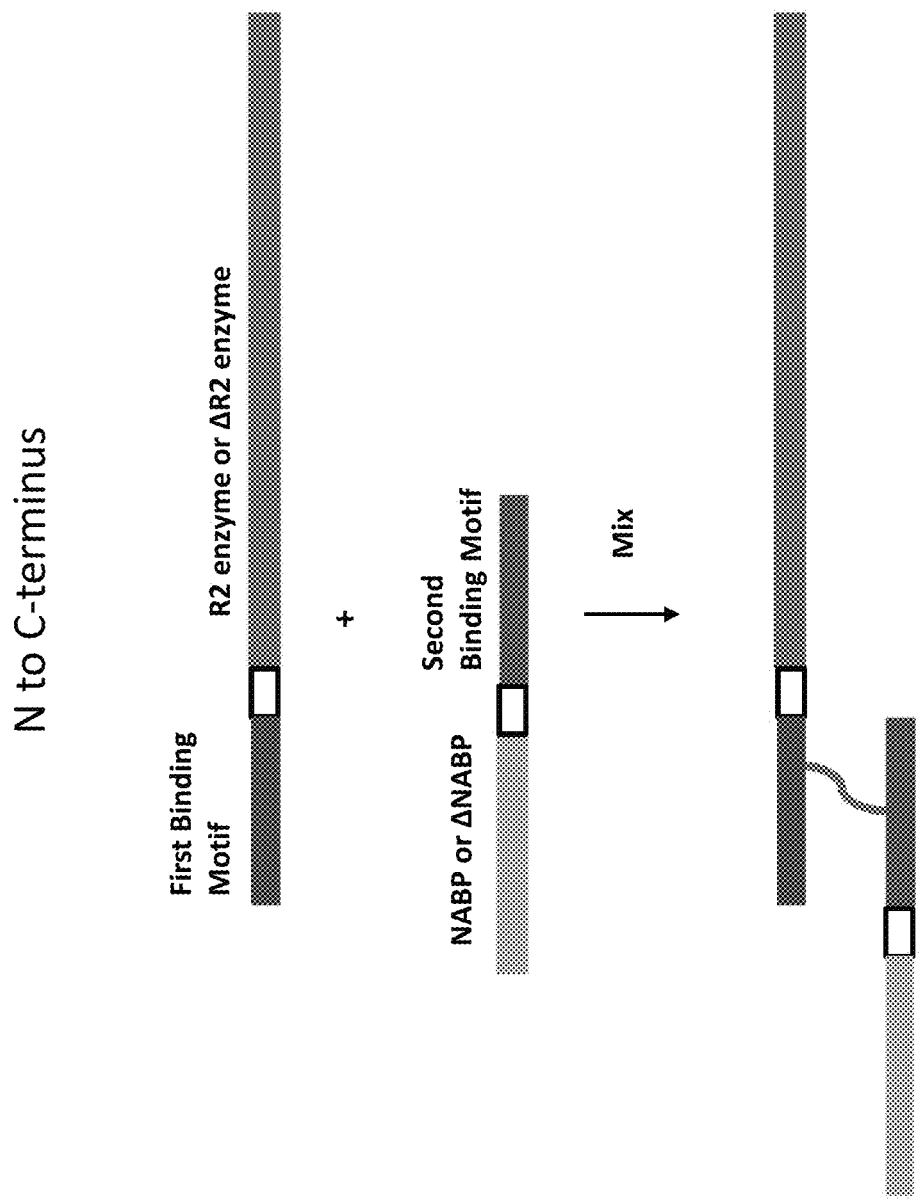
Figure 2D:
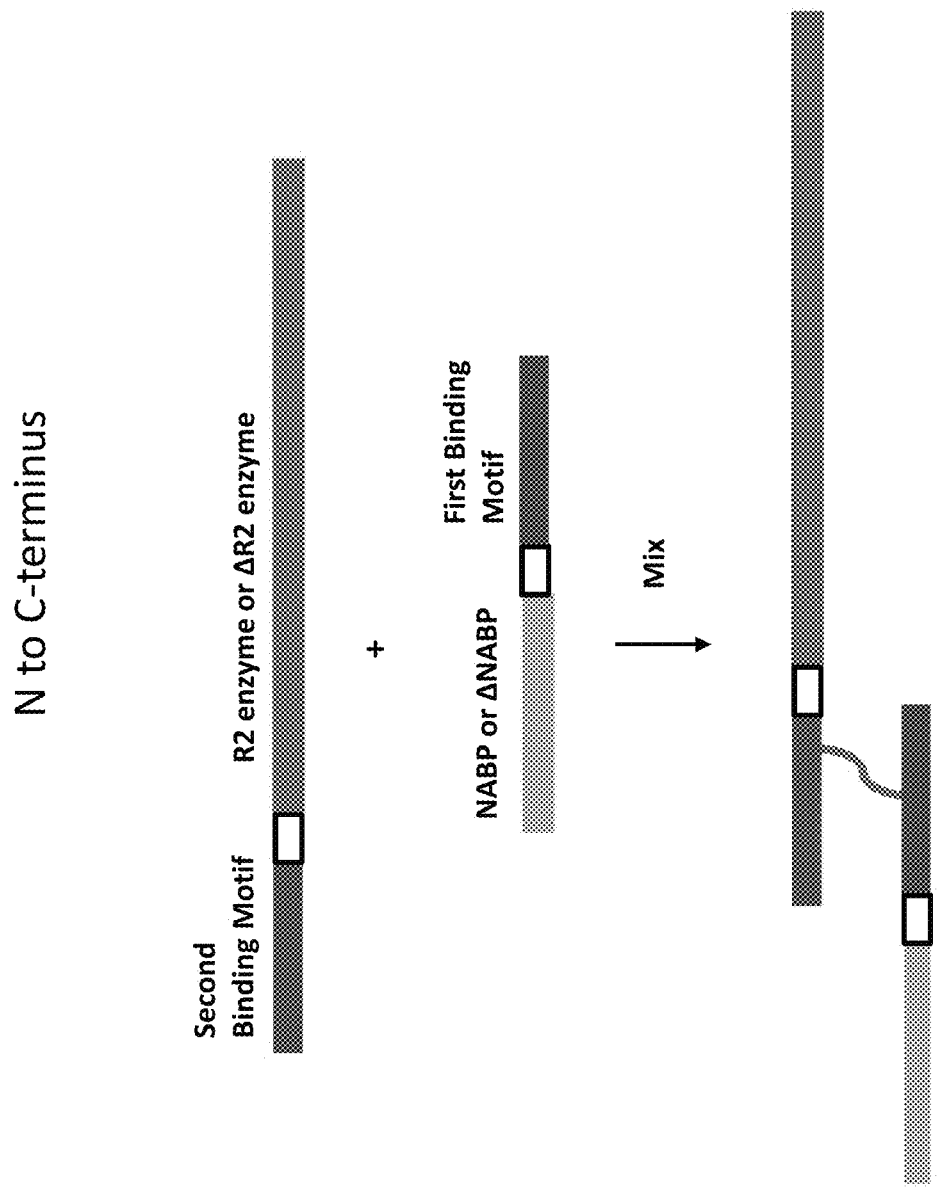

To produce the hybrid reverse transcriptase, the first and second fusion proteins are mixed with each other under appropriate conditions to allow the first and second binding motifs in the first and second fusion proteins, respectively, to covalently join via protein ligation, either spontaneously or with the help of an enzyme. In an embodiment, the hybrid reverse transcriptase comprises a first fusion protein having a C-terminal or N-terminal binding motif conjugated to a C-terminal or N-terminal binding motif of the second fusion protein in any combination, i.e., the first and second fusion proteins can be attached via C-terminus to N-terminus, N-terminus to C-terminus, N-terminus to N-terminus, or C-terminus to C-terminus via the binding motifs (FIGS. 2A-5C). For example, in an embodiment using an R2 enzyme lacking an N-terminal DNA binding domain (i.e., ΔR2 enzyme) and a SpyTag/SpyCatcher binding motif pair, a ΔR2 enzyme-SpyTag fusion protein is mixed with a SpyCatcher-nucleic acid binding protein fusion to produce a hybrid reverse transcriptase having the ΔR2 enzyme with the C-terminal SpyTag conjugated to the N-terminal Spy-Catcher of the nucleic acid binding protein (FIG. 2A). Cognate binding motif pairs are interchangeable; thus, in some embodiments, a ΔR2 enzyme-SpyCatcher fusion protein is mixed with a SpyTag-nucleic acid binding protein fusion to produce a hybrid reverse transcriptase having the ΔR2 enzyme with the C-terminal SpyCatcher conjugated to the N-terminal SpyTag of the nucleic acid binding protein (FIG. 2B). Alternatively, a SpyTag-ΔR2 enzyme fusion protein can be mixed with a nucleic acid binding protein-SpyCatcher fusion protein to produce a hybrid reverse transcriptase having the ΔR2 enzyme with the N-terminal SpyTag conjugated to the C-terminal SpyCatcher of the nucleic acid binding protein (FIG. 2C). Also, a SpyCatcher-ΔR2 enzyme fusion protein can be mixed with a nucleic acid binding protein-SpyTag fusion protein to produce a hybrid reverse transcriptase having the ΔR2 enzyme with the N-terminal SpyCatcher conjugated to the C-terminal SpyTag of the nucleic acid binding protein (FIG. 2D).

Figure 3A:
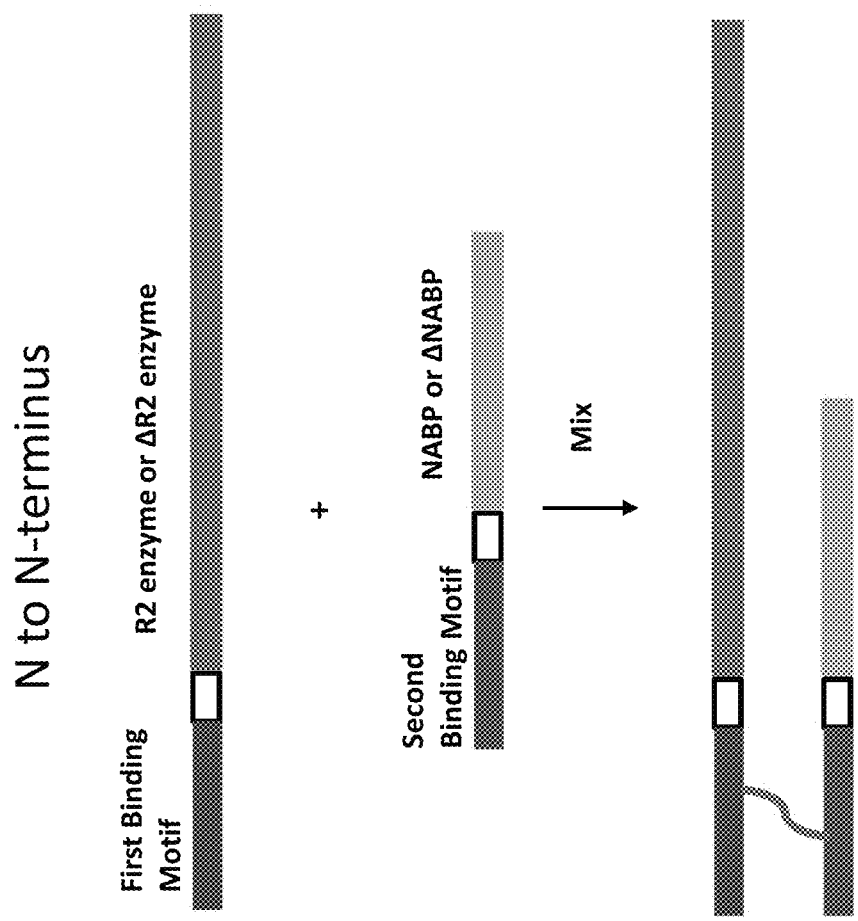
Figure 3B:
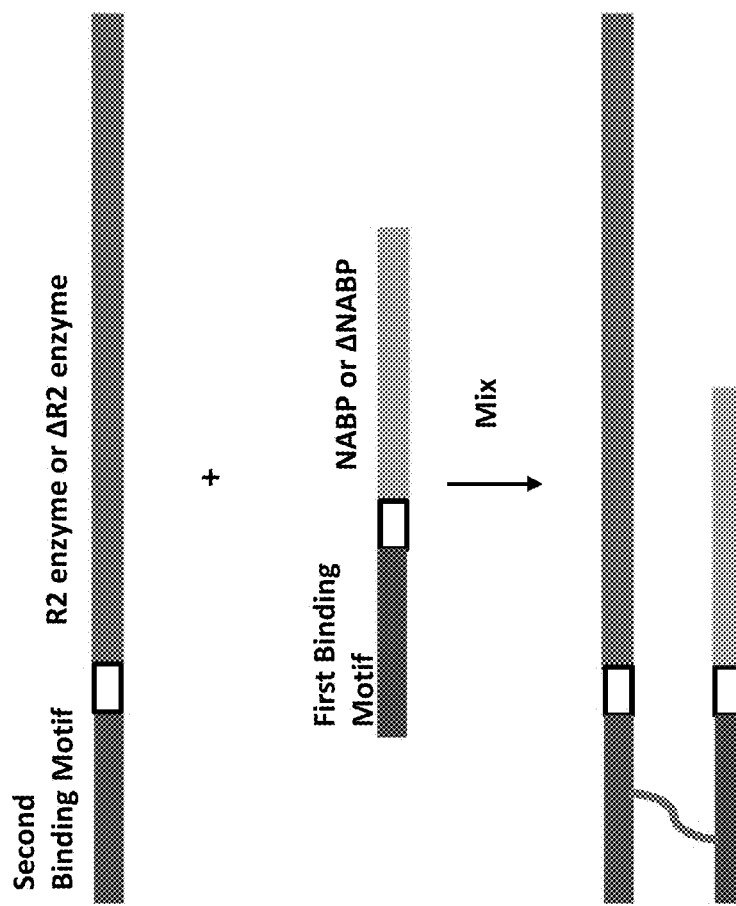
Figure 4A:
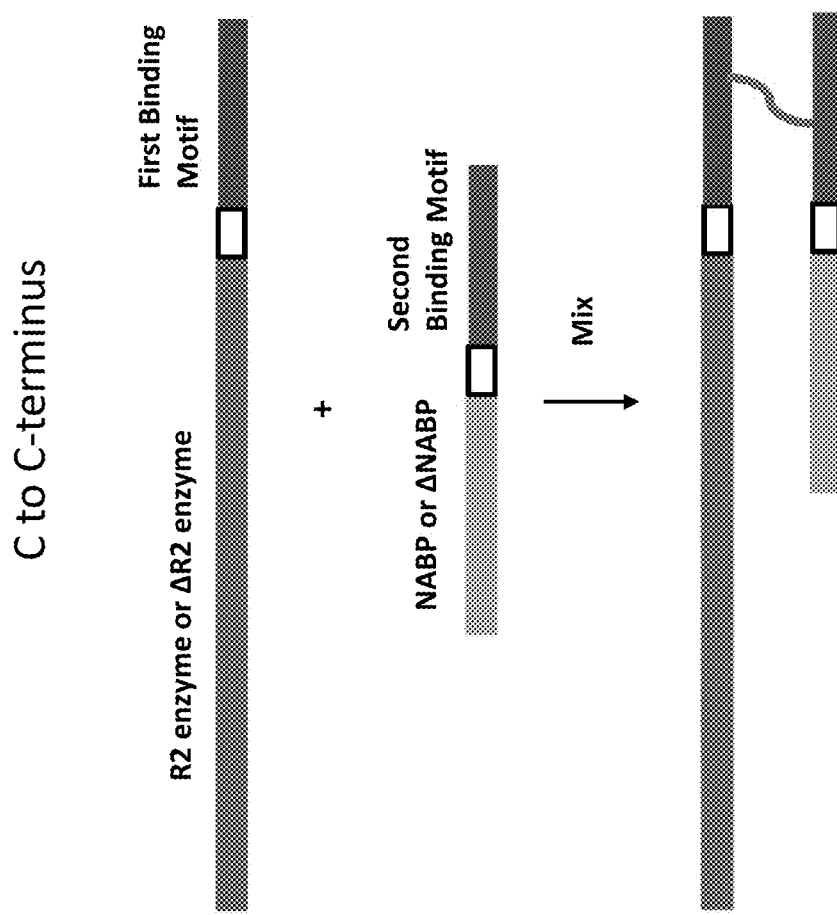
Figure 4B:
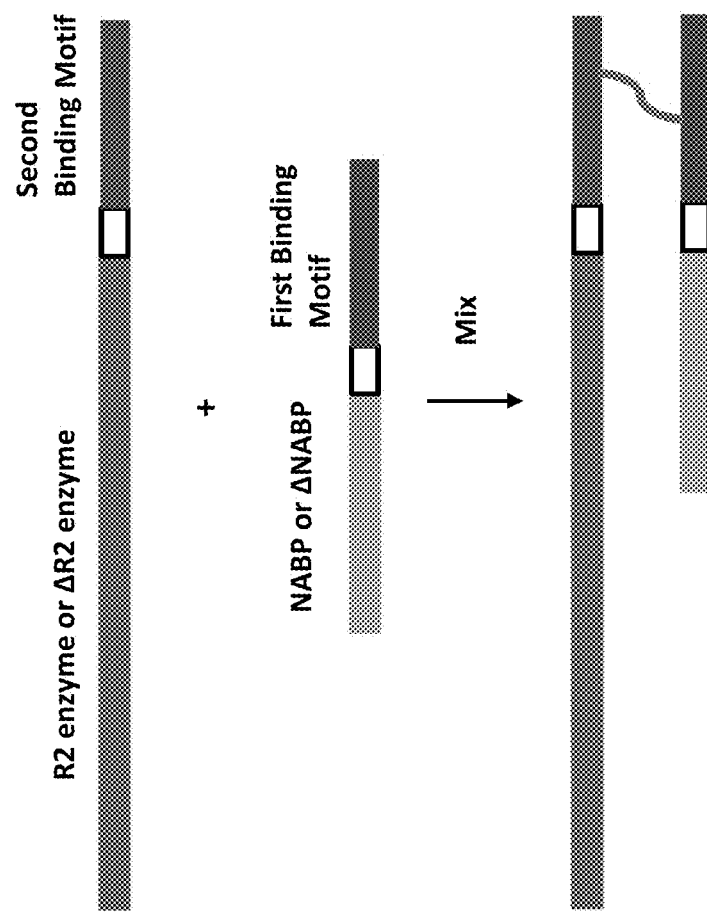

In some embodiments, a SpyTag-ΔR2 enzyme fusion protein is mixed with a SpyCatcher-nucleic acid binding protein fusion protein to produce a hybrid reverse transcriptase having the ΔR2 enzyme with the N-terminal SpyTag conjugated to the N-terminal SpyCatcher of the nucleic acid binding protein (FIG. 3A). Likewise, a SpyCatcher-ΔR2 enzyme fusion protein can be mixed with a SpyTag-nucleic acid binding protein fusion protein to produce a hybrid reverse transcriptase having the ΔR2 enzyme with the N-terminal SpyCatcher conjugated to the N-terminal SpyTag of the nucleic acid binding protein (FIG. 3B). In certain embodiments, a ΔR2 enzyme-SpyTag fusion protein is mixed with a nucleic acid binding protein-SpyCatcher fusion protein to produce a hybrid reverse transcriptase having the ΔR2 enzyme with the C-terminal SpyTag conjugated to the C-terminal SpyCatcher of the nucleic acid binding protein (FIG. 4A). Likewise, a ΔR2 enzyme-SpyCatcher fusion protein can be mixed with a nucleic acid binding protein-SpyTag fusion protein to produce a hybrid reverse transcriptase having the ΔR2 enzyme with the C-terminal SpyCatcher conjugated to the C-terminal SpyTag of the nucleic acid binding protein-SpyTag fusion protein (FIG. 4B).

Figure 5A:
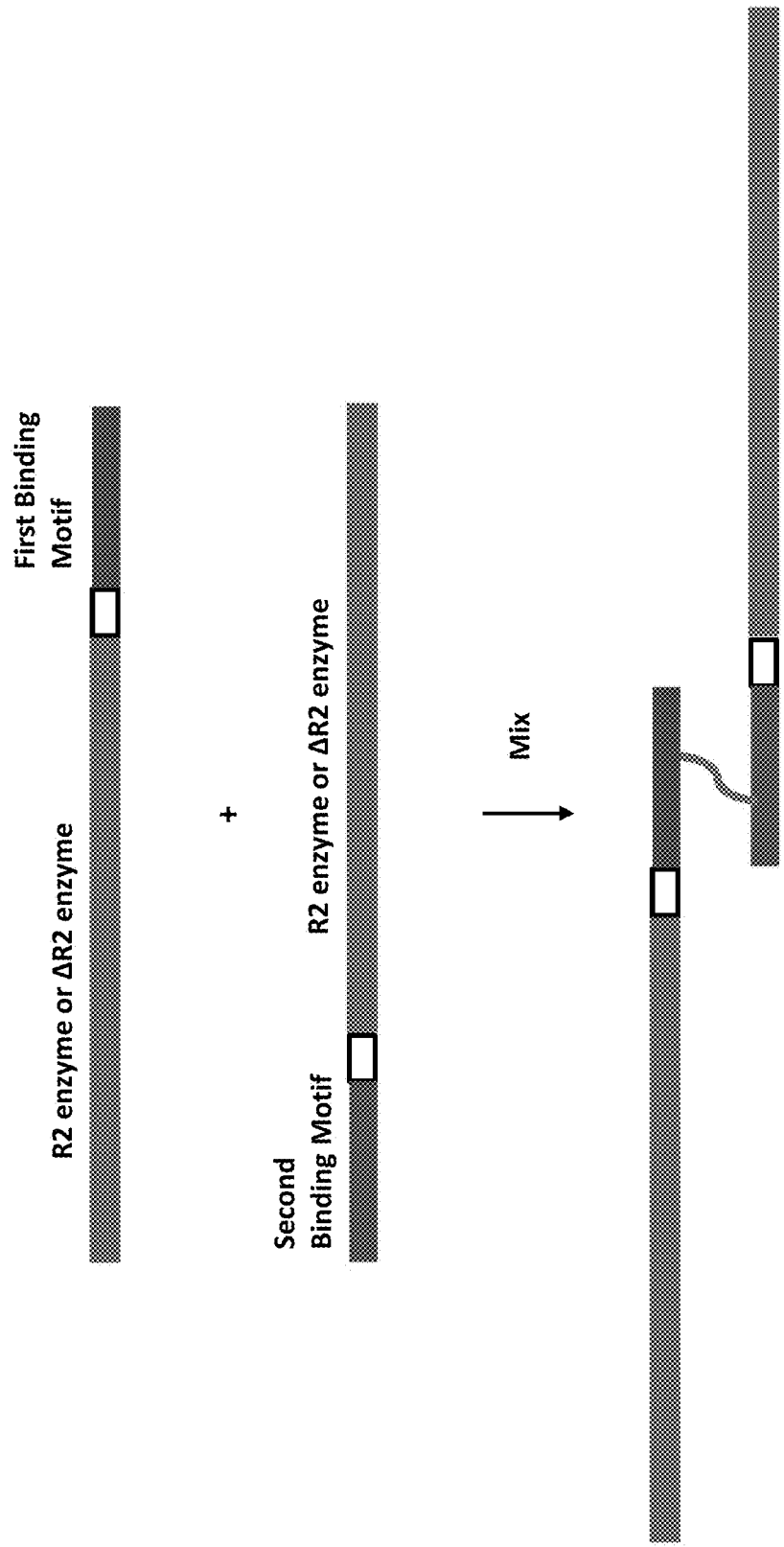
FIGS. 5A-5C illustrate methods of producing hybrid reverse transcriptases according to embodiments in which a first nonviral retrotransposon or a first fragment of the nonviral retrotransposon is joined via protein ligation to a second nonviral retrotransposon or a second fragment of the nonviral retrotransposon.
Figure 5B:
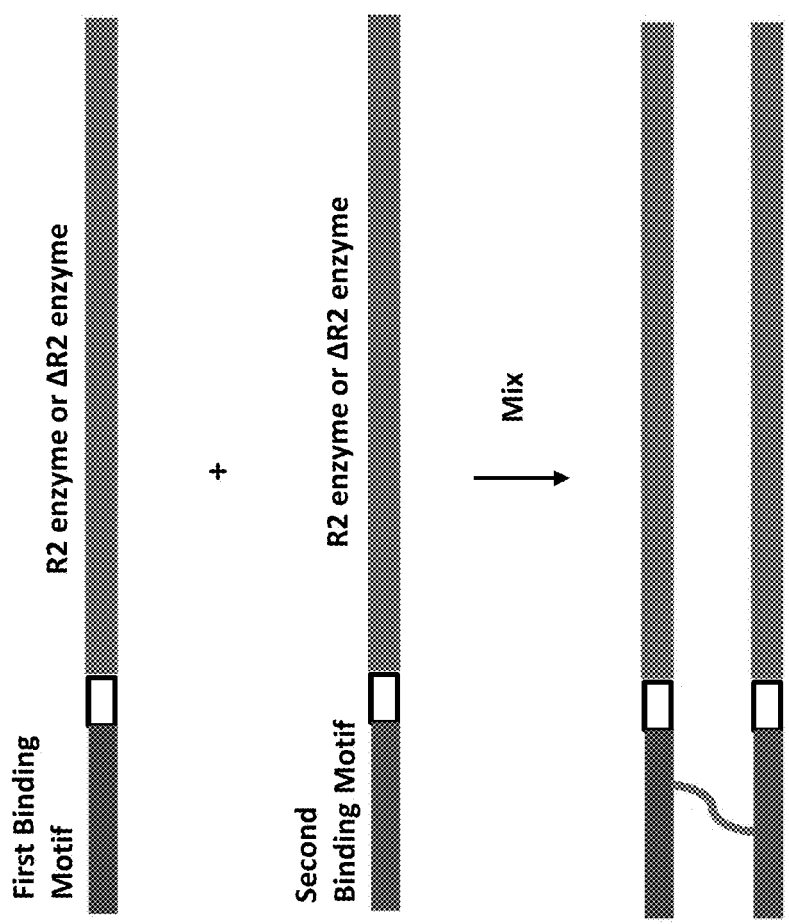
Figure 5C:
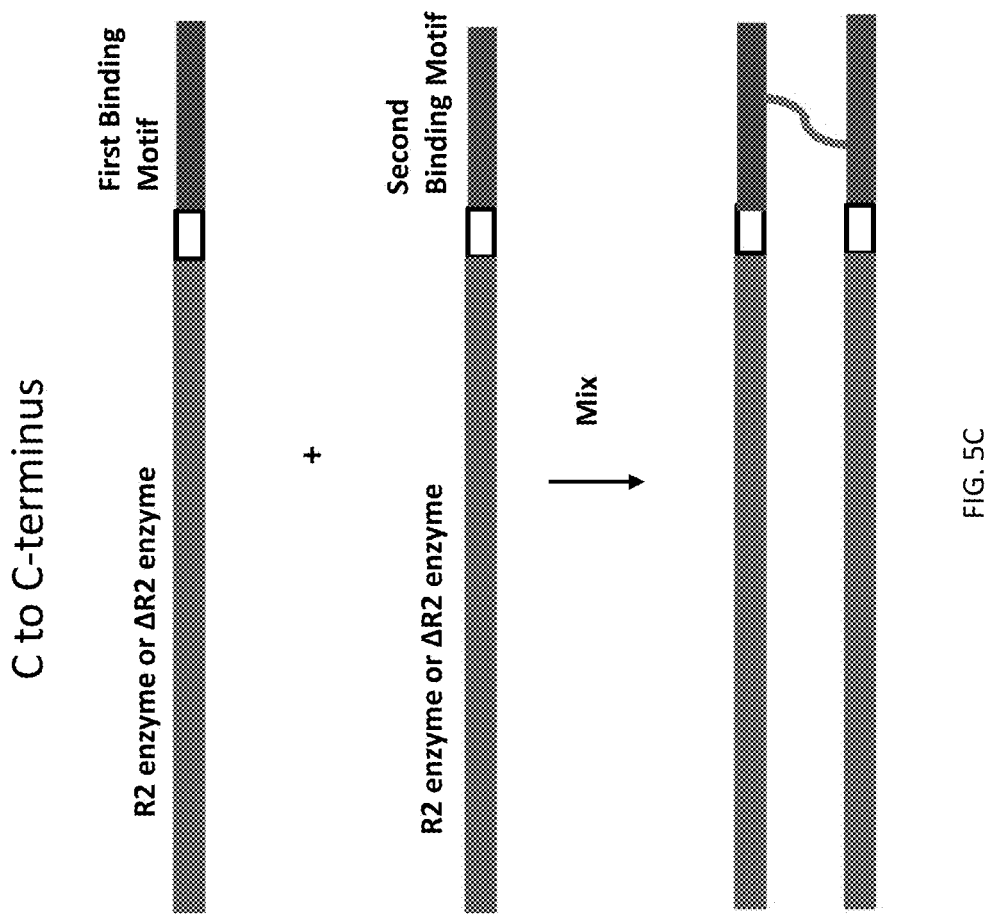

In some embodiments, the produced hybrid reverse transcriptase comprises a first non-retroviral retrotransposon, or a first fragment of the non-retroviral retrotransposon, conjugated to a second non-retroviral retrotransposon, or a second fragment of the non-retroviral retrotransposon (i.e., a dimer) via C-terminus to N-terminus N-terminus to N-terminus, or C-terminus to C-terminus by protein ligation (FIGS. 5A-5C). For example, in an embodiment, a first ΔR2 enzyme-SpyTag fusion protein is mixed with a SpyCatcher-second ΔR2 enzyme fusion protein to produce a hybrid reverse transcriptase having the first ΔR2 enzyme with the C-terminal SpyTag conjugated to the N-terminal Spy-Catcher of the second ΔR2 enzyme (FIG. 5A). The Spy Tag and SpyCatcher binding motifs are interchangeable; thus, in some embodiments, a first ΔR2 enzyme-SpyCatcher fusion protein is mixed with a SpyTag-second ΔR2 enzyme fusion protein to produce a hybrid reverse transcriptase having the first ΔR2 enzyme with the C-terminal SpyCatcher conjugated to the N-terminal SpyTag of the second ΔR2 enzyme. In some embodiments, a SpyTag-first ΔR2 enzyme fusion protein is mixed with a SpyCatcher-second ΔR2 enzyme fusion protein to produce a hybrid reverse transcriptase having the first ΔR2 enzyme with the N-terminal Spy Tag conjugated to the N-terminal SpyCatcher of the nucleic acid binding protein (FIG. 5B). In certain embodiments, a first ΔR2 enzyme-SpyTag fusion protein is mixed with a second ΔR2 enzyme-SpyCatcher fusion protein to produce a hybrid reverse transcriptase having the first ΔR2 enzyme with the C-terminal SpyTag conjugated to the C-terminal SpyCatcher of the second ΔR2 enzyme (FIG. 5C).

In some embodiments, a SnoopTag/SnoopCatcher protein ligation system (Veggiani et al., 2016) is used to produce a hybrid reverse transcriptase. In such embodiments, a non-retroviral retrotransposon, or a fragment of the non-retroviral retrotransposon having reverse transcriptase activity fused to SnoopTag or SnoopCatcher and a nucleic acid binding protein, or a fragment of the nucleic acid binding protein, fused to SnoopCatcher or SnoopTag, respectively, is produced as described previously. The fusion proteins are then mixed under appropriate conditions to allow ligation of SnoopTag to SnoopCatcher.

In certain embodiments, an Isopeptag/Split Spy0128 protein ligation system (Abe et al., 2013) is used to produce a hybrid reverse transcriptase. In such embodiments, a non-retroviral retrotransposon, or a fragment of the non-retroviral retrotransposon having reverse transcriptase activity fused to Isopeptag or Split Spy0128 and a nucleic acid binding protein fused to Split Spy0128 or Isopeptag, respectively, is produced as described previously. The fusion proteins are then mixed under appropriate conditions to allow ligation of Isopeptag to Split Spy0128.

In some embodiments, a SdyTag/SdyCatcherDANG short protein ligation system (Tan et al., 2016) is used to produce a hybrid reverse transcriptase. In such embodiments, a non-retroviral retrotransposon, or a fragment of the non-retroviral retrotransposon having reverse transcriptase activity fused to SdyTag or SdyCatcherDANG short and a nucleic acid binding protein, or a fragment of the nucleic acid binding protein, fused to SdyCatcherDANG short or SdyTag, respectively, is produced as described previously. The fusion proteins are then mixed under appropriate conditions to allow ligation of SdyTag to SdyCatcherDANG short.

In certain embodiments, the SpyLigase or SnoopLigase protein ligation systems can be used to create a hybrid reverse transcriptase. For example, if the SpyLigase protein ligation system is used, a non-retroviral retrotransposon, or a fragment of the non-retroviral retrotransposon having reverse transcriptase activity fused to Spy Tag can be produced as described previously. The second binding motif (SpyCatcher) in the nucleic acid binding protein, or a fragment of the nucleic acid binding protein, is replaced by the 10 amino acid K-Tag binding motif (SEQ ID NO: 55). The fusion proteins are then mixed in the presence of SpyLigase under conditions that permit the ligation of Spy Tag and K-tag. Alternatively, if the SnoopLigase protein ligation system is used, the SnoopTag binding motif is replaced with SnoopTagJr and the SnoopCatcher binding motif is replaced with the 23 amino acid DogTag binding motif (SEQ ID NO: 61). First and second fusion proteins having SnoopTagJr and DogTag binding motifs, respectively, are mixed in the presence of SnoopLigase under conditions that permit ligation of SnoopTagJr and DogTag. For example, a non-retroviral retrotransposon, or a fragment of the non-retroviral retrotransposon having reverse transcriptase activity fused to SnoopTagJr can be mixed with a nucleic acid binding protein fused to DogTag in the presence of SnoopLigase under conditions that allow ligation of SnoopTagJr and DogTag to produce a hybrid reverse transcriptase.

In further embodiments, the Sortase system is used to produce a hybrid reverse transcriptase. For example, a non-retroviral retrotransposon, or a fragment of the non-retroviral retrotransposon having reverse transcriptase activity fused to sortase recognition domain (i.e., any of SEQ ID NOs: 62-68) and a nucleic acid binding protein fused to a sortase bridging domain (i.e., any of Gly, $(Gly)_2$, $(Gly)_3$, $(Gly)_4$, or $(Gly)_x$, where x is an integer of 1-20) can be produced as described above. The fusion proteins are then mixed in the presence of sortase to allow covalent coupling of the sortase recognition and bridging domains.

Production of Hybrid Reverse Transcriptases Using Biotinylated Acceptor Peptides and Biotin-Binding Protein The invention also provides methods for producing the disclosed hybrid reverse transcriptases. To produce a hybrid reverse transcriptase, an acceptor peptide is first recombinantly fused to the non-retroviral retrotransposon, or the fragment of the non-retroviral retrotransposon having reverse transcriptase activity, and to the nucleic acid binding protein, or a fragment of the nucleic acid binding protein.

In some embodiments, a first fusion protein is produced with a first acceptor peptide N- or C-terminally fused to a non-retroviral retrotransposon, or a fragment of the non-retroviral retrotransposon having reverse transcriptase activity. A second fusion protein is also produced with a second acceptor peptide N- or C-terminally fused to a nucleic acid binding protein, or a fragment of the nucleic acid binding protein, depending on which ends of the fusion proteins are to be attached to a biotin-binding protein.

In certain embodiments of the hybrid reverse transcriptase, a first fusion protein is produced with a first acceptor peptide N- or C-terminally fused to a first non-retroviral retrotransposon, or a first fragment of the non-retroviral retrotransposon having reverse transcriptase activity. A second fusion protein is also produced with a second acceptor peptide N- or C-terminally fused to a second non-retroviral retrotransposon, or a second fragment of the non-retroviral retrotransposon having reverse transcriptase activity, depending on which ends of the fusion proteins are to be attached to a biotin-binding protein.

The first and second acceptor peptides can be identical or different and are any of SEQ ID NOS: 85-89.

In an embodiment, the first and second fusion proteins are produced by recombinant expression of nucleic acids encoding the fusion proteins. Such proteins are made by fusing the appropriate nucleic acid sequences encoding the desired amino acid sequences to each other in the proper coding frame and then expressing the product in an appropriate expression system and by processes described previously. The expressed fusion proteins can then be purified by methods described previously.

In some embodiments, the first and second acceptor peptides are biotinylated in vitro by contacting the fusion proteins with biotin in the presence of biotin ligase and ATP to form biotinylated first and second acceptor peptides.

Figure 6:
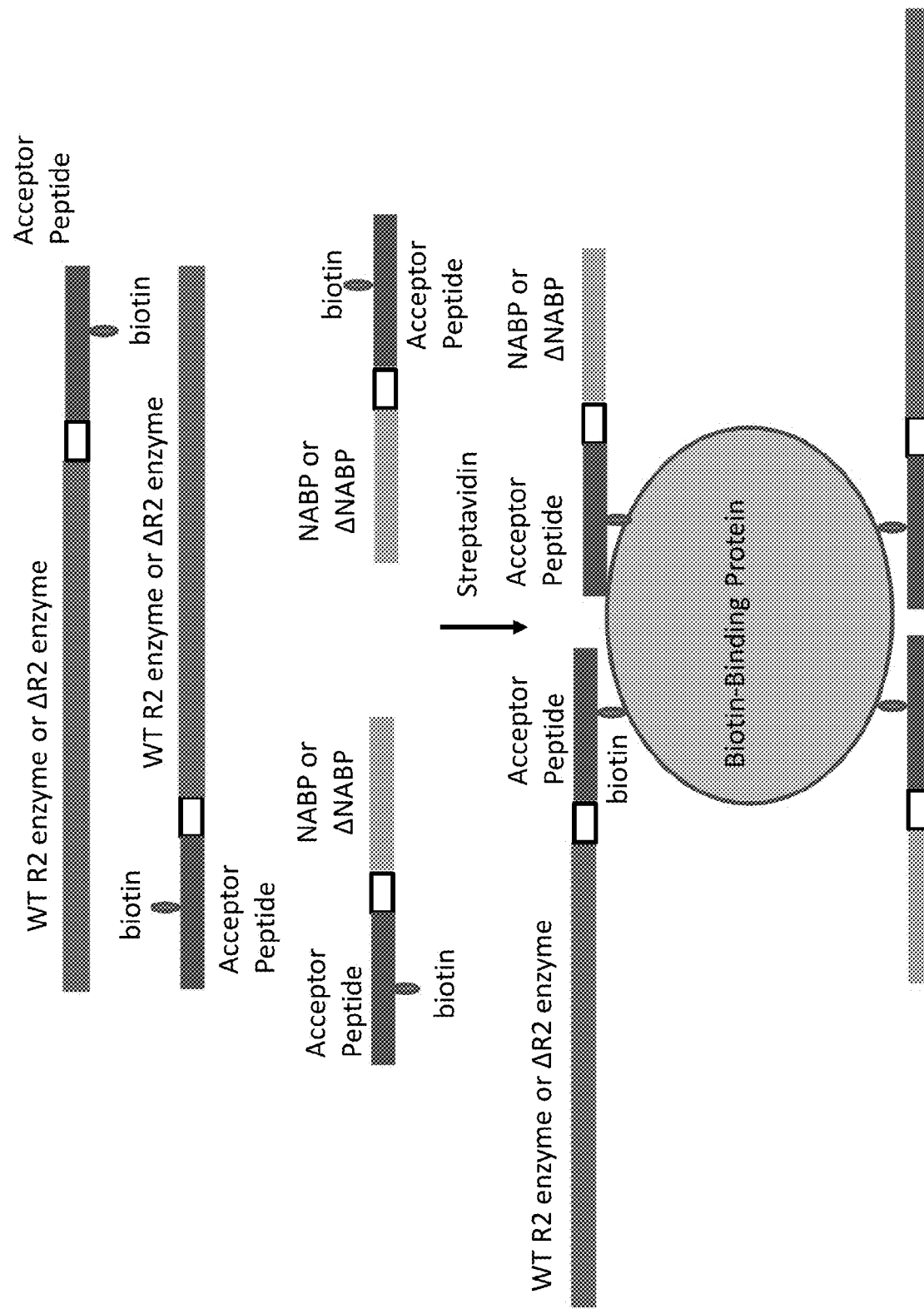
FIG. 6 illustrates a method of producing hybrid reverse transcriptase according to an embodiment. In the embodiment, a biotinylated nonviral retrotransposon or a biotinylated fragment of the nonviral retrotransposon and a biotinylated nucleic acid binding protein or a biotinylated fragment of the nucleic acid binding protein are joined to a biotin-binding protein via non-covalent interactions.
Figure 7:
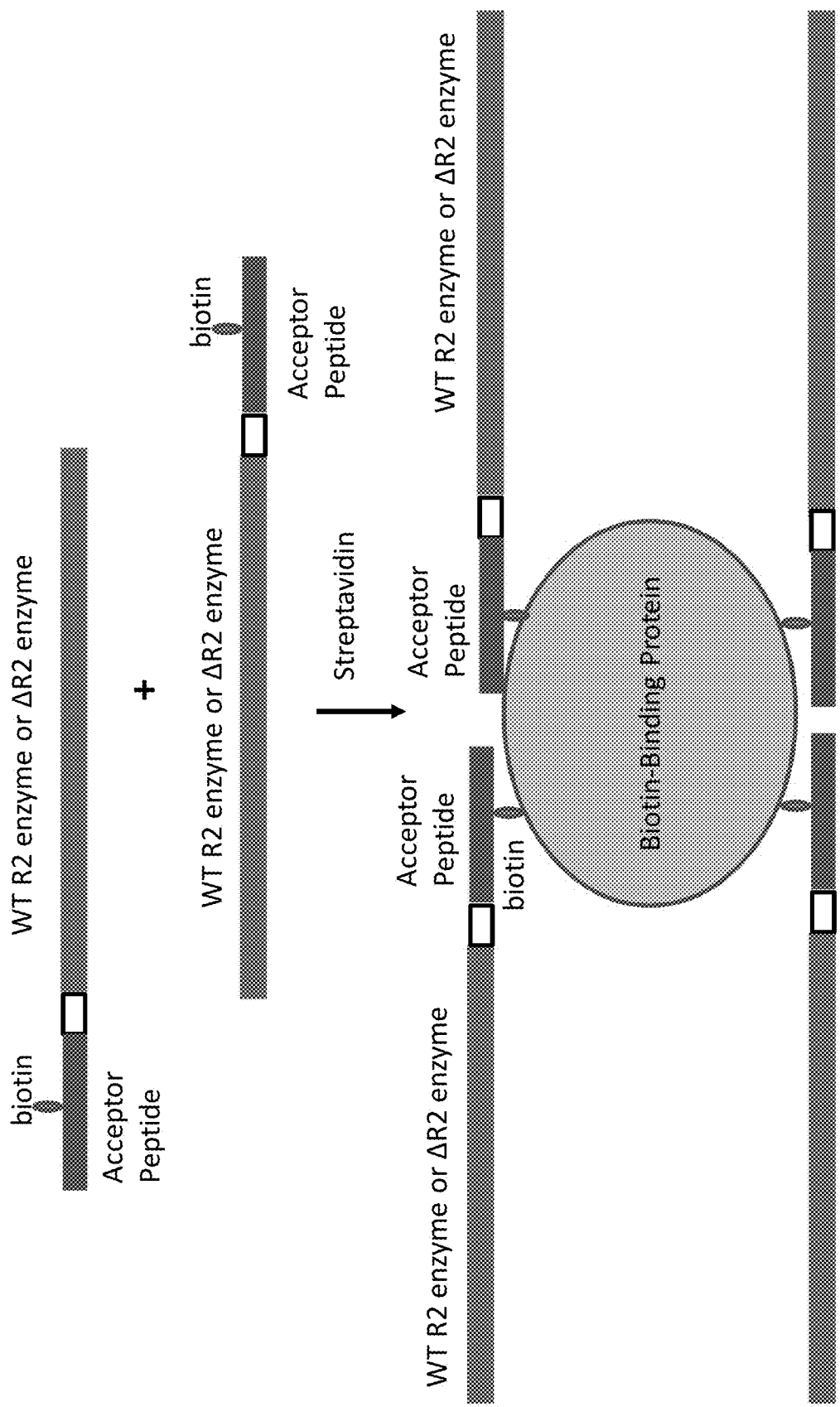
FIG. 7 illustrate a method of producing hybrid reverse transcriptase according to an embodiment in which a first biotinylated nonviral retrotransposon or a first biotinylated fragment of the nonviral retrotransposon and a second biotinylated nonviral retrotransposon or a second biotinylated fragment of the nonviral retrotransposon are joined to a biotin-binding protein via non-covalent interactions.

To produce the hybrid reverse transcriptase, the biotinylated first and second fusion proteins are mixed with a biotin-binding protein under appropriate conditions to allow the first and second acceptor peptides in the respective first and second fusion proteins to non-covalently bind to the biotin-binding protein. In an embodiment, the hybrid reverse transcriptase comprises a first fusion protein having a C-terminal or N-terminal biotinylated acceptor peptide and a second fusion protein having a C-terminal or N-terminal biotinylated acceptor peptide non-covalently bound to the biotin-binding protein via biotin (FIGS. 6-7). For example, in an embodiment using an R2 enzyme lacking an N-terminal DNA binding domain (i.e., ΔR2 enzyme), a ΔR2 enzyme-biotinylated acceptor peptide fusion protein, a biotinylated acceptor peptide-ΔR2 enzyme fusion protein, a biotinylated acceptor peptide-nucleic acid binding protein (NABP) fusion, a nucleic acid binding protein-biotinylated acceptor peptide fusion protein, and a biotin-binding protein are mixed together to produce a hybrid reverse transcriptase having ΔR2 enzymes with C- and N-terminal biotinylated acceptor peptides and nucleic acid binding proteins with C- and N-terminal biotinylated acceptor peptides bound to biotin-binding protein (FIG. 6). In an embodiment using wild type R2 enzyme (i.e., WT R2 enzyme; SEQ ID NO: 1), an WT R2 enzyme-biotinylated acceptor peptide fusion protein, a biotinylated acceptor peptide-WT R2 enzyme fusion protein, a biotinylated acceptor peptide-nucleic acid binding protein fusion, a nucleic acid binding protein-biotinylated acceptor peptide fusion protein, and a biotin-binding protein are mixed together to produce a hybrid reverse transcriptase having the WT R2 enzymes with C- and N-terminal biotinylated acceptor peptides and nucleic acid binding proteins with C- and N-terminal biotinylated acceptor peptides bound to biotin-binding protein. In some embodiments, a fragment of the nucleic acid binding protein (i.e., ΔNABP) N- or C-terminally fused to biotinylated acceptor peptide is used in place of the nucleic acid binding protein N- or C-terminally fused to biotinylated acceptor peptide (FIG. 6).

In some embodiments, the produced hybrid reverse transcriptase comprises a first non-retroviral retrotransposon, or a first fragment of the non-retroviral retrotransposon, comprising a biotinylated first acceptor peptide, and a second non-retroviral retrotransposon, or a second fragment of the non-retroviral retrotransposon, comprising a biotinylated second acceptor peptide are non-covalently bound to a biotin-binding protein (FIG. 7). For example, in an embodiment, a first ΔR2 enzyme-biotinylated first acceptor peptide fusion protein, a biotinylated second acceptor peptide-second ΔR2 enzyme fusion protein, and a biotin-binding protein are mixed together to produce a hybrid reverse transcriptase in which the biotinylated acceptor peptides from the fusion proteins are non-covalently bound to the biotin-binding protein. In another embodiment, a first WT R2 enzyme-biotinylated-first acceptor peptide fusion protein, a biotinylated second acceptor peptide-second WT R2 enzyme fusion protein, and a biotin-binding protein are mixed together to produce a hybrid reverse transcriptase in which the biotinylated acceptor peptides from the fusion proteins are non-covalently bound to the biotin-binding protein.

Methods of Using Hybrid Reverse Transcriptases

Also provided are methods of using the disclosed hybrid reverse transcriptases to prepare a cDNA molecule or a cDNA library from total-RNA, messenger RNA (mRNA), micro RNA (miRNA), ribosomal RNAs, transfer RNAs (tRNAs), long non-coding RNA, cell free-RNA or from a single cell. RNA used in the disclosed methods can be synthetic or derived from naturally occurring sources. In one embodiment, RNA is isolated from a biological sample containing a variety of other components, such as proteins, lipids and non-template nucleic acids. RNA can be obtained from any cellular material from an animal, plant, bacterium, fungus, or any other cellular organism. RNA can be obtained directly from an organism or from a biological sample obtained from an organism, e.g., from blood, urine, cerebrospinal fluid, seminal fluid, saliva, sputum, stool and tissue. Any tissue or body fluid specimen may be used as a source of RNA. RNA can also be isolated from cultured cells, such as a primary cell culture or a cell line. The cells or tissues from which RNA is obtained can be infected with a virus or other intracellular pathogen. In addition, RNA can be obtained from non-cellular or non-tissue samples, such as viral samples, or environmental samples. Generally, RNA can be extracted from a biological sample by a variety of techniques such as those described by Sambrook and Russell, *Molecular Cloning: A Laboratory Manual*, Third Edition, Cold Spring Harbor, N.Y. (2001).

In methods of using the disclosed hybrid reverse transcriptases to prepare a cDNA molecule or a cDNA library, reverse transcription is initiated from a primer that optionally hybridizes or partially hybridizes with a template RNA molecule (i.e., the primer may or may not be complementary to the template RNA molecule). In methods in which the primer hybridizes or partially hybridizes with the template RNA molecule, the hybrid reverse transcriptase comprises a dsDNA binding protein. In methods in which the primer does not hybridize with the template RNA molecule (i.e., the primer is not complementary to the template RNA molecule), the hybrid reverse transcriptase comprises a ssDNA binding protein. In the methods, after transcribing the template RNA molecule, the hybrid reverse transcriptase jumps from a 5' end of the template RNA molecule to a 3'-end of an acceptor-adapter and continues reverse transcribing the acceptor-adaptor. Such template jumping produces full length reverse transcripts of the template RNA molecule. In some embodiments, the jumping of the hybrid reverse transcriptase to the 3'-end of the acceptor-adapter is independent of sequence identity between the template RNA molecule(s) and the acceptor-adapter.

Methods in which Hybrid Reverse Transcriptase Comprises a dsDNA Binding Protein

Figure 8:
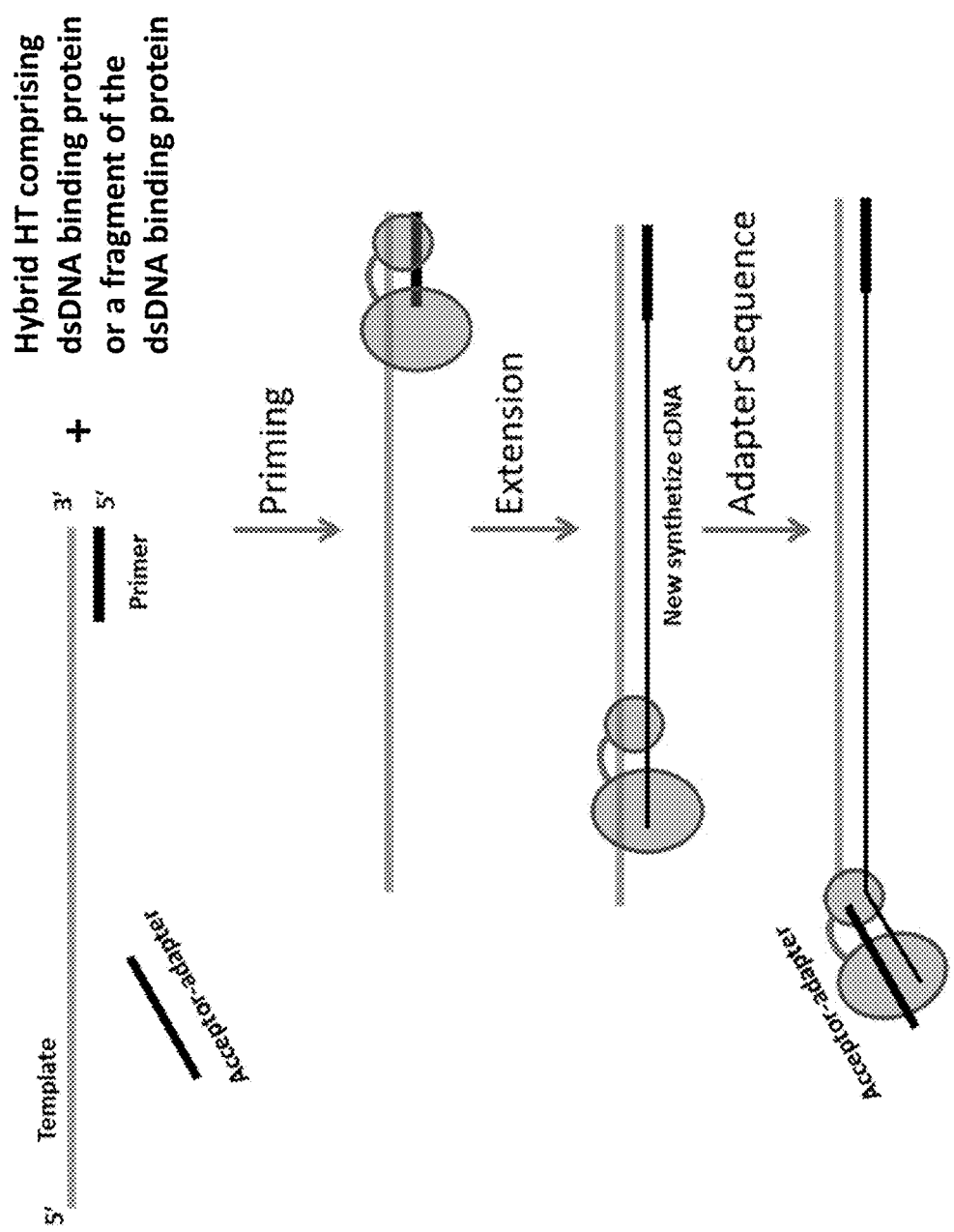
FIG. 8 illustrates a method of preparing a cDNA molecule using a hybrid reverse transcriptase comprising a dsDNA binding protein or a fragment of the dsDNA binding protein.

In an embodiment, a method of preparing a cDNA molecule comprises contacting a template RNA molecule and free nucleotides, with a primer that is complementary to the template RNA molecule, an acceptor-adapter, and a hybrid reverse transcriptase comprising a dsDNA binding protein or a fragment of a dsDNA binding protein (FIG. 8). The hybrid reverse transcriptase is then allowed to transcribe the template RNA molecule under conditions effective to produce a cDNA molecule complementary to the template RNA molecule and, optionally, to the acceptor-adapter. In some embodiments, the template RNA molecule comprises a poly (A) tail.

Figure 9:
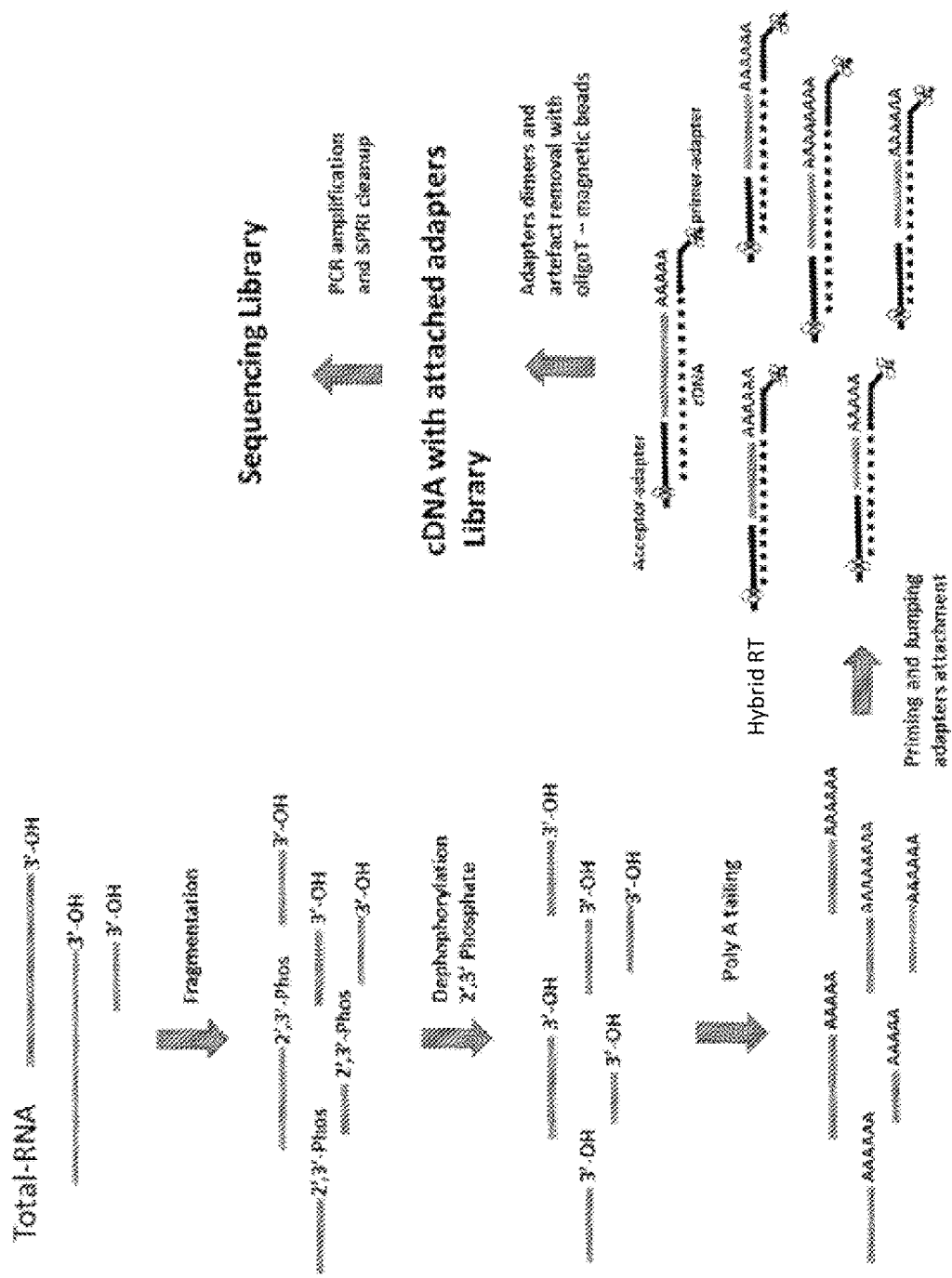
FIG. 9 illustrates a method of preparing a cDNA molecule library using a hybrid reverse transcriptase comprising a dsDNA binding protein or a fragment of the dsDNA binding protein. The method uses fragmented template RNA.

Referring to FIG. 9, in some embodiments, step (a) of a method for preparing a cDNA molecule library comprises fragmenting a template RNA molecule (e.g., total RNA) to produce RNA fragments. The template RNA can be fragmented by enzymatic or non-enzymatic methods. Enzymatic methods can use endonucleases with RNase activity (e.g., RNase A, RNase P, RNase H, RNase III, RNase T1, RNase T2, RNase U2, RNase VI, RNase I, RNase L, RNase PhyM, RNase V, dicer, or argonaute). Non-enzymatic methods take advantage of the natural chemical instability of RNAs. RNA can undergo spontaneous non-enzymatic fragmentation as a result of internal transphosphorylation. Breaking of phosphodiester bonds of RNA can be brought about by various conditions such as high pH or high temperature (e.g., about 70° C.-100° C.). RNA can also be fragmented in the presence of metals (e.g., Mg, Mn, Pb), polyamines, or cofactors, such as polyvinylpyrrolidone or polyethylene glycol. Non-enzymatic methods of fragmenting template RNA are more simple, are independent of enzyme activity or shelf life, and can be conducted under conditions compatible with the majority of the subsequent steps in the method.

The RNA fragments from the step (a) are a mixture of RNA fragments having a 3'-OH, a 2',3'-cyclic phosphate, or a 3'-phosphate. The 2',3'-cyclic phosphate can occur naturally (i.e., via cell free RNA degradation) or as a result of sample treatment or storage. RNA samples bearing 2',3'-cyclic phosphate or 3'-phosphate cannot be subsequently poly-tailed or ligated because the presence of a free 3'-OH is required for both. Accordingly, in step (b) of the method, the 2',3'-cyclic phosphate and the 3'-phosphate is removed from the RNA fragments by treating the RNA fragments with a phosphatase to generate dephosphorylated RNA fragments that can have a poly (A) tail added to the 3'-OH in step (c) of the method. In some embodiments, the phosphatase is T4 polynucleotide kinase (PNK). Other exemplary phosphatases include, but are not limited to, T4 polynucleotide kinase/phosphatase (Pnkp), *Clostridium thermocellum* Pnkp, yeast and plant tRNA ligase, and *E. coli* RtcB (Das and Shuman, "Mechanism of RNA 2',3'-cyclic phosphate end healing by T4 polynucleotide kinase phosphatase," *Nucleic Acids Research,* 2013, Vol. 41, No. 1, pp. 355-365).

In step (c) of the method, a poly (A) tail is added to the 3'-hydroxyl of the dephosphorylated RNA fragments by treating the dephosphorylated RNA fragments with, for example, poly-A polymerase.

A primer-adapter comprising an oligo-T sequence, an acceptor-adapter, nucleotides, and a hybrid reverse transcriptase comprising a dsDNA binding protein, or a fragment of the dsDNA binding protein, are then added to the poly-A tailed RNA fragments in step (d) of the method.

In step (e) of the method, the hybrid reverse transcriptase is allowed to transcribe the poly-A tailed RNA fragments under conditions effective to produce a cDNA molecule library. The hybrid reverse transcriptase then jumps to a 3'-end of the acceptor-adapter upon reaching the 5' end of the poly-A tailed RNA fragments.

Figure 10:
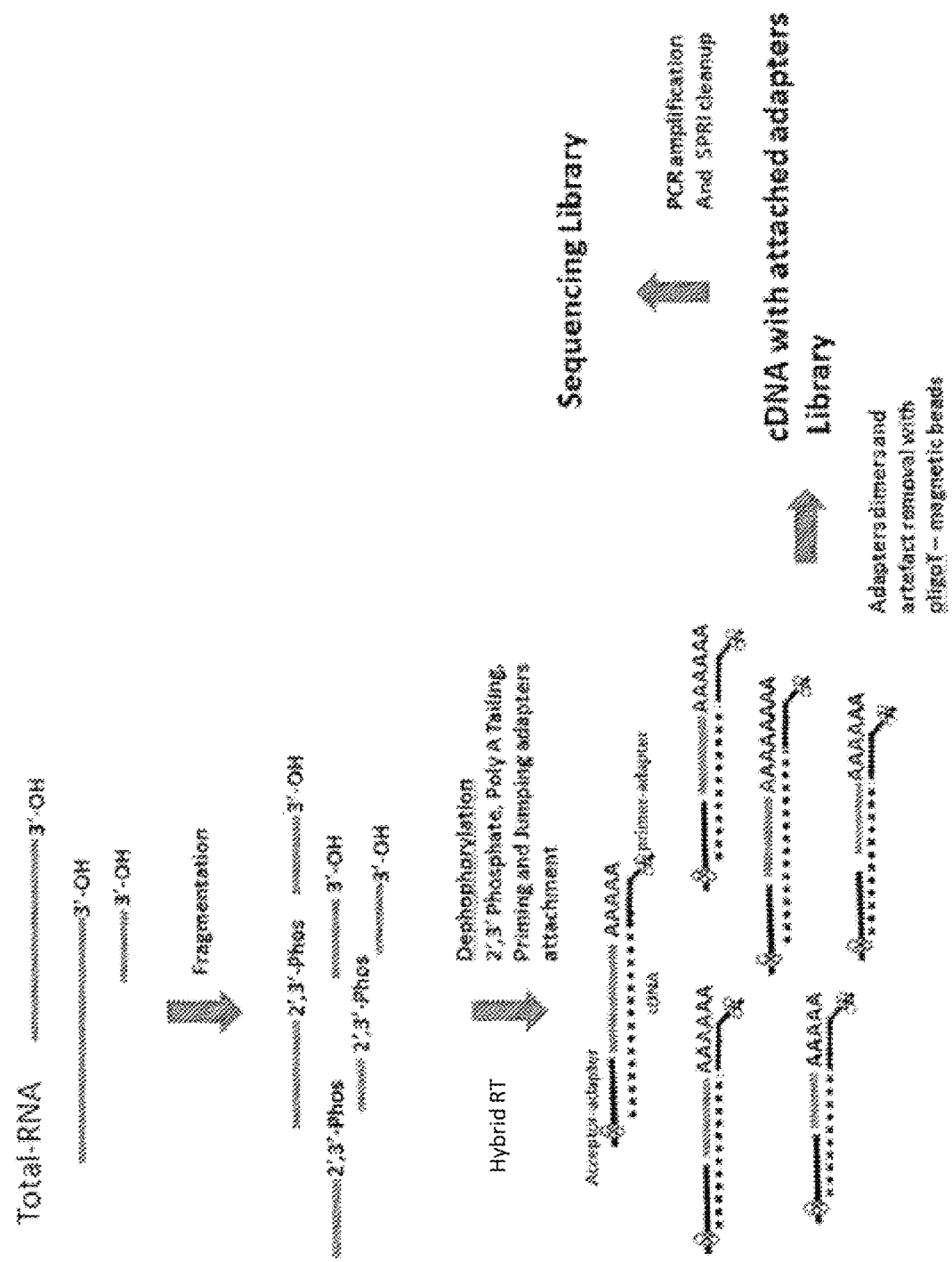
FIG. 10 illustrates a method of preparing a cDNA molecule library using a hybrid reverse transcriptase comprising a dsDNA binding protein or a fragment of the dsDNA binding protein. In the method, template RNA molecule end repair and poly A tailing steps are combined into one step.

In some embodiments (FIG. 10), steps (b) and (c) are combined into one step by using a mutant form of T4 PNK in which the kinase enzymatic activity is removed. Kinase enzymatic activity can be removed by, for example, modifying one or more amino acid in the kinase domain of the enzyme (Wang and Shuman, "Domain Structure and Mutational Analysis of T4 Polynucleotide Kinase," *J. Biol. Chem.* 2001, vol. 279, No. 29, pp 26868-26874).

Figure 11:
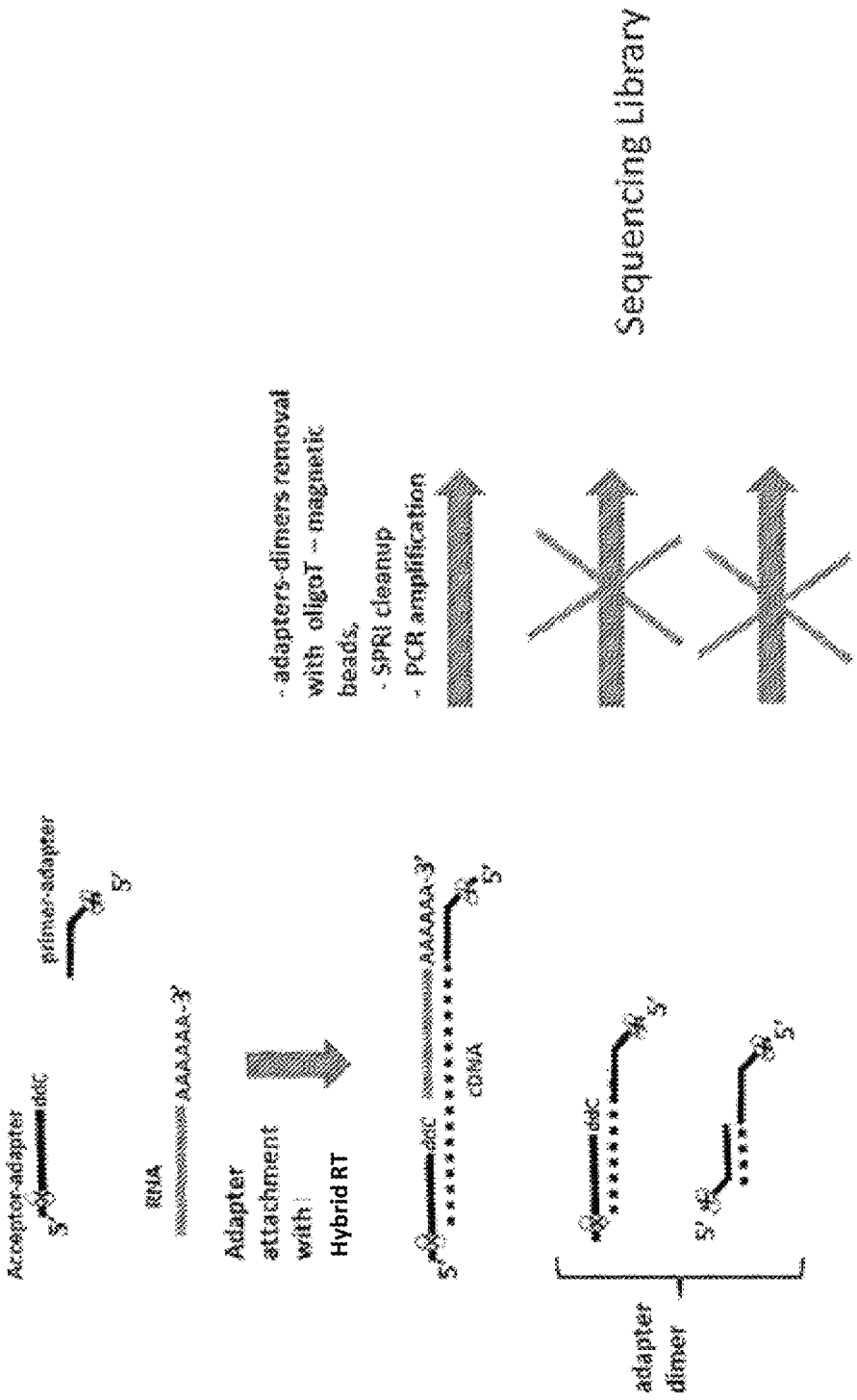
FIG. 11 illustrates a method of removing adapter-dimer artifacts generated in methods of preparing cDNA molecules according to embodiments.

During the transcription (i.e., step (e)), non-annealed primer-adapter artifacts can be generated. Such artifacts include primer-adapter-acceptor-adapter dimers or homogenous primer-adapter dimers. Generation of primer-adapter-acceptor-adapter dimers can be prevented by including a 3'-dideoxy nucleotide at the 3' end of the acceptor-adapter, which prevents acceptor-adapter extension. In some embodiments, one or more non-annealed primer-adapters are removed after the last step with an immobilized poly A oligonucleotide (e.g., oligo A attached to magnetic beads; FIG. 11) that hybridizes to an poly T sequence at the 3'end of the primer-adapter. Solid phase reverse immobilization (SPRI) can also be used in place of or after the immobilized poly A oligonucleotide are used to remove the non-annealed primer-adapter artifacts.

Figure 12:
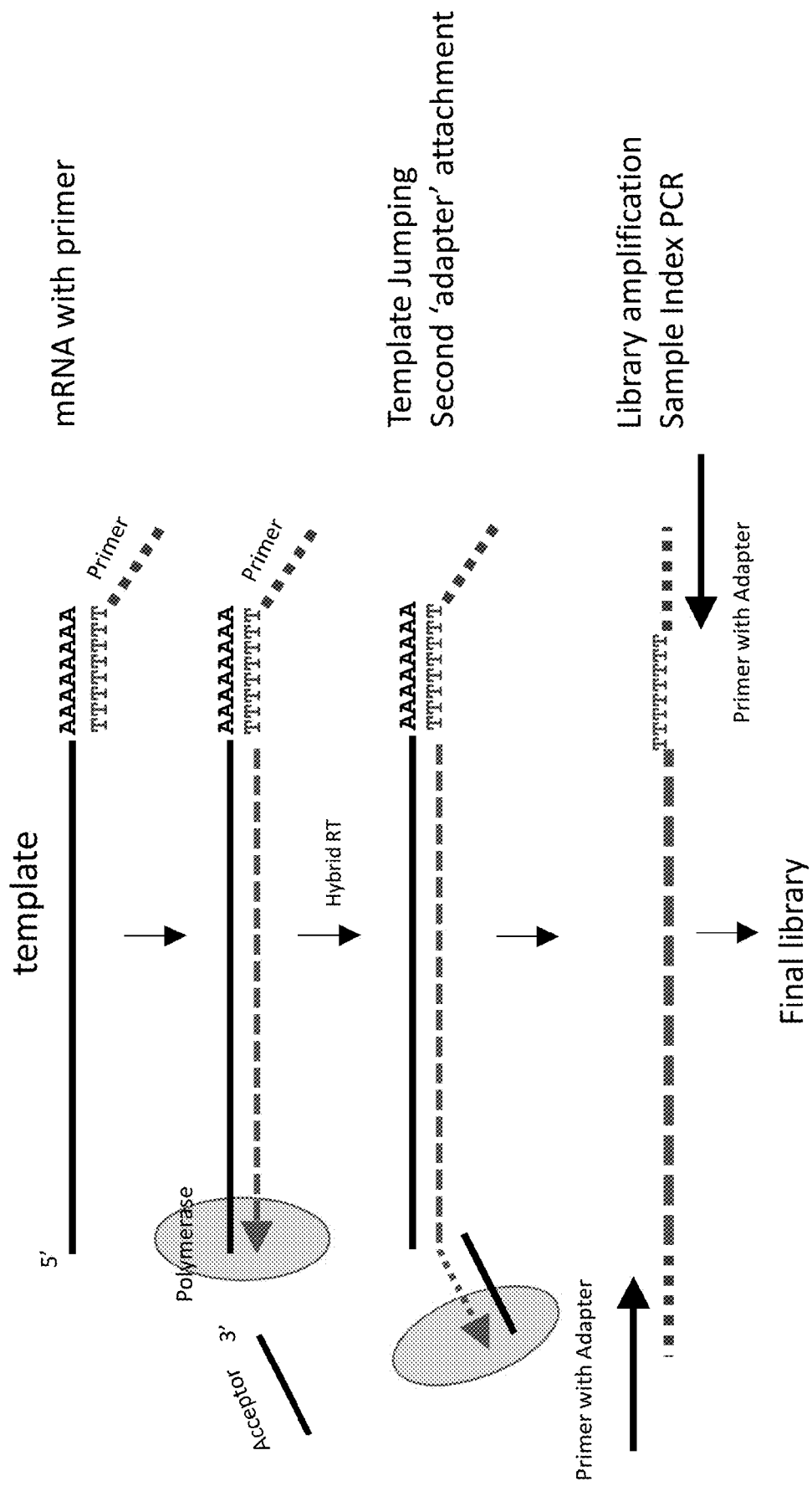
FIG. 12 illustrates a method of preparing a cDNA molecule library using a hybrid reverse transcriptase comprising a dsDNA binding protein or a fragment of the dsDNA binding protein. The method uses a messenger RNA template comprising a poly A tail and a primer-adapter comprising a poly T tail.
Figure 13:
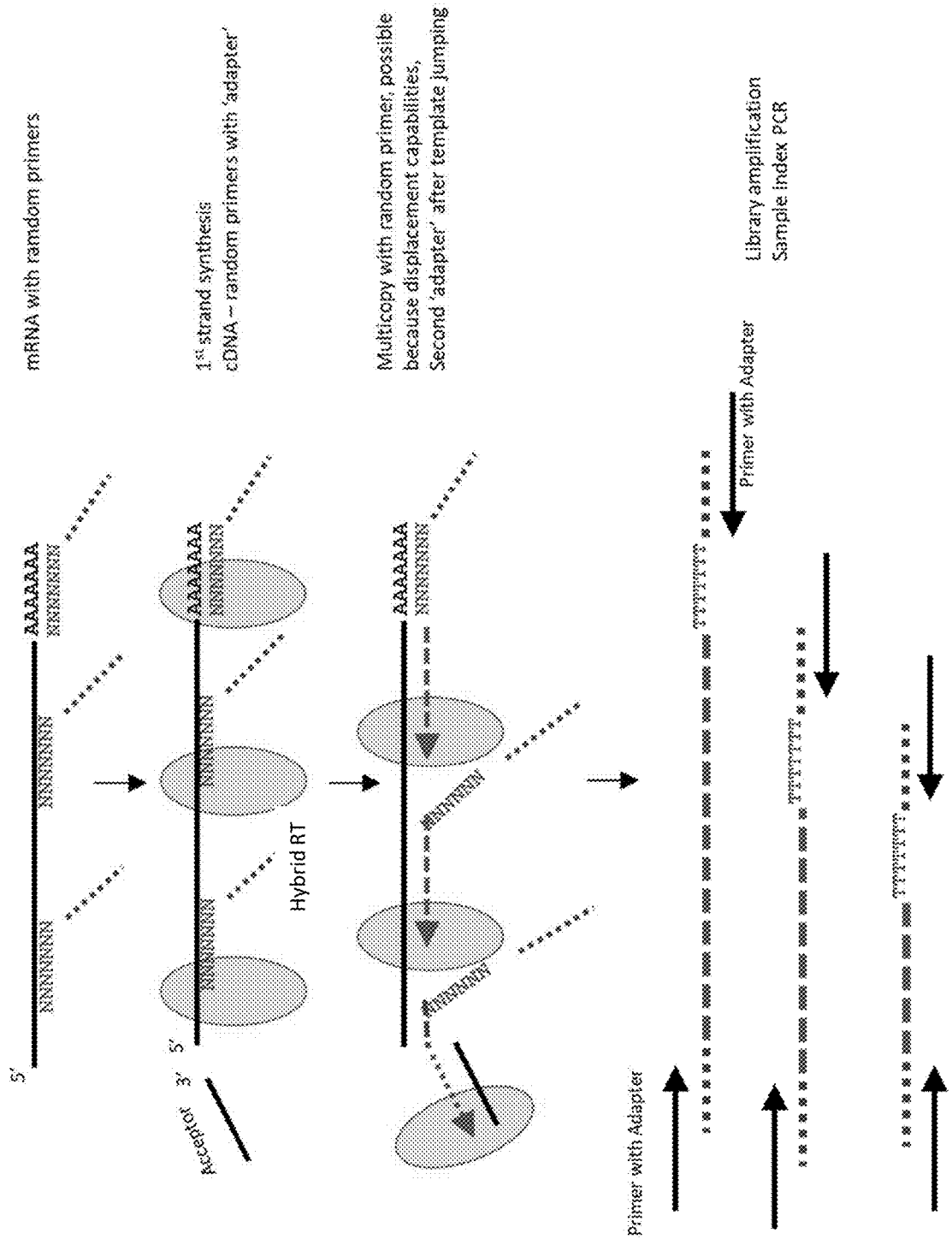
FIG. 13 illustrates a method of preparing a cDNA molecule library using a hybrid reverse transcriptase comprising a dsDNA binding protein or a fragment of the dsDNA binding protein. The method uses a messenger RNA template comprising a poly A tail and one or more random primer-adapters.

The disclosed hybrid reverse transcriptases can also be used to prepare cDNA from an mRNA template with a single primer-adapter (FIG. 12) or with random primer-adapters (FIG. 13). Referring to FIG. 12, in certain embodiments, step (a) of a method of preparing a cDNA molecule library using a single primer-adapter comprises annealing a primer-adapter comprising a poly (T) tail to a template RNA molecule comprising a poly (A) tail (e.g., a messenger RNA molecule comprising a poly (A) tail), thereby generating an annealed RNA molecule. In step (b) of the method, the annealed RNA molecule and free nucleotides are mixed, with an acceptor-adapter and a hybrid reverse transcriptase comprising a dsDNA binding protein, or a fragment of the dsDNA binding protein. In the next step (i.e., step (c)) of the method, the hybrid reverse transcriptase is allowed to transcribe the annealed RNA molecule at a temperature from about 12° C. to about 42° C. to produce a cDNA molecule library. In some embodiments, in step (c), the hybrid reverse transcriptase transcribes the annealed RNA molecule at a temperature of about 4° C. to about 50° C. (e.g., about 4° C., about 15° C., about 20° C., about 25° C., about 30° C., about 35° C., about 40° C., about 45° C., about 48° C.). In some embodiments, steps (a)-(c) are performed in a single reaction vessel. In certain embodiments, step (a) or step (b) further comprises adding hot start thermostable polymerase.

Referring to FIG. 13, in some embodiments, step (a) of a method for preparing a cDNA molecule library using random primers (i.e., primers with random base sequences) comprises annealing one or more random primer-adapters to template RNA molecules comprising a poly (A) tail, thereby generating annealed RNA molecules. In step (b) of the method, the one or more annealed RNA molecules are mixed, in the presence of nucleotides, with one or more acceptor-adapters and a hybrid reverse transcriptase comprising a dsDNA binding protein, or a fragment of the dsDNA binding protein. In step (c) of the method, the hybrid reverse transcriptase is allowed to transcribe the annealed RNA molecule without thermal cycling to produce a cDNA molecule library. In some embodiments, steps (a)-(c) are performed in a single reaction vessel. In certain embodiments, step (a) or step (b) further comprises adding hot start thermostable polymerase. In some embodiments, the template RNA molecules do not comprise a poly (A) tail.

In methods in which the hybrid reverse transcriptase comprises a dsDNA binding protein, the hybrid reverse transcriptase comprises SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 40, SEQ ID NO: 41, SEQ ID NO: 42, or SEQ ID NO: 43 or a sequence at least 75% identical to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 40, SEQ ID NO: 41, SEQ ID NO: 42, or SEQ ID NO: 43.

Methods in which Hybrid Reverse Transcriptase Comprises a ssDNA Binding Protein

Figure 14:
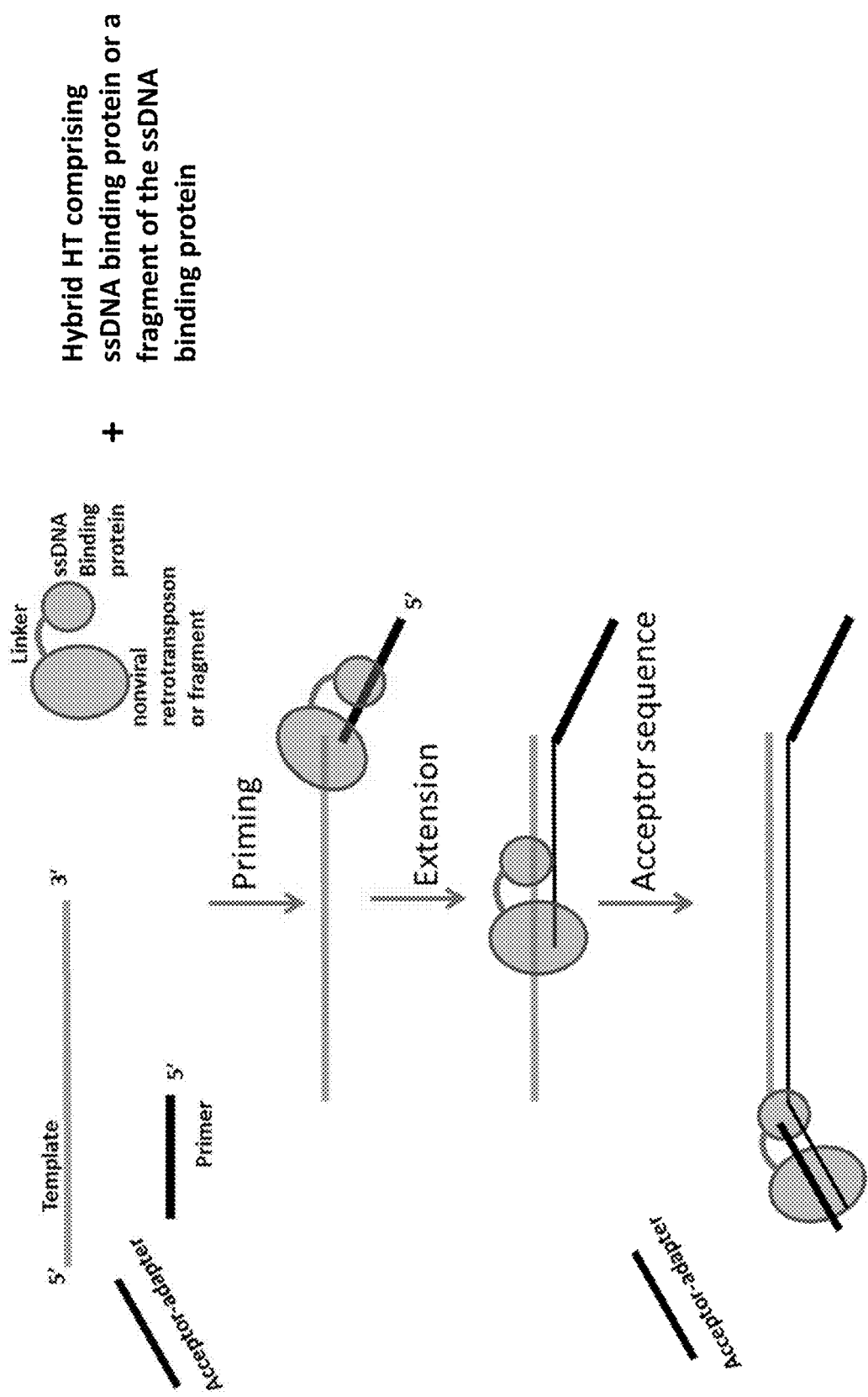
FIG. 14 illustrates a method of preparing a cDNA molecule using a hybrid reverse transcriptase comprising a ssDNA binding protein or a fragment of the ssDNA binding protein.

In some embodiments (FIG. 14), a method of preparing a cDNA molecule comprises contacting a template RNA molecule and free nucleotides with a primer that is not complementary (or has limited complementarity, i.e., 1 to 3 base pair complementarity) to the template RNA molecule, an acceptor-adapter; and a hybrid reverse transcriptase comprising a ssDNA binding protein or a fragment of the ssDNA binding protein. The hybrid reverse transcriptase is then allowed to transcribe the template RNA molecule under conditions effective for producing a cDNA molecule complementary to the template RNA molecule and, optionally, to the acceptor-adapter. An advantage to this method and subsequent methods in which the hybrid reverse transcriptase comprises a ssDNA binding protein is that template RNA dephosphorylation and poly (A) tailing steps are absent.

Figure 15:
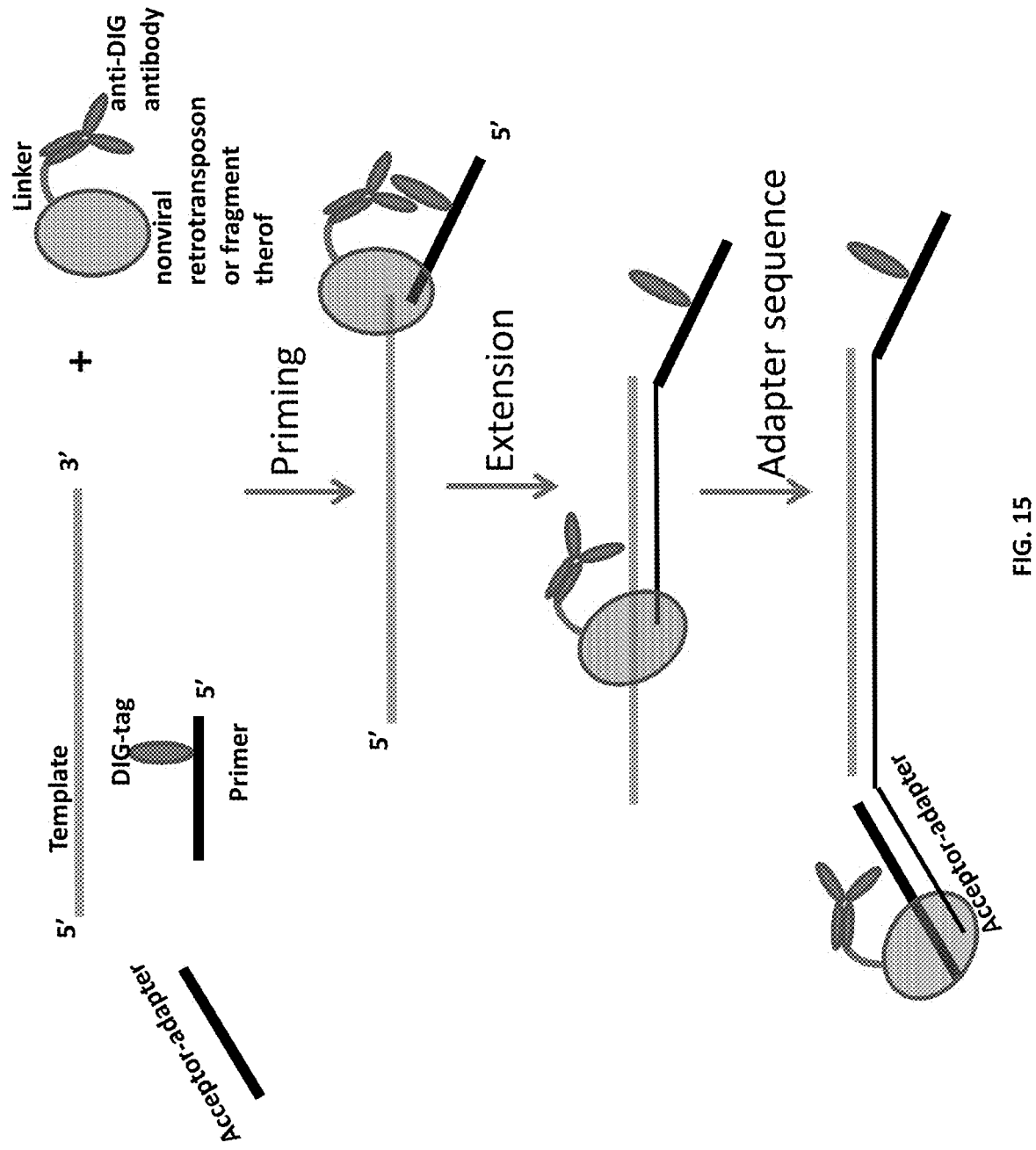
FIG. 15 illustrates a method of preparing a cDNA molecule using a hybrid reverse transcriptase comprising a ssDNA binding protein. The hybrid reverse transcriptase is a fusion protein. The ssDNA binding protein is an anti-Digoxigenin antibody and the ssDNA or ssRNA primer comprises a Digoxigenin tag.

In certain embodiments, the primer-adapter comprises ssDNA or ssRNA. In some embodiments in which the hybrid reverse transcriptase is a fusion protein (FIG. 15), the ssDNA binding protein is an anti-Digoxigenin antibody and the primer-adapter comprises a Digoxigenin-tag (DIG-tag). During the transcription step of the method, the anti-digoxigenin antibody binds non-covalently to the DIG-tag in the primer-adapter, and may enhance the ability of the hybrid reverse transcriptase to transcribe the template RNA molecule.

Figure 16:
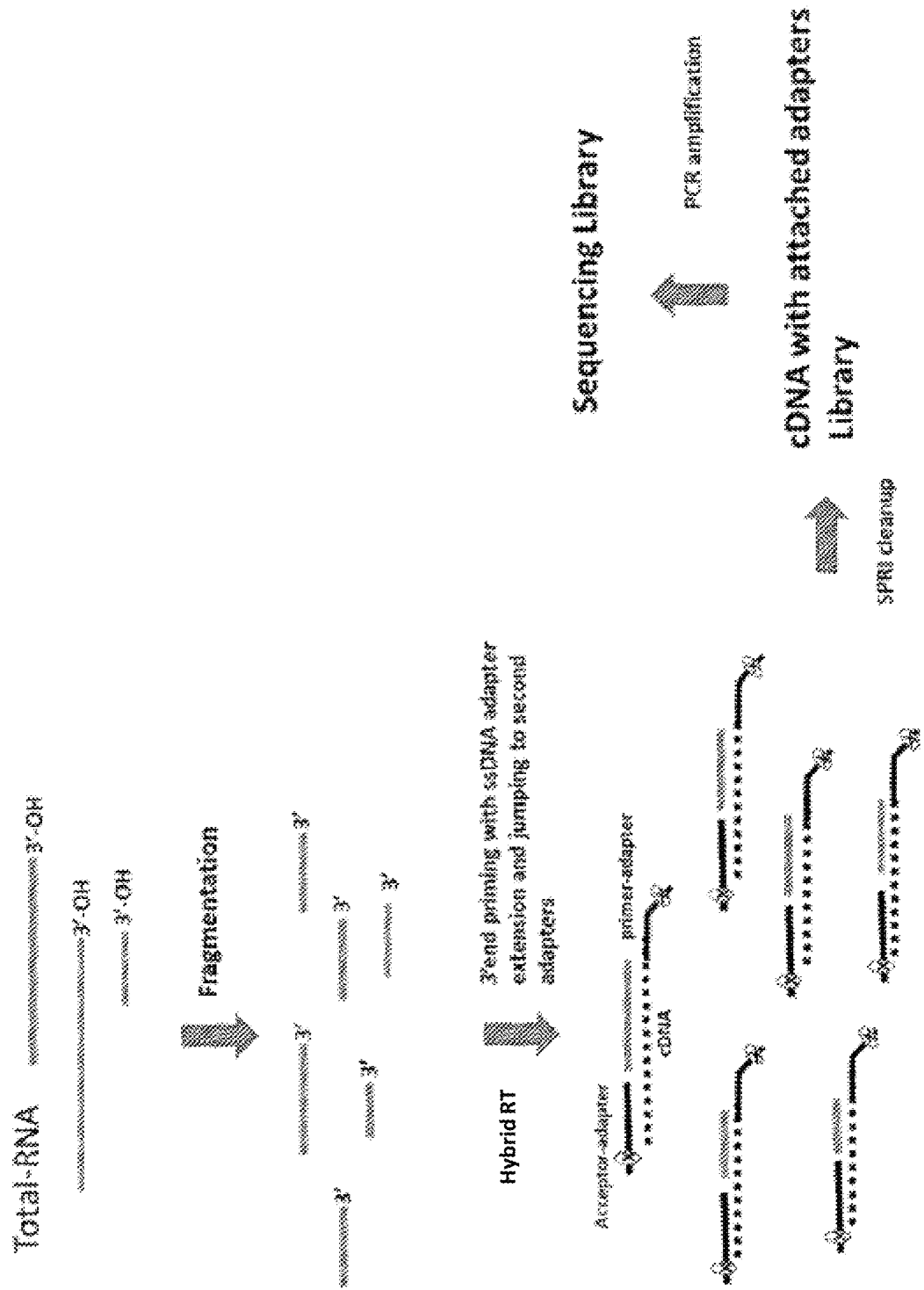
FIG. 16 illustrates a method of preparing a cDNA molecule library using a hybrid reverse transcriptase comprising a ssDNA binding protein, or a fragment of the ssDNA binding protein, in which a primer-adapter is not complementary to the template RNA molecule. Template RNA molecule end repair and poly A tailing steps are absent.
Figure 17:
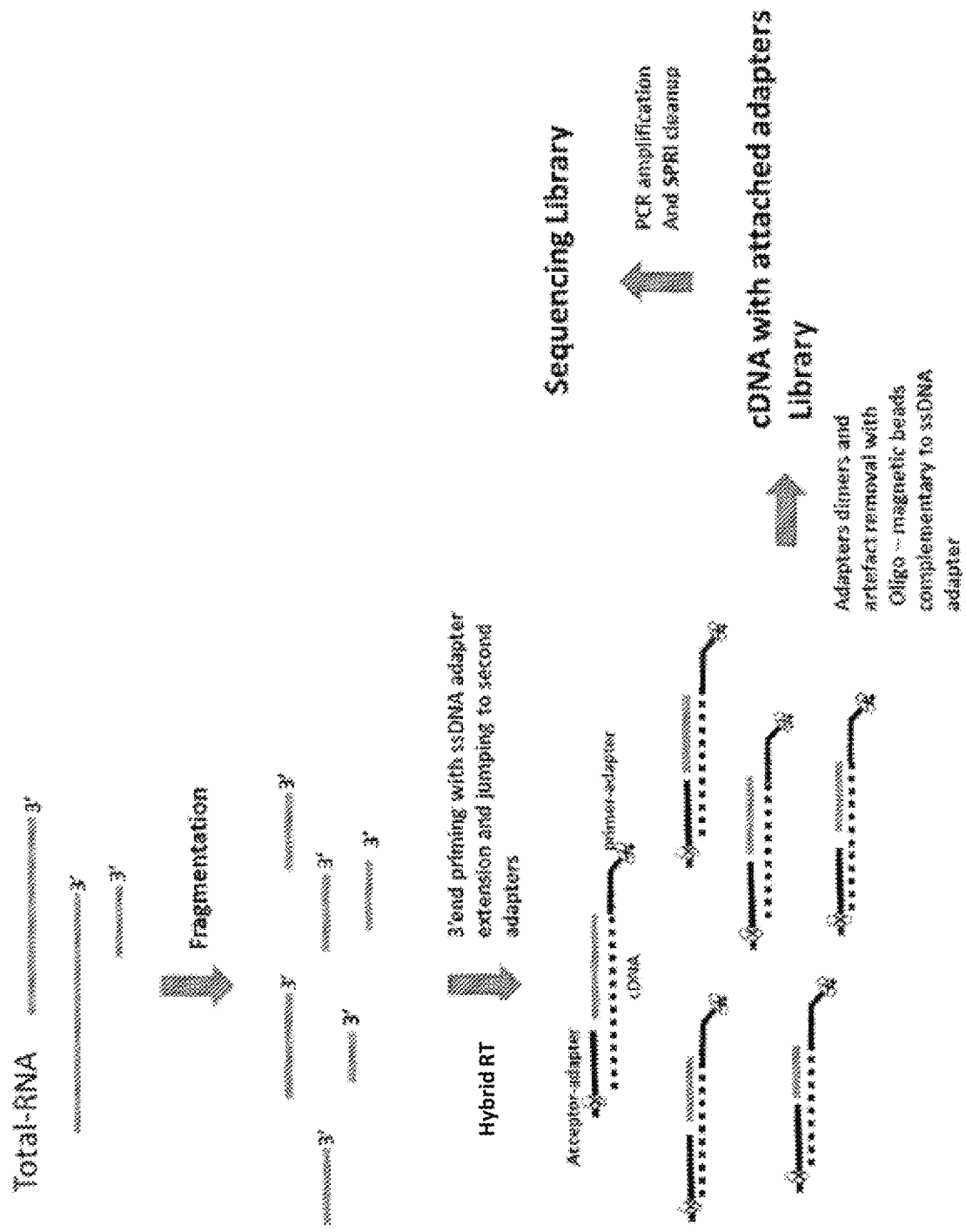
FIG. 17 illustrates a method of preparing a cDNA molecule library using a hybrid reverse transcriptase comprising a ssDNA binding protein, or a fragment of the ssDNA binding protein, in which the primer-adapter is not complementary to the template RNA molecule. Template RNA molecule end repair and poly A tailing steps are absent. The method illustrated in FIG. 11 is used to remove adapter-dimer artifacts.
Figure 18:
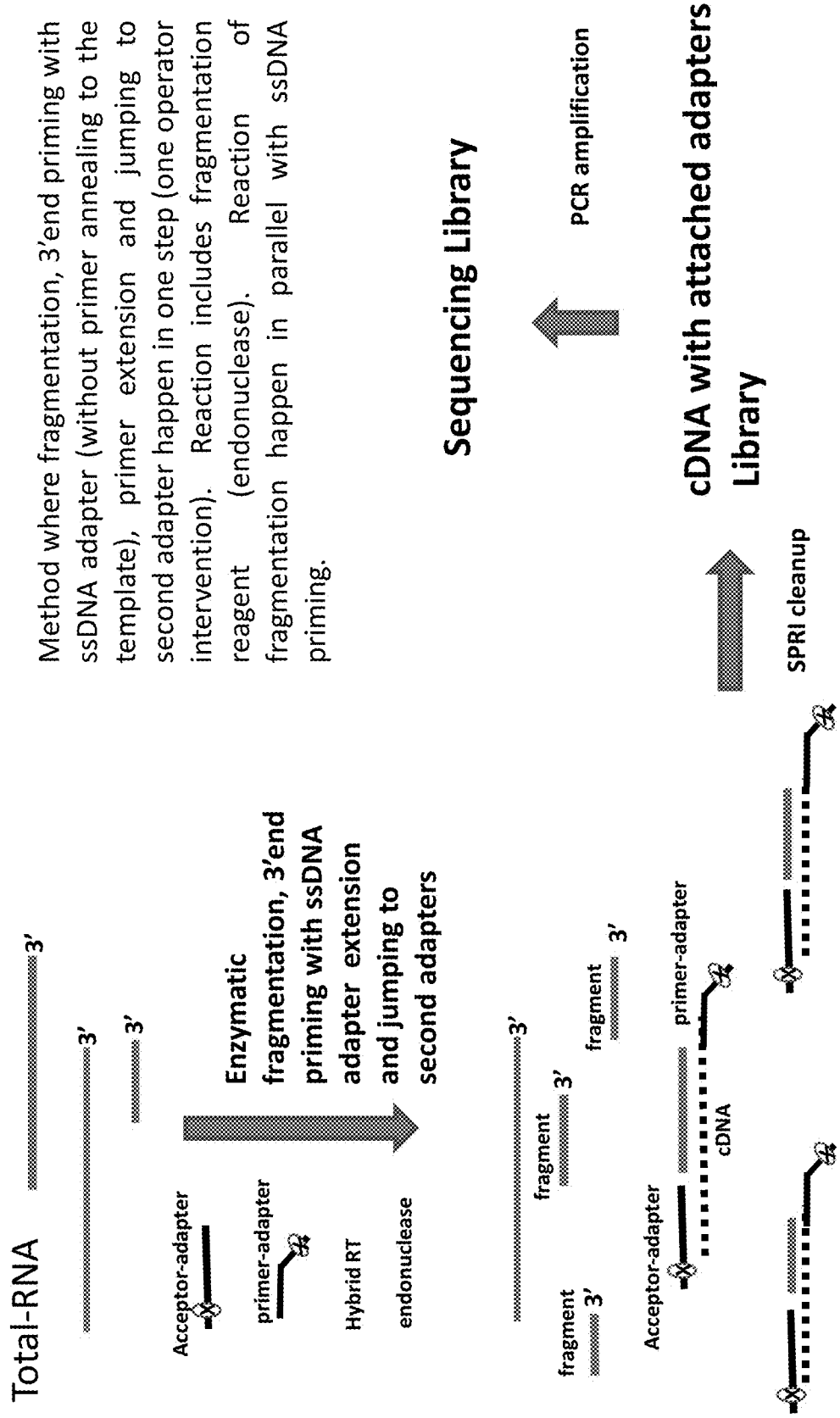
FIG. 18 illustrates a method of preparing a cDNA molecule library using a hybrid reverse transcriptase comprising a ssDNA binding protein, or a fragment of the ssDNA binding protein, in which a primer-adapter is not complementary to the template RNA molecule. Fragmentation, 3' end priming with the primer-adapter, primer extension, and jumping of the hybrid reverse transcriptase to an acceptor-adapter occur in one step.

In certain embodiments (FIG. 16), step (a) of a method of preparing a cDNA molecule library comprises fragmenting a template RNA molecule to produce RNA fragments. In step (b) of the method, the RNA fragments and free nucleotides are contacted with a primer-adapter that is not complementary to the RNA fragments, an acceptor-adapter, and a hybrid reverse transcriptase comprising a ssDNA binding protein or a fragment of the ssDNA binding protein. The hybrid reverse transcriptase is then allowed to transcribe the RNA fragments under conditions effective to produce a cDNA molecule library in step (c) of the method. In some embodiments, the method further comprises removing one or more non-annealed primer-adapter after the last step by, for example, size fractionation via electrophoresis or chromatography. In some embodiments, one or more non-annealed primer-adapters are removed after the last step with an immobilized poly A oligonucleotide that hybridizes to a poly T sequence at the 3'end of the primer-adapter (FIG. 17). Solid phase reverse immobilization (SPRI) can also be used in place of or after the immobilized poly A oligonucleotide are used to remove the non-annealed primer-adapter artifacts. In some embodiments, steps (a)-(c) are combined into one step by further including an endonuclease which fragments the template RNA (FIG. 18). In certain embodiments, any or all of the steps are performed in a partition.

Figure 19:
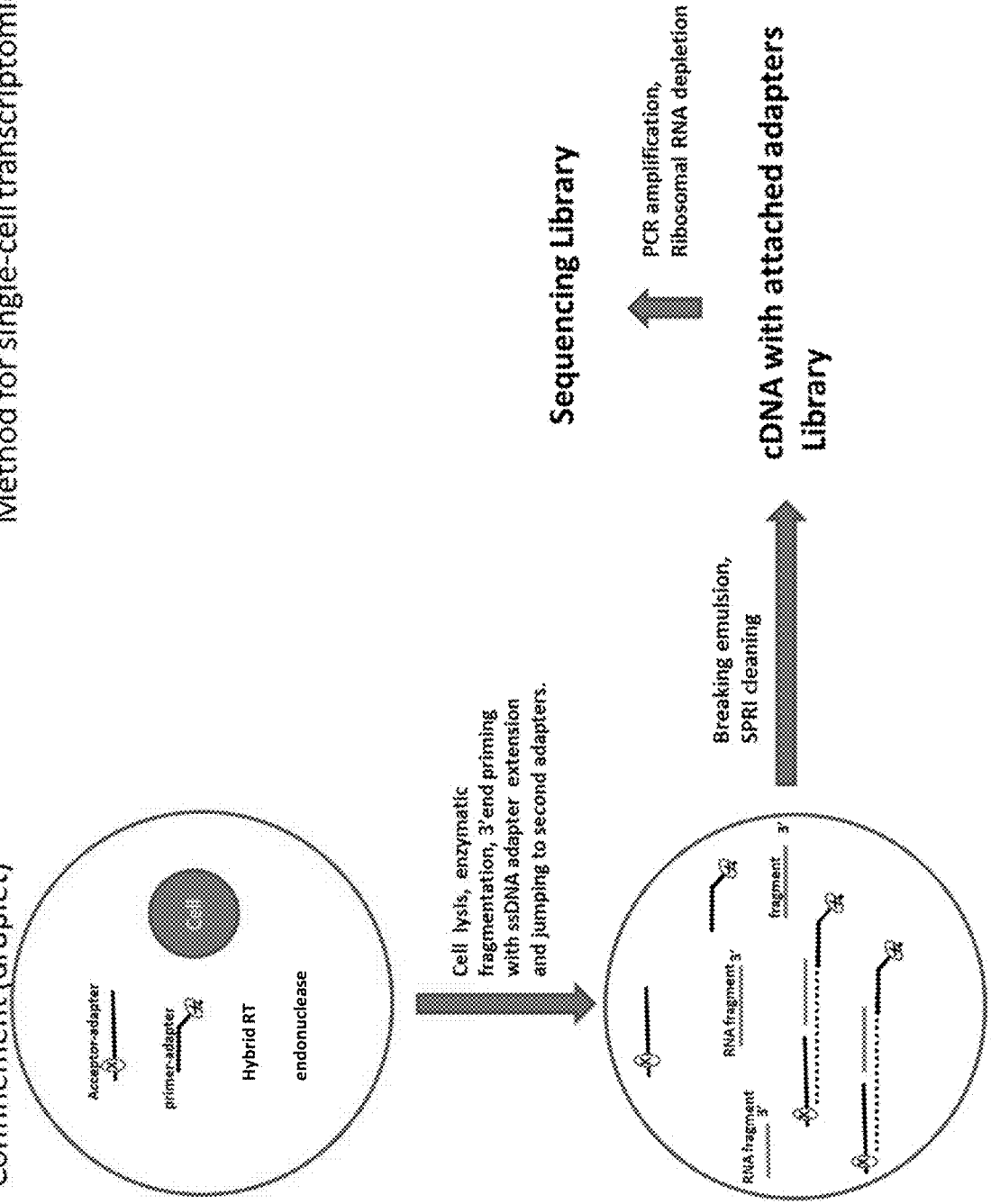
FIG. 19 illustrates a method of preparing a cDNA molecule using a hybrid reverse transcriptase comprising a ssDNA binding protein, or a fragment of the ssDNA binding protein, in which a primer-adapter is not complementary to the template RNA molecule. Fragmentation, 3' end priming with the primer-adapter, primer extension, and jumping of the hybrid reverse transcriptase to an acceptor-adapter occur in a droplet. The method is used for single-cell transcriptomics.

The hybrid reverse transcriptases can also be used in methods performed in a partition. In some embodiments (FIG. 19), step (a) of a method of preparing a cDNA molecule library comprises providing a partition comprising a cell comprising template RNA molecules, nucleotides, a primer-adapter that is not complementary to the template RNA molecules, an acceptor-adapter, an endonuclease, and a hybrid reverse transcriptase comprising a non-retroviral retrotransposon, or a fragment of the non-retroviral retrotransposon having reverse transcriptase activity, joined to a ssDNA binding protein. In the partition, template RNA molecules are released from the cell (step (b)), the RNA molecules are fragmented to form RNA fragments (step (c)), and the hybrid reverse transcriptase is allowed to transcribe the RNA fragments under conditions effective to produce a cDNA molecule library (step (d)).

The term "partitioning" or "partitioned" refers to separating an aqueous solution having one or more of a sample and reactants into a plurality of portions, or "partitions." Partitions can be solid or fluid. In some embodiments, a partition is a solid partition, e.g., a microchannel. In some embodiments, a partition is a fluid partition (e.g., a droplet). In some embodiments, a fluid partition is a mixture of immiscible fluids (e.g., water and oil). In some embodiments, a fluid partition is an aqueous droplet that is surrounded by an immiscible carrier fluid (e.g., oil).

The partition can include any of a number of types of partitions, including solid partitions (e.g., wells or tubes) and fluid partitions (e.g., aqueous phase or droplet within an oil phase). In some embodiments, the partitions are droplets. In some embodiments, the partitions are microchannels. Methods and compositions for partitioning a sample are described, for example, in published patent application WO 2010/036352 and issued U.S. Pat. No. 9,156,010, the entire content of each of which is incorporated by reference herein.

In an embodiment, the droplet is formed by flowing an oil phase through an aqueous phase. The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

In some embodiments, the droplet is formed by flowing an oil phase through an aqueous phase having a sample (e.g., a cell) and one or more components (e.g., reagents) that are used to prepare a cDNA library. In some embodiments, the one or more components used to prepare the cDNA library in the aqueous droplet are soluble and/or miscible in water including, but not limited to, one or more salts, buffering agents, reagents (e.g., nucleotides, a primer-adapter, an acceptor-adapter, an endonuclease, and a hybrid reverse transcriptase), surfactants, and/or whatever additional components may be necessary for a desired reaction(s) that may be intended to occur within a formed droplet. All such additional components may be selected to be compatible with the desired reaction.

In methods in which the hybrid reverse transcriptase comprises a ssDNA binding protein, the hybrid reverse transcriptase comprises SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100, or a sequence at least 75% identical to SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100.

In some embodiments, the cDNA molecule or cDNA library is prepared in about 1-3 hours (e.g., 2 hours) or less.

In some embodiments, the method further comprises amplifying the cDNA molecule(s) by polymerase chain reaction (PCR), thereby forming one or more amplicons. PCR techniques are described in, for example, Walker-Daniels (2012) "Current PCR Methods," Mater. Methods, Vol. 2, No. 119. PCR techniques that may be used to amplify the cDNA molecule(s) include, but are not limited to, RT-PCR (in which reverse transcription and PCR are performed in the same reaction vessel), real-time PCR, nested PCR, quantitative PCR, multiplexed PCR, digital PCR, and assembly PCR. In certain embodiments, the amplifying is performed at a temperature sufficient to inactivate the reverse transcriptase.

In some embodiments, the method further comprises adding a label (e.g., a fluorescent dye) to the template RNA molecule(s), thereby generating a labeled cDNA molecule(s). In some embodiments, the method further comprises sequencing the labeled cDNA molecule(s). Sequencing the labeled cDNA molecule(s) may be performed by sequencing methods including, but not limited to, Helioscope® single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLID sequencing, Ion Torrent, Ion semiconductor sequencing, Single Molecule SMRT® sequencing, Polony sequencing, DNA nanoball sequencing, and VisiGen Biotechnologies approach. Alternatively, determining the sequence of the labeled nucleic acid or any product thereof may use sequencing platforms, including, but not limited to, Genome Analyzer IN, HiSeq, and MiSeq offered by Illumina, Single Molecule Real Time (SMRT®) technology, such as the PacBio RS system offered by Pacific Biosciences (California) and the Solexa Sequencer, True Single Molecule Sequencing (tSMS®) technology such as the HeliScope® Sequencer offered by Helicos Inc. (Cambridge, Mass.). The sequencing reaction can occur on a solid or semi-solid support, in a gel, in an emulsion, on a surface, on a bead, in a drop, in a continuous follow, in a dilution, or in one or more physically separate volumes.

Kits

Also provided are kits for preparing cDNA from RNA. In some embodiments, such kits include a hybrid reverse transcriptase according to embodiments. In some embodiments, the kits further include suitable buffers, substrates for DNA synthesis such as the deoxynucleotide triphosphates (e.g., dATP, dCTP, dGTP, and dTTP) either individually or collectively in a suitable solution, a terminal transferase in solution, primer-adapter RNA having a known nucleotide sequence for use as a reverse transcription primer to obtain a 3' end of RNA, and acceptor-adapter RNA having a known nucleotide sequence to obtain a 5' end of RNA. In certain embodiments, the kits also include reagents for PCR (e.g., PCR primers, polymerase, buffers) and/or reagents for sequencing (e.g., fluorescently labeled dNTPs, sequencing primers). Any combination of the kit components may be provided in solution or in lyophilized form. The kits may also include instructions for using the kit components.

Various non-limiting embodiments include:
1. A hybrid reverse transcriptase comprising a non-retroviral retrotransposon, or a fragment of the non-retroviral retrotransposon having reverse transcriptase activity, joined to a nucleic acid binding protein or a fragment of the nucleic acid binding protein that binds to nucleic acid.
2. The hybrid reverse transcriptase of embodiment 1, wherein the nucleic acid binding protein is a single stranded deoxyribonucleic acid (ssDNA) binding protein or a fragment of a ssDNA binding protein.
3. The hybrid reverse transcriptase of embodiment 1, wherein the nucleic acid binding protein is a double stranded deoxyribonucleic acid (dsDNA) binding protein or a fragment of a dsDNA binding protein.

4. The hybrid reverse transcriptase of embodiment 1, wherein the nucleic acid binding protein is a nucleic acid tag binding protein.
5. The hybrid reverse transcriptase of any one of the preceding embodiments, wherein the non-retroviral retrotransposon, or the fragment of the non-retroviral retrotransposon, is an R2 reverse transcriptase or a fragment of the R2 reverse transcriptase, respectively.
6. The hybrid reverse transcriptase of embodiment 5, wherein the R2 reverse transcriptase comprises domains from two or more arthropods.
7. The hybrid reverse transcriptase of any one of embodiments 1-6, wherein the non-retroviral retrotransposon, or the fragment of the non-retroviral retrotransposon, is optionally joined via a linker to the nucleic acid binding protein or a fragment of the nucleic acid binding protein.
8. The hybrid reverse transcriptase of any one of embodiments 1-6, wherein the non-retroviral retrotransposon, or the fragment of the non-retroviral retrotransposon, is joined via a linker to the nucleic acid binding protein or a fragment of the nucleic acid binding protein.
9. The hybrid reverse transcriptase of embodiment 7 or 8, wherein the linker lacks a secondary structure.
10. The hybrid reverse transcriptase of embodiment 8 or 9, wherein the linker is selected from the group consisting of VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), VGTGGGSGGGTGGGSA (SEQ ID NO: 107), (GGGS)n (SEQ ID NO: 108), (GGS)n, (GGGGS)n (SEQ ID NO: 109), and (EAAAK)n (SEQ ID NO: 110) and n is 1, 2, 3, 4, or 5.
11. The hybrid reverse transcriptase of embodiment 2, wherein the nucleic acid binding protein is *Sulfolobus* SSB, a fragment of *Sulfolobus* SSB, or an anti-Digoxigenin antibody.
12. The hybrid reverse transcriptase of embodiment 3, wherein the nucleic acid binding protein is Sso7d, a fragment of Sso7d, Cren7, or a fragment of Cren 7.
13. The hybrid reverse transcriptase of any one of the preceding embodiments, wherein the nucleic acid binding protein, or the fragment of the nucleic acid binding protein, is joined to the N-terminus or C-terminus of the non-retroviral retrotransposon or the fragment of the non-retroviral retrotransposon.
14. The hybrid reverse transcriptase of any one of the preceding embodiments, wherein the nucleic acid binding protein is two or more nucleic acid binding proteins or fragments of two or more nucleic acid binding proteins and the two or more nucleic acid binding proteins or fragments of two or more nucleic acid binding proteins are identical or non-identical.
15. The hybrid reverse transcriptase of embodiment 14, wherein the two or more nucleic acid binding proteins or fragments of two or more nucleic acid binding proteins are in sequential or random order.
16. The hybrid reverse transcriptase of any one of the preceding embodiments, wherein the non-retroviral retrotransposon, or the fragment of the non-retroviral retrotransposon, is covalently joined to the nucleic acid binding protein or the fragment of the nucleic acid binding protein.
17. A hybrid reverse transcriptase comprising two or more non-retroviral retrotransposons, or two or more fragments of the non-retroviral retrotransposon having reverse transcriptase activity, optionally joined by a linker.
18. The hybrid reverse transcriptase of embodiment 17, wherein the two or more non-retroviral retrotransposons, or the two or more fragments of the non-retroviral retrotransposon having reverse transcriptase activity are joined by a linker.
19. The hybrid reverse transcriptase of embodiment 17 or 18, wherein the linker lacks a secondary structure.
20. The hybrid reverse transcriptase of any one of embodiments 17-19, wherein the linker is selected from the group consisting of VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), VGTGGGSGGGTGGGSA (SEQ ID NO: 107), (GGGS)n (SEQ ID NO: 108), (GGS)n, (GGGGS)n (SEQ ID NO: 109), and (EAAAK)n (SEQ ID NO: 110) and n is 1, 2, 3, 4, or 5.
21. The hybrid reverse transcriptase of any one of embodiments 17-20, wherein the two or more non-retroviral retrotransposons, or the two or more fragments of the non-retroviral retrotransposon, are an R2 reverse transcriptase or a fragment of the R2 reverse transcriptase, respectively.
22. The hybrid reverse transcriptase of any one of embodiments 17-21, wherein the two or more non-retroviral retrotransposons, or the two or more fragments of the non-retroviral retrotransposon, are covalently joined.
23. The hybrid reverse transcriptase of any one of the preceding embodiments, further comprising a purification tag at an N-terminus or a C-terminus.
24. A hybrid reverse transcriptase comprising a non-retroviral retrotransposon having at least 75% sequence identity to SEQ ID NO: 1 joined to a nucleic acid binding protein or a fragment of the nucleic acid binding protein.
25. A hybrid reverse transcriptase comprising a fragment of a non-retroviral retrotransposon having at least 75% sequence identity to SEQ ID NO: 2 joined to a nucleic acid binding protein or a fragment of the nucleic acid binding protein.
26. A hybrid reverse transcriptase comprising SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100 or a sequence with at least 75% identity to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 47, SEQ ID NO: 98, SEQ ID NO: 99, or SEQ ID NO: 100.

27. A nucleic acid construct comprising a polynucleotide sequence encoding the hybrid reverse transcriptase of any one of the preceding embodiments.

28. A vector comprising the nucleic acid construct of embodiment 27.

29. A host cell comprising a nucleic acid construct and/or a vector as defined in embodiment 27 or 28.

30. A method of preparing a cDNA molecule comprising:
(a) contacting a template RNA molecule and free nucleotides with:
  i. a primer that is complementary to the template RNA molecule;
  ii. an acceptor-adapter; and
  iii. a hybrid reverse transcriptase comprising a non-retroviral retrotransposon, or a fragment of the non-retroviral retrotransposon having reverse transcriptase activity, joined to a dsDNA binding protein or a fragment of a dsDNA binding protein; and
(b) allowing the hybrid reverse transcriptase to transcribe the template RNA molecule under conditions effective to produce a cDNA molecule complementary to the RNA molecule and, optionally, to the acceptor-adapter,
wherein the hybrid reverse transcriptase jumps to a 3'-end of the acceptor-adapter upon reaching a 5' end of the RNA molecule.

31. A method of preparing a cDNA molecule library comprising:
(a) fragmenting a template RNA molecule to produce RNA fragments;
(b) removing a 2', 3'-cyclic phosphate and a 3'-phosphate from the RNA fragments, thereby generating dephosphorylated RNA fragments;
(c) adding a poly-A tail to the dephosphorylated RNA fragments to form poly-A tailed RNA fragments;
(d) adding to the poly-A tailed RNA fragments:
  i. a primer-adapter comprising an oligo-T sequence;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, joined to a dsDNA binding protein or a fragment of a dsDNA binding protein; and
(e) allowing the hybrid reverse transcriptase to transcribe the poly-A tailed RNA fragments under conditions effective to produce a cDNA molecule library,
wherein the hybrid reverse transcriptase jumps to a 3'-end of the acceptor-adapter upon reaching a 5' end of the poly-A tailed RNA fragments.

32. The method of embodiment 30, wherein steps (b) and (c) are combined into one step.

33. A method of preparing a cDNA molecule library comprising:
(a) annealing a primer adapter comprising a poly (T) tail to a template RNA molecule comprising a poly (A) tail, thereby generating an annealed RNA molecule;
(b) mixing:
  i. the annealed RNA molecule;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, joined to a dsDNA binding protein or a fragment of a dsDNA binding protein; and
(c) allowing the hybrid reverse transcriptase to transcribe the annealed RNA molecule at a temperature from about 12° C. to about 42° C. to produce a cDNA molecule library,
wherein the hybrid reverse transcriptase jumps to a 3'-end of the acceptor-adapter upon reaching a 5' end of the annealed RNA molecule.

34. The method of embodiment 33, wherein the template RNA molecule is a messenger RNA molecule.

35. A method of preparing a cDNA molecule library comprising:
(a) annealing one or more random primer adapters to template RNA molecules comprising a poly (A) tail, thereby generating annealed RNA molecules;
(b) mixing:
  i. the one or more annealed RNA molecules;
  ii. one or more acceptor-adapters;
  iii. nucleotides; and
  iv. a hybrid reverse transcriptase comprising a non-retroviral retrotransposon, or a fragment of the non-retroviral retrotransposon having reverse transcriptase activity, joined to a dsDNA binding protein or a fragment of a dsDNA binding protein; and
(c) allowing the hybrid reverse transcriptase to transcribe the annealed RNA molecule without thermal cycling to produce a cDNA molecule library,
wherein the hybrid reverse transcriptase jumps to a 3'-end of the acceptor-adapter upon reaching a 5' end of the annealed RNA molecules.

36. The method of embodiment 35, wherein the steps (a)-(c) are performed in a single reaction vessel.

37. The method of embodiment 35 or 36, wherein the template RNA molecules comprise messenger RNAs, ribosomal RNAs, transfer RNAs (tRNAs), micro RNAs, and/or long non-coding RNAs.

38. The method of any one of embodiments 30-37, wherein the hybrid reverse transcriptase comprises SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 40, SEQ ID NO: 41, SEQ ID NO: 42, or SEQ ID NO: 43 or a sequence at least 75% identical to SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 40, SEQ ID NO: 41, SEQ ID NO: 42, or SEQ ID NO: 43.

39. A method of preparing a cDNA molecule comprising:
(a) contacting a template RNA molecule and free nucleotides with:
   i. a primer that is not complementary to the template RNA molecule;
   ii. an acceptor-adapter; and
   iii. a hybrid reverse transcriptase comprising a non-retroviral retrotransposon, or a fragment of the non-retroviral retrotransposon having reverse transcriptase activity, joined to a ssDNA binding protein or a fragment of a ssDNA binding protein; and
(b) allowing the hybrid reverse transcriptase to transcribe the template RNA molecule under conditions effective for producing a cDNA molecule complementary to the RNA molecule and, optionally, to the acceptor-adapter,
wherein the hybrid reverse transcriptase jumps to a 3'-end of the acceptor-adapter upon reaching a 5' end of the RNA molecule.

40. The method of embodiment 39, wherein the primer comprises ssDNA or ssRNA.

41. The method of embodiment 39, wherein the ssDNA binding protein is an anti-Digoxigenin antibody and the primer comprises a Digoxigenin tag.

42. A method of preparing a cDNA molecule library comprising:
(a) fragmenting a template RNA molecule to produce RNA fragments;
(b) contacting the RNA fragments and free nucleotides, with:
   i. a primer-adapter that is not complementary to the RNA fragments;
   ii. an acceptor-adapter; and
   iii. a hybrid reverse transcriptase comprising a non-retroviral retrotransposon, or a fragment of the non-retroviral retrotransposon having reverse transcriptase activity, joined to a ssDNA binding protein or a fragment of a ssDNA binding protein; and
(c) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the RNA fragments.

43. The method of embodiment 42, wherein steps (a)-(c) are combined into one step.

44. The method of any one of embodiments 30-43, wherein any or all of the steps are performed in a partition.

45. A method of preparing a cDNA molecule library comprising:
(a) providing a partition comprising:
   i. a cell comprising template RNA molecules;
   ii. nucleotides;
   iii. a primer adapter that is not complementary to the RNA molecules;
   iv. an acceptor-adapter;
   v. an endonuclease; and
   vi. a hybrid reverse transcriptase comprising a non-retroviral retrotransposon, or a fragment of the non-retroviral retrotransposon having reverse transcriptase activity, joined to a ssDNA binding protein or a fragment of a ssDNA binding protein;
in the partition:
(b) releasing template RNA molecules from the cell;
(c) fragmenting the template RNA molecules to form RNA fragments; and
(d) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the dephosphorylated RNA fragments.

46. The method of any one of embodiments 39-45, wherein the hybrid reverse transcriptase comprises SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100, or a sequence at least 75% identical to SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100.

47. A hybrid reverse transcriptase comprising:
a non-retroviral retrotransposon, or a fragment of the non-retroviral retrotransposon having reverse transcriptase activity, in either case comprising a first binding motif; and
a nucleic acid binding protein, or a fragment of the nucleic acid binding protein, in either case comprising a second binding motif,
wherein the first binding motif is covalently joined to the second binding motif via protein ligation.

48. The hybrid reverse transcriptase of embodiment 47, wherein the nucleic acid binding protein is a single stranded deoxyribonucleic acid (ssDNA) binding protein or a fragment of the ssDNA binding protein.

49. The hybrid reverse transcriptase of embodiment 47, wherein the nucleic acid binding protein is a double stranded deoxyribonucleic acid (dsDNA) binding protein or a fragment of the dsDNA binding protein.

50. The hybrid reverse transcriptase of any one of embodiments 47-49, wherein a binding motif is located at a C terminus or an N-terminus of the non-retroviral retrotransposon, the fragment of the non-retroviral retrotransposon, the nucleic acid binding protein, or the fragment of the nucleic acid binding protein.

51. The hybrid reverse transcriptase of embodiment 50, wherein the binding motif is joined to the non-retroviral retrotransposon, the fragment of the non-retroviral retrotransposon, the nucleic acid binding protein, or the fragment of the nucleic acid binding protein via a linker.

52. The hybrid reverse transcriptase of embodiment 51, wherein the linker is selected from the group consisting of VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), VGTGGGSGGGTGGGSA (SEQ ID NO: 107), (GGGS)n (SEQ ID NO: 108), (GGS)n, (GGGGS)n (SEQ ID NO: 109), and (EAAAK)n (SEQ ID NO: 110) and n is 1, 2, 3, 4, or 5.

53. The hybrid reverse transcriptase of embodiment 48, wherein the nucleic acid binding protein is *Sulfolobus* SSB or a fragment of *Sulfolobus* SSB.
54. The hybrid reverse transcriptase of embodiment 49, wherein the nucleic acid binding protein is Sso7d, a fragment of Sso7d, Cren7, or a fragment of Cren7.
55. The hybrid reverse transcriptase of any one of embodiments 47-54, further comprising a purification tag at an N-terminus or C-terminus of the non-retroviral retrotransposon, the fragment of the non-retroviral retrotransposon, the nucleic acid binding protein, or the fragment of the nucleic acid binding protein.
56. The hybrid reverse transcriptase of any one of embodiments 47-55, wherein the non-retroviral retrotransposons, or the fragment of the non-retroviral retrotransposon, is an R2 reverse transcriptase or a fragment of the R2 reverse transcriptase, respectively.
57. The hybrid reverse transcriptase of embodiment 56, wherein the R2 reverse transcriptase comprises domains from two or more arthropods.
58. A hybrid reverse transcriptase comprising:
a first non-retroviral retrotransposon, or a first fragment of the non-retroviral retrotransposon having reverse transcriptase activity, in either case comprising a first binding motif; and
a second non-retroviral retrotransposon, or a second fragment of the non-retroviral retrotransposon having reverse transcriptase activity, in either case comprising a second binding motif,
wherein the first binding motif is covalently joined to the second binding motif via protein ligation.
59. The hybrid reverse transcriptase of embodiment 58, wherein the first and second non-retroviral retrotransposons, or the first and second fragments of the non-retroviral retrotransposon, are an R2 reverse transcriptase or a fragment of the R2 reverse transcriptase, respectively.
60. The hybrid reverse transcriptase of any one of embodiments 47-59, wherein:
(a) the first binding motif comprises SEQ ID NO: 48, 49, or 50 or a sequence with at least 60% identity to 48, 49, or 50 and the second binding motif comprises SEQ ID NO: 51, 52, 53, 54, or 55 or a sequence with at least 60% identity to 51, 52, 53, 54, or 55; or
(b) the first binding motif comprises SEQ ID NO: 51, 52, 53, 54, or 55 or a sequence with at least 60% identity to 51, 52, 53, 54, or 55 and the second binding motif comprises SEQ ID NO: 48, 49, or 50 or a sequence with at least 60% identity to 48, 49, or 50.
61. The hybrid reverse transcriptase of any one of embodiments 47-59, wherein:
(a) the first binding motif comprises SEQ ID NO: 56, 57, or 58 or a sequence with at least 60% identity to 56, 57, or 58 and the second binding motif comprises SEQ ID NO: 59, 60, or 61 or a sequence with at least 60% identity to 59, 60, or 61; or
(b) the first binding motif comprises SEQ ID NO: 59, 60, or 61 or a sequence with at least 60% identity to 59, 60, or 61 and the second binding motif comprises SEQ ID NO: 56, 57, or 58 or a sequence with at least 60% identity to 56, 57, or 58.
62. The hybrid reverse transcriptase of any one of embodiments 47-59, wherein the first binding motif comprises a sortase recognition domain comprising the amino acid sequence: LPTGAA (SEQ ID NO: 62), LPTGGG (SEQ ID NO: 63), LPKTGG (SEQ ID NO: 64), LPETG (SEQ ID NO: 65), LPXTG (SEQ ID NO: 66) or LPXTG(X)$_n$ (SEQ ID NO: 67), where X is any amino acid, and n is 0, 1, 2, 3, 4, 5, 7, 8, 9, 10, in the range of 0-5 or 0-10, or any integer up to 100, or NPX1TX2 (SEQ ID NO: 68), where X1 is glutamine or lysine; X2 is asparagine or glycine; N is asparagine; P is proline and T is threonine, and the second binding motif comprises a sortase bridging domain comprising: Gly, (Gly)2, (Gly)3, (Gly)4, or (Gly) x, where x is an integer of 1-20.
63. A hybrid reverse transcriptase comprising a non-retroviral retrotransposon having at least 75% sequence identity to SEQ ID NO: 1 joined via protein ligation to a nucleic acid binding protein or a fragment of the nucleic acid binding protein.
64. A hybrid reverse transcriptase comprising a fragment of a non-retroviral retrotransposon having at least 75% sequence identity to SEQ ID NO: 2 joined via protein ligation to a nucleic acid binding protein or a fragment of the nucleic acid binding protein.
65. A pair of nucleic acid constructs comprising:
a) a first nucleic acid construct comprising a polynucleotide sequence encoding a non-retroviral retrotransposon, or a fragment of the non-retroviral retrotransposon having reverse transcriptase activity, fused to a first binding motif; and
b) a second nucleic acid construct comprising a polynucleotide sequence encoding a nucleic acid binding protein, or a fragment of the nucleic acid binding protein, fused to a second binding motif, wherein the first binding motif and the second binding motif form a covalent bond via protein ligation when brought into contact with one another either spontaneously or with the help of an enzyme.
66. A pair of nucleic acid constructs comprising:
a) a first nucleic acid construct comprising a polynucleotide sequence encoding a first non-retroviral retrotransposon, or a first fragment of the non-retroviral retrotransposon having reverse transcriptase activity, fused to a first binding motif; and
b) a second nucleic acid construct comprising a polynucleotide sequence encoding a second non-retroviral retrotransposon, or a second fragment of the non-retroviral retrotransposon having reverse transcriptase activity, fused to a second binding motif, wherein the first binding motif and the second binding motif form a covalent bond via protein ligation when brought into contact with one another either spontaneously or with the help of an enzyme.
67. A vector comprising the nucleic acid constructs of embodiment 65 or 66.
68. A host cell comprising a nucleic acid constructs and/or a vector as defined in any one of embodiments 65-67.
69. A method of producing a hybrid reverse transcriptase, the method comprising contacting a non-retroviral retrotransposon, or a fragment of the non-retroviral retrotransposon having reverse transcriptase activity, in either case comprising a first binding motif, with a nucleic acid binding protein, or a fragment of the nucleic acid binding protein, in either case comprising a second binding motif, wherein the contacting is performed under conditions that allow the first binding motif to covalently join via protein ligation, either spontaneously or with the help of an enzyme, to the second binding motif.
70. A method of producing a hybrid reverse transcriptase, the method comprising contacting a first non-retroviral retrotransposon, or a first fragment of the non-retroviral retrotransposon having reverse transcriptase activity, in either case comprising a first binding motif, with a second non-retroviral retrotransposon, or a second fragment of the non-retroviral retrotransposon, in either case comprising a second binding motif, wherein the contacting is performed under conditions that allow the first binding motif to covalently join via protein ligation, either spontaneously or with the help of an enzyme, to the second binding motif.

71. A method of preparing a cDNA molecule comprising:
(a) contacting a template RNA molecule and free nucleotides with:
  i. a primer that is complementary to the template RNA molecule;
  ii. an acceptor-adapter; and
  iii. a hybrid reverse transcriptase comprising a non-retroviral retrotransposon, or a fragment of the non-retroviral retrotransposon having reverse transcriptase activity, in either case comprising a first binding motif and a dsDNA binding protein, or a fragment of the dsDNA binding protein, in either case comprising a second binding motif,
    wherein the first binding motif is covalently joined to the second binding motif via protein ligation; and
(b) allowing the hybrid reverse transcriptase to transcribe the template RNA molecule under conditions effective to produce a cDNA molecule complementary to the RNA molecule and, optionally, to the acceptor-adapter,
wherein the hybrid reverse transcriptase jumps to a 3'-end of the acceptor-adapter upon reaching a 5' end of the RNA molecule.

72. A method of preparing a cDNA molecule library comprising:
(a) fragmenting a template RNA molecule to produce RNA fragments;
(b) removing a 2', 3'-cyclic phosphate and a 3'-phosphate from the RNA fragments, thereby generating dephosphorylated RNA fragments;
(c) adding a poly-A tail to the dephosphorylated RNA fragments to form poly-A tailed RNA fragments;
(d) adding to the poly-A tailed RNA fragments:
  i. a primer-adapter comprising an oligo-T sequence;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, in either case comprising a first binding motif and a dsDNA binding protein, or a fragment of the dsDNA binding protein, in either case comprising a second binding motif,
    wherein the first binding motif is covalently joined to the second binding motif via protein ligation; and
(e) allowing the hybrid reverse transcriptase to transcribe the poly-A tailed RNA fragments under conditions effective to produce a cDNA molecule library,
wherein the hybrid reverse transcriptase jumps to a 3'-end of the acceptor-adapter upon reaching a 5' end of the poly-A tailed RNA fragments.

73. The method of embodiment 72, wherein steps (b) and (c) are combined into one step.

74. A method of preparing a cDNA molecule library comprising:
(a) annealing a primer adapter comprising a poly (T) tail to a template RNA molecule comprising a poly (A) tail, thereby generating an annealed RNA molecule;
(b) mixing:
  i. the annealed RNA molecule;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, comprising a first binding motif and a dsDNA binding protein, or a fragment of the dsDNA binding protein, in either case comprising a second binding motif,
    wherein the first binding motif is covalently joined to the second binding motif via protein ligation; and
(c) allowing the hybrid reverse transcriptase to transcribe the annealed RNA molecule at a temperature from about 12° C. to about 42° C. to produce a cDNA molecule library,
wherein the hybrid reverse transcriptase jumps to a 3'-end of the acceptor-adapter upon reaching a 5' end of the annealed RNA molecule.

75. The method of embodiment 74, wherein the template RNA molecule is a messenger RNA molecule.

76. A method of preparing a cDNA molecule library comprising:
(a) annealing one or more random primer adapters to template RNA molecules comprising a poly (A) tail, thereby generating annealed RNA molecules;
(b) mixing:
  i. the one or more annealed RNA molecules;
  ii. one or more acceptor-adapters;
  iii. nucleotides; and
  iv. a hybrid reverse transcriptase comprising a non-retroviral retrotransposon, or a fragment of the non-retroviral retrotransposon having reverse transcriptase activity, in either case comprising a first binding motif and a dsDNA binding protein, or a fragment of the dsDNA binding protein, in either case comprising a second binding motif,
    wherein the first binding motif is covalently joined to the second binding motif via protein ligation; and
(c) allowing the hybrid reverse transcriptase to transcribe the annealed RNA molecule without thermal cycling to produce a cDNA molecule library,
wherein the hybrid reverse transcriptase jumps to a 3'-end of the acceptor-adapter upon reaching a 5' end of the annealed RNA molecules.

77. The method of embodiment 76, wherein the steps (a)-(c) are performed in a single reaction vessel.

78. The method of embodiment 76 or 77, wherein the template RNA molecules comprise messenger RNAs, ribosomal RNAs, transfer RNAs (tRNAs), micro RNAs, and/or long non-coding RNAs.

79. A method of preparing a cDNA molecule comprising:
(a) contacting a template RNA molecule and free nucleotides with:
  i. a primer that is not complementary to the template RNA molecule;
  ii. an acceptor-adapter; and
  iii. a hybrid reverse transcriptase comprising a non-retroviral retrotransposon, or a fragment of the non-retroviral retrotransposon having reverse transcriptase activity, in either case comprising a first binding motif and a ssDNA binding protein, or a fragment of the ssDNA binding protein, in either case comprising a second binding motif,
    wherein the first binding motif is covalently joined to the second binding motif via protein ligation; and (b) allowing the hybrid reverse transcriptase to transcribe the template RNA molecule under conditions effective for producing a cDNA molecule complementary to the RNA molecule and, optionally, to the acceptor-adapter, wherein the hybrid reverse transcriptase jumps to a 3'-end of the acceptor-adapter upon reaching a 5' end of the RNA molecule.

80. The method of embodiment 79, wherein the primer comprises ssDNA or ssRNA.

81. A method of preparing a cDNA molecule library comprising:
(a) fragmenting a template RNA molecule to produce RNA fragments;
(b) contacting the RNA fragments and free nucleotides with:
  i. a primer-adapter that is not complementary to the RNA fragments;
  ii. an acceptor-adapter; and
  iii. a hybrid reverse transcriptase comprising a non-retroviral retrotransposon, or a fragment of the non-retroviral retrotransposon having reverse transcriptase activity, in either case comprising a first binding motif and a ssDNA binding protein, or a fragment of the ssDNA binding protein, in either case comprising a second binding motif, wherein the first binding motif is covalently joined to the second binding motif via protein ligation; and
(c) allowing the hybrid reverse transcriptase to transcribe the RNA fragments under conditions effective to produce a cDNA molecule library, wherein the hybrid reverse transcriptase jumps to a 3'-end of the acceptor-adapter upon reaching a 5' end of the RNA fragments.

82. The method of embodiment 81, wherein steps (a)-(c) are combined into one step.

83. The method of any one of embodiments 71-82, wherein any or all of the steps are performed in a partition.

84. A method of preparing a cDNA molecule library comprising:
(a) providing a partition comprising:
  i. a cell comprising template RNA molecules;
  ii. nucleotides;
  iii. a primer adapter that is not complementary to the RNA molecules;
  iv. an acceptor-adapter;
  v. an endonuclease; and
  vi. a hybrid reverse transcriptase comprising a non-retroviral retrotransposon, or a fragment of the non-retroviral retrotransposon having reverse transcriptase activity, in either case comprising a first binding motif and a ssDNA binding protein, or a fragment of the ssDNA binding protein, in either case comprising a second binding motif, wherein the first binding motif is covalently joined to the second binding motif via protein ligation; and
in the partition:
(b) releasing template RNA molecules from the cell;
(c) fragmenting the template RNA molecules to form RNA fragments; and
(d) allowing the hybrid reverse transcriptase to transcribe the RNA fragments under conditions effective to produce a cDNA molecule library, wherein the hybrid reverse transcriptase jumps to a 3'-end of the acceptor-adapter upon reaching a 5' end of the dephosphorylated RNA fragments.

85. The method of any one of embodiments 71-84, wherein:
(a) the first binding motif comprises SEQ ID NO: 48, 49, or 50 or a sequence with at least 60% identity to 48, 49, or 50 and the second binding motif comprises SEQ ID NO: 51, 52, 53, 54, or 55 or a sequence with at least 60% identity to 51, 52, 53, 54, or 55; or
(b) the first binding motif comprises SEQ ID NO: 51, 52, 53, 54, or 55 or a sequence with at least 60% identity to 51, 52, 53, 54, or 55 and the second binding motif comprises SEQ ID NO: 48, 49, or 50 or a sequence with at least 60% identity to 48, 49, or 50.

86. The method of any one of embodiments 71-84, wherein:
(a) the first binding motif comprises SEQ ID NO: 56, 57, or 58 or a sequence with at least 60% identity to 56, 57, or 58 and the second binding motif comprises SEQ ID NO: 59, 60, or 61 or a sequence with at least 60% identity to 59, 60, or 61; or
(b) the first binding motif comprises SEQ ID NO: 59, 60, or 61 or a sequence with at least 60% identity to 59, 60, or 61 and the second binding motif comprises SEQ ID NO: 56, 57, or 58 or a sequence with at least 60% identity to 56, 57, or 58.

87. The method of any one of embodiments 71-84, wherein the first binding motif comprises a sortase recognition domain comprising the amino acid sequence: LPTGAA (SEQ ID NO: 62), LPTGGG (SEQ ID NO: 63), LPKTGG (SEQ ID NO: 64), LPETG (SEQ ID NO: 65), LPXTG (SEQ ID NO: 66) or LPXTG(X)n (SEQ ID NO: 67), where X is any amino acid, and n is 0, 1, 2, 3, 4, 5, 7, 8, 9, 10, in the range of 0-5 or 0-10, or any integer up to 100, or NPX1TX2 (SEQ ID NO: 68), where X1 is glutamine or lysine; X2 is asparagine or glycine; N is asparagine; P is proline and T is threonine, and the second binding motif comprises a sortase bridging domain comprising: Gly, (Gly)2, (Gly)3, (Gly)4, or (Gly) x, where x is an integer of 1-20.

88. A hybrid reverse transcriptase comprising:
a non-retroviral retrotransposon, or a fragment of the non-retroviral retrotransposon having reverse transcriptase activity, in either case comprising a biotinylated first acceptor peptide;
a nucleic acid binding protein, or a fragment of the nucleic acid binding protein, in either case comprising a biotinylated second acceptor peptide; and
a biotin-binding protein,
wherein the biotinylated first and second acceptor peptides are joined to the biotin-binding protein via non-covalent interactions.

89. The hybrid reverse transcriptase of embodiment 88, wherein the nucleic acid binding protein is a single stranded deoxyribonucleic acid (ssDNA) binding protein or a fragment of the ssDNA binding protein.

90. The hybrid reverse transcriptase of embodiment 88, wherein the nucleic acid binding protein is a double stranded deoxyribonucleic acid (dsDNA) binding protein, or a fragment of the dsDNA binding protein.

91. The hybrid reverse transcriptase of any one of embodiments 88-90, wherein a biotinylated acceptor peptide is located at a C terminus or an N-terminus of the non-retroviral retrotransposon, the fragment of the non-retroviral retrotransposon, the nucleic acid binding protein, or the fragment of the nucleic acid binding protein.

92. The hybrid reverse transcriptase of embodiment 91, wherein the biotinylated acceptor peptide is joined to the non-retroviral retrotransposon, the fragment of the non-retroviral retrotransposon, the nucleic acid binding protein, or the fragment of the nucleic acid binding protein via a linker.

93. The hybrid reverse transcriptase of embodiment 92, wherein the linker is selected from the group consisting of VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NO: 104), VGTGGGSGGGEAAAKEAAAKSGGGSA (SEQ ID NO: 105), VGTGGGSGGGTGGGS (SEQ ID NO: 106), VGTGGGSGGGTGGGSA (SEQ ID NO: 107), (GGGS)n (SEQ ID NO: 108), (GGS)n, (GGGGS)n (SEQ ID NO: 109), and (EAAAK)n (SEQ ID NO: 110) wherein n is 1, 2, 3, 4, or 5.

94. The hybrid reverse transcriptase of embodiment 89, wherein the nucleic acid binding protein is *Sulfolobus* SSB or a fragment of *Sulfolobus* SSB.

95. The hybrid reverse transcriptase of embodiment 90, wherein the nucleic acid binding protein is Sso7d, a fragment of Sso7d, Cren7, or a fragment of Cren 7.

96. The hybrid reverse transcriptase of any one of embodiments 88-95, further comprising a purification tag at an N-terminus or C-terminus of the non-retroviral retrotransposon, the fragment of the non-retroviral retrotransposon, the nucleic acid binding protein, or the fragment of the nucleic acid binding protein.

97. The hybrid reverse transcriptase of any of embodiments 88-96, wherein the non-retroviral retrotransposons, or the fragment of the non-retroviral retrotransposon, is an R2 reverse transcriptase or a fragment of the R2 reverse transcriptase, respectively.

98. A hybrid reverse transcriptase comprising:
a first non-retroviral retrotransposon, or a first fragment of the non-retroviral retrotransposon having reverse transcriptase activity, in either case comprising a biotinylated first acceptor peptide; and
a second non-retroviral retrotransposon, or a second fragment of the non-retroviral retrotransposon having reverse transcriptase activity, in either case comprising a biotinylated second acceptor peptide; and
a biotin-binding protein,
wherein the biotinylated first and second acceptor peptides are joined to the biotin-binding protein via non-covalent interactions.

99. The hybrid reverse transcriptase of embodiment 98, wherein the first and second non-retroviral retrotransposons, or the first and second fragments of the non-retroviral retrotransposon, are an R2 reverse transcriptase or a fragment of the R2 reverse transcriptase, respectively.

100. The hybrid reverse transcriptase of any one of embodiments 88-99, wherein the biotinylated acceptor peptide comprises an acceptor peptide selected from the group consisting of SEQ ID NO: 85, 86, 87, 88, and 89.

101. A hybrid reverse transcriptase comprising a non-retroviral retrotransposon having at least 75% sequence identity to SEQ ID NO: 1 and a nucleic acid binding protein, or a fragment of the nucleic acid binding protein, non-covalently joined to a biotin-binding protein.

102. A hybrid reverse transcriptase comprising a fragment of a non-retroviral retrotransposon having at least 75% sequence identity to SEQ ID NO: 2 and a nucleic acid binding protein, or a fragment of the nucleic acid binding protein, non-covalently joined to a biotin-binding protein.

103. The hybrid reverse transcriptase of any one of embodiments 88-102, wherein the biotin-binding protein is streptavidin, traptavidin, or neutravidin.

104. A pair of nucleic acid constructs comprising:
a) a first nucleic acid construct comprising a polynucleotide sequence encoding a non-retroviral retrotransposon, or a fragment of the non-retroviral retrotransposon having reverse transcriptase activity, fused to a first acceptor peptide; and
b) a second nucleic acid construct comprising a polynucleotide sequence encoding a nucleic acid binding protein, or a fragment of the nucleic acid binding protein, fused to a second acceptor peptide,
wherein the first and second acceptor peptides are biotinylated in the presence of biotin, a biotin ligase, and ATP to form biotinylated first and second acceptor peptides; and
wherein the biotinylated first and second acceptor peptides bind to a biotin-binding protein via non-covalent interactions when brought into contact with one another.

105. A pair of nucleic acid constructs comprising:
a) a first nucleic acid construct comprising a polynucleotide sequence encoding a first non-retroviral retrotransposon, or a first fragment of the non-retroviral retrotransposon having reverse transcriptase activity, fused to a first acceptor peptide; and
b) a second nucleic acid construct comprising a polynucleotide sequence encoding a second non-retroviral retrotransposon, or a second fragment of the non-retroviral retrotransposon having reverse transcriptase activity, fused to a second acceptor peptide,
wherein the first and second acceptor peptides are biotinylated in the presence of biotin, a biotin ligase, and ATP to form biotinylated first and second acceptor peptides; and
wherein the biotinylated first and second acceptor peptides bind to a biotin-binding protein via non-covalent interactions when brought into contact with one another.

106. A vector comprising the nucleic acid constructs of embodiment 104 or 105.

107. A host cell comprising a nucleic acid constructs and/or a vector as defined in any one of embodiments 104-106.

108. A method of producing a hybrid reverse transcriptase, the method comprising contacting a non-retroviral retrotransposon, or a fragment of the non-retroviral retrotransposon having reverse transcriptase activity, in either case comprising a first acceptor peptide and a nucleic acid binding protein, or a fragment of the nucleic acid binding protein, in either case comprising a second acceptor peptide, with biotin in the presence of biotin ligase and ATP to form biotinylated first and second acceptor peptides; and
contacting the biotinylated first and second acceptor peptides with a biotin-binding protein to allow the biotinylated first and second biotin acceptor peptides to bind to the biotin-binding protein via non-covalent interactions.

109. A method of producing a hybrid reverse transcriptase, the method comprising contacting a first non-retroviral retrotransposon, or a first fragment of the non-retroviral retrotransposon having reverse transcriptase activity, in either case comprising a first acceptor peptide and a second non-retroviral retrotransposon, or a second fragment of the non-retroviral retrotransposon, in either case comprising a second acceptor peptide with biotin in the presence of biotin ligase and ATP to form biotinylated first and second acceptor peptides; and contacting the biotinylated first and second acceptor peptides with a biotin-binding protein to allow the biotinylated first and second acceptor peptides to bind to the biotin-binding protein via non-covalent interactions.

110. A method of preparing a cDNA molecule comprising:
(a) contacting a template RNA molecule and free nucleotides with:
  i. a primer that is complementary to the template RNA molecule;
  ii. an acceptor-adapter; and
  iii. a hybrid reverse transcriptase comprising a non-retroviral retrotransposon, or a fragment of the non-retroviral retrotransposon having reverse transcriptase activity, in either case comprising a biotinylated first acceptor peptide and a dsDNA binding protein, or a fragment of the dsDNA binding protein, in either case comprising a biotinylated second acceptor peptide,
  wherein the biotinylated first and second acceptor peptides are joined to a biotin-binding protein via non-covalent interactions; and
(b) allowing the hybrid reverse transcriptase to transcribe the template RNA molecule under conditions effective to produce a cDNA molecule complementary to the RNA molecule and, optionally, to the acceptor-adapter,
wherein the hybrid reverse transcriptase jumps to a 3'-end of the acceptor-adapter upon reaching a 5' end of the RNA molecule.

111. A method of preparing a cDNA molecule library comprising:
(a) fragmenting a template RNA molecule to produce RNA fragments;
(b) removing a 2', 3'-cyclic phosphate and a 3'-phosphate from the RNA fragments, thereby generating dephosphorylated RNA fragments;
(c) adding a poly-A tail to the dephosphorylated RNA fragments to form poly-A tailed RNA fragments;
(d) adding to the poly-A tailed RNA fragments:
  i. a primer-adapter comprising an oligo-T sequence;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, in either case comprising a biotinylated first acceptor peptide and a dsDNA binding protein, or a fragment of the dsDNA binding protein, in either case comprising a biotinylated second acceptor peptide,
  wherein the biotinylated first and second acceptor peptides are joined to a biotin-binding protein via non-covalent interactions; and
(e) allowing the hybrid reverse transcriptase to transcribe the poly-A tailed RNA fragments under conditions effective to produce a cDNA molecule library,
wherein the hybrid reverse transcriptase jumps to a 3'-end of the acceptor-adapter upon reaching a 5' end of the poly-A tailed RNA fragments.

112. The method of embodiment 111, wherein steps (b) and (c) are combined into one step.

113. A method of preparing a cDNA molecule library comprising:
(a) annealing a primer adapter comprising a poly (T) tail to a template RNA molecule comprising a poly (A) tail, thereby generating an annealed RNA molecule;
(b) mixing:
  i. the annealed RNA molecule;
  ii. an acceptor-adapter;
  iii. nucleotides; and
  iv. a hybrid reverse transcriptase comprising a non-retroviral retrotransposon, or a fragment of the non-retroviral retrotransposon having reverse transcriptase activity, in either case comprising a biotinylated first acceptor peptide and a dsDNA binding protein, or a fragment of the dsDNA binding protein, in either case comprising a biotinylated second acceptor peptide,
  wherein the biotinylated first and second acceptor peptides are joined to a biotin-binding protein via non-covalent interactions; and
(c) allowing the hybrid reverse transcriptase to transcribe the annealed RNA molecule at a temperature from about 12° C. to about 42° C. to produce a cDNA molecule library,
wherein the hybrid reverse transcriptase jumps to a 3'-end of the acceptor-adapter upon reaching a 5' end of the annealed RNA molecule.

114. The method of embodiment 113, wherein the template RNA molecule is a messenger RNA molecule.

115. A method of preparing a cDNA molecule library comprising:
(a) annealing one or more random primer adapters to template RNA molecules comprising a poly (A) tail, thereby generating annealed RNA molecules;
(b) mixing:
  i. the one or more annealed RNA molecules;
  ii. one or more acceptor-adapters;
  iii. nucleotides; and
  iv. a hybrid reverse transcriptase comprising a non-retroviral retrotransposon, or a fragment of the non-retroviral retrotransposon having reverse transcriptase activity, in either case comprising a biotinylated first acceptor peptide and a dsDNA binding protein, or a fragment of the dsDNA binding protein, in either case comprising a biotinylated second acceptor peptide,
  wherein the biotinylated first and second acceptor peptides are joined to a biotin-binding protein via non-covalent interactions; and
(c) allowing the hybrid reverse transcriptase to transcribe the annealed RNA molecule without thermal cycling to produce a cDNA molecule library,
wherein the hybrid reverse transcriptase jumps to a 3'-end of the acceptor-adapter upon reaching a 5' end of the annealed RNA molecules.

116. The method of embodiment 115, wherein the steps (a)-(c) are performed in a single reaction vessel.

117. The method of embodiment 115 or 116, wherein the template RNA molecules comprise messenger RNAs, ribosomal RNAs, transfer RNAs (tRNAs), micro RNAs, and/or long non-coding RNAs.

118. A method of preparing a cDNA molecule comprising:
(a) contacting a template RNA molecule and free nucleotides with:
   i. a primer that is not complementary to the template RNA molecule;
   ii. an acceptor-adapter; and
   iii. a hybrid reverse transcriptase comprising a non-retroviral retrotransposon, or a fragment of the non-retroviral retrotransposon having reverse transcriptase activity, in either case comprising a biotinylated first acceptor peptide and a ssDNA binding protein, or a fragment of the ssDNA binding protein, in either case comprising a biotinylated second acceptor peptide,
   wherein the biotinylated first and second acceptor peptides are joined to a biotin-binding protein via non-covalent interactions; and
(b) allowing the hybrid reverse transcriptase to transcribe the template RNA molecule under conditions effective for producing a cDNA molecule complementary to the RNA molecule and, optionally, to the acceptor-adapter,
   wherein the hybrid reverse transcriptase jumps to a 3'-end of the acceptor-adapter upon reaching a 5' end of the RNA molecule.

119. The method of embodiment 118, wherein the primer comprises ssDNA or ssRNA.

120. A method of preparing a cDNA molecule library comprising:
(a) fragmenting a template RNA molecule to produce RNA fragments;
(b) contacting the RNA fragments and free nucleotides with:
   i. a primer-adapter that is not complementary to the RNA fragments;
   ii. an acceptor-adapter; and
   iii. a hybrid reverse transcriptase comprising a non-retroviral retrotransposon, or a fragment of the non-retroviral retrotransposon having reverse transcriptase activity, in either case comprising a biotinylated first acceptor peptide and a ssDNA binding protein, or a fragment of the ssDNA binding protein, in either case comprising a biotinylated second acceptor peptide,
   wherein the biotinylated first and second acceptor peptides are joined to a biotin-binding protein via non-covalent interactions; and
(c) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the RNA fragments.

121. The method of embodiment 120, wherein steps (a)-(c) are combined into one step.

122. The method of any one of embodiments 110-121, wherein any or all of the steps are performed in a partition.

123. A method of preparing a cDNA molecule library comprising:
(a) providing a partition comprising:
   i. a cell comprising template RNA molecules;
   ii. nucleotides;
   iii. a primer adapter that is not complementary to the RNA molecules;
   iv. an acceptor-adapter;
   v. an endonuclease; and
   vi. a hybrid reverse transcriptase comprising a non-retroviral retrotransposon, or a fragment of the non-retroviral retrotransposon having reverse transcriptase activity, in either case comprising a biotinylated first acceptor peptide and a ssDNA binding protein, or a fragment of the ssDNA binding protein, in either case comprising a biotinylated second acceptor peptide,
   wherein the biotinylated first and second acceptor peptides are joined to a biotin-binding protein via non-covalent interactions; and
in the partition:
(b) releasing template RNA molecules from the cell;
(c) fragmenting the template RNA molecules to form RNA fragments; and
(d) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the dephosphorylated RNA fragments.

124. The method of any one of embodiments 110-123, wherein the biotinylated acceptor peptide comprises an acceptor peptide selected from the group consisting of SEQ ID NO: 85, 86, 87, 88, and 89.

125. The method of any one of embodiments 30-45, 71-87, or 110-124, further comprising removing one or more non-annealed primer adapter after the last step.

126. The method of embodiment 125, wherein the one or more non-annealed primer-adapter is removed with an immobilized poly A oligo.

127. The method of any one of embodiments 30-45, 71-87, or 110-124, wherein the jumping of the hybrid reverse transcriptase to the 3'-end of the acceptor-adapter is independent of sequence identity between the template RNA molecule(s) and the acceptor-adapter.

128. The method of any one of embodiments 30-45, 71-87, or 110-124, wherein the cDNA molecule or cDNA library is prepared in about 2 hours or less.

129. The method of any one of embodiments 30-45, 71-87, or 110-124, further comprising amplifying the cDNA molecule(s) by polymerase chain reaction, thereby forming one or more amplicons.

130. The method of embodiment 129, wherein the amplifying is performed at a temperature sufficient to inactivate the reverse transcriptase.

131. The method of embodiment 128 or 129, wherein producing and amplifying the cDNA molecule(s) is performed in the same reaction vessel.

132. The method of embodiment 129 or 130, further comprising adding a label to the template RNA molecule(s), thereby generating a labeled cDNA molecule(s).

133. The method of embodiment 132, further comprising sequencing the labeled cDNA molecule(s).

134. The method of any one of embodiments 30-45, 71-87, or 110-124, wherein the acceptor-adapter, the primer adapter, or both the acceptor-adapter and primer adapter comprise a nucleotide analogue that stops the reverse transcription by the hybrid reverse transcriptase.

135. The method of embodiment 134, wherein the nucleotide analogue is at the 5' end of the acceptor-adapter.

136. The method of embodiment 134, wherein the nucleotide analogue is at the 5' end of the primer adapter.

137. The method of any one of embodiments 30-45, 71-87, or 110-124, wherein the acceptor-adapter comprises a 3'-dideoxynucleotide.
138. The method of any one of embodiments 30-45, 71-87, or 110-124, wherein the non-retroviral retrotransposon comprises SEQ ID NO: 1 or a sequence with at least 75% identity to SEQ ID NO: 1 joined to a nucleic acid binding protein, or a fragment of the nucleic acid binding protein.
139. The method of any one of embodiments 30-45, 71-87, or 110-124, wherein the fragment of the non-retroviral retrotransposon comprises SEQ ID NO: 2 or a sequence with at least 75% sequence identity to SEQ ID NO: 2 joined to a nucleic acid binding protein, or a fragment of the nucleic acid binding protein.
140. The method of embodiment 38, 48, 71-87, 110-124, wherein the hybrid reverse transcriptase comprises at least one improved property selected from the group consisting of higher processivity, longer shelf life, higher strand displacement, higher end-to-end template jumping, and higher affinity as compared to a non-retroviral retrotransposon, or a fragment of the non-retroviral retrotransposon, that is not joined to a nucleic acid binding protein, or a fragment of the nucleic acid binding protein.
141. The method of embodiment 140, wherein the processivity of the hybrid reverse transcriptase is about 20 or more nucleotides.

EXAMPLES

The following examples are provided by way of illustration only and not by way of limitation. Those of skill in the art will readily recognize a variety of non-critical parameters that could be changed or modified to yield essentially the same or similar results.

Figure 20:
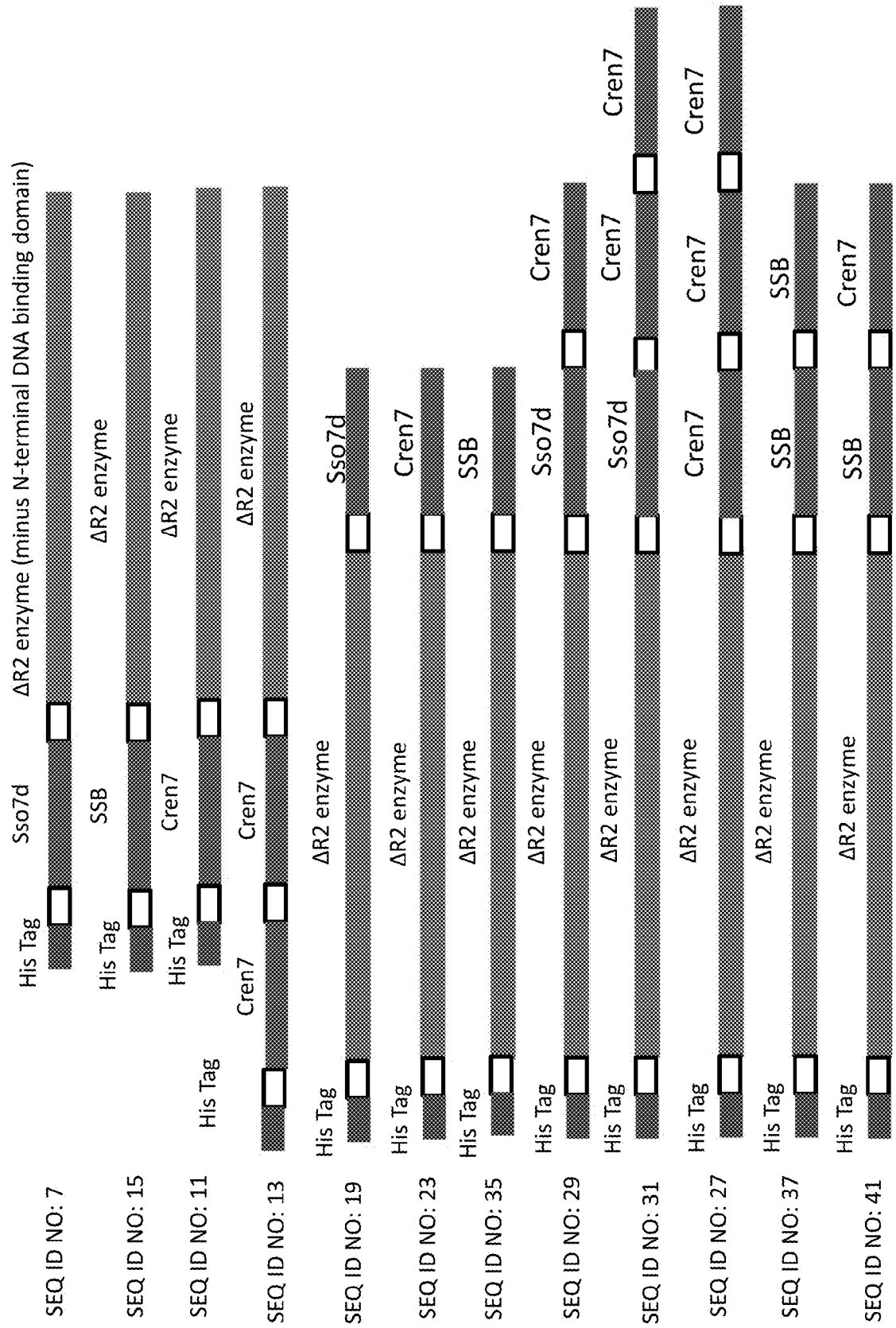
FIG. 20 illustrates hybrid reverse transcriptase constructs used in expression studies as described in Example 1. ΔR2 enzyme is R2 enzyme minus the N-terminal DNA binding domain.

Example 1—Expression and Purification of Hybrid Reverse Transcriptases Comprising ΔR2 Enzyme Recombinantly Fused to Nucleic Acid Binding Protein Expression vector pET-45b carrying the constructs shown in FIG. 20 were transformed into E. coli BL21 (DE3). For expression of each construct, a pre-culture was setup in 2 mL LB with 100 µM Corbenicillin and was grown for about 8-12 hours at room temperature. After about 8-12 hours, 550 µL of the pre-cultures were transferred to 25 mL auto-induction expression media (Overnight Express TB from Novagen) including 0.08 mg/ml Corbenicillin and shaker-incubated at 280-290 RPM at room temperature for 48 hours. Cells were harvested by centrifugation at 8000×g for 10 min at 4-8° C. The biomass-pellets were frozen at −20° C. for a minimum of 1 hour.

The pellets were re-suspended in 0.8 mL lysis buffer (0.8 ml lysis buffer per 10% of the biomass) and were incubated for 45 minutes at room temperature. Lysis buffer composition: 1× BugBuster (Millipore), 100 mM Sodium Phosphate, 0.2% Tween, 2.5 mM Tris (2-carboxyethyl) phosphine (TCEP), 6 µl Protease inhibitor mix (Roche), 0.1 mg/ml lysozyme, 0.5 ul DNaseI (2,000 units/ml, from NEB). After incubation, the lysates were mixed with equal volume (0.8 mL) of His-binding buffer (50 mM Sodium Phosphate pH 7.7, 1.5 M Sodium Chloride, 5 mM TCEP, 0.2% Tween, 0.03% Triton X-100, 10 mM Imidazole) and incubated at room temperature for 30 minutes. After incubation, the lysates were centrifuged at 13000×g for 40 minutes at 80° C.

The pellets were each mixed with 250 µl of His-Affinity Gel (His-Spin Protein Miniprep by Zymo Research) per the manufacturer's protocol. After the binding step, for each pellet, the His-Affinity Gel was washed five times with Washing buffer (50 mM Sodium Phosphate pH7.7, 1.2M Sodium Chloride, 0.2% Tween, 0.03% Triton X-100, 2.5 mM TCEP, 50 mM Imidazole). Finally fusion proteins were eluted with 250 µL of elution buffer (50 mM Sodium Phosphate pH7.7, 300 mM Sodium Chloride, 2.5 mM TCEP, 0.2% Tween and 250 mM Imidazole). The preparations were frozen at −20° C. in 50% glycerol, 50 mM Sodium Phosphate pH 7.7, 300 mM Sodium Chloride, 5 mM TCEP, 0.2% Tween and 125 mM Imidazole.

The following fusion proteins were analyzed by SDS-PAGE using 4-12% Bis-Tris polyacrylamide gels with SYPRO Orange fluorescent stain (Bio-Rad):
1. Nucleic acid binding protein fused to the N-terminus of truncated R2 enzyme (i.e., R2 enzyme minus the N-terminal DNA binding domain):
   Lane 1N is sso7d-ΔR2 enzyme (SEQ ID NO: 7)
   Lane 2N is Cren7-ΔR2 enzyme (SEQ ID NO: 11)
   Lane 3N is Cren7-Cren7-ΔR2 enzyme (SEQ ID NO: 13)
   Lane 4N is SSB-ΔR2 enzyme (SEQ ID NO: 15)
   Lane 5N is ΔR2 enzyme (SEQ ID NO: 2)
2. Nucleic acid binding protein fused to the C-terminus of truncated R2 enzyme
   Lane 1C is ΔR2 enzyme-Sso7d (SEQ ID NO: 19)
   Lane 2C is ΔR2 enzyme-SSB (SEQ ID NO: 35)
   Lane 3C is ΔR2 enzyme-Cren7 (SEQ ID NO: 23)
   Lane 4C is ΔR2 enzyme (SEQ ID NO: 2)

Figure 21B:
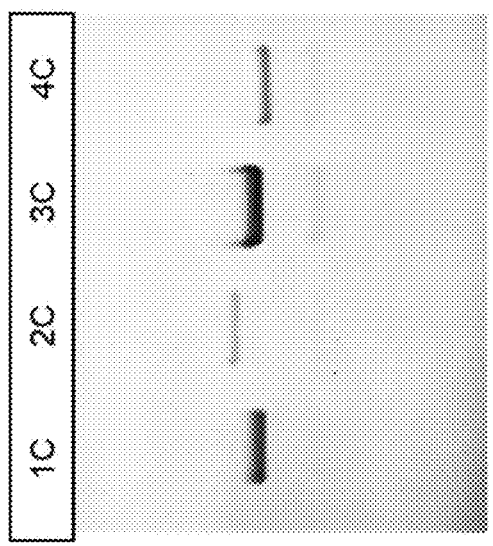
FIGS. 21A and 21B are images of SDS-PAGE gels of expressed hybrid reverse transcriptases in which a nucleic acid binding protein is joined to the N-terminus or C-terminus, respectively, of ΔR2 enzyme.
Figure 21A:
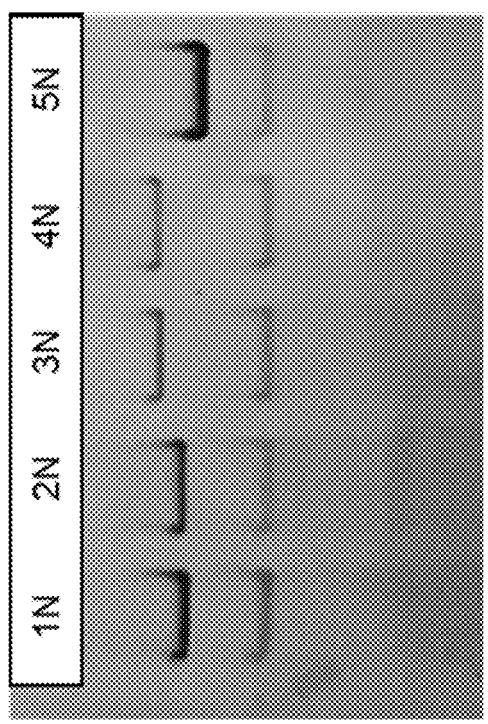

Images of the gels are shown in FIG. 21A (N-terminal fusions) and 21B (C-terminal fusions). The results show that all of the fusion proteins were expressed.

Example 2—qPCR with the Hybrid Reverse Transcriptases from Example 1

This example compares the qPCR performance of hybrid reverse transcriptases from Example 1 to truncated R2 enzyme that is not fused to a nucleic acid binding protein.
Materials:
1. ΔR2 Enzyme (SEQ ID NO: 2) and the following hybrid reverse transcriptases (with a nucleic acid binding protein fused to the C-terminus of ΔR2 enzyme):
   a) ΔR2 enzyme-Sso7d (SEQ ID NO: 19)
   b) ΔR2 enzyme-Cren7 (SEQ ID NO: 23)
   c) ΔR2 enzyme-SSB (SEQ ID NO: 35)
2. 10× Fragmentation Buffer: 700 mM Tris-HCl, 100 mM MgCl$_2$, 50 mM DTT, pH 7.6
3. 100×dNTP: 90 mM dNTP in water
4. 5× Total RNA Buffer:

TABLE 9

| 5× Total RNA Buffer | Volume (µL) |
| --- | --- |
| H2O | 885 |
| 1000 mM Tris-HCl pH7.5 | 10 |
| 5000 mM NaCl2 | 60 |
| 1000 mM MgCl2 | 5 |
| 10% Tween | 25 |
| 1000 mM DTT | 15 |

5. nB Mix:

TABLE 10

| nB Mix | Final Concentration | Volume (μL) |
|---|---|---|
| Water | | 212.3 |
| 5× Total RNA Buffer | 1× | 150 |
| 100 μM Primer P591 | 0.2 μM | 1.5 |
| 100× dNTPs | 1× | 7.5 |
| 100 μM P423 Acceptor Oligo | 0.5 μM | 3.75 |

6. nC Mix: 56.25 μL ΔR2 enzyme or Hybrid Reverse Transcriptase and 18.75 μL water.
7. cDNA elution buffer: 10 mM Tris, 1 mM EDTA pH 7.5 or water

```
8. RNA template External RNA Controls
Consortium (ERCC) 00074:
TGGACATTAATTAGGGCTGAAAGCCCTAACTTAATGGACGGGAG

GTATCCCAATAGGAGGTTTCCTCCTATGGTTTTCAAAACAATCA

CCATCATGCTATTAATGATATTAAAATCCCAACTATACCAAAGA

ATATCCCAATTATCCATAAAACTGTAACTAAGTGAGGCTCTCTC

ATTGGTTTATACTTCAATATAAGCCTTGGTAGGGATAGATAGCC

ACCTATATAGTATAGCTTCCCATCTTCTTTGAGAGTTGTTGGTT

TATGCTCATCCCTACTCATAACCCCAGCACTTAGATATTTTAAA

GAGGCATCTATCACATAAGGCATCATTATAACTAAAAATGGGAT

ATATTCCTTATAAACTACTGCTAAGACAGCTAAGAAAGCTCCAA

TTGGTAGAGTTCCAACATCTCCTGGAAAAACCTTTGCTGGATAT

TTGTTAAATATCAATAGCCCTAAATAGGATGCAGAGAATATCAA

AGCGGAAAAAATCCAAAAAAAAAAAAAAAAAAAAAAAA
(SEQ ID NO: 111)

9. RNA template ERCC 00002:
TCCAGATTACTTCCATTTCCGCCCAAGCTGCTCACAGTATACGG

GCGTCGGCATCCAGACCGTCGGCTGATCGTGGTTTTACTAGGCT

AGACTAGCGTACGAGCACTATGGTCAGTAATTCCTGGAGGAATA

GGTACCAAGAAAAAAACGAACCTTTGGGTTCCAGAGCTGTACGG

TCGCACTGAACTCGGATAGGTCTCAGAAAAACGAAATATAGGCT

TACGGTAGGTCCGAATGGCACAAAGCTTGTTCCGTTAGCTGGCA

TAAGATTCCATGCCTAGATGTGATACACGTTTCTGGAAACTGCC

TCGTCATGCGACTGTTCCCCGGGGTCAGGGCCGCTGGTATTTGC

TGTAAAGAGGGCGTTGAGTCCGTCCGACTTCACTGCCCCTTT

CAGCCTTTTGGGTCCTGTATCCCAATTCTCAGAGGTCCCGCCGT

ACGCTGAGGACCACCTGAAACGGGCATCGTCGCTCTTCGTTGTT

CGTCGACTTCTAGTGTGGAGACGAATTGCCAGAATTATTAACTG

CGCAGTTAGGGCAGCGTCTGAGGAAGTTTGCTGCGGTTTCGCCT

TGACCGCGGGAAGGAGACATAACGATAGCGACTCTGTCTCAGGG

GATCTGCATATGTTTGCAGCATACTTTAGGTGGGCCTTGGCTTC

CTTCCGCAGTCAAAACCGCGCAATTATCCCCGTCCTGATTTACT
```

```
GGACTCGCAACGTGGGTCCATCAGTTGTCCGTATACCAAGACGT

CTAAGGGCGGTGTACACCCTTTTGAGCAATGATTGCACAACCTG

CGATCACCTTATACAGAATTATCAATCAAGCTCCCCGAGGAGCG

GACTTGTAAGGACCGCCGCTTTCGCTCGGGTCTGCGGGTTATAG

CTTTTCAGTCTCGACGGGCTAGCACACATCTGGTTGACTAGGCG

CATAGTCGCCATTCACAGATTTGCTCGGCAATCAGTACTGGTAG

GCGTTAGACCCCGTGACTCGTGGCTGAACGGCCGTACAACTCGA

CAGCCGGTGCTTGCGTTTTACCCTTAAAAAAAAAAAAAAAAAAA

AAAAA (SEQ ID NO: 112)

10. Acceptor-adapter P423:
AA/iSp9/ACACTCTTTCCCTACACGACGCTCTTCCGATCT/
3ddC/ (SEQ ID NO: 113)

11. Primer-adapter P591:
/5Sp9/GTGACTGGAGTTCAGACGTGTGCTCTTCCGATCT
(SEQ ID NO: 114)

12. PCR primer P312:
ACACTCTTTCCCTACACGACGCT (SEQ ID NO: 115)

13. PCR primer G9:
CTGAGACCTATCCGAGTTCAGTGC (SEQ ID NO: 116)

14. PCR primer C2:
GTGGCTATCTATCCCTACCAAGGCTTATATTG
(SEQ ID NO: 117)

15. Rotor-Gene® Q Real-Time PCR
cycler (Qiagen)
```

Method:
1. cDNA preparation: For each enzyme and template RNA tested, 4 μL of 1/50 diluted template RNA, 5 μL water, and 1 μL of 10× Fragmentation Buffer was added to the enzyme in a tube and the solution was mixed. Heat was used to fragment the template RNA by incubating the solutions at 94° C. for 4 minutes, followed by 4° C. for 2 minutes. Next, 12.5 μL of nB was added to each solution, followed by mixing. Then, 2.5 μL of nC was added to each solution, followed by mixing. Each solution was then incubated at 34° C. for 45 minutes and stored at 4° C. until use.
2. SPRI cleanup (Beckman Coulter) was performed on each solution per manufacturer's instructions. For each solution, cDNA was eluted in 12 μL elution buffer and 3 μL was transferred to a new PCR tubes
3. qPCR: 3 μL of the eluted cDNA from Step 2 was mixed with 7.5 μL Luna® Universal qPCR Master Mix (NEB) and 4.5 μL water. qPCR was conducted according to the NEB protocol for Luna® Universal qPCR Master Mix using the Rotor-Gene® Q Real-Time PCR cycler (Qiagen). For RNA template ERCC 00074, primers P312 and C2 were used. For RNA template ERC 00002, primers P312 and G9 were used.

Results: The qPCR results in Table 8 show a yield improvement with the ΔR2 enzyme-SSB fusion and the ΔR2-Cren7 fusion.

TABLE 11

| | $C_T$ values | |
|---|---|---|
| Enzyme | RNA Template ERCC 00074 | RNA Template ERCC 00002 |
| ΔR2 enzyme | 26 | 20 |
| ΔR2 enzyme-Sso7d | 26 | 20 |

TABLE 11-continued

| | $C_T$ values | |
|---|---|---|
| Enzyme | RNA Template ERCC 00074 | RNA Template ERCC 00002 |
| ΔR2 enzyme-Cren7 | 24 | 19 |
| ΔR2 enzyme-SSB | 22 | 16 |

Example 3—Processivity of Hybrid Reverse Transcriptases from Examples 1, 6, and 8

For each hybrid reverse transcriptase from Examples 1, 6, and 8, qPCR is used to quantify the amount (or yield) of cDNA copies obtained with an External RNA Controls Consortium (ERCC) standard mix of 90 different RNA templates having known concentrations, lengths, and secondary structure (or GC content). Appropriate primers for the RNA templates are used. The ratio of amount of long to short transcripts and/or high to low secondary structure-containing transcripts is measured. Highly processive and strand displacing enzymes with high affinity will generate exact cDNA copies of the RNA templates with the original ratio of long to short RNA templates or high to low secondary structure. Enzymes that exhibit low processivity, strand displacement, and low affinity will predominantly copy short RNA templates having low amounts of secondary structure.

Example 4-Expression and Purification of a Dimer of Truncated SSB Recombinantly Fused to the C-Terminus of ΔR2 Enzyme (SEQ ID NO: 47)

23.3 grams of cell biomass containing a dimer of truncated SSB fused to the C-terminus of ΔR2 enzyme was re-suspended in 233 mL (10 mL per gram biomass) lysis buffer (1λ BugBuster, 100 mM sodium phosphate pH 7.7, 0.1% Tween 20, 2.5 mM Tris (2-carboxyethyl) phosphine (TCEP), 0.1 mg/mL lysozyme, 1.25 units/mL DNase. The suspension was incubated for 45 minutes at room temperature (RT) with gently mixing. The lysate was then diluted 1:1 with Immobilized Metal Affinity Chromatography (IMAC) buffer A (50 mM sodium phosphate pH 7.7, 1.5 M NaCl, 2.5 mM TCEP, 0.1% Tween 20, 0.03% Triton X100, 10 mM imidazole) and was incubated at RT for 30 minutes with gentle rocking. The diluted lysate was sonicated and was clarified by centrifugation at 12,000 g for 40 minutes at 8° C. The supernatant was allowed to bind by gentle stirring to 10 mL Ni Sepharose FF6 resin (GE Healthcare) equilibrated with IMAC buffer A for 2 hours at 4° C. The resin was collected by centrifugation and poured onto a XK16 column (GE Healthcare). To step elute the fusion protein, the resin in the XK16 column was washed with 5 column volumes (CV) of IMAC buffer B (50 mM sodium phosphate pH 7.7, 300 mM M NaCl, 2.5 mM TCEP, 0.1% Tween 20, 250 mM imidazole). Fractions were pooled based on SDS-PAGE (not shown) and Western blot using (anti-histidine; not shown). The pooled fractions were then diluted 4-fold in heparin buffer (50 mM sodium phosphate pH 7.7, 100 mM NaCl, 2.5 mM TCEP, 0.1% Tween 20) and was loaded onto a 5 mM HiTrap Heparin HP column (GE Healthcare) equilibrated in heparin buffer. The column was washed with 10 CV heparin buffer followed by 10 CV heparin buffer with 300 mM NaCl. The bound fusion protein was eluted with a 20 CV gradient to heparin buffer with 1200 mM NaCl. Fractions to pool were determined by SDS-PAGE (not shown). The pooled heparin fractions were dialyzed at 4° C. overnight versus 20 mM sodium phosphate pH 7.7, 300 mM NaCl, 5 mM TCEP, 0.3% Tween 20, 10% glycerol.

Figure 22:
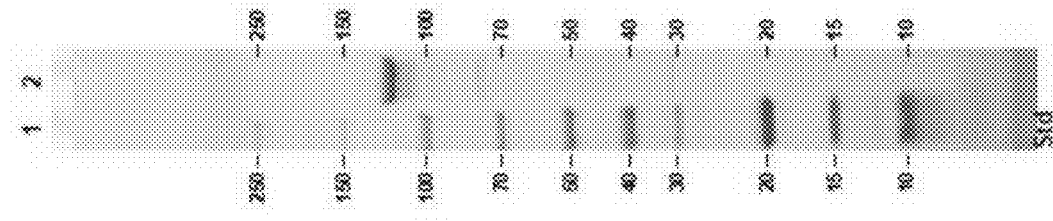
FIG. 22 is an image of an SDS-PAGE gel of a purified hybrid reverse transcriptase in which a dimer of a fragment of *Sulfolobus* SSB is joined to the C-terminus of ΔR2 enzyme.

The resulting purified fusion protein was analyzed by SDS-PAGE using 4-12% Bis-Tris polyacrylamide gels with Coomassie stain (see FIG. 22 for an image of the gel). The results show that the dimer of truncated SSB fused to the C-terminus of ΔR2 enzyme was expressed.

Example 5—Expression and Purification of Fusion Proteins Comprising SpyTag and SpyCatcher Binding Motifs Expression vector pET-45b carrying the constructs shown in Table 12 are transformed into *E. coli* BL21 (DE3).

TABLE 12

| SEQ ID NO: | N-terminal ORF | Linker ORF | C-terminal ORF |
|---|---|---|---|
| 69-70 | ΔR2 enzyme | Linker | SpyTag-linker-His Tag and Spy Catcher-linker-His Tag |
| 71-72 | Sso7d | Linker | SpyTag-linker-His Tag and Spy Catcher-linker-His Tag |
| 73-74 | Cren7 | Linker | SpyTag-linker-His Tag and Spy Catcher-linker-His Tag |
| 75-76 | SSB | Linker | SpyTag-linker-His Tag and Spy Catcher-linker-His Tag |
| 77-78 | His Tag-linker-SpyTag and His Tag-linker-Spy Catcher | Linker | ΔR2 enzyme |
| 79-80 | His Tag-linker-SpyTag and His Tag-linker-Spy Catcher | Linker | Sso7d |
| 81-82 | His Tag-linker-SpyTag and His Tag-linker-Spy Catcher | Linker | Cren7 |
| 83-84 | His Tag-linker-SpyTag and His Tag-linker-Spy Catcher | Linker | SSB |

For expression of each construct, a pre-culture are setup in 2 mL LB with 100 μM Corbenicillin and re grown for about 8-12 hours at room temperature. After about 8-12 hours, 550 μL of the pre-cultures are transferred to 25 mL auto-induction expression media (Overnight Express TB from Novagen) including 0.08 mg/ml Corbenicillin and shaker-incubated at 280-290 RPM at room temperature for 48 hours. Cells are harvested by centrifugation at 8000×g for 10 min at 4-8° C. The biomass-pellets are frozen at −20° C. for a minimum of 1 hour.

The pellets are re-suspended in 0.8 mL lysis buffer (0.8 ml lysis buffer per 10% of the biomass) and were incubated for 45 minutes at room temperature. Lysis buffer composition: 1× BugBuster (Millipore), 100 mM Sodium Phosphate, 0.2% Tween, 2.5 mM TCEP, 6 ul Protease inhibitor mix (Roche), 0.1 mg/ml lysozyme, 0.5 ul DNaseI (2,000 units/ml, from NEB). After incubation, the lysates are mixed with equal volume (0.8 mL) of His-binding buffer (50 mM Sodium Phosphate pH 7.7, 1.5 M Sodium Chloride, 5 mM TCEP, 0.2% Tween, 0.03% Triton X-100, 10 mM Imidazole) and incubated at room temperature for 30 minutes. After incubation, the lysates are centrifuged at 13000×g for 40 minutes at 80° C. The pellets are each mixed with 250 μl of His-Affinity Gel (His-Spin Protein Miniprep by Zymo Research) per the manufacturer's protocol. After the binding step, for each pellet, the His-Affinity Gel is washed five times with Washing buffer (50 mM Sodium Phosphate pH7.7, 1.2M Sodium Chloride, 0.2% Tween, 0.03% Triton X-100, 2.5 mM TCEP, 50 mM Imidazole). Finally fusion proteins are eluted with 250 µL of elution buffer (50 mM Sodium Phosphate pH7.7, 300 mM Sodium Chloride, 2.5 mM TCEP, 0.2% Tween and 250 mM Imidazole). The preparations are frozen at −20° C. in 50% glycerol, 50 mM Sodium Phosphate pH 7.7, 300 mM Sodium Chloride, 5 mM TCEP, 0.2% Tween and 125 mM Imidazole.

The fusion proteins are analyzed by SDS-PAGE using 4-12% Bis-Tris polyacrylamide gels with SYPRO Orange fluorescent stain (Bio-Rad).

Example 6-Ligation of ΔR2 Enzyme-SpyTag and Sso7d-SpyCatcher, Cren7-SpyCatcher, or SSB-SpyCatcher to Form Hybrid Reverse Transcriptases ΔR2 enzyme-SpyTag is ligated to Sso7d-SpyCatcher, Cren7-SpyCatcher, or SSB-SpyCatcher by reacting equimolar amounts of ΔR2 enzyme-SpyTag with Sso7d-SpyCatcher, Cren7-SpyCatcher, or SSB-SpyCatcher. The ligation reaction is allowed to proceed for about 16 hours at room temperature. For analysis, SDS loading buffer is added to the reaction mixture and the mixture is heated for 5 minutes at 95° C. prior to SDS-PAGE on 4-20% polyacrylamide gels. An image of the gel is obtained and shows that ΔR2 enzyme-SpyTag ligates with Sso7d-SpyCatcher, Cren7-SpyCatcher, or SSB-SpyCatcher.

Example 7-Expression and Purification of Fusion Proteins Comprising AviTag Acceptor Peptide Expression vector pET-45b carrying the constructs shown in Table 13 are transformed into *E. coli* BL21 (DE3).

TABLE 13

| SEQ ID NO: | N-terminal ORF | Linker ORF | C-terminal ORF |
|---|---|---|---|
| 90 | His Tag-linker-ΔR2 enzyme | Linker | AviTag |
| 91 | His Tag-linker-Sso7d | Linker | AviTag |
| 92 | His Tag-linker-Cren7 | Linker | AviTag |
| 93 | His Tag-linker-SSB | Linker | AviTag |
| 94 | His Tag-linker-AviTag | Linker | ΔR2 enzyme |
| 95 | His Tag-linker-AviTag | Linker | Sso7d |
| 96 | His Tag-linker-AviTag | Linker | Cren7 |
| 97 | His Tag-linker-AviTag | Linker | SSB |

For expression of each construct, a pre-culture are setup in 2 mL LB with 100 µM Corbenicillin and re grown for about 8-12 hours at room temperature. After about 8-12 hours, 550 µL of the pre-cultures are transferred to 25 mL auto-induction expression media (Overnight Express TB from Novagen) including 0.08 mg/ml Corbenicillin and shaker-incubated at 280-290 RPM at room temperature for 48 hours. Cells are harvested by centrifugation at 8000×g for 10 min at 4-8° C. The biomass-pellets are frozen at −20° C. for a minimum of 1 hour.

The pellets are re-suspended in 0.8 mL lysis buffer (0.8 ml lysis buffer per 10% of the biomass) and were incubated for 45 minutes at room temperature. Lysis buffer composition: 1× BugBuster (Millipore), 100 mM Sodium Phosphate, 0.2% Tween, 2.5 mM TCEP, 6 µl Protease inhibitor mix (Roche), 0.1 mg/ml lysozyme, 0.5 ul DNaseI (2,000 units/ml, from NEB). After incubation, the lysates are mixed with equal volume (0.8 mL) of His-binding buffer (50 mM Sodium Phosphate pH 7.7, 1.5 M Sodium Chloride, 5 mM TCEP, 0.2% Tween, 0.03% Triton X-100, 10 mM Imidazole) and incubated at room temperature for 30 minutes. After incubation, the lysates are centrifuged at 13000×g for 40 minutes at 80° C. The pellets are each mixed with 250 µl of His-Affinity Gel (His-Spin Protein Miniprep by Zymo Research) per the manufacturer's protocol. After the binding step, for each pellet, the His-Affinity Gel is washed five times with Washing buffer (50 mM Sodium Phosphate pH7.7, 1.2M Sodium Chloride, 0.2% Tween, 0.03% Triton X-100, 2.5 mM TCEP, 50 mM Imidazole). Finally fusion proteins are eluted with 250 µL of elution buffer (50 mM Sodium Phosphate pH7.7, 300 mM Sodium Chloride, 2.5 mM TCEP, 0.2% Tween and 250 mM Imidazole). The preparations are frozen at −20° C. in 50% glycerol, 50 mM Sodium Phosphate pH 7.7, 300 mM Sodium Chloride, 5 mM TCEP, 0.2% Tween and 125 mM Imidazole.

The fusion proteins are analyzed by SDS-PAGE using 4-12% Bis-Tris polyacrylamide gels with SYPRO Orange fluorescent stain (Bio-Rad).

Example 8—Preparation of Hybrid Reverse Transcriptases with Biotinylated Fusion Protein Non-Covalently Bound to Streptavidin To biotinylate the AviTag portion of the fusion proteins from Example 7, each fusion protein is mixed with 0.1 mM biotin and 30 nM BirA enzyme in the presence of 1 mM ATP and 5 mM $MgCl_2$ and allowed to incubate at 37° C. for 2 hours. The levels of biotinylation are analyzed via western blot using Strepavidin-HRP and HRP conjugated secondary antibody.

To non-covalently bind the biotinylated fusion proteins to streptavidin, different combinations of biotinylated fusion proteins are mixed with streptavidin in an appropriate ratio and incubated at 4° C. for 1 hour. Table 14 lists the combinations of ΔR2 enzyme comprising biotinylated AviTag and nucleic acid binding protein comprising biotinylated AviTag that are mixed with streptavidin along with the molar ratios to be used (i.e., that takes into the tetrameric structure of streptavidin):

TABLE 14

| 1st Fusion Protein or 1st and 2nd fusion protein | 2nd Fusion Protein or 3rd and 4th fusion protein | Molar Ratio |
|---|---|---|
| ΔR2 enzyme-biotinylated AviTag | biotinylated AviTag-Sso7d, biotinylated AviTag-Cren7, or biotinylated AviTag-SSB | 2 moles 1st fusion: 2 moles 2nd fusion: 1 mole streptavidin |
| biotinylated AviTag-ΔR2 enzyme | Sso7d-biotinylated AviTag, Cren7-biotinylated AviTag, or SSB-biotinylated AviTag | 2 moles 1st fusion: 2 moles 2nd fusion: 1 mole streptavidin |
| ΔR2 enzyme-biotinylated AviTag + biotinylated AviTag-ΔR2 enzyme | Sso7d-biotinylated AviTag + biotinylated AviTag-Sso7d, Cren7-biotinylated AviTag + biotinylated AviTag-Cren7, or SSB-biotinylated AviTag + biotinylated AviTag-SSB | 1 mole 1st fusion: 1 moles 2nd fusion: 1 mole 3rd fusion: 1 moles 4th fusion: 1 mole streptavidin |
| ΔR2 enzyme-biotinylated AviTag | biotinylated AviTag-ΔR2 enzyme | 2 moles 1st fusion: 2 moles 2nd fusion: 1 mole streptavidin |

For analysis, SDS loading buffer is added to the reaction mixture and the mixture is heated for 5 minutes at 95° C. prior to SDS-PAGE on 4-20% polyacrylamide gels under non-reducing conditions. An image of the gel is obtained and shows biotinylated fusion proteins non-covalently bind to streptavidin. After SDS-PAGE analysis, unreacted biotinylated fusion protein and streptavidin are removed from each reaction by size exclusion chromatography, resulting in purified hybrid reverse transcriptases.

All patents, patent applications, and other published reference materials cited in this specification are hereby incorporated herein by reference in their entirety.

The invention claimed is:

1. A hybrid reverse transcriptase comprising a non-retroviral retrotransposon, or a fragment of the non-retroviral retrotransposon having reverse transcriptase activity, joined to a nucleic acid binding protein or a fragment of the nucleic acid binding protein that binds to nucleic acid, wherein the nucleic acid binding protein is *Sulfolobus* SSB, a fragment of *Sulfolobus* SSB, an anti-Digoxigenin antibody, Sso7d, a fragment of Sso7d, Cren7, or a fragment of Cren7.

2. The hybrid reverse transcriptase of claim 1, wherein the nucleic acid binding protein is a single stranded deoxyribonucleic acid (ssDNA) binding protein or a fragment of the ssDNA binding protein.

3. The hybrid reverse transcriptase of claim 1, wherein the nucleic acid binding protein is a double stranded deoxyribonucleic acid (dsDNA) binding protein or a fragment of the dsDNA binding protein.

4. The hybrid reverse transcriptase of claim 1, wherein the non-retroviral retrotransposon, or the fragment of the non-retroviral retrotransposon, is an R2 reverse transcriptase or a fragment of the R2 reverse transcriptase, respectively.

5. The hybrid reverse transcriptase of claim 1, wherein the non-retroviral retrotransposon, or the fragment of the non-retroviral retrotransposon, is joined via a linker to the nucleic acid binding protein or the fragment of the nucleic acid binding protein.

6. The hybrid reverse transcriptase of claim 5, wherein the linker is selected from the group consisting of VGTVGTGGGSGGASTAL (SEQ ID NO: 101), VGTVGTGGGSEAAAKGGASTAL (SEQ ID NO: 102), VGTGGGSEAAAKGGASTAL (SEQ ID NO: 103), VGTGGGSGGGEAAAKEAAAKSGGGS (SEQ ID NOL 104), VGTGGGSGGGEAAAKEAAAKSGGGSA (SEQ ID NOL 105), VGTGGGSGGGTGGGS (SEQ ID NO: 106), VGTGGGSGGGTGGGSA (SEQ ID NO: 107), (GGGS)$_n$ (SEQ ID NO: 108), (GGS)$_n$, (GGGGS)$_n$ (SEQ ID NO: 109), and (EAAAK)$_n$ (SEQ ID NO: 100) and n is 1, 2, 3, 4, or 5.

7. The hybrid reverse transcriptase of claim 1, wherein the nucleic acid binding protein, or the fragment of the nucleic acid binding protein, is joined to the N-terminus or C-terminus of the non-retroviral retrotransposon or the fragment of the non-retroviral retrotransposon.

8. The hybrid reverse transcriptase of claim 1, wherein the nucleic acid binding protein is two or more nucleic acid binding proteins or fragments of two or more nucleic acid binding proteins and the two or more nucleic acid binding proteins or fragments of two or more nucleic acid binding proteins are identical or non-identical.

9. The hybrid reverse transcriptase of claim 8, wherein the two or more nucleic acid binding proteins or fragments of two or more nucleic acid binding proteins are in sequential or random order.

10. The hybrid reverse transcriptase of claim 1, wherein the non-retroviral retrotransposon, or the fragment of the non-retroviral retrotransposon, is covalently joined to the nucleic acid binding protein or the fragment of the nucleic acid binding protein.

11. A hybrid reverse transcriptase comprising a non-retroviral retrotransposon having at least 75% sequence identity to SEQ ID NO: 1 joined to a nucleic acid binding protein or a fragment of the nucleic acid binding protein, wherein the nucleic acid binding protein is *Sulfolobus* SSB, a fragment of *Sulfolobus* SSB, an anti-Digoxigenin antibody, Sso7d, a fragment of Sso7d, Cren7, or a fragment of Cren7.

12. A hybrid reverse transcriptase comprising a fragment of a non-retroviral retrotransposon having at least 75% sequence identity to SEQ ID NO: 2 joined to a nucleic acid binding protein or a fragment of the nucleic acid binding protein, wherein the nucleic acid binding protein is *Sulfolobus* SSB, a fragment of *Sulfolobus* SSB, an anti-Digoxigenin antibody, Sso7d, a fragment of Sso7d, Cren7, or a fragment of Cren7.

13. A nucleic acid construct comprising a polynucleotide sequence encoding the hybrid reverse transcriptase of claim 1.

14. A vector comprising the nucleic acid construct of claim 13.

15. A host cell comprising a vector as defined in claim 14.

16. A method of preparing a cDNA molecule comprising:
(a) contacting a template RNA molecule and free nucleotides with:
  i. a primer that is not complementary to the template RNA molecule;
  ii. an acceptor-adapter; and
  iii. the hybrid reverse transcriptase of claim 2; and
(b) allowing the hybrid reverse transcriptase to transcribe the template RNA molecule under conditions effective for producing a cDNA molecule complementary to the RNA molecule and, optionally, to the acceptor-adapter,
wherein the hybrid reverse transcriptase jumps to a 3'-end of the acceptor-adapter upon reaching a 5' end of the RNA molecule.

17. A method of preparing a cDNA molecule library comprising:
(a) fragmenting a template RNA molecule to produce RNA fragments;
(b) contacting the RNA fragments and free nucleotides, with:
  i. a primer-adapter that is not complementary to the RNA fragments;
  ii. an acceptor-adapter; and
  iii. the hybrid reverse transcriptase of claim 2; and
(c) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the RNA fragments.

18. A method of preparing a cDNA molecule library comprising:
(a) providing a partition comprising:
  i. a cell comprising template RNA molecules;
  ii. nucleotides;
  iii. a primer adapter that is not complementary to the RNA molecules;
  iv. an acceptor-adapter;
  v. an endonuclease; and
  vi. the hybrid reverse transcriptase of claim 2;
in the partition:
(b) releasing template RNA molecules from the cell;
(c) fragmenting the template RNA molecules to form RNA fragments; and
(d) allowing the hybrid reverse transcriptase to transcribe the RNA fragments under conditions effective to produce a cDNA molecule library,
wherein the hybrid reverse transcriptase jumps to a 3'-end of the acceptor-adapter upon reaching a 5' end of the dephosphorylated RNA fragments.

19. The method of claim 16, wherein the hybrid reverse transcriptase comprises SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100, or a sequence at least 75% identical to SEQ ID NO: 14, SEQ ID NO: 15, SEQ ID NO: 16, SEQ ID NO: 17, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 47, SEQ ID NO: 98, SEQ ID NO: 99, or SEQ ID NO: 100.

20. The method of claim 19, wherein the hybrid reverse transcriptase comprises at least one improved property selected from the group consisting of higher processivity, longer shelf life, higher strand displacement, higher end-to-end template jumping, and higher affinity as compared to a non-retroviral retrotransposon, or a fragment of the non-retroviral retrotransposon, that is not joined to a nucleic acid binding protein.

21. The method of claim 20, wherein the improved property of the hybrid reverse transcriptase is higher affinity.

* * * * *

SEQUENCE LISTING

<160> NUMBER OF SEQ ID NOS: 124

<210> SEQ ID NO 1
<211> LENGTH: 1114
<212> TYPE: PRT
<213> ORGANISM: Bombyx mori
<220> FEATURE:
<221> NAME/KEY: misc_feature
<223> OTHER INFORMATION: wild type R2 enzyme

<400> SEQUENCE: 1

```
Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
            115                 120                 125

Val His Lys Arg Arg Ala His Pro Val Glu Thr Asn Thr Asp Ala Ala
        130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
            195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320
```

```
Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
                340                 345                 350

Pro Ile Leu Glu Arg Val Ser Asp Ala Pro Gly Pro Thr Pro Glu Ala
                355                 360                 365

Leu His Ala Leu Gly Arg Ala Glu Trp His Gly Gly Asn Arg Asp Tyr
                370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
                420                 425                 430

Met Ala Arg Gly Glu Ile Pro Glu Ile Leu Arg Gln Cys Arg Thr Val
                435                 440                 445

Phe Val Pro Lys Val Glu Arg Pro Gly Gly Pro Gly Glu Tyr Arg Pro
                450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
                500                 505                 510

Leu Gly Asp Ser Arg Lys Lys Leu Arg Glu Cys His Val Ala Val Leu
                515                 520                 525

Asp Phe Ala Lys Ala Phe Asp Thr Val Ser His Glu Ala Leu Val Glu
                530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
                580                 585                 590

Ser Pro Ile Leu Phe Asn Val Val Met Asp Leu Ile Leu Ala Ser Leu
                595                 600                 605

Pro Glu Arg Val Gly Tyr Arg Leu Glu Met Glu Leu Val Ser Ala Leu
                610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
                660                 665                 670

His Arg Lys Lys His His Tyr Leu Thr Glu Arg Thr Phe Asn Ile Gly
                675                 680                 685

Gly Lys Pro Leu Arg Gln Val Ser Cys Val Glu Arg Trp Arg Tyr Leu
                690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735
```

-continued

```
Arg Leu Glu Ile Leu Arg Ala His Leu Ile Pro Arg Phe Gln His Gly
            740                 745                 750

Phe Val Leu Gly Asn Ile Ser Asp Arg Leu Arg Met Leu Asp Val
        755                 760                 765

Gln Ile Arg Lys Ala Val Gly Gln Trp Leu Arg Leu Pro Ala Asp Val
770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
            915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly

<210> SEQ ID NO 2
<211> LENGTH: 829
<212> TYPE: PRT
```

<213> ORGANISM: Artificial Sequence
<220> FEATURE:
<223> OTHER INFORMATION: deltaR2 enzyme or R2 enzyme minus N-terminal DNA binding domain

<400> SEQUENCE: 2

```
Lys Thr Ala Gly Arg Arg Asn Asp Leu His Asp Asp Arg Thr Ala Ser
1               5                   10                  15

Ala His Lys Thr Ser Arg Gln Lys Arg Arg Ala Glu Tyr Ala Arg Val
            20                  25                  30

Gln Glu Leu Tyr Lys Lys Cys Arg Ser Arg Ala Ala Ala Glu Val Ile
        35                  40                  45

Asp Gly Ala Cys Gly Gly Val Gly His Ser Leu Glu Glu Met Glu Thr
    50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Gly Asn
                85                  90                  95

Arg Asp Tyr Thr Gln Leu Trp Lys Pro Ile Ser Val Glu Glu Ile Lys
            100                 105                 110

Ala Ser Arg Phe Asp Trp Arg Thr Ser Pro Gly Pro Asp Gly Ile Arg
        115                 120                 125

Ser Gly Gln Trp Arg Ala Val Pro Val His Leu Lys Ala Glu Met Phe
    130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
            180                 185                 190

Ile Leu Ala Arg Arg Leu Leu Ala Cys Cys Pro Pro Asp Ala Arg Gln
        195                 200                 205

Arg Gly Phe Ile Cys Ala Asp Gly Thr Leu Glu Asn Ser Ala Val Leu
    210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
            260                 265                 270

Tyr Ile Ala His Leu Tyr Asp Thr Ala Ser Thr Thr Leu Ala Val Asn
        275                 280                 285

Asn Glu Met Ser Ser Pro Val Lys Val Gly Arg Gly Val Arg Gln Gly
    290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Leu Val Leu Leu Ala Gly Ser Lys
            340                 345                 350

Val Gly Met Gln Glu Ser Ile Ser Ala Val Asp Cys Val Gly Arg Gln
        355                 360                 365

Met Gly Leu Arg Leu Asn Cys Arg Lys Ser Ala Val Leu Ser Met Ile
    370                 375                 380
```

```
Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
            405                 410                 415

Arg Tyr Leu Gly Val Asp Phe Glu Ala Ser Gly Cys Val Thr Leu Glu
        420                 425                 430

His Ser Ile Ser Ser Ala Leu Asn Asn Ile Ser Arg Ala Pro Leu Lys
    435                 440                 445

Pro Gln Gln Arg Leu Glu Ile Leu Arg Ala His Leu Ile Pro Arg Phe
450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
            500                 505                 510

Leu Ala Ile Pro Ser Val Arg Ala Thr Ile Pro Asp Leu Ile Val Arg
        515                 520                 525

Arg Phe Gly Gly Leu Asp Ser Ser Pro Trp Ser Val Ala Arg Ala Ala
530                 535                 540

Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
        595                 600                 605

Arg Cys Ala Gln Ile Thr Gly Arg Asp Phe Val Gln Phe Val His Thr
610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
            660                 665                 670

Arg Ile Leu Arg His Asn Lys Ile Val Ser Phe Val Ala Lys Ala Met
        675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
        755                 760                 765

Ala Thr Ser Cys Thr Ile Ser Trp Arg Gly Val Trp Ser Leu Thr Ser
770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
```

```
                        805                 810                 815
Phe Asn Gln Met Thr Ser Val Met Gly Gly Gly Val Gly
                820                 825

<210> SEQ ID NO 3
<211> LENGTH: 63
<212> TYPE: PRT
<213> ORGANISM: Artificial Sequence
<220> FEATURE:
<223> OTHER INFORMATION: Sso7d

<400> SEQUENCE: 3

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 4
<211> LENGTH: 59
<212> TYPE: PRT
<213> ORGANISM: Artificial Sequence
<220> FEATURE:
<223> OTHER INFORMATION: Cren7

<400> SEQUENCE: 4

Ser Ser Gly Lys Lys Pro Val Lys Val Lys Thr Pro Ala Gly Lys Glu
1               5                   10                  15

Ala Glu Leu Val Pro Glu Lys Val Trp Ala Leu Ala Pro Lys Gly Arg
            20                  25                  30

Lys Gly Val Lys Ile Gly Leu Phe Lys Asp Pro Glu Thr Gly Lys Tyr
        35                  40                  45

Phe Arg His Lys Leu Pro Asp Asp Tyr Pro Ile
    50                  55

<210> SEQ ID NO 5
<211> LENGTH: 148
<212> TYPE: PRT
<213> ORGANISM: Artificial Sequence
<220> FEATURE:
<223> OTHER INFORMATION: Sulfolobus SSB

<400> SEQUENCE: 5

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Gln Ile Pro Glu Asn Thr Pro
            100                 105                 110
```

Thr Ala Pro Gln Gln Met Arg Gly Gly Gly Arg Gly Phe Arg Gly Gly
        115                 120                 125

Gly Arg Arg Tyr Gly Arg Gly Gly Arg Arg Gln Glu Asn Glu Glu
    130                 135                 140

Gly Glu Glu Glu
145

<210> SEQ ID NO 6
<211> LENGTH: 1194
<212> TYPE: PRT
<213> ORGANISM: Artificial Sequence
<220> FEATURE:
<223> OTHER INFORMATION: Sso7d joined via a linker to the N-terminus of
      wild type R2 enzyme

<400> SEQUENCE: 6

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys Val
    50                  55                  60

Gly Thr Val Gly Thr Gly Gly Ser Gly Gly Ala Ser Thr Ala Leu
65                  70                  75                  80

Met Met Ala Ser Thr Ala Leu Ser Leu Met Gly Arg Cys Asn Pro Asp
                85                  90                  95

Gly Cys Thr Arg Gly Lys His Val Thr Ala Ala Pro Met Asp Gly Pro
            100                 105                 110

Arg Gly Pro Ser Ser Leu Ala Gly Thr Phe Gly Trp Gly Leu Ala Ile
        115                 120                 125

Pro Ala Gly Glu Pro Cys Gly Arg Val Cys Ser Pro Ala Thr Val Gly
    130                 135                 140

Phe Phe Pro Val Ala Lys Lys Ser Asn Lys Glu Asn Arg Pro Glu Ala
145                 150                 155                 160

Ser Gly Leu Pro Leu Glu Ser Glu Arg Thr Gly Asp Asn Pro Thr Val
                165                 170                 175

Arg Gly Ser Ala Gly Ala Asp Pro Val Gly Gln Asp Ala Pro Gly Trp
            180                 185                 190

Thr Cys Gln Phe Cys Glu Arg Thr Phe Ser Thr Asn Arg Gly Leu Gly
        195                 200                 205

Val His Lys Arg Arg Ala His Pro Val Glu Thr Asn Thr Asp Ala Ala
    210                 215                 220

Pro Met Met Val Lys Arg Arg Trp His Gly Glu Glu Ile Asp Leu Leu
225                 230                 235                 240

Ala Arg Thr Glu Ala Arg Leu Leu Ala Glu Arg Gly Gln Cys Ser Gly
                245                 250                 255

Gly Asp Leu Phe Gly Ala Leu Pro Gly Phe Gly Arg Thr Leu Glu Ala
            260                 265                 270

Ile Lys Gly Gln Arg Arg Arg Glu Pro Tyr Arg Ala Leu Val Gln Ala
        275                 280                 285

His Leu Ala Arg Phe Gly Ser Gln Pro Gly Pro Ser Ser Gly Gly Cys
    290                 295                 300

Ser Ala Glu Pro Asp Phe Arg Arg Ala Ser Gly Ala Glu Glu Ala Gly

```
            305                 310                 315                 320
        Glu Glu Arg Cys Ala Glu Asp Ala Ala Ala Tyr Asp Pro Ser Ala Val
                        325                 330                 335
        Gly Gln Met Ser Pro Asp Ala Ala Arg Val Leu Ser Glu Leu Leu Glu
                        340                 345                 350
        Gly Ala Gly Arg Arg Ala Cys Arg Ala Met Arg Pro Lys Thr Ala
                        355                 360                 365
        Gly Arg Arg Asn Asp Leu His Asp Asp Arg Thr Ala Ser Ala His Lys
                        370                 375                 380
        Thr Ser Arg Gln Lys Arg Arg Ala Glu Tyr Ala Arg Val Gln Glu Leu
        385                 390                 395                 400
        Tyr Lys Lys Cys Arg Ser Arg Ala Ala Ala Glu Val Ile Asp Gly Ala
                        405                 410                 415
        Cys Gly Gly Val Gly His Ser Leu Glu Glu Met Glu Thr Tyr Trp Arg
                        420                 425                 430
        Pro Ile Leu Glu Arg Val Ser Asp Ala Pro Gly Pro Thr Pro Glu Ala
                        435                 440                 445
        Leu His Ala Leu Gly Arg Ala Glu Trp His Gly Gly Asn Arg Asp Tyr
                        450                 455                 460
        Thr Gln Leu Trp Lys Pro Ile Ser Val Glu Ile Lys Ala Ser Arg
        465                 470                 475                 480
        Phe Asp Trp Arg Thr Ser Pro Gly Pro Asp Gly Ile Arg Ser Gly Gln
                        485                 490                 495
        Trp Arg Ala Val Pro Val His Leu Lys Ala Glu Met Phe Asn Ala Trp
                        500                 505                 510
        Met Ala Arg Gly Glu Ile Pro Glu Ile Leu Arg Gln Cys Arg Thr Val
                        515                 520                 525
        Phe Val Pro Lys Val Glu Arg Pro Gly Gly Pro Gly Glu Tyr Arg Pro
                        530                 535                 540
        Ile Ser Ile Ala Ser Ile Pro Leu Arg His Phe His Ser Ile Leu Ala
        545                 550                 555                 560
        Arg Arg Leu Leu Ala Cys Cys Pro Pro Asp Ala Arg Gln Arg Gly Phe
                        565                 570                 575
        Ile Cys Ala Asp Gly Thr Leu Glu Asn Ser Ala Val Leu Asp Ala Val
                        580                 585                 590
        Leu Gly Asp Ser Arg Lys Lys Leu Arg Glu Cys His Val Ala Val Leu
                        595                 600                 605
        Asp Phe Ala Lys Ala Phe Asp Thr Val Ser His Glu Ala Leu Val Glu
                        610                 615                 620
        Leu Leu Arg Leu Arg Gly Met Pro Glu Gln Phe Cys Gly Tyr Ile Ala
        625                 630                 635                 640
        His Leu Tyr Asp Thr Ala Ser Thr Thr Leu Ala Val Asn Asn Glu Met
                        645                 650                 655
        Ser Ser Pro Val Lys Val Gly Arg Gly Val Arg Gln Gly Asp Pro Leu
                        660                 665                 670
        Ser Pro Ile Leu Phe Asn Val Val Met Asp Leu Ile Leu Ala Ser Leu
                        675                 680                 685
        Pro Glu Arg Val Gly Tyr Arg Leu Glu Met Glu Leu Val Ser Ala Leu
                        690                 695                 700
        Ala Tyr Ala Asp Asp Leu Val Leu Leu Ala Gly Ser Lys Val Gly Met
        705                 710                 715                 720
        Gln Glu Ser Ile Ser Ala Val Asp Cys Val Gly Arg Gln Met Gly Leu
                        725                 730                 735
        Arg Leu Asn Cys Arg Lys Ser Ala Val Leu Ser Met Ile Pro Asp Gly
```

```
                740              745              750
His Arg Lys Lys His Tyr Leu Thr Glu Arg Thr Phe Asn Ile Gly
            755              760              765

Gly Lys Pro Leu Arg Gln Val Ser Cys Val Glu Arg Trp Arg Tyr Leu
            770              775              780

Gly Val Asp Phe Glu Ala Ser Gly Cys Val Thr Leu Glu His Ser Ile
785              790              795              800

Ser Ser Ala Leu Asn Asn Ile Ser Arg Ala Pro Leu Lys Pro Gln Gln
            805              810              815

Arg Leu Glu Ile Leu Arg Ala His Leu Ile Pro Arg Phe Gln His Gly
            820              825              830

Phe Val Leu Gly Asn Ile Ser Asp Asp Arg Leu Arg Met Leu Asp Val
            835              840              845

Gln Ile Arg Lys Ala Val Gly Gln Trp Leu Arg Leu Pro Ala Asp Val
            850              855              860

Pro Lys Ala Tyr Tyr His Ala Ala Val Gln Asp Gly Gly Leu Ala Ile
865              870              875              880

Pro Ser Val Arg Ala Thr Ile Pro Asp Leu Ile Val Arg Arg Phe Gly
            885              890              895

Gly Leu Asp Ser Ser Pro Trp Ser Val Ala Arg Ala Ala Ala Lys Ser
            900              905              910

Asp Lys Ile Arg Lys Leu Arg Trp Ala Trp Lys Gln Leu Arg Arg
            915              920              925

Phe Ser Arg Val Asp Ser Thr Thr Gln Arg Pro Ser Val Arg Leu Phe
            930              935              940

Trp Arg Glu His Leu His Ala Ser Val Asp Gly Arg Glu Leu Arg Glu
945              950              955              960

Ser Thr Arg Thr Pro Thr Ser Thr Lys Trp Ile Arg Glu Arg Cys Ala
            965              970              975

Gln Ile Thr Gly Arg Asp Phe Val Gln Phe Val His Thr His Ile Asn
            980              985              990

Ala Leu Pro Ser Arg Ile Arg Gly  Ser Arg Gly Arg Arg  Gly Gly Gly
            995              1000              1005

Glu Ser  Ser Leu Thr Cys Arg  Ala Gly Cys Lys Val  Arg Glu Thr
    1010             1015              1020

Thr Ala  His Ile Leu Gln Gln  Cys His Arg Thr His  Gly Gly Arg
    1025             1030              1035

Ile Leu  Arg His Asn Lys Ile  Val Ser Phe Val Ala  Lys Ala Met
    1040             1045              1050

Glu Glu  Asn Lys Trp Thr Val  Glu Leu Glu Pro Arg  Leu Arg Thr
    1055             1060              1065

Ser Val  Gly Leu Arg Lys Pro  Asp Ile Ile Ala Ser  Arg Asp Gly
    1070             1075              1080

Val Gly  Val Ile Val Asp Val  Gln Val Val Ser Gly  Gln Arg Ser
    1085             1090              1095

Leu Asp  Glu Leu His Arg Glu  Lys Arg Asn Lys Tyr  Gly Asn His
    1100             1105              1110

Gly Glu  Leu Val Glu Leu Val  Ala Gly Arg Leu Gly  Leu Pro Lys
    1115             1120              1125

Ala Glu  Cys Val Arg Ala Thr  Ser Cys Thr Ile Ser  Trp Arg Gly
    1130             1135              1140

Val Trp  Ser Leu Thr Ser Tyr  Lys Glu Leu Arg Ser  Ile Ile Gly
    1145             1150              1155
```

-continued

```
Leu Arg Glu Pro Thr Leu Gln Ile Val Pro Ile Leu Ala Leu Arg
    1160                1165                1170

Gly Ser His Met Asn Trp Thr Arg Phe Asn Gln Met Thr Ser Val
1175                1180                1185

Met Gly Gly Gly Val Gly
    1190

<210> SEQ ID NO 7
<211> LENGTH: 934
<212> TYPE: PRT
<213> ORGANISM: Artificial Sequence
<220> FEATURE:
<223> OTHER INFORMATION: His Tag joined via a linker to Sso7d joined via
      a linker to the N-terminus of deltaR2 enzyme

<400> SEQUENCE: 7

Met Ala His His His His His Val Gly Thr Val Gly Thr Gly Gly
1               5                   10                  15

Gly Ser Gly Gly Ala Ser Thr Ala Leu Ala Thr Val Lys Phe Lys Tyr
            20                  25                  30

Lys Gly Glu Glu Lys Glu Val Asp Ile Ser Lys Ile Lys Lys Val Trp
            35                  40                  45

Arg Val Gly Lys Met Ile Ser Phe Thr Tyr Asp Glu Gly Gly Gly Lys
50                  55                  60

Thr Gly Arg Gly Ala Val Ser Glu Lys Asp Ala Pro Lys Glu Leu Leu
65                  70                  75                  80

Gln Met Leu Glu Lys Gln Lys Lys Val Gly Thr Val Gly Thr Gly Gly
                85                  90                  95

Gly Ser Gly Gly Ala Ser Thr Ala Leu Lys Thr Ala Gly Arg Arg Asn
            100                 105                 110

Asp Leu His Asp Asp Arg Thr Ala Ser Ala His Lys Thr Ser Arg Gln
            115                 120                 125

Lys Arg Arg Ala Glu Tyr Ala Arg Val Gln Glu Leu Tyr Lys Lys Cys
            130                 135                 140

Arg Ser Arg Ala Ala Ala Glu Val Ile Asp Gly Ala Cys Gly Gly Val
145                 150                 155                 160

Gly His Ser Leu Glu Glu Met Glu Thr Tyr Trp Arg Pro Ile Leu Glu
                165                 170                 175

Arg Val Ser Asp Ala Pro Gly Pro Thr Pro Glu Ala Leu His Ala Leu
            180                 185                 190

Gly Arg Ala Glu Trp His Gly Gly Asn Arg Asp Tyr Thr Gln Leu Trp
            195                 200                 205

Lys Pro Ile Ser Val Glu Glu Ile Lys Ala Ser Arg Phe Asp Trp Arg
            210                 215                 220

Thr Ser Pro Gly Pro Asp Gly Ile Arg Ser Gly Gln Trp Arg Ala Val
225                 230                 235                 240

Pro Val His Leu Lys Ala Glu Met Phe Asn Ala Trp Met Ala Arg Gly
                245                 250                 255

Glu Ile Pro Glu Ile Leu Arg Gln Cys Arg Thr Val Phe Val Pro Lys
            260                 265                 270

Val Glu Arg Pro Gly Gly Pro Gly Glu Tyr Arg Pro Ile Ser Ile Ala
            275                 280                 285

Ser Ile Pro Leu Arg His Phe His Ser Ile Leu Ala Arg Arg Leu Leu
            290                 295                 300

Ala Cys Cys Pro Pro Asp Ala Arg Gln Arg Gly Phe Ile Cys Ala Asp
```

-continued

```
          305                 310                 315                 320
        Gly Thr Leu Glu Asn Ser Ala Val Leu Asp Ala Val Leu Gly Asp Ser
                        325                 330                 335
        Arg Lys Lys Leu Arg Glu Cys His Val Ala Val Leu Asp Phe Ala Lys
                        340                 345                 350
        Ala Phe Asp Thr Val Ser His Glu Ala Leu Val Glu Leu Leu Arg Leu
                        355                 360                 365
        Arg Gly Met Pro Glu Gln Phe Cys Gly Tyr Ile Ala His Leu Tyr Asp
                        370                 375                 380
        Thr Ala Ser Thr Thr Leu Ala Val Asn Asn Glu Met Ser Ser Pro Val
        385                 390                 395                 400
        Lys Val Gly Arg Gly Val Arg Gln Gly Asp Pro Leu Ser Pro Ile Leu
                        405                 410                 415
        Phe Asn Val Val Met Asp Leu Ile Leu Ala Ser Leu Pro Glu Arg Val
                        420                 425                 430
        Gly Tyr Arg Leu Glu Met Glu Leu Val Ser Ala Leu Ala Tyr Ala Asp
                        435                 440                 445
        Asp Leu Val Leu Leu Ala Gly Ser Lys Val Gly Met Gln Glu Ser Ile
            450                 455                 460
        Ser Ala Val Asp Cys Val Gly Arg Gln Met Gly Leu Arg Leu Asn Cys
        465                 470                 475                 480
        Arg Lys Ser Ala Val Leu Ser Met Ile Pro Asp Gly His Arg Lys Lys
                        485                 490                 495
        His His Tyr Leu Thr Glu Arg Thr Phe Asn Ile Gly Gly Lys Pro Leu
                        500                 505                 510
        Arg Gln Val Ser Cys Val Glu Arg Trp Arg Tyr Leu Gly Val Asp Phe
                        515                 520                 525
        Glu Ala Ser Gly Cys Val Thr Leu Glu His Ser Ile Ser Ser Ala Leu
                        530                 535                 540
        Asn Asn Ile Ser Arg Ala Pro Leu Lys Pro Gln Gln Arg Leu Glu Ile
        545                 550                 555                 560
        Leu Arg Ala His Leu Ile Pro Arg Phe Gln His Gly Phe Val Leu Gly
                        565                 570                 575
        Asn Ile Ser Asp Asp Arg Leu Arg Met Leu Asp Val Gln Ile Arg Lys
                        580                 585                 590
        Ala Val Gly Gln Trp Leu Arg Leu Pro Ala Asp Val Pro Lys Ala Tyr
                        595                 600                 605
        Tyr His Ala Ala Val Gln Asp Gly Gly Leu Ala Ile Pro Ser Val Arg
            610                 615                 620
        Ala Thr Ile Pro Asp Leu Ile Val Arg Arg Phe Gly Gly Leu Asp Ser
        625                 630                 635                 640
        Ser Pro Trp Ser Val Ala Arg Ala Ala Lys Ser Asp Lys Ile Arg
                        645                 650                 655
        Lys Lys Leu Arg Trp Ala Trp Lys Gln Leu Arg Arg Phe Ser Arg Val
                        660                 665                 670
        Asp Ser Thr Thr Gln Arg Pro Ser Val Arg Leu Phe Trp Arg Glu His
                        675                 680                 685
        Leu His Ala Ser Val Asp Gly Arg Glu Leu Arg Glu Ser Thr Arg Thr
                        690                 695                 700
        Pro Thr Ser Thr Lys Trp Ile Arg Glu Arg Cys Ala Gln Ile Thr Gly
        705                 710                 715                 720
        Arg Asp Phe Val Gln Phe Val His Thr His Ile Asn Ala Leu Pro Ser
                        725                 730                 735
```

```
Arg Ile Arg Gly Ser Arg Gly Arg Gly Gly Glu Ser Ser Leu
            740                 745                 750

Thr Cys Arg Ala Gly Cys Lys Val Arg Glu Thr Thr Ala His Ile Leu
            755                 760                 765

Gln Gln Cys His Arg Thr His Gly Gly Arg Ile Leu Arg His Asn Lys
            770                 775                 780

Ile Val Ser Phe Val Ala Lys Ala Met Glu Glu Asn Lys Trp Thr Val
785                 790                 795                 800

Glu Leu Glu Pro Arg Leu Arg Thr Ser Val Gly Leu Arg Lys Pro Asp
            805                 810                 815

Ile Ile Ala Ser Arg Asp Gly Val Gly Val Ile Val Asp Val Gln Val
            820                 825                 830

Val Ser Gly Gln Arg Ser Leu Asp Glu Leu His Arg Glu Lys Arg Asn
            835                 840                 845

Lys Tyr Gly Asn His Gly Glu Leu Val Glu Leu Val Ala Gly Arg Leu
850                 855                 860

Gly Leu Pro Lys Ala Glu Cys Val Arg Ala Thr Ser Cys Thr Ile Ser
865                 870                 875                 880

Trp Arg Gly Val Trp Ser Leu Thr Ser Tyr Lys Glu Leu Arg Ser Ile
            885                 890                 895

Ile Gly Leu Arg Glu Pro Thr Leu Gln Ile Val Pro Ile Leu Ala Leu
            900                 905                 910

Arg Gly Ser His Met Asn Trp Thr Arg Phe Asn Gln Met Thr Ser Val
            915                 920                 925

Met Gly Gly Gly Val Gly
        930

<210> SEQ ID NO 8
<211> LENGTH: 1287
<212> TYPE: PRT
<213> ORGANISM: Artificial Sequence
<220> FEATURE:
<223> OTHER INFORMATION: Sso7d-Sso7d joined via a linker to the
      N-terminus of wild type R2 enzyme

<400> SEQUENCE: 8

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
            35                  40                  45

Asp Ala Pro Lys Glu Leu Leu Gln Met Leu Glu Lys Gln Lys Lys Val
        50                  55                  60

Gly Thr Gly Gly Gly Ser Gly Gly Glu Ala Ala Lys Glu Ala
65                  70                  75                  80

Ala Ala Lys Ser Gly Gly Ser Ala Thr Val Lys Phe Lys Tyr Lys
                85                  90                  95

Gly Glu Glu Lys Glu Val Asp Ile Ser Lys Ile Lys Lys Val Trp Arg
            100                 105                 110

Val Gly Lys Met Ile Ser Phe Thr Tyr Asp Glu Gly Gly Gly Lys Thr
            115                 120                 125

Gly Arg Gly Ala Val Ser Glu Lys Asp Ala Pro Lys Glu Leu Leu Gln
        130                 135                 140

Met Leu Glu Lys Gln Lys Lys Val Gly Thr Val Gly Thr Gly Gly Gly
```

```
            145                 150                 155                 160
Ser Glu Ala Ala Lys Gly Ala Ser Thr Ala Leu Met Met Ala
                165                 170                 175
Ser Thr Ala Leu Ser Leu Met Gly Arg Cys Asn Pro Asp Gly Cys Thr
                180                     185                 190
Arg Gly Lys His Val Thr Ala Ala Pro Met Asp Gly Pro Arg Gly Pro
                195                 200                 205
Ser Ser Leu Ala Gly Thr Phe Gly Trp Gly Leu Ala Ile Pro Ala Gly
        210                 215                 220
Glu Pro Cys Gly Arg Val Cys Ser Pro Ala Thr Val Gly Phe Phe Pro
225                 230                 235                 240
Val Ala Lys Lys Ser Asn Lys Glu Asn Arg Pro Glu Ala Ser Gly Leu
                    245                 250                 255
Pro Leu Glu Ser Glu Arg Thr Gly Asp Asn Pro Thr Val Arg Gly Ser
                260                 265                 270
Ala Gly Ala Asp Pro Val Gly Gln Asp Ala Pro Gly Trp Thr Cys Gln
            275                 280                 285
Phe Cys Glu Arg Thr Phe Ser Thr Asn Arg Gly Leu Gly Val His Lys
        290                 295                 300
Arg Arg Ala His Pro Val Glu Thr Asn Thr Asp Ala Ala Pro Met Met
305                 310                 315                 320
Val Lys Arg Arg Trp His Gly Glu Glu Ile Asp Leu Leu Ala Arg Thr
                325                 330                 335
Glu Ala Arg Leu Leu Ala Glu Arg Gly Gln Cys Ser Gly Gly Asp Leu
                340                 345                 350
Phe Gly Ala Leu Pro Gly Phe Gly Arg Thr Leu Glu Ala Ile Lys Gly
        355                 360                 365
Gln Arg Arg Arg Glu Pro Tyr Arg Ala Leu Val Gln Ala His Leu Ala
        370                 375                 380
Arg Phe Gly Ser Gln Pro Gly Pro Ser Ser Gly Gly Cys Ser Ala Glu
385                 390                 395                 400
Pro Asp Phe Arg Arg Ala Ser Gly Ala Glu Glu Ala Gly Glu Glu Arg
                405                 410                 415
Cys Ala Glu Asp Ala Ala Ala Tyr Asp Pro Ser Ala Val Gly Gln Met
                420                 425                 430
Ser Pro Asp Ala Ala Arg Val Leu Ser Glu Leu Leu Glu Gly Ala Gly
            435                 440                 445
Arg Arg Arg Ala Cys Arg Ala Met Arg Pro Lys Thr Ala Gly Arg Arg
450                 455                 460
Asn Asp Leu His Asp Asp Arg Thr Ala Ser Ala His Lys Thr Ser Arg
465                 470                 475                 480
Gln Lys Arg Arg Ala Glu Tyr Ala Arg Val Gln Glu Leu Tyr Lys Lys
                485                 490                 495
Cys Arg Ser Arg Ala Ala Ala Glu Val Ile Asp Gly Ala Cys Gly Gly
                500                 505                 510
Val Gly His Ser Leu Glu Glu Met Glu Thr Tyr Trp Arg Pro Ile Leu
        515                 520                 525
Glu Arg Val Ser Asp Ala Pro Gly Pro Thr Pro Glu Ala Leu His Ala
        530                 535                 540
Leu Gly Arg Ala Glu Trp His Gly Gly Asn Arg Asp Tyr Thr Gln Leu
545                 550                 555                 560
Trp Lys Pro Ile Ser Val Glu Glu Ile Lys Ala Ser Arg Phe Asp Trp
                565                 570                 575
```

```
Arg Thr Ser Pro Gly Pro Asp Gly Ile Arg Ser Gly Gln Trp Arg Ala
            580                 585                 590

Val Pro Val His Leu Lys Ala Glu Met Phe Asn Ala Trp Met Ala Arg
            595                 600                 605

Gly Glu Ile Pro Glu Ile Leu Arg Gln Cys Arg Thr Val Phe Val Pro
            610                 615                 620

Lys Val Glu Arg Pro Gly Gly Pro Gly Glu Tyr Arg Pro Ile Ser Ile
625                 630                 635                 640

Ala Ser Ile Pro Leu Arg His Phe His Ser Ile Leu Ala Arg Arg Leu
                    645                 650                 655

Leu Ala Cys Cys Pro Pro Asp Ala Arg Gln Arg Gly Phe Ile Cys Ala
            660                 665                 670

Asp Gly Thr Leu Glu Asn Ser Ala Val Leu Asp Ala Val Leu Gly Asp
            675                 680                 685

Ser Arg Lys Lys Leu Arg Glu Cys His Val Ala Val Leu Asp Phe Ala
    690                 695                 700

Lys Ala Phe Asp Thr Val Ser His Glu Ala Leu Val Glu Leu Leu Arg
705                 710                 715                 720

Leu Arg Gly Met Pro Glu Gln Phe Cys Gly Tyr Ile Ala His Leu Tyr
                    725                 730                 735

Asp Thr Ala Ser Thr Thr Leu Ala Val Asn Asn Glu Met Ser Ser Pro
            740                 745                 750

Val Lys Val Gly Arg Gly Val Arg Gln Gly Asp Pro Leu Ser Pro Ile
            755                 760                 765

Leu Phe Asn Val Val Met Asp Leu Ile Leu Ala Ser Leu Pro Glu Arg
            770                 775                 780

Val Gly Tyr Arg Leu Glu Met Glu Leu Val Ser Ala Leu Ala Tyr Ala
785                 790                 795                 800

Asp Asp Leu Val Leu Leu Ala Gly Ser Lys Val Gly Met Gln Glu Ser
            805                 810                 815

Ile Ser Ala Val Asp Cys Val Gly Arg Gln Met Gly Leu Arg Leu Asn
            820                 825                 830

Cys Arg Lys Ser Ala Val Leu Ser Met Ile Pro Asp Gly His Arg Lys
            835                 840                 845

Lys His His Tyr Leu Thr Glu Arg Thr Phe Asn Ile Gly Gly Lys Pro
            850                 855                 860

Leu Arg Gln Val Ser Cys Val Glu Arg Trp Arg Tyr Leu Gly Val Asp
865                 870                 875                 880

Phe Glu Ala Ser Gly Cys Val Thr Leu Glu His Ser Ile Ser Ser Ala
                    885                 890                 895

Leu Asn Asn Ile Ser Arg Ala Pro Leu Lys Pro Gln Gln Arg Leu Glu
            900                 905                 910

Ile Leu Arg Ala His Leu Ile Pro Arg Phe Gln His Gly Phe Val Leu
            915                 920                 925

Gly Asn Ile Ser Asp Asp Arg Leu Arg Met Leu Asp Val Gln Ile Arg
            930                 935                 940

Lys Ala Val Gly Gln Trp Leu Arg Leu Pro Ala Asp Val Pro Lys Ala
945                 950                 955                 960

Tyr Tyr His Ala Ala Val Gln Asp Gly Gly Leu Ala Ile Pro Ser Val
                    965                 970                 975

Arg Ala Thr Ile Pro Asp Leu Ile Val Arg Arg Phe Gly Gly Leu Asp
            980                 985                 990
```

```
Ser Ser Pro Trp Ser Val Ala Arg Ala Ala Ala Lys Ser Asp Lys Ile
            995                 1000                1005

Arg Lys Lys Leu Arg Trp Ala Trp Lys Gln Leu Arg Arg Phe Ser
        1010                1015                1020

Arg Val Asp Ser Thr Thr Gln Arg Pro Ser Val Arg Leu Phe Trp
        1025                1030                1035

Arg Glu His Leu His Ala Ser Val Asp Gly Arg Glu Leu Arg Glu
        1040                1045                1050

Ser Thr Arg Thr Pro Thr Ser Thr Lys Trp Ile Arg Glu Arg Cys
        1055                1060                1065

Ala Gln Ile Thr Gly Arg Asp Phe Val Gln Phe Val His Thr His
        1070                1075                1080

Ile Asn Ala Leu Pro Ser Arg Ile Arg Gly Ser Arg Gly Arg Arg
        1085                1090                1095

Gly Gly Gly Glu Ser Ser Leu Thr Cys Arg Ala Gly Cys Lys Val
        1100                1105                1110

Arg Glu Thr Thr Ala His Ile Leu Gln Gln Cys His Arg Thr His
        1115                1120                1125

Gly Gly Arg Ile Leu Arg His Asn Lys Ile Val Ser Phe Val Ala
        1130                1135                1140

Lys Ala Met Glu Glu Asn Lys Trp Thr Val Glu Leu Glu Pro Arg
        1145                1150                1155

Leu Arg Thr Ser Val Gly Leu Arg Lys Pro Asp Ile Ile Ala Ser
        1160                1165                1170

Arg Asp Gly Val Gly Val Ile Val Asp Val Gln Val Val Ser Gly
        1175                1180                1185

Gln Arg Ser Leu Asp Glu Leu His Arg Glu Lys Arg Asn Lys Tyr
        1190                1195                1200

Gly Asn His Gly Glu Leu Val Glu Leu Val Ala Gly Arg Leu Gly
        1205                1210                1215

Leu Pro Lys Ala Glu Cys Val Arg Ala Thr Ser Cys Thr Ile Ser
        1220                1225                1230

Trp Arg Gly Val Trp Ser Leu Thr Ser Tyr Lys Glu Leu Arg Ser
        1235                1240                1245

Ile Ile Gly Leu Arg Glu Pro Thr Leu Gln Ile Val Pro Ile Leu
        1250                1255                1260

Ala Leu Arg Gly Ser His Met Asn Trp Thr Arg Phe Asn Gln Met
        1265                1270                1275

Thr Ser Val Met Gly Gly Gly Val Gly
        1280                1285

<210> SEQ ID NO 9
<211> LENGTH: 1002
<212> TYPE: PRT
<213> ORGANISM: Artificial Sequence
<220> FEATURE:
<223> OTHER INFORMATION: Sso7d-Sso7d joined via a linker to the
      N-terminus of deltaR2 enzyme

<400> SEQUENCE: 9

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
                20                  25                  30

Tyr Asp Glu Gly Gly Gly Lys Thr Gly Arg Gly Ala Val Ser Glu Lys
                35                  40                  45
```

```
Asp Ala Pro Lys Glu Leu Leu Gln Met Leu Glu Lys Gln Lys Lys Val
    50                  55                  60
Gly Thr Gly Gly Gly Ser Gly Gly Gly Glu Ala Ala Lys Glu Ala
65                  70                  75                  80
Ala Ala Lys Ser Gly Gly Gly Ser Ala Thr Val Lys Phe Lys Tyr Lys
                85                  90                  95
Gly Glu Glu Lys Glu Val Asp Ile Ser Lys Ile Lys Lys Val Trp Arg
                100                 105                 110
Val Gly Lys Met Ile Ser Phe Thr Tyr Asp Glu Gly Gly Gly Lys Thr
                115                 120                 125
Gly Arg Gly Ala Val Ser Glu Lys Asp Ala Pro Lys Glu Leu Leu Gln
            130                 135                 140
Met Leu Glu Lys Gln Lys Lys Val Gly Thr Val Gly Thr Gly Gly Gly
145                 150                 155                 160
Ser Glu Ala Ala Ala Lys Gly Gly Ala Ser Thr Ala Leu Lys Thr Ala
                165                 170                 175
Gly Arg Arg Asn Asp Leu His Asp Asp Arg Thr Ala Ser Ala His Lys
            180                 185                 190
Thr Ser Arg Gln Lys Arg Arg Ala Glu Tyr Ala Arg Val Gln Glu Leu
        195                 200                 205
Tyr Lys Lys Cys Arg Ser Arg Ala Ala Ala Glu Val Ile Asp Gly Ala
        210                 215                 220
Cys Gly Gly Val Gly His Ser Leu Glu Glu Met Glu Thr Tyr Trp Arg
225                 230                 235                 240
Pro Ile Leu Glu Arg Val Ser Asp Ala Pro Gly Pro Thr Pro Glu Ala
                245                 250                 255
Leu His Ala Leu Gly Arg Ala Glu Trp His Gly Gly Asn Arg Asp Tyr
            260                 265                 270
Thr Gln Leu Trp Lys Pro Ile Ser Val Glu Glu Ile Lys Ala Ser Arg
        275                 280                 285
Phe Asp Trp Arg Thr Ser Pro Gly Pro Asp Gly Ile Arg Ser Gly Gln
        290                 295                 300
Trp Arg Ala Val Pro Val His Leu Lys Ala Glu Met Phe Asn Ala Trp
305                 310                 315                 320
Met Ala Arg Gly Glu Ile Pro Glu Ile Leu Arg Gln Cys Arg Thr Val
                325                 330                 335
Phe Val Pro Lys Val Glu Arg Pro Gly Gly Pro Gly Glu Tyr Arg Pro
                340                 345                 350
Ile Ser Ile Ala Ser Ile Pro Leu Arg His Phe His Ser Ile Leu Ala
            355                 360                 365
Arg Arg Leu Leu Ala Cys Cys Pro Pro Asp Ala Arg Gln Arg Gly Phe
        370                 375                 380
Ile Cys Ala Asp Gly Thr Leu Glu Asn Ser Ala Val Leu Asp Ala Val
385                 390                 395                 400
Leu Gly Asp Ser Arg Lys Lys Leu Arg Glu Cys His Val Ala Val Leu
                405                 410                 415
Asp Phe Ala Lys Ala Phe Asp Thr Val Ser His Glu Ala Leu Val Glu
            420                 425                 430
Leu Leu Arg Leu Arg Gly Met Pro Glu Gln Phe Cys Gly Tyr Ile Ala
        435                 440                 445
His Leu Tyr Asp Thr Ala Ser Thr Thr Leu Ala Val Asn Asn Glu Met
    450                 455                 460
```

```
Ser Ser Pro Val Lys Val Gly Arg Gly Val Arg Gln Gly Asp Pro Leu
465                 470                 475                 480

Ser Pro Ile Leu Phe Asn Val Val Met Asp Leu Ile Leu Ala Ser Leu
            485                 490                 495

Pro Glu Arg Val Gly Tyr Arg Leu Glu Met Glu Leu Val Ser Ala Leu
        500                 505                 510

Ala Tyr Ala Asp Asp Leu Val Leu Leu Ala Gly Ser Lys Val Gly Met
            515                 520             525

Gln Glu Ser Ile Ser Ala Val Asp Cys Val Gly Arg Gln Met Gly Leu
530                 535                 540

Arg Leu Asn Cys Arg Lys Ser Ala Val Leu Ser Met Ile Pro Asp Gly
545                 550                 555                 560

His Arg Lys Lys His His Tyr Leu Thr Glu Arg Thr Phe Asn Ile Gly
                565                 570                 575

Gly Lys Pro Leu Arg Gln Val Ser Cys Val Glu Arg Trp Arg Tyr Leu
                580                 585                 590

Gly Val Asp Phe Glu Ala Ser Gly Cys Val Thr Leu Glu His Ser Ile
            595                 600                 605

Ser Ser Ala Leu Asn Asn Ile Ser Arg Ala Pro Leu Lys Pro Gln Gln
610                 615                 620

Arg Leu Glu Ile Leu Arg Ala His Leu Ile Pro Arg Phe Gln His Gly
625                 630                 635                 640

Phe Val Leu Gly Asn Ile Ser Asp Asp Arg Leu Arg Met Leu Asp Val
                645                 650                 655

Gln Ile Arg Lys Ala Val Gly Gln Trp Leu Arg Leu Pro Ala Asp Val
            660                 665                 670

Pro Lys Ala Tyr Tyr His Ala Ala Val Gln Asp Gly Gly Leu Ala Ile
        675                 680                 685

Pro Ser Val Arg Ala Thr Ile Pro Asp Leu Ile Val Arg Arg Phe Gly
        690                 695                 700

Gly Leu Asp Ser Ser Pro Trp Ser Val Ala Arg Ala Ala Ala Lys Ser
705                 710                 715                 720

Asp Lys Ile Arg Lys Lys Leu Arg Trp Ala Trp Lys Gln Leu Arg Arg
                725                 730                 735

Phe Ser Arg Val Asp Ser Thr Thr Gln Arg Pro Ser Val Arg Leu Phe
            740                 745                 750

Trp Arg Glu His Leu His Ala Ser Val Asp Gly Arg Glu Leu Arg Glu
        755                 760                 765

Ser Thr Arg Thr Pro Thr Ser Thr Lys Trp Ile Arg Glu Arg Cys Ala
770                 775                 780

Gln Ile Thr Gly Arg Asp Phe Val Gln Phe Val His Thr His Ile Asn
785                 790                 795                 800

Ala Leu Pro Ser Arg Ile Arg Gly Ser Arg Gly Arg Gly Gly
                805                 810                 815

Glu Ser Ser Leu Thr Cys Arg Ala Gly Cys Lys Val Arg Glu Thr Thr
            820                 825                 830

Ala His Ile Leu Gln Gln Cys His Arg Thr His Gly Gly Arg Ile Leu
        835                 840                 845

Arg His Asn Lys Ile Val Ser Phe Val Ala Lys Ala Met Glu Glu Asn
850                 855                 860

Lys Trp Thr Val Glu Leu Glu Pro Arg Leu Arg Thr Ser Val Gly Leu
865                 870                 875                 880

Arg Lys Pro Asp Ile Ile Ala Ser Arg Asp Gly Val Gly Val Ile Val
```

```
                    885                 890                 895
Asp Val Gln Val Val Ser Gly Gln Arg Ser Leu Asp Glu Leu His Arg
            900                 905                 910

Glu Lys Arg Asn Lys Tyr Gly Asn His Gly Glu Leu Val Glu Leu Val
            915                 920                 925

Ala Gly Arg Leu Gly Leu Pro Lys Ala Glu Cys Val Arg Ala Thr Ser
            930                 935                 940

Cys Thr Ile Ser Trp Arg Gly Val Trp Ser Leu Thr Ser Tyr Lys Glu
945                 950                 955                 960

Leu Arg Ser Ile Ile Gly Leu Arg Glu Pro Thr Leu Gln Ile Val Pro
                965                 970                 975

Ile Leu Ala Leu Arg Gly Ser His Met Asn Trp Thr Arg Phe Asn Gln
            980                 985                 990

Met Thr Ser Val Met Gly Gly Gly  Val Gly
            995                 1000

<210> SEQ ID NO 10
<211> LENGTH: 1195
<212> TYPE: PRT
<213> ORGANISM: Artificial Sequence
<220> FEATURE:
<223> OTHER INFORMATION: Cren7 joined via a linker to the N-terminus of
      wild type R2 enzyme

<400> SEQUENCE: 10

Ser Ser Gly Lys Lys Pro Val Lys Val Lys Thr Pro Ala Gly Lys Glu
1               5                   10                  15

Ala Glu Leu Val Pro Glu Lys Val Trp Ala Leu Ala Pro Lys Gly Arg
                20                  25                  30

Lys Gly Val Lys Ile Gly Leu Phe Lys Asp Pro Glu Thr Gly Lys Tyr
            35                  40                  45

Phe Arg His Lys Leu Pro Asp Asp Tyr Pro Ile Val Gly Thr Val Gly
        50                  55                  60

Thr Gly Gly Gly Ser Glu Ala Ala Lys Gly Gly Ala Ser Thr Ala
65                  70                  75                  80

Leu Met Met Ala Ser Thr Ala Leu Ser Leu Met Gly Arg Cys Asn Pro
                85                  90                  95

Asp Gly Cys Thr Arg Gly Lys His Val Thr Ala Ala Pro Met Asp Gly
            100                 105                 110

Pro Arg Gly Pro Ser Ser Leu Ala Gly Thr Phe Gly Trp Gly Leu Ala
        115                 120                 125

Ile Pro Ala Gly Glu Pro Cys Gly Arg Val Cys Ser Pro Ala Thr Val
130                 135                 140

Gly Phe Phe Pro Val Ala Lys Lys Ser Asn Lys Glu Asn Arg Pro Glu
145                 150                 155                 160

Ala Ser Gly Leu Pro Leu Glu Ser Glu Arg Thr Gly Asp Asn Pro Thr
                165                 170                 175

Val Arg Gly Ser Ala Gly Ala Asp Pro Val Gly Gln Asp Ala Pro Gly
            180                 185                 190

Trp Thr Cys Gln Phe Cys Glu Arg Thr Phe Ser Thr Asn Arg Gly Leu
        195                 200                 205

Gly Val His Lys Arg Arg Ala His Pro Val Glu Thr Asn Thr Asp Ala
    210                 215                 220

Ala Pro Met Met Val Lys Arg Arg Trp His Gly Glu Glu Ile Asp Leu
225                 230                 235                 240
```

```
Leu Ala Arg Thr Glu Ala Arg Leu Leu Ala Glu Arg Gly Gln Cys Ser
            245                 250                 255

Gly Gly Asp Leu Phe Gly Ala Leu Pro Gly Phe Gly Arg Thr Leu Glu
        260                 265                 270

Ala Ile Lys Gly Gln Arg Arg Glu Pro Tyr Arg Ala Leu Val Gln
    275                 280                 285

Ala His Leu Ala Arg Phe Gly Ser Gln Pro Gly Pro Ser Ser Gly Gly
        290                 295                 300

Cys Ser Ala Glu Pro Asp Phe Arg Arg Ala Ser Gly Ala Glu Glu Ala
305                 310                 315                 320

Gly Glu Glu Arg Cys Ala Glu Asp Ala Ala Tyr Asp Pro Ser Ala
                325                 330                 335

Val Gly Gln Met Ser Pro Asp Ala Ala Arg Val Leu Ser Glu Leu Leu
            340                 345                 350

Glu Gly Ala Gly Arg Arg Ala Cys Arg Ala Met Arg Pro Lys Thr
                355                 360                 365

Ala Gly Arg Arg Asn Asp Leu His Asp Asp Arg Thr Ala Ser Ala His
        370                 375                 380

Lys Thr Ser Arg Gln Lys Arg Arg Ala Glu Tyr Ala Arg Val Gln Glu
385                 390                 395                 400

Leu Tyr Lys Lys Cys Arg Ser Arg Ala Ala Ala Glu Val Ile Asp Gly
                405                 410                 415

Ala Cys Gly Gly Val Gly His Ser Leu Glu Glu Met Glu Thr Tyr Trp
            420                 425                 430

Arg Pro Ile Leu Glu Arg Val Ser Asp Ala Pro Gly Pro Thr Pro Glu
                435                 440                 445

Ala Leu His Ala Leu Gly Arg Ala Glu Trp His Gly Gly Asn Arg Asp
        450                 455                 460

Tyr Thr Gln Leu Trp Lys Pro Ile Ser Val Glu Glu Ile Lys Ala Ser
465                 470                 475                 480

Arg Phe Asp Trp Arg Thr Ser Pro Gly Pro Asp Gly Ile Arg Ser Gly
                485                 490                 495

Gln Trp Arg Ala Val Pro Val His Leu Lys Ala Glu Met Phe Asn Ala
        500                 505                 510

Trp Met Ala Arg Gly Glu Ile Pro Glu Ile Leu Arg Gln Cys Arg Thr
        515                 520                 525

Val Phe Val Pro Lys Val Glu Arg Pro Gly Gly Pro Gly Glu Tyr Arg
        530                 535                 540

Pro Ile Ser Ile Ala Ser Ile Pro Leu Arg His Phe His Ser Ile Leu
545                 550                 555                 560

Ala Arg Arg Leu Leu Ala Cys Cys Pro Pro Asp Ala Arg Gln Arg Gly
                565                 570                 575

Phe Ile Cys Ala Asp Gly Thr Leu Glu Asn Ser Ala Val Leu Asp Ala
        580                 585                 590

Val Leu Gly Asp Ser Arg Lys Lys Leu Arg Glu Cys His Val Ala Val
        595                 600                 605

Leu Asp Phe Ala Lys Ala Phe Asp Thr Val Ser His Glu Ala Leu Val
        610                 615                 620

Glu Leu Leu Arg Leu Arg Gly Met Pro Glu Gln Phe Cys Gly Tyr Ile
625                 630                 635                 640

Ala His Leu Tyr Asp Thr Ala Ser Thr Thr Leu Ala Val Asn Asn Glu
                645                 650                 655

Met Ser Ser Pro Val Lys Val Gly Arg Gly Val Arg Gln Gly Asp Pro
```

-continued

```
                660                 665                 670
Leu Ser Pro Ile Leu Phe Asn Val Val Met Asp Leu Ile Leu Ala Ser
            675                 680                 685
Leu Pro Glu Arg Val Gly Tyr Arg Leu Glu Met Glu Leu Val Ser Ala
    690                 695                 700
Leu Ala Tyr Ala Asp Asp Leu Val Leu Leu Ala Gly Ser Lys Val Gly
705                 710                 715                 720
Met Gln Glu Ser Ile Ser Ala Val Asp Cys Val Gly Arg Gln Met Gly
                725                 730                 735
Leu Arg Leu Asn Cys Arg Lys Ser Ala Val Leu Ser Met Ile Pro Asp
            740                 745                 750
Gly His Arg Lys Lys His His Tyr Leu Thr Glu Arg Thr Phe Asn Ile
        755                 760                 765
Gly Gly Lys Pro Leu Arg Gln Val Ser Cys Val Glu Arg Trp Arg Tyr
    770                 775                 780
Leu Gly Val Asp Phe Glu Ala Ser Gly Cys Val Thr Leu Glu His Ser
785                 790                 795                 800
Ile Ser Ser Ala Leu Asn Asn Ile Ser Arg Ala Pro Leu Lys Pro Gln
                805                 810                 815
Gln Arg Leu Glu Ile Leu Arg Ala His Leu Ile Pro Arg Phe Gln His
            820                 825                 830
Gly Phe Val Leu Gly Asn Ile Ser Asp Asp Arg Leu Arg Met Leu Asp
        835                 840                 845
Val Gln Ile Arg Lys Ala Val Gly Gln Trp Leu Arg Leu Pro Ala Asp
    850                 855                 860
Val Pro Lys Ala Tyr Tyr His Ala Ala Val Gln Asp Gly Gly Leu Ala
865                 870                 875                 880
Ile Pro Ser Val Arg Ala Thr Ile Pro Asp Leu Ile Val Arg Arg Phe
                885                 890                 895
Gly Gly Leu Asp Ser Ser Pro Trp Ser Val Ala Arg Ala Ala Ala Lys
            900                 905                 910
Ser Asp Lys Ile Arg Lys Lys Leu Arg Trp Ala Trp Lys Gln Leu Arg
        915                 920                 925
Arg Phe Ser Arg Val Asp Ser Thr Thr Gln Arg Pro Ser Val Arg Leu
    930                 935                 940
Phe Trp Arg Glu His Leu His Ala Ser Val Asp Gly Arg Glu Leu Arg
945                 950                 955                 960
Glu Ser Thr Arg Thr Pro Thr Ser Thr Lys Trp Ile Arg Glu Arg Cys
                965                 970                 975
Ala Gln Ile Thr Gly Arg Asp Phe Val Gln Phe Val His Thr His Ile
            980                 985                 990
Asn Ala Leu Pro Ser Arg Ile Arg  Gly Ser Arg Gly Arg  Arg Gly Gly
        995                 1000                1005
Gly Glu  Ser Ser Leu Thr Cys  Arg Ala Gly Cys Lys  Val Arg Glu
    1010                1015                1020
Thr Thr  Ala His Ile Leu Gln  Gln Cys His Arg Thr  His Gly Gly
    1025                1030                1035
Arg Ile  Leu Arg His Asn Lys  Ile Val Ser Phe Val  Ala Lys Ala
    1040                1045                1050
Met Glu  Glu Asn Lys Trp Thr  Val Glu Leu Glu Pro  Arg Leu Arg
    1055                1060                1065
Thr Ser  Val Gly Leu Arg Lys  Pro Asp Ile Ile Ala  Ser Arg Asp
    1070                1075                1080
```

```
Gly Val Gly Val Ile Val Asp Val Gln Val Val Ser Gly Gln Arg
    1085                1090                1095

Ser Leu Asp Glu Leu His Arg Glu Lys Arg Asn Lys Tyr Gly Asn
    1100                1105                1110

His Gly Glu Leu Val Glu Leu Val Ala Gly Arg Leu Gly Leu Pro
    1115                1120                1125

Lys Ala Glu Cys Val Arg Ala Thr Ser Cys Thr Ile Ser Trp Arg
    1130                1135                1140

Gly Val Trp Ser Leu Thr Ser Tyr Lys Glu Leu Arg Ser Ile Ile
    1145                1150                1155

Gly Leu Arg Glu Pro Thr Leu Gln Ile Val Pro Ile Leu Ala Leu
    1160                1165                1170

Arg Gly Ser His Met Asn Trp Thr Arg Phe Asn Gln Met Thr Ser
    1175                1180                1185

Val Met Gly Gly Gly Val Gly
    1190            1195

<210> SEQ ID NO 11
<211> LENGTH: 935
<212> TYPE: PRT
<213> ORGANISM: Artificial Sequence
<220> FEATURE:
<223> OTHER INFORMATION: His Tag joined via a linker to Cren7 joined via
      a linker to the N-terminus of deltaR2 enzyme

<400> SEQUENCE: 11

Met Ala His His His His His His Val Gly Thr Val Gly Thr Gly Gly
1               5                   10                  15

Gly Ser Gly Gly Ala Ser Thr Ala Leu Ser Ser Gly Lys Lys Pro Val
                20                  25                  30

Lys Val Lys Thr Pro Ala Gly Lys Glu Ala Glu Leu Val Pro Glu Lys
            35                  40                  45

Val Trp Ala Leu Ala Pro Lys Gly Arg Lys Gly Val Lys Ile Gly Leu
        50                  55                  60

Phe Lys Asp Pro Glu Thr Gly Lys Tyr Phe Arg His Lys Leu Pro Asp
65                  70                  75                  80

Asp Tyr Pro Ile Val Gly Thr Val Gly Thr Gly Gly Ser Glu Ala
                85                  90                  95

Ala Ala Lys Gly Gly Ala Ser Thr Ala Leu Lys Thr Ala Gly Arg Arg
            100                 105                 110

Asn Asp Leu His Asp Asp Arg Thr Ala Ser Ala His Lys Thr Ser Arg
        115                 120                 125

Gln Lys Arg Arg Ala Glu Tyr Ala Arg Val Gln Glu Leu Tyr Lys Lys
    130                 135                 140

Cys Arg Ser Arg Ala Ala Ala Glu Val Ile Asp Gly Ala Cys Gly Gly
145                 150                 155                 160

Val Gly His Ser Leu Glu Glu Met Glu Thr Tyr Trp Arg Pro Ile Leu
                165                 170                 175

Glu Arg Val Ser Asp Ala Pro Gly Pro Thr Pro Glu Ala Leu His Ala
            180                 185                 190

Leu Gly Arg Ala Glu Trp His Gly Gly Asn Arg Asp Tyr Thr Gln Leu
        195                 200                 205

Trp Lys Pro Ile Ser Val Glu Glu Ile Lys Ala Ser Arg Phe Asp Trp
    210                 215                 220

Arg Thr Ser Pro Gly Pro Asp Gly Ile Arg Ser Gly Gln Trp Arg Ala
```

```
            225                 230                 235                 240
Val Pro Val His Leu Lys Ala Glu Met Phe Asn Ala Trp Met Ala Arg
                245                 250                 255
Gly Glu Ile Pro Glu Ile Leu Arg Gln Cys Arg Thr Val Phe Val Pro
                260                 265                 270
Lys Val Glu Arg Pro Gly Gly Pro Gly Tyr Arg Pro Ile Ser Ile
                275                 280                 285
Ala Ser Ile Pro Leu Arg His Phe His Ser Ile Leu Ala Arg Arg Leu
            290                 295                 300
Leu Ala Cys Cys Pro Pro Asp Ala Arg Gln Arg Gly Phe Ile Cys Ala
305                 310                 315                 320
Asp Gly Thr Leu Glu Asn Ser Ala Val Leu Asp Ala Val Leu Gly Asp
                325                 330                 335
Ser Arg Lys Lys Leu Arg Glu Cys His Val Ala Val Leu Asp Phe Ala
                340                 345                 350
Lys Ala Phe Asp Thr Val Ser His Glu Ala Leu Val Glu Leu Leu Arg
                355                 360                 365
Leu Arg Gly Met Pro Glu Gln Phe Cys Gly Tyr Ile Ala His Leu Tyr
            370                 375                 380
Asp Thr Ala Ser Thr Thr Leu Ala Val Asn Asn Glu Met Ser Ser Pro
385                 390                 395                 400
Val Lys Val Gly Arg Gly Val Arg Gln Gly Asp Pro Leu Ser Pro Ile
                405                 410                 415
Leu Phe Asn Val Val Met Asp Leu Ile Leu Ala Ser Leu Pro Glu Arg
                420                 425                 430
Val Gly Tyr Arg Leu Glu Met Glu Leu Val Ser Ala Leu Ala Tyr Ala
            435                 440                 445
Asp Asp Leu Val Leu Leu Ala Gly Ser Lys Val Gly Met Gln Glu Ser
            450                 455                 460
Ile Ser Ala Val Asp Cys Val Gly Arg Gln Met Gly Leu Arg Leu Asn
465                 470                 475                 480
Cys Arg Lys Ser Ala Val Leu Ser Met Ile Pro Asp Gly His Arg Lys
                485                 490                 495
Lys His His Tyr Leu Thr Glu Arg Thr Phe Asn Ile Gly Gly Lys Pro
                500                 505                 510
Leu Arg Gln Val Ser Cys Val Glu Arg Trp Arg Tyr Leu Gly Val Asp
                515                 520                 525
Phe Glu Ala Ser Gly Cys Val Thr Leu Glu His Ser Ile Ser Ser Ala
            530                 535                 540
Leu Asn Asn Ile Ser Arg Ala Pro Leu Lys Pro Gln Gln Arg Leu Glu
545                 550                 555                 560
Ile Leu Arg Ala His Leu Ile Pro Arg Phe Gln His Gly Phe Val Leu
                565                 570                 575
Gly Asn Ile Ser Asp Asp Arg Leu Arg Met Leu Asp Val Gln Ile Arg
                580                 585                 590
Lys Ala Val Gly Gln Trp Leu Arg Leu Pro Ala Asp Val Pro Lys Ala
                595                 600                 605
Tyr Tyr His Ala Ala Val Gln Asp Gly Gly Leu Ala Ile Pro Ser Val
            610                 615                 620
Arg Ala Thr Ile Pro Asp Leu Ile Val Arg Arg Phe Gly Gly Leu Asp
625                 630                 635                 640
Ser Ser Pro Trp Ser Val Ala Arg Ala Ala Lys Ser Asp Lys Ile
                645                 650                 655
```

-continued

```
Arg Lys Lys Leu Arg Trp Ala Trp Lys Gln Leu Arg Arg Phe Ser Arg
            660                 665                 670

Val Asp Ser Thr Thr Gln Arg Pro Ser Val Arg Leu Phe Trp Arg Glu
        675                 680                 685

His Leu His Ala Ser Val Asp Gly Arg Glu Leu Arg Glu Ser Thr Arg
    690                 695                 700

Thr Pro Thr Ser Thr Lys Trp Ile Arg Glu Arg Cys Ala Gln Ile Thr
705                 710                 715                 720

Gly Arg Asp Phe Val Gln Phe Val His Thr His Ile Asn Ala Leu Pro
                725                 730                 735

Ser Arg Ile Arg Gly Ser Arg Gly Arg Gly Gly Glu Ser Ser
            740                 745                 750

Leu Thr Cys Arg Ala Gly Cys Lys Val Arg Glu Thr Thr Ala His Ile
        755                 760                 765

Leu Gln Gln Cys His Arg Thr His Gly Gly Arg Ile Leu Arg His Asn
    770                 775                 780

Lys Ile Val Ser Phe Val Ala Lys Ala Met Glu Glu Asn Lys Trp Thr
785                 790                 795                 800

Val Glu Leu Glu Pro Arg Leu Arg Thr Ser Val Gly Leu Arg Lys Pro
                805                 810                 815

Asp Ile Ile Ala Ser Arg Asp Gly Val Gly Val Ile Val Asp Val Gln
            820                 825                 830

Val Val Ser Gly Gln Arg Ser Leu Asp Glu Leu His Arg Glu Lys Arg
        835                 840                 845

Asn Lys Tyr Gly Asn His Gly Glu Leu Val Glu Leu Val Ala Gly Arg
    850                 855                 860

Leu Gly Leu Pro Lys Ala Glu Cys Val Arg Ala Thr Ser Cys Thr Ile
865                 870                 875                 880

Ser Trp Arg Gly Val Trp Ser Leu Thr Ser Tyr Lys Glu Leu Arg Ser
                885                 890                 895

Ile Ile Gly Leu Arg Glu Pro Thr Leu Gln Ile Val Pro Ile Leu Ala
            900                 905                 910

Leu Arg Gly Ser His Met Asn Trp Thr Arg Phe Asn Gln Met Thr Ser
        915                 920                 925

Val Met Gly Gly Gly Val Gly
    930                 935

<210> SEQ ID NO 12
<211> LENGTH: 1280
<212> TYPE: PRT
<213> ORGANISM: Artificial Sequence
<220> FEATURE:
<223> OTHER INFORMATION: Cren7-Cren7 joined via a linker to the
      N-terminus of wild type R2 enzyme

<400> SEQUENCE: 12

Ser Ser Gly Lys Lys Pro Val Lys Val Lys Thr Pro Ala Gly Lys Glu
1               5                   10                  15

Ala Glu Leu Val Pro Glu Lys Val Trp Ala Leu Ala Pro Lys Gly Arg
                20                  25                  30

Lys Gly Val Lys Ile Gly Leu Phe Lys Asp Pro Glu Thr Gly Lys Tyr
            35                  40                  45

Phe Arg His Lys Leu Pro Asp Asp Tyr Pro Ile Val Gly Thr Gly Gly
        50                  55                  60

Gly Ser Gly Gly Gly Glu Ala Ala Ala Lys Glu Ala Ala Ala Lys Ser
```

```
                65                  70                  75                  80
Gly Gly Gly Ser Ala Ser Ser Gly Lys Lys Pro Val Lys Val Lys Thr
                        85                  90                  95

Pro Ala Gly Lys Glu Ala Glu Leu Val Pro Glu Lys Val Trp Ala Leu
                100                 105                 110

Ala Pro Lys Gly Arg Lys Gly Val Lys Ile Gly Leu Phe Lys Asp Pro
            115                 120                 125

Glu Thr Gly Lys Tyr Phe Arg His Lys Leu Pro Asp Asp Tyr Pro Ile
        130                 135                 140

Val Gly Thr Val Gly Thr Gly Gly Ser Glu Ala Ala Lys Gly
145                 150                 155                 160

Gly Ala Ser Thr Ala Leu Met Met Ala Ser Thr Ala Leu Ser Leu Met
                    165                 170                 175

Gly Arg Cys Asn Pro Asp Gly Cys Thr Arg Gly Lys His Val Thr Ala
                180                 185                 190

Ala Pro Met Asp Gly Pro Arg Gly Pro Ser Ser Leu Ala Gly Thr Phe
            195                 200                 205

Gly Trp Gly Leu Ala Ile Pro Ala Gly Glu Pro Cys Gly Arg Val Cys
        210                 215                 220

Ser Pro Ala Thr Val Gly Phe Phe Pro Val Ala Lys Lys Ser Asn Lys
225                 230                 235                 240

Glu Asn Arg Pro Glu Ala Ser Gly Leu Pro Leu Glu Ser Glu Arg Thr
                    245                 250                 255

Gly Asp Asn Pro Thr Val Arg Gly Ser Ala Gly Ala Asp Pro Val Gly
                260                 265                 270

Gln Asp Ala Pro Gly Trp Thr Cys Gln Phe Cys Glu Arg Thr Phe Ser
            275                 280                 285

Thr Asn Arg Gly Leu Gly Val His Lys Arg Arg Ala His Pro Val Glu
        290                 295                 300

Thr Asn Thr Asp Ala Ala Pro Met Met Val Lys Arg Arg Trp His Gly
305                 310                 315                 320

Glu Glu Ile Asp Leu Leu Ala Arg Thr Glu Ala Arg Leu Leu Ala Glu
                    325                 330                 335

Arg Gly Gln Cys Ser Gly Gly Asp Leu Phe Gly Ala Leu Pro Gly Phe
                340                 345                 350

Gly Arg Thr Leu Glu Ala Ile Lys Gly Gln Arg Arg Glu Pro Tyr
            355                 360                 365

Arg Ala Leu Val Gln Ala His Leu Ala Arg Phe Gly Ser Gln Pro Gly
        370                 375                 380

Pro Ser Ser Gly Gly Cys Ser Ala Glu Pro Asp Phe Arg Arg Ala Ser
385                 390                 395                 400

Gly Ala Glu Glu Ala Gly Glu Glu Arg Cys Ala Glu Asp Ala Ala Ala
                    405                 410                 415

Tyr Asp Pro Ser Ala Val Gly Gln Met Ser Pro Asp Ala Ala Arg Val
                420                 425                 430

Leu Ser Glu Leu Leu Glu Gly Ala Gly Arg Arg Ala Cys Arg Ala
            435                 440                 445

Met Arg Pro Lys Thr Ala Gly Arg Arg Asn Asp Leu His Asp Asp Arg
        450                 455                 460

Thr Ala Ser Ala His Lys Thr Ser Arg Gln Lys Arg Arg Ala Glu Tyr
465                 470                 475                 480

Ala Arg Val Gln Glu Leu Tyr Lys Lys Cys Arg Ser Arg Ala Ala Ala
                    485                 490                 495
```

```
Glu Val Ile Asp Gly Ala Cys Gly Gly Val Gly His Ser Leu Glu Glu
            500                 505                 510

Met Glu Thr Tyr Trp Arg Pro Ile Leu Glu Arg Val Ser Asp Ala Pro
            515                 520                 525

Gly Pro Thr Pro Glu Ala Leu His Ala Leu Gly Arg Ala Glu Trp His
            530                 535                 540

Gly Gly Asn Arg Asp Tyr Thr Gln Leu Trp Lys Pro Ile Ser Val Glu
545                 550                 555                 560

Glu Ile Lys Ala Ser Arg Phe Asp Trp Arg Thr Ser Pro Gly Pro Asp
                565                 570                 575

Gly Ile Arg Ser Gly Gln Trp Arg Ala Val Pro Val His Leu Lys Ala
            580                 585                 590

Glu Met Phe Asn Ala Trp Met Ala Arg Gly Glu Ile Pro Glu Ile Leu
            595                 600                 605

Arg Gln Cys Arg Thr Val Phe Val Pro Lys Val Glu Arg Pro Gly Gly
        610                 615                 620

Pro Gly Glu Tyr Arg Pro Ile Ser Ile Ala Ser Ile Pro Leu Arg His
625                 630                 635                 640

Phe His Ser Ile Leu Ala Arg Arg Leu Leu Ala Cys Cys Pro Pro Asp
                645                 650                 655

Ala Arg Gln Arg Gly Phe Ile Cys Ala Asp Gly Thr Leu Glu Asn Ser
                660                 665                 670

Ala Val Leu Asp Ala Val Leu Gly Asp Ser Arg Lys Lys Leu Arg Glu
            675                 680                 685

Cys His Val Ala Val Leu Asp Phe Ala Lys Ala Phe Asp Thr Val Ser
            690                 695                 700

His Glu Ala Leu Val Glu Leu Leu Arg Leu Arg Gly Met Pro Glu Gln
705                 710                 715                 720

Phe Cys Gly Tyr Ile Ala His Leu Tyr Asp Thr Ala Ser Thr Thr Leu
                725                 730                 735

Ala Val Asn Asn Glu Met Ser Ser Pro Val Lys Val Gly Arg Gly Val
            740                 745                 750

Arg Gln Gly Asp Pro Leu Ser Pro Ile Leu Phe Asn Val Val Met Asp
            755                 760                 765

Leu Ile Leu Ala Ser Leu Pro Glu Arg Val Gly Tyr Arg Leu Glu Met
770                 775                 780

Glu Leu Val Ser Ala Leu Ala Tyr Ala Asp Asp Leu Val Leu Leu Ala
785                 790                 795                 800

Gly Ser Lys Val Gly Met Gln Glu Ser Ile Ser Ala Val Asp Cys Val
                805                 810                 815

Gly Arg Gln Met Gly Leu Arg Leu Asn Cys Arg Lys Ser Ala Val Leu
            820                 825                 830

Ser Met Ile Pro Asp Gly His Arg Lys Lys His Tyr Leu Thr Glu
            835                 840                 845

Arg Thr Phe Asn Ile Gly Gly Lys Pro Leu Arg Gln Val Ser Cys Val
            850                 855                 860

Glu Arg Trp Arg Tyr Leu Gly Val Asp Phe Glu Ala Ser Gly Cys Val
865                 870                 875                 880

Thr Leu Glu His Ser Ile Ser Ser Ala Leu Asn Asn Ile Ser Arg Ala
                885                 890                 895

Pro Leu Lys Pro Gln Gln Arg Leu Glu Ile Leu Arg Ala His Leu Ile
            900                 905                 910
```

-continued

```
Pro Arg Phe Gln His Gly Phe Val Leu Gly Asn Ile Ser Asp Asp Arg
            915                 920                 925

Leu Arg Met Leu Asp Val Gln Ile Arg Lys Ala Val Gly Gln Trp Leu
    930                 935                 940

Arg Leu Pro Ala Asp Val Pro Lys Ala Tyr Tyr His Ala Ala Val Gln
945                 950                 955                 960

Asp Gly Gly Leu Ala Ile Pro Ser Val Arg Ala Thr Ile Pro Asp Leu
                965                 970                 975

Ile Val Arg Arg Phe Gly Gly Leu Asp Ser Ser Pro Trp Ser Val Ala
            980                 985                 990

Arg Ala Ala Ala Lys Ser Asp Lys Ile Arg Lys Lys Leu Arg Trp Ala
        995                 1000                1005

Trp Lys Gln Leu Arg Arg Phe Ser Arg Val Asp Ser Thr Thr Gln
    1010                1015                1020

Arg Pro Ser Val Arg Leu Phe Trp Arg Glu His Leu His Ala Ser
    1025                1030                1035

Val Asp Gly Arg Glu Leu Arg Glu Ser Thr Arg Thr Pro Thr Ser
    1040                1045                1050

Thr Lys Trp Ile Arg Glu Arg Cys Ala Gln Ile Thr Gly Arg Asp
    1055                1060                1065

Phe Val Gln Phe Val His Thr His Ile Asn Ala Leu Pro Ser Arg
    1070                1075                1080

Ile Arg Gly Ser Arg Gly Arg Gly Gly Gly Glu Ser Ser Leu
    1085                1090                1095

Thr Cys Arg Ala Gly Cys Lys Val Arg Glu Thr Thr Ala His Ile
    1100                1105                1110

Leu Gln Gln Cys His Arg Thr His Gly Gly Arg Ile Leu Arg His
    1115                1120                1125

Asn Lys Ile Val Ser Phe Val Ala Lys Ala Met Glu Glu Asn Lys
    1130                1135                1140

Trp Thr Val Glu Leu Glu Pro Arg Leu Arg Thr Ser Val Gly Leu
    1145                1150                1155

Arg Lys Pro Asp Ile Ile Ala Ser Arg Asp Gly Val Gly Val Ile
    1160                1165                1170

Val Asp Val Gln Val Val Ser Gly Gln Arg Ser Leu Asp Glu Leu
    1175                1180                1185

His Arg Glu Lys Arg Asn Lys Tyr Gly Asn His Gly Glu Leu Val
    1190                1195                1200

Glu Leu Val Ala Gly Arg Leu Gly Leu Pro Lys Ala Glu Cys Val
    1205                1210                1215

Arg Ala Thr Ser Cys Thr Ile Ser Trp Arg Gly Val Trp Ser Leu
    1220                1225                1230

Thr Ser Tyr Lys Glu Leu Arg Ser Ile Ile Gly Leu Arg Glu Pro
    1235                1240                1245

Thr Leu Gln Ile Val Pro Ile Leu Ala Leu Arg Gly Ser His Met
    1250                1255                1260

Asn Trp Thr Arg Phe Asn Gln Met Thr Ser Val Met Gly Gly Gly
    1265                1270                1275

Val Gly
    1280

<210> SEQ ID NO 13
<211> LENGTH: 1020
<212> TYPE: PRT
```

<213> ORGANISM: Artificial Sequence
<220> FEATURE:
<223> OTHER INFORMATION: His Tag joined via a linker to Cren7-Cren7
      joined via a linker to the N-terminus of deltaR2 enzyme

<400> SEQUENCE: 13

```
Met Ala His His His His His Val Gly Thr Val Gly Thr Gly Gly
1               5                   10                  15

Gly Ser Gly Gly Ala Ser Thr Ala Leu Ser Ser Gly Lys Lys Pro Val
            20                  25                  30

Lys Val Lys Thr Pro Ala Gly Lys Glu Ala Glu Leu Val Pro Glu Lys
            35                  40                  45

Val Trp Ala Leu Ala Pro Lys Gly Arg Lys Gly Val Lys Ile Gly Leu
50                  55                  60

Phe Lys Asp Pro Glu Thr Gly Lys Tyr Phe Arg His Lys Leu Pro Asp
65                  70                  75                  80

Asp Tyr Pro Ile Val Gly Thr Gly Gly Ser Gly Gly Gly Glu Ala
                85                  90                  95

Ala Ala Lys Glu Ala Ala Ala Lys Ser Gly Gly Ser Ala Ser Ser
            100                 105                 110

Gly Lys Lys Pro Val Lys Val Lys Thr Pro Ala Gly Lys Glu Ala Glu
            115                 120                 125

Leu Val Pro Glu Lys Val Trp Ala Leu Ala Pro Lys Gly Arg Lys Gly
130                 135                 140

Val Lys Ile Gly Leu Phe Lys Asp Pro Glu Thr Gly Lys Tyr Phe Arg
145                 150                 155                 160

His Lys Leu Pro Asp Asp Tyr Pro Ile Val Gly Thr Val Gly Thr Gly
                165                 170                 175

Gly Gly Ser Glu Ala Ala Ala Lys Gly Gly Ala Ser Thr Ala Leu Lys
            180                 185                 190

Thr Ala Gly Arg Arg Asn Asp Leu His Asp Asp Arg Thr Ala Ser Ala
            195                 200                 205

His Lys Thr Ser Arg Gln Lys Arg Arg Ala Glu Tyr Ala Arg Val Gln
            210                 215                 220

Glu Leu Tyr Lys Lys Cys Arg Ser Arg Ala Ala Ala Glu Val Ile Asp
225                 230                 235                 240

Gly Ala Cys Gly Gly Val Gly His Ser Leu Glu Glu Met Glu Thr Tyr
                245                 250                 255

Trp Arg Pro Ile Leu Glu Arg Val Ser Asp Ala Pro Gly Pro Thr Pro
                260                 265                 270

Glu Ala Leu His Ala Leu Gly Arg Ala Glu Trp His Gly Gly Asn Arg
            275                 280                 285

Asp Tyr Thr Gln Leu Trp Lys Pro Ile Ser Val Glu Glu Ile Lys Ala
            290                 295                 300

Ser Arg Phe Asp Trp Arg Thr Ser Pro Gly Pro Asp Gly Ile Arg Ser
305                 310                 315                 320

Gly Gln Trp Arg Ala Val Pro Val His Leu Lys Ala Glu Met Phe Asn
                325                 330                 335

Ala Trp Met Ala Arg Gly Glu Ile Pro Glu Ile Leu Arg Gln Cys Arg
                340                 345                 350

Thr Val Phe Val Pro Lys Val Glu Arg Pro Gly Gly Pro Gly Glu Tyr
            355                 360                 365

Arg Pro Ile Ser Ile Ala Ser Ile Pro Leu Arg His Phe His Ser Ile
            370                 375                 380
```

```
Leu Ala Arg Arg Leu Leu Ala Cys Cys Pro Pro Asp Ala Arg Gln Arg
385                 390                 395                 400

Gly Phe Ile Cys Ala Asp Gly Thr Leu Glu Asn Ser Ala Val Leu Asp
            405                 410                 415

Ala Val Leu Gly Asp Ser Arg Lys Leu Arg Glu Cys His Val Ala
        420                 425                 430

Val Leu Asp Phe Ala Lys Ala Phe Asp Thr Val Ser His Glu Ala Leu
        435                 440                 445

Val Glu Leu Leu Arg Leu Arg Gly Met Pro Glu Gln Phe Cys Gly Tyr
    450                 455                 460

Ile Ala His Leu Tyr Asp Thr Ala Ser Thr Thr Leu Ala Val Asn Asn
465                 470                 475                 480

Glu Met Ser Ser Pro Val Lys Val Gly Arg Gly Val Arg Gln Gly Asp
                485                 490                 495

Pro Leu Ser Pro Ile Leu Phe Asn Val Val Met Asp Leu Ile Leu Ala
                500                 505                 510

Ser Leu Pro Glu Arg Val Gly Tyr Arg Leu Glu Met Glu Leu Val Ser
        515                 520                 525

Ala Leu Ala Tyr Ala Asp Asp Leu Val Leu Leu Ala Gly Ser Lys Val
        530                 535                 540

Gly Met Gln Glu Ser Ile Ser Ala Val Asp Cys Val Gly Arg Gln Met
545                 550                 555                 560

Gly Leu Arg Leu Asn Cys Arg Lys Ser Ala Val Leu Ser Met Ile Pro
                565                 570                 575

Asp Gly His Arg Lys Lys His His Tyr Leu Thr Glu Arg Thr Phe Asn
            580                 585                 590

Ile Gly Gly Lys Pro Leu Arg Gln Val Ser Cys Val Glu Arg Trp Arg
        595                 600                 605

Tyr Leu Gly Val Asp Phe Glu Ala Ser Gly Cys Val Thr Leu Glu His
    610                 615                 620

Ser Ile Ser Ser Ala Leu Asn Asn Ile Ser Arg Ala Pro Leu Lys Pro
625                 630                 635                 640

Gln Gln Arg Leu Glu Ile Leu Arg Ala His Leu Ile Pro Arg Phe Gln
                645                 650                 655

His Gly Phe Val Leu Gly Asn Ile Ser Asp Asp Arg Leu Arg Met Leu
            660                 665                 670

Asp Val Gln Ile Arg Lys Ala Val Gly Gln Trp Leu Arg Leu Pro Ala
        675                 680                 685

Asp Val Pro Lys Ala Tyr Tyr His Ala Ala Val Gln Asp Gly Gly Leu
        690                 695                 700

Ala Ile Pro Ser Val Arg Ala Thr Ile Pro Asp Leu Ile Val Arg Arg
705                 710                 715                 720

Phe Gly Gly Leu Asp Ser Ser Pro Trp Ser Val Ala Arg Ala Ala Ala
                725                 730                 735

Lys Ser Asp Lys Ile Arg Lys Lys Leu Arg Trp Ala Trp Lys Gln Leu
            740                 745                 750

Arg Arg Phe Ser Arg Val Asp Ser Thr Thr Gln Arg Pro Ser Val Arg
        755                 760                 765

Leu Phe Trp Arg Glu His Leu His Ala Ser Val Asp Gly Arg Glu Leu
        770                 775                 780

Arg Glu Ser Thr Arg Thr Pro Thr Ser Thr Lys Trp Ile Arg Glu Arg
785                 790                 795                 800

Cys Ala Gln Ile Thr Gly Arg Asp Phe Val Gln Phe Val His Thr His
```

```
                805                 810                 815

Ile Asn Ala Leu Pro Ser Arg Ile Arg Gly Ser Arg Gly Arg Gly
            820                 825                 830

Gly Gly Glu Ser Ser Leu Thr Cys Arg Ala Gly Cys Lys Val Arg Glu
            835                 840                 845

Thr Thr Ala His Ile Leu Gln Gln Cys His Arg Thr His Gly Gly Arg
    850                 855                 860

Ile Leu Arg His Asn Lys Ile Val Ser Phe Val Ala Lys Ala Met Glu
865                 870                 875                 880

Glu Asn Lys Trp Thr Val Glu Leu Glu Pro Arg Leu Arg Thr Ser Val
                885                 890                 895

Gly Leu Arg Lys Pro Asp Ile Ile Ala Ser Arg Asp Gly Val Gly Val
            900                 905                 910

Ile Val Asp Val Gln Val Val Ser Gly Gln Arg Ser Leu Asp Glu Leu
        915                 920                 925

His Arg Glu Lys Arg Asn Lys Tyr Gly Asn His Gly Glu Leu Val Glu
    930                 935                 940

Leu Val Ala Gly Arg Leu Gly Leu Pro Lys Ala Glu Cys Val Arg Ala
945                 950                 955                 960

Thr Ser Cys Thr Ile Ser Trp Arg Gly Val Trp Ser Leu Thr Ser Tyr
                965                 970                 975

Lys Glu Leu Arg Ser Ile Ile Gly Leu Arg Glu Pro Thr Leu Gln Ile
            980                 985                 990

Val Pro Ile Leu Ala Leu Arg Gly  Ser His Met Asn Trp  Thr Arg Phe
            995                 1000                1005

Asn Gln  Met Thr Ser Val Met  Gly Gly Gly Val Gly
    1010            1015                1020

<210> SEQ ID NO 14
<211> LENGTH: 1283
<212> TYPE: PRT
<213> ORGANISM: Artificial Sequence
<220> FEATURE:
<223> OTHER INFORMATION: SSB joined via a linker to the N-terminus of
      wild type R2 enzyme

<400> SEQUENCE: 14

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140
```

```
Gly Glu Glu Glu Gly Thr Val Gly Thr Gly Gly Ser Glu Ala Ala
145                 150                 155                 160

Ala Lys Gly Gly Ala Ser Thr Ala Leu Met Met Ala Ser Thr Ala Leu
            165                 170                 175

Ser Leu Met Gly Arg Cys Asn Pro Asp Gly Cys Thr Arg Gly Lys His
            180                 185                 190

Val Thr Ala Ala Pro Met Asp Gly Pro Arg Gly Pro Ser Ser Leu Ala
            195                 200                 205

Gly Thr Phe Gly Trp Gly Leu Ala Ile Pro Ala Gly Glu Pro Cys Gly
            210                 215                 220

Arg Val Cys Ser Pro Ala Thr Val Gly Phe Phe Pro Val Ala Lys Lys
225                 230                 235                 240

Ser Asn Lys Glu Asn Arg Pro Glu Ala Ser Gly Leu Pro Leu Glu Ser
            245                 250                 255

Glu Arg Thr Gly Asp Asn Pro Thr Val Arg Gly Ser Ala Gly Ala Asp
            260                 265                 270

Pro Val Gly Gln Asp Ala Pro Gly Trp Thr Cys Gln Phe Cys Glu Arg
            275                 280                 285

Thr Phe Ser Thr Asn Arg Gly Leu Gly Val His Lys Arg Arg Ala His
290                 295                 300

Pro Val Glu Thr Asn Thr Asp Ala Ala Pro Met Met Val Lys Arg Arg
305                 310                 315                 320

Trp His Gly Glu Glu Ile Asp Leu Leu Ala Arg Thr Glu Ala Arg Leu
            325                 330                 335

Leu Ala Glu Arg Gly Gln Cys Ser Gly Gly Asp Leu Phe Gly Ala Leu
            340                 345                 350

Pro Gly Phe Gly Arg Thr Leu Glu Ala Ile Lys Gly Gln Arg Arg Arg
            355                 360                 365

Glu Pro Tyr Arg Ala Leu Val Gln Ala His Leu Ala Arg Phe Gly Ser
            370                 375                 380

Gln Pro Gly Pro Ser Ser Gly Cys Ser Ala Glu Pro Asp Phe Arg
385                 390                 395                 400

Arg Ala Ser Gly Ala Glu Glu Ala Gly Glu Glu Arg Cys Ala Glu Asp
            405                 410                 415

Ala Ala Ala Tyr Asp Pro Ser Ala Val Gly Gln Met Ser Pro Asp Ala
            420                 425                 430

Ala Arg Val Leu Ser Glu Leu Leu Glu Gly Ala Gly Arg Arg Arg Ala
            435                 440                 445

Cys Arg Ala Met Arg Pro Lys Thr Ala Gly Arg Asn Asp Leu His
450                 455                 460

Asp Asp Arg Thr Ala Ser Ala His Lys Thr Ser Arg Gln Lys Arg Arg
465                 470                 475                 480

Ala Glu Tyr Ala Arg Val Gln Glu Leu Tyr Lys Lys Cys Arg Ser Arg
            485                 490                 495

Ala Ala Ala Glu Val Ile Asp Gly Ala Cys Gly Val Gly His Ser
            500                 505                 510

Leu Glu Glu Met Glu Thr Tyr Trp Arg Pro Ile Leu Glu Arg Val Ser
            515                 520                 525

Asp Ala Pro Gly Pro Thr Pro Glu Ala Leu His Leu Gly Arg Ala
            530                 535                 540

Glu Trp His Gly Gly Asn Arg Asp Tyr Thr Gln Leu Trp Lys Pro Ile
545                 550                 555                 560

Ser Val Glu Glu Ile Lys Ala Ser Arg Phe Asp Trp Arg Thr Ser Pro
```

```
                565                 570                 575
Gly Pro Asp Gly Ile Arg Ser Gly Gln Trp Arg Ala Val Pro Val His
            580                 585                 590
Leu Lys Ala Glu Met Phe Asn Ala Trp Met Ala Arg Gly Glu Ile Pro
            595                 600                 605
Glu Ile Leu Arg Gln Cys Arg Thr Val Phe Val Pro Lys Val Glu Arg
            610                 615                 620
Pro Gly Pro Gly Glu Tyr Arg Pro Ile Ser Ile Ala Ser Ile Pro
625                 630                 635                 640
Leu Arg His Phe His Ser Ile Leu Ala Arg Arg Leu Leu Ala Cys Cys
                645                 650                 655
Pro Pro Asp Ala Arg Gln Arg Gly Phe Ile Cys Ala Asp Gly Thr Leu
                660                 665                 670
Glu Asn Ser Ala Val Leu Asp Ala Val Leu Gly Asp Ser Arg Lys Lys
                675                 680                 685
Leu Arg Glu Cys His Val Ala Val Leu Asp Phe Ala Lys Ala Phe Asp
            690                 695                 700
Thr Val Ser His Glu Ala Leu Val Glu Leu Leu Arg Leu Arg Gly Met
705                 710                 715                 720
Pro Glu Gln Phe Cys Gly Tyr Ile Ala His Leu Tyr Asp Thr Ala Ser
                725                 730                 735
Thr Thr Leu Ala Val Asn Asn Glu Met Ser Ser Pro Val Lys Val Gly
                740                 745                 750
Arg Gly Val Arg Gln Gly Asp Pro Leu Ser Pro Ile Leu Phe Asn Val
            755                 760                 765
Val Met Asp Leu Ile Leu Ala Ser Leu Pro Glu Arg Val Gly Tyr Arg
770                 775                 780
Leu Glu Met Glu Leu Val Ser Ala Leu Ala Tyr Ala Asp Asp Leu Val
785                 790                 795                 800
Leu Leu Ala Gly Ser Lys Val Gly Met Gln Glu Ser Ile Ser Ala Val
                805                 810                 815
Asp Cys Val Gly Arg Gln Met Gly Leu Arg Leu Asn Cys Arg Lys Ser
                820                 825                 830
Ala Val Leu Ser Met Ile Pro Asp Gly His Arg Lys Lys His His Tyr
                835                 840                 845
Leu Thr Glu Arg Thr Phe Asn Ile Gly Gly Lys Pro Leu Arg Gln Val
            850                 855                 860
Ser Cys Val Glu Arg Trp Arg Tyr Leu Gly Val Asp Phe Glu Ala Ser
865                 870                 875                 880
Gly Cys Val Thr Leu Glu His Ser Ile Ser Ser Ala Leu Asn Asn Ile
                885                 890                 895
Ser Arg Ala Pro Leu Lys Pro Gln Gln Arg Leu Glu Ile Leu Arg Ala
            900                 905                 910
His Leu Ile Pro Arg Phe Gln His Gly Phe Val Leu Gly Asn Ile Ser
            915                 920                 925
Asp Asp Arg Leu Arg Met Leu Asp Val Gln Ile Arg Lys Ala Val Gly
            930                 935                 940
Gln Trp Leu Arg Leu Pro Ala Asp Val Pro Lys Ala Tyr Tyr His Ala
945                 950                 955                 960
Ala Val Gln Asp Gly Gly Leu Ala Ile Pro Ser Val Arg Ala Thr Ile
                965                 970                 975
Pro Asp Leu Ile Val Arg Arg Phe Gly Gly Leu Asp Ser Ser Pro Trp
                980                 985                 990
```

-continued

```
Ser Val Ala Arg Ala Ala Ala Lys  Ser Asp Lys Ile Arg  Lys Lys Leu
        995               1000                1005

Arg Trp Ala Trp Lys Gln Leu Arg  Arg Phe Ser Arg  Val Asp Ser
   1010              1015                1020

Thr Thr Gln Arg Pro Ser Val Arg Leu Phe Trp Arg  Glu His Leu
   1025              1030                1035

His Ala Ser Val Asp Gly Arg  Glu Leu Arg Glu Ser  Thr Arg Thr
   1040              1045                1050

Pro Thr Ser Thr Lys Trp Ile  Arg Glu Arg Cys Ala  Gln Ile Thr
   1055              1060                1065

Gly Arg Asp Phe Val Gln Phe  Val His Thr His Ile  Asn Ala Leu
   1070              1075                1080

Pro Ser Arg Ile Arg Gly Ser  Arg Gly Arg Arg Gly  Gly Gly Glu
   1085              1090                1095

Ser Ser Leu Thr Cys Arg Ala  Gly Cys Lys Val Arg  Glu Thr Thr
   1100              1105                1110

Ala His Ile Leu Gln Gln Cys  His Arg Thr His Gly  Gly Arg Ile
   1115              1120                1125

Leu Arg His Asn Lys Ile Val  Ser Phe Val Ala Lys  Ala Met Glu
   1130              1135                1140

Glu Asn Lys Trp Thr Val Glu  Leu Glu Pro Arg Leu  Arg Thr Ser
   1145              1150                1155

Val Gly Leu Arg Lys Pro Asp  Ile Ile Ala Ser Arg  Asp Gly Val
   1160              1165                1170

Gly Val Ile Val Asp Val Gln  Val Val Ser Gly Gln  Arg Ser Leu
   1175              1180                1185

Asp Glu Leu His Arg Glu Lys  Arg Asn Lys Tyr Gly  Asn His Gly
   1190              1195                1200

Glu Leu Val Glu Leu Val Ala  Gly Arg Leu Gly Leu  Pro Lys Ala
   1205              1210                1215

Glu Cys Val Arg Ala Thr Ser  Cys Thr Ile Ser Trp  Arg Gly Val
   1220              1225                1230

Trp Ser Leu Thr Ser Tyr Lys  Glu Leu Arg Ser Ile  Ile Gly Leu
   1235              1240                1245

Arg Glu Pro Thr Leu Gln Ile  Val Pro Ile Leu Ala  Leu Arg Gly
   1250              1255                1260

Ser His Met Asn Trp Thr Arg  Phe Asn Gln Met Thr  Ser Val Met
   1265              1270                1275

Gly Gly Gly Val Gly
   1280
```

<210> SEQ ID NO 15
<211> LENGTH: 1023
<212> TYPE: PRT
<213> ORGANISM: Artificial Sequence
<220> FEATURE:
<223> OTHER INFORMATION: His Tag joined via a linker to SSB joined via a
      linker to the N-terminus of deltaR2 enzyme

<400> SEQUENCE: 15

```
Met Ala His His His His His His Val Gly Thr Val Gly Thr Gly Gly
1               5                   10                  15

Gly Ser Gly Gly Ala Ser Thr Ala Leu Met Glu Glu Lys Val Gly Asn
            20                  25                  30

Leu Lys Pro Asn Met Glu Ser Val Asn Val Thr Val Arg Val Leu Glu
```

-continued

```
            35                  40                  45
Ala Ser Glu Ala Arg Gln Ile Gln Thr Lys Asn Gly Val Arg Thr Ile
 50                  55                  60

Ser Glu Ala Ile Val Gly Asp Glu Thr Gly Arg Val Lys Leu Thr Leu
 65                  70                  75                  80

Trp Gly Lys His Ala Gly Ser Ile Lys Glu Gly Gln Val Val Lys Ile
                 85                  90                  95

Glu Asn Ala Trp Thr Thr Ala Phe Lys Gly Gln Val Gln Leu Asn Ala
                100                 105                 110

Gly Ser Lys Thr Lys Ile Ala Glu Ala Ser Glu Asp Gly Phe Pro Glu
            115                 120                 125

Ser Ser Gln Ile Pro Glu Asn Thr Pro Thr Ala Pro Gln Gln Met Arg
130                 135                 140

Gly Gly Gly Arg Gly Phe Arg Gly Gly Gly Arg Arg Tyr Gly Arg Arg
145                 150                 155                 160

Gly Gly Arg Arg Gln Glu Asn Glu Glu Gly Glu Glu Glu Gly Thr Val
                165                 170                 175

Gly Thr Gly Gly Gly Ser Glu Ala Ala Ala Lys Gly Gly Ala Ser Thr
            180                 185                 190

Ala Leu Lys Thr Ala Gly Arg Arg Asn Asp Leu His Asp Asp Arg Thr
            195                 200                 205

Ala Ser Ala His Lys Thr Ser Arg Gln Lys Arg Arg Ala Glu Tyr Ala
            210                 215                 220

Arg Val Gln Glu Leu Tyr Lys Lys Cys Arg Ser Arg Ala Ala Ala Glu
225                 230                 235                 240

Val Ile Asp Gly Ala Cys Gly Gly Val Gly His Ser Leu Glu Glu Met
                245                 250                 255

Glu Thr Tyr Trp Arg Pro Ile Leu Glu Arg Val Ser Asp Ala Pro Gly
                260                 265                 270

Pro Thr Pro Glu Ala Leu His Ala Leu Gly Arg Ala Glu Trp His Gly
            275                 280                 285

Gly Asn Arg Asp Tyr Thr Gln Leu Trp Lys Pro Ile Ser Val Glu Glu
290                 295                 300

Ile Lys Ala Ser Arg Phe Asp Trp Arg Thr Ser Pro Gly Pro Asp Gly
305                 310                 315                 320

Ile Arg Ser Gly Gln Trp Arg Ala Val Pro Val His Leu Lys Ala Glu
                325                 330                 335

Met Phe Asn Ala Trp Met Ala Arg Gly Glu Ile Pro Glu Ile Leu Arg
                340                 345                 350

Gln Cys Arg Thr Val Phe Val Pro Lys Val Glu Arg Pro Gly Gly Pro
            355                 360                 365

Gly Glu Tyr Arg Pro Ile Ser Ile Ala Ser Ile Pro Leu Arg His Phe
            370                 375                 380

His Ser Ile Leu Ala Arg Arg Leu Leu Ala Cys Cys Pro Pro Asp Ala
385                 390                 395                 400

Arg Gln Arg Gly Phe Ile Cys Ala Asp Gly Thr Leu Glu Asn Ser Ala
                405                 410                 415

Val Leu Asp Ala Val Leu Gly Asp Ser Arg Lys Lys Leu Arg Glu Cys
            420                 425                 430

His Val Ala Val Leu Asp Phe Ala Lys Ala Phe Asp Thr Val Ser His
            435                 440                 445

Glu Ala Leu Val Glu Leu Leu Arg Leu Arg Gly Met Pro Glu Gln Phe
450                 455                 460
```

```
Cys Gly Tyr Ile Ala His Leu Tyr Asp Thr Ala Ser Thr Thr Leu Ala
465                 470                 475                 480

Val Asn Asn Glu Met Ser Ser Pro Val Lys Val Gly Arg Gly Val Arg
                485                 490                 495

Gln Gly Asp Pro Leu Ser Pro Ile Leu Phe Asn Val Val Met Asp Leu
            500                 505                 510

Ile Leu Ala Ser Leu Pro Glu Arg Val Gly Tyr Arg Leu Glu Met Glu
        515                 520                 525

Leu Val Ser Ala Leu Ala Tyr Ala Asp Asp Leu Val Leu Leu Ala Gly
    530                 535                 540

Ser Lys Val Gly Met Gln Glu Ser Ile Ser Ala Val Asp Cys Val Gly
545                 550                 555                 560

Arg Gln Met Gly Leu Arg Leu Asn Cys Arg Lys Ser Ala Val Leu Ser
                565                 570                 575

Met Ile Pro Asp Gly His Arg Lys Lys His His Tyr Leu Thr Glu Arg
            580                 585                 590

Thr Phe Asn Ile Gly Gly Lys Pro Leu Arg Gln Val Ser Cys Val Glu
        595                 600                 605

Arg Trp Arg Tyr Leu Gly Val Asp Phe Glu Ala Ser Gly Cys Val Thr
    610                 615                 620

Leu Glu His Ser Ile Ser Ser Ala Leu Asn Asn Ile Ser Arg Ala Pro
625                 630                 635                 640

Leu Lys Pro Gln Gln Arg Leu Glu Ile Leu Arg Ala His Leu Ile Pro
                645                 650                 655

Arg Phe Gln His Gly Phe Val Leu Gly Asn Ile Ser Asp Asp Arg Leu
            660                 665                 670

Arg Met Leu Asp Val Gln Ile Arg Lys Ala Val Gly Gln Trp Leu Arg
        675                 680                 685

Leu Pro Ala Asp Val Pro Lys Ala Tyr Tyr His Ala Ala Val Gln Asp
    690                 695                 700

Gly Gly Leu Ala Ile Pro Ser Val Arg Ala Thr Ile Pro Asp Leu Ile
705                 710                 715                 720

Val Arg Arg Phe Gly Gly Leu Asp Ser Ser Pro Trp Ser Val Ala Arg
                725                 730                 735

Ala Ala Ala Lys Ser Asp Lys Ile Arg Lys Lys Leu Arg Trp Ala Trp
            740                 745                 750

Lys Gln Leu Arg Arg Phe Ser Arg Val Asp Ser Thr Thr Gln Arg Pro
        755                 760                 765

Ser Val Arg Leu Phe Trp Arg Glu His Leu His Ala Ser Val Asp Gly
    770                 775                 780

Arg Glu Leu Arg Glu Ser Thr Arg Thr Pro Thr Ser Thr Lys Trp Ile
785                 790                 795                 800

Arg Glu Arg Cys Ala Gln Ile Thr Gly Arg Asp Phe Val Gln Phe Val
                805                 810                 815

His Thr His Ile Asn Ala Leu Pro Ser Arg Ile Arg Gly Ser Arg Gly
            820                 825                 830

Arg Arg Gly Gly Gly Glu Ser Ser Leu Thr Cys Arg Ala Gly Cys Lys
        835                 840                 845

Val Arg Glu Thr Thr Ala His Ile Leu Gln Gln Cys His Arg Thr His
    850                 855                 860

Gly Gly Arg Ile Leu Arg His Asn Lys Ile Val Ser Phe Val Ala Lys
865                 870                 875                 880
```

```
Ala Met Glu Glu Asn Lys Trp Thr Val Glu Leu Pro Arg Leu Arg
                885                 890                 895

Thr Ser Val Gly Leu Arg Lys Pro Asp Ile Ile Ala Ser Arg Asp Gly
            900                 905                 910

Val Gly Val Ile Val Asp Val Gln Val Val Ser Gly Gln Arg Ser Leu
        915                 920                 925

Asp Glu Leu His Arg Glu Lys Arg Asn Lys Tyr Gly Asn His Gly Glu
    930                 935                 940

Leu Val Glu Leu Val Ala Gly Arg Leu Gly Leu Pro Lys Ala Glu Cys
945                 950                 955                 960

Val Arg Ala Thr Ser Cys Thr Ile Ser Trp Arg Gly Val Trp Ser Leu
                965                 970                 975

Thr Ser Tyr Lys Glu Leu Arg Ser Ile Ile Gly Leu Arg Glu Pro Thr
            980                 985                 990

Leu Gln Ile Val Pro Ile Leu Ala Leu Arg Gly Ser His Met Asn Trp
        995                1000                1005

Thr Arg Phe Asn Gln Met Thr Ser Val Met Gly Gly Gly Val Gly
    1010                1015                1020

<210> SEQ ID NO 16
<211> LENGTH: 1456
<212> TYPE: PRT
<213> ORGANISM: Artificial Sequence
<220> FEATURE:
<223> OTHER INFORMATION: SSB-SSB joined via a linker to the N-terminus
      of wild type R2 enzyme

<400> SEQUENCE: 16

Met Glu Glu Lys Val Gly Asn Leu Lys Pro Asn Met Glu Ser Val Asn
1               5                  10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140

Gly Glu Glu Glu Val Gly Thr Gly Gly Ser Gly Gly Gly Glu Ala
145                 150                 155                 160

Ala Ala Lys Glu Ala Ala Ala Lys Ser Gly Gly Ser Met Glu Glu
                165                 170                 175

Lys Val Gly Asn Leu Lys Pro Asn Met Glu Ser Val Asn Val Thr Val
            180                 185                 190

Arg Val Leu Glu Ala Ser Glu Ala Arg Gln Ile Gln Thr Lys Asn Gly
        195                 200                 205

Val Arg Thr Ile Ser Glu Ala Ile Val Gly Asp Glu Thr Gly Arg Val
    210                 215                 220
```

```
Lys Leu Thr Leu Trp Gly Lys His Ala Gly Ser Ile Lys Glu Gly Gln
225                 230                 235                 240

Val Val Lys Ile Glu Asn Ala Trp Thr Thr Ala Phe Lys Gly Gln Val
                245                 250                 255

Gln Leu Asn Ala Gly Ser Lys Thr Lys Ile Ala Glu Ala Ser Glu Asp
            260                 265                 270

Gly Phe Pro Glu Ser Ser Gln Ile Pro Glu Asn Thr Pro Thr Ala Pro
        275                 280                 285

Gln Gln Met Arg Gly Gly Arg Gly Phe Arg Gly Gly Arg Arg
    290                 295                 300

Tyr Gly Arg Arg Gly Gly Arg Arg Gln Glu Asn Glu Glu Gly Glu Glu
305                 310                 315                 320

Glu Gly Thr Val Gly Thr Gly Gly Ser Glu Ala Ala Ala Lys Gly
                325                 330                 335

Gly Ala Ser Thr Ala Leu Met Met Ala Ser Thr Ala Leu Ser Leu Met
            340                 345                 350

Gly Arg Cys Asn Pro Asp Gly Cys Thr Arg Gly Lys His Val Thr Ala
        355                 360                 365

Ala Pro Met Asp Gly Pro Arg Gly Pro Ser Ser Leu Ala Gly Thr Phe
370                 375                 380

Gly Trp Gly Leu Ala Ile Pro Ala Gly Glu Pro Cys Gly Arg Val Cys
385                 390                 395                 400

Ser Pro Ala Thr Val Gly Phe Phe Pro Val Ala Lys Lys Ser Asn Lys
                405                 410                 415

Glu Asn Arg Pro Glu Ala Ser Gly Leu Pro Leu Glu Ser Glu Arg Thr
            420                 425                 430

Gly Asp Asn Pro Thr Val Arg Gly Ser Ala Gly Ala Asp Pro Val Gly
        435                 440                 445

Gln Asp Ala Pro Gly Trp Thr Cys Gln Phe Cys Glu Arg Thr Phe Ser
450                 455                 460

Thr Asn Arg Gly Leu Gly Val His Lys Arg Arg Ala His Pro Val Glu
465                 470                 475                 480

Thr Asn Thr Asp Ala Ala Pro Met Met Val Lys Arg Arg Trp His Gly
                485                 490                 495

Glu Glu Ile Asp Leu Leu Ala Arg Thr Glu Ala Arg Leu Leu Ala Glu
            500                 505                 510

Arg Gly Gln Cys Ser Gly Gly Asp Leu Phe Gly Ala Leu Pro Gly Phe
        515                 520                 525

Gly Arg Thr Leu Glu Ala Ile Lys Gly Gln Arg Arg Glu Pro Tyr
530                 535                 540

Arg Ala Leu Val Gln Ala His Leu Ala Arg Phe Gly Ser Gln Pro Gly
545                 550                 555                 560

Pro Ser Ser Gly Gly Cys Ser Ala Glu Pro Asp Phe Arg Arg Ala Ser
                565                 570                 575

Gly Ala Glu Glu Ala Gly Glu Glu Arg Cys Ala Glu Asp Ala Ala Ala
            580                 585                 590

Tyr Asp Pro Ser Ala Val Gly Gln Met Ser Pro Asp Ala Ala Arg Val
        595                 600                 605

Leu Ser Glu Leu Leu Glu Gly Ala Gly Arg Arg Ala Cys Arg Ala
610                 615                 620

Met Arg Pro Lys Thr Ala Gly Arg Arg Asn Asp Leu His Asp Asp Arg
625                 630                 635                 640
```

```
Thr Ala Ser Ala His Lys Thr Ser Arg Gln Lys Arg Ala Glu Tyr
                645                 650                 655

Ala Arg Val Gln Glu Leu Tyr Lys Lys Cys Arg Ser Arg Ala Ala Ala
            660                 665                 670

Glu Val Ile Asp Gly Ala Cys Gly Gly Val Gly His Ser Leu Glu Glu
            675                 680                 685

Met Glu Thr Tyr Trp Arg Pro Ile Leu Glu Arg Val Ser Asp Ala Pro
    690                 695                 700

Gly Pro Thr Pro Glu Ala Leu His Ala Leu Gly Arg Ala Glu Trp His
705                 710                 715                 720

Gly Gly Asn Arg Asp Tyr Thr Gln Leu Trp Lys Pro Ile Ser Val Glu
                725                 730                 735

Glu Ile Lys Ala Ser Arg Phe Asp Trp Arg Thr Ser Pro Gly Pro Asp
            740                 745                 750

Gly Ile Arg Ser Gly Gln Trp Arg Ala Val Pro Val His Leu Lys Ala
            755                 760                 765

Glu Met Phe Asn Ala Trp Met Ala Arg Gly Glu Ile Pro Glu Ile Leu
    770                 775                 780

Arg Gln Cys Arg Thr Val Phe Val Pro Lys Val Glu Arg Pro Gly Gly
785                 790                 795                 800

Pro Gly Glu Tyr Arg Pro Ile Ser Ile Ala Ser Ile Pro Leu Arg His
                805                 810                 815

Phe His Ser Ile Leu Ala Arg Arg Leu Leu Ala Cys Cys Pro Pro Asp
            820                 825                 830

Ala Arg Gln Arg Gly Phe Ile Cys Ala Asp Gly Thr Leu Glu Asn Ser
            835                 840                 845

Ala Val Leu Asp Ala Val Leu Gly Asp Ser Arg Lys Lys Leu Arg Glu
850                 855                 860

Cys His Val Ala Val Leu Asp Phe Ala Lys Ala Phe Asp Thr Val Ser
865                 870                 875                 880

His Glu Ala Leu Val Glu Leu Leu Arg Leu Arg Gly Met Pro Glu Gln
                885                 890                 895

Phe Cys Gly Tyr Ile Ala His Leu Tyr Asp Thr Ala Ser Thr Thr Leu
            900                 905                 910

Ala Val Asn Asn Glu Met Ser Ser Pro Val Lys Val Gly Arg Gly Val
            915                 920                 925

Arg Gln Gly Asp Pro Leu Ser Pro Ile Leu Phe Asn Val Val Met Asp
    930                 935                 940

Leu Ile Leu Ala Ser Leu Pro Glu Arg Val Gly Tyr Arg Leu Glu Met
945                 950                 955                 960

Glu Leu Val Ser Ala Leu Ala Tyr Ala Asp Asp Leu Val Leu Leu Ala
                965                 970                 975

Gly Ser Lys Val Gly Met Gln Glu Ser Ile Ser Ala Val Asp Cys Val
            980                 985                 990

Gly Arg Gln Met Gly Leu Arg Leu Asn Cys Arg Lys Ser Ala Val Leu
            995                1000                1005

Ser Met Ile Pro Asp Gly His Arg Lys Lys His His Tyr Leu Thr
   1010                1015                1020

Glu Arg Thr Phe Asn Ile Gly Gly Lys Pro Leu Arg Gln Val Ser
   1025                1030                1035

Cys Val Glu Arg Trp Arg Tyr Leu Gly Val Asp Phe Glu Ala Ser
   1040                1045                1050

Gly Cys Val Thr Leu Glu His Ser Ile Ser Ser Ala Leu Asn Asn
```

```
                   1055                1060                1065
Ile Ser Arg Ala Pro Leu Lys Pro Gln Gln Arg Leu Glu Ile Leu
               1070                1075                1080

Arg Ala His Leu Ile Pro Arg Phe Gln His Gly Phe Val Leu Gly
               1085                1090                1095

Asn Ile Ser Asp Asp Arg Leu Arg Met Leu Asp Val Gln Ile Arg
               1100                1105                1110

Lys Ala Val Gly Gln Trp Leu Arg Leu Pro Ala Asp Val Pro Lys
               1115                1120                1125

Ala Tyr Tyr His Ala Ala Val Gln Asp Gly Gly Leu Ala Ile Pro
               1130                1135                1140

Ser Val Arg Ala Thr Ile Pro Asp Leu Ile Val Arg Arg Phe Gly
               1145                1150                1155

Gly Leu Asp Ser Ser Pro Trp Ser Val Ala Arg Ala Ala Ala Lys
               1160                1165                1170

Ser Asp Lys Ile Arg Lys Lys Leu Arg Trp Ala Trp Lys Gln Leu
               1175                1180                1185

Arg Arg Phe Ser Arg Val Asp Ser Thr Thr Gln Arg Pro Ser Val
               1190                1195                1200

Arg Leu Phe Trp Arg Glu His Leu His Ala Ser Val Asp Gly Arg
               1205                1210                1215

Glu Leu Arg Glu Ser Thr Arg Thr Pro Thr Ser Thr Lys Trp Ile
               1220                1225                1230

Arg Glu Arg Cys Ala Gln Ile Thr Gly Arg Asp Phe Val Gln Phe
               1235                1240                1245

Val His Thr His Ile Asn Ala Leu Pro Ser Arg Ile Arg Gly Ser
               1250                1255                1260

Arg Gly Arg Arg Gly Gly Glu Ser Ser Leu Thr Cys Arg Ala
               1265                1270                1275

Gly Cys Lys Val Arg Glu Thr Thr Ala His Ile Leu Gln Gln Cys
               1280                1285                1290

His Arg Thr His Gly Gly Arg Ile Leu Arg His Asn Lys Ile Val
               1295                1300                1305

Ser Phe Val Ala Lys Ala Met Glu Glu Asn Lys Trp Thr Val Glu
               1310                1315                1320

Leu Glu Pro Arg Leu Arg Thr Ser Val Gly Leu Arg Lys Pro Asp
               1325                1330                1335

Ile Ile Ala Ser Arg Asp Gly Val Gly Val Ile Val Asp Val Gln
               1340                1345                1350

Val Val Ser Gly Gln Arg Ser Leu Asp Glu Leu His Arg Glu Lys
               1355                1360                1365

Arg Asn Lys Tyr Gly Asn His Gly Glu Leu Val Glu Leu Val Ala
               1370                1375                1380

Gly Arg Leu Gly Leu Pro Lys Ala Glu Cys Val Arg Ala Thr Ser
               1385                1390                1395

Cys Thr Ile Ser Trp Arg Gly Val Trp Ser Leu Thr Ser Tyr Lys
               1400                1405                1410

Glu Leu Arg Ser Ile Ile Gly Leu Arg Glu Pro Thr Leu Gln Ile
               1415                1420                1425

Val Pro Ile Leu Ala Leu Arg Gly Ser His Met Asn Trp Thr Arg
               1430                1435                1440

Phe Asn Gln Met Thr Ser Val Met Gly Gly Gly Val Gly
               1445                1450                1455
```

```
<210> SEQ ID NO 17
<211> LENGTH: 1171
<212> TYPE: PRT
<213> ORGANISM: Artificial Sequence
<220> FEATURE:
<223> OTHER INFORMATION: SSB-SSB joined via a linker to the N-terminus
      of deltaR2 enzyme

<400> SEQUENCE: 17

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Arg Gly Phe Arg Gly Gly
        115                 120                 125

Gly Arg Arg Tyr Gly Arg Arg Gly Gly Arg Gln Glu Asn Glu Glu
    130                 135                 140

Gly Glu Glu Glu Val Gly Thr Gly Gly Ser Gly Gly Gly Glu Ala
145                 150                 155                 160

Ala Ala Lys Glu Ala Ala Ala Lys Ser Gly Gly Gly Ser Met Glu Glu
                165                 170                 175

Lys Val Gly Asn Leu Lys Pro Asn Met Glu Ser Val Asn Val Thr Val
            180                 185                 190

Arg Val Leu Glu Ala Ser Glu Ala Arg Gln Ile Gln Thr Lys Asn Gly
        195                 200                 205

Val Arg Thr Ile Ser Glu Ala Ile Val Gly Asp Glu Thr Gly Arg Val
    210                 215                 220

Lys Leu Thr Leu Trp Gly Lys His Ala Gly Ser Ile Lys Glu Gly Gln
225                 230                 235                 240

Val Val Lys Ile Glu Asn Ala Trp Thr Thr Ala Phe Lys Gly Gln Val
                245                 250                 255

Gln Leu Asn Ala Gly Ser Lys Thr Lys Ile Ala Glu Ala Ser Glu Asp
            260                 265                 270

Gly Phe Pro Glu Ser Ser Gln Ile Pro Glu Asn Thr Pro Thr Ala Pro
        275                 280                 285

Gln Gln Met Arg Gly Gly Gly Arg Gly Phe Arg Gly Gly Arg Arg
    290                 295                 300

Tyr Gly Arg Arg Gly Gly Arg Gln Glu Asn Glu Glu Gly Glu Glu
305                 310                 315                 320

Glu Gly Thr Val Gly Thr Gly Gly Ser Glu Ala Ala Lys Gly
                325                 330                 335

Gly Ala Ser Thr Ala Leu Lys Thr Ala Gly Arg Arg Asn Asp Leu His
            340                 345                 350

Asp Asp Arg Thr Ala Ser Ala His Lys Thr Ser Arg Gln Lys Arg Arg
```

```
                355                 360                 365
Ala Glu Tyr Ala Arg Val Gln Glu Leu Tyr Lys Lys Cys Arg Ser Arg
    370                 375                 380

Ala Ala Ala Glu Val Ile Asp Gly Ala Cys Gly Val Gly His Ser
385                 390                 395                 400

Leu Glu Glu Met Glu Thr Tyr Trp Arg Pro Ile Leu Glu Arg Val Ser
                405                 410                 415

Asp Ala Pro Gly Pro Thr Pro Glu Ala Leu His Ala Leu Gly Arg Ala
            420                 425                 430

Glu Trp His Gly Gly Asn Arg Asp Tyr Thr Gln Leu Trp Lys Pro Ile
        435                 440                 445

Ser Val Glu Glu Ile Lys Ala Ser Arg Phe Asp Trp Arg Thr Ser Pro
    450                 455                 460

Gly Pro Asp Gly Ile Arg Ser Gly Gln Trp Arg Ala Val Pro Val His
465                 470                 475                 480

Leu Lys Ala Glu Met Phe Asn Ala Trp Met Ala Arg Gly Glu Ile Pro
                485                 490                 495

Glu Ile Leu Arg Gln Cys Arg Thr Val Phe Val Pro Lys Val Glu Arg
            500                 505                 510

Pro Gly Gly Pro Gly Glu Tyr Arg Pro Ile Ser Ile Ala Ser Ile Pro
        515                 520                 525

Leu Arg His Phe His Ser Ile Leu Ala Arg Arg Leu Leu Ala Cys Cys
    530                 535                 540

Pro Pro Asp Ala Arg Gln Arg Gly Phe Ile Cys Ala Asp Gly Thr Leu
545                 550                 555                 560

Glu Asn Ser Ala Val Leu Asp Ala Val Leu Gly Asp Ser Arg Lys Lys
                565                 570                 575

Leu Arg Glu Cys His Val Ala Val Leu Asp Phe Ala Lys Ala Phe Asp
            580                 585                 590

Thr Val Ser His Glu Ala Leu Val Glu Leu Leu Arg Leu Arg Gly Met
        595                 600                 605

Pro Glu Gln Phe Cys Gly Tyr Ile Ala His Leu Tyr Asp Thr Ala Ser
    610                 615                 620

Thr Thr Leu Ala Val Asn Asn Glu Met Ser Ser Pro Val Lys Val Gly
625                 630                 635                 640

Arg Gly Val Arg Gln Gly Asp Pro Leu Ser Pro Ile Leu Phe Asn Val
                645                 650                 655

Val Met Asp Leu Ile Leu Ala Ser Leu Pro Glu Arg Val Gly Tyr Arg
            660                 665                 670

Leu Glu Met Glu Leu Val Ser Ala Leu Ala Tyr Ala Asp Asp Leu Val
        675                 680                 685

Leu Leu Ala Gly Ser Lys Val Gly Met Gln Glu Ser Ile Ser Ala Val
    690                 695                 700

Asp Cys Val Gly Arg Gln Met Gly Leu Arg Leu Asn Cys Arg Lys Ser
705                 710                 715                 720

Ala Val Leu Ser Met Ile Pro Asp Gly His Arg Lys Lys His His Tyr
                725                 730                 735

Leu Thr Glu Arg Thr Phe Asn Ile Gly Gly Lys Pro Leu Arg Gln Val
            740                 745                 750

Ser Cys Val Glu Arg Trp Arg Tyr Leu Gly Val Asp Phe Glu Ala Ser
        755                 760                 765

Gly Cys Val Thr Leu Glu His Ser Ile Ser Ser Ala Leu Asn Asn Ile
    770                 775                 780
```

Ser Arg Ala Pro Leu Lys Pro Gln Gln Arg Leu Glu Ile Leu Arg Ala
785                 790                 795                 800

His Leu Ile Pro Arg Phe Gln His Gly Phe Val Leu Gly Asn Ile Ser
                805                 810                 815

Asp Asp Arg Leu Arg Met Leu Asp Val Gln Ile Arg Lys Ala Val Gly
            820                 825                 830

Gln Trp Leu Arg Leu Pro Ala Asp Val Pro Lys Ala Tyr Tyr His Ala
        835                 840                 845

Ala Val Gln Asp Gly Gly Leu Ala Ile Pro Ser Val Arg Ala Thr Ile
850                 855                 860

Pro Asp Leu Ile Val Arg Arg Phe Gly Gly Leu Asp Ser Ser Pro Trp
865                 870                 875                 880

Ser Val Ala Arg Ala Ala Lys Ser Asp Lys Ile Arg Lys Lys Leu
                885                 890                 895

Arg Trp Ala Trp Lys Gln Leu Arg Arg Phe Ser Arg Val Asp Ser Thr
            900                 905                 910

Thr Gln Arg Pro Ser Val Arg Leu Phe Trp Arg Glu His Leu His Ala
        915                 920                 925

Ser Val Asp Gly Arg Glu Leu Arg Glu Ser Thr Arg Thr Pro Thr Ser
930                 935                 940

Thr Lys Trp Ile Arg Glu Arg Cys Ala Gln Ile Thr Gly Arg Asp Phe
945                 950                 955                 960

Val Gln Phe Val His Thr His Ile Asn Ala Leu Pro Ser Arg Ile Arg
                965                 970                 975

Gly Ser Arg Gly Arg Arg Gly Gly Glu Ser Ser Leu Thr Cys Arg
            980                 985                 990

Ala Gly Cys Lys Val Arg Glu Thr Thr Ala His Ile Leu Gln Gln Cys
        995                 1000                1005

His Arg Thr His Gly Gly Arg Ile Leu Arg His Asn Lys Ile Val
    1010                1015                1020

Ser Phe Val Ala Lys Ala Met Glu Glu Asn Lys Trp Thr Val Glu
    1025                1030                1035

Leu Glu Pro Arg Leu Arg Thr Ser Val Gly Leu Arg Lys Pro Asp
    1040                1045                1050

Ile Ile Ala Ser Arg Asp Gly Val Gly Val Ile Val Asp Val Gln
    1055                1060                1065

Val Val Ser Gly Gln Arg Ser Leu Asp Glu Leu His Arg Glu Lys
    1070                1075                1080

Arg Asn Lys Tyr Gly Asn His Gly Glu Leu Val Glu Leu Val Ala
    1085                1090                1095

Gly Arg Leu Gly Leu Pro Lys Ala Glu Cys Val Arg Ala Thr Ser
    1100                1105                1110

Cys Thr Ile Ser Trp Arg Gly Val Trp Ser Leu Thr Ser Tyr Lys
    1115                1120                1125

Glu Leu Arg Ser Ile Ile Gly Leu Arg Glu Pro Thr Leu Gln Ile
    1130                1135                1140

Val Pro Ile Leu Ala Leu Arg Gly Ser His Met Asn Trp Thr Arg
    1145                1150                1155

Phe Asn Gln Met Thr Ser Val Met Gly Gly Val Gly
    1160                1165                1170

<210> SEQ ID NO 18
<211> LENGTH: 1192

```
<212> TYPE: PRT
<213> ORGANISM: Artificial Sequence
<220> FEATURE:
<223> OTHER INFORMATION: Sso7d joined via a linker to the C-terminus of
      wild type R2 enzyme

<400> SEQUENCE: 18
```

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Arg Val Leu Ser Glu Leu Leu Glu
            260                 265                 270

Gly Ala Gly Arg Arg Arg Ala Cys Arg Ala Met Arg Pro Lys Thr Ala
            275                 280                 285

Gly Arg Arg Asn Asp Leu His Asp Asp Arg Thr Ser Ala His Lys
290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
            325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Gly Asn Arg Asp Tyr
        370                 375                 380

```
Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
        435                 440                 445

Phe Val Pro Lys Val Glu Arg Pro Gly Gly Pro Gly Glu Tyr Arg Pro
    450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
        515                 520                 525

Asp Phe Ala Lys Ala Phe Asp Thr Val Ser His Glu Ala Leu Val Glu
    530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Val Gln Asp Gly Gly Leu Ala Ile
785                 790                 795                 800
```

-continued

```
Pro Ser Val Arg Ala Thr Ile Pro Asp Leu Ile Val Arg Arg Phe Gly
            805                 810                 815

Gly Leu Asp Ser Ser Pro Trp Ser Val Ala Arg Ala Ala Lys Ser
        820                 825                 830

Asp Lys Ile Arg Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
        930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser  Arg Asp Gly Val Gly  Val Ile Val
        995                 1000                1005

Asp Val  Gln Val Val Ser Gly  Gln Arg Ser Leu Asp  Glu Leu His
    1010                1015                1020

Arg Glu  Lys Arg Asn Lys Tyr  Gly Asn His Gly Glu  Leu Val Glu
    1025                1030                1035

Leu Val  Ala Gly Arg Leu Gly  Leu Pro Lys Ala Glu  Cys Val Arg
    1040                1045                1050

Ala Thr  Ser Cys Thr Ile Ser  Trp Arg Gly Val Trp  Ser Leu Thr
    1055                1060                1065

Ser Tyr  Lys Glu Leu Arg Ser  Ile Ile Gly Leu Arg  Glu Pro Thr
    1070                1075                1080

Leu Gln  Ile Val Pro Ile Leu  Ala Leu Arg Gly Ser  His Met Asn
    1085                1090                1095

Trp Thr  Arg Phe Asn Gln Met  Thr Ser Val Met Gly  Gly Gly Val
    1100                1105                1110

Gly Val  Gly Thr Gly Gly Gly  Ser Gly Gly Gly Thr  Gly Gly Gly
    1115                1120                1125

Ser Ala  Thr Val Lys Phe Lys  Tyr Lys Gly Glu Glu  Lys Glu Val
    1130                1135                1140

Asp Ile  Ser Lys Ile Lys Lys  Val Trp Arg Val Gly  Lys Met Ile
    1145                1150                1155

Ser Phe  Thr Tyr Asp Glu Gly  Gly Gly Lys Thr Gly  Arg Gly Ala
    1160                1165                1170

Val Ser  Glu Lys Asp Ala Pro  Lys Glu Leu Leu Gln  Met Leu Glu
    1175                1180                1185

Lys Gln  Lys Lys
    1190
```

```
<210> SEQ ID NO 19
<211> LENGTH: 932
<212> TYPE: PRT
<213> ORGANISM: Artificial Sequence
<220> FEATURE:
<223> OTHER INFORMATION: His Tag joined via a linker to Sso7d joined via
      a linker to the C-terminus of deltaR2 enzyme

<400> SEQUENCE: 19
```

| | | | | | | | | | | | | | | | |
|---|---|---|---|---|---|---|---|---|---|---|---|---|---|---|---|
| Met | Ala | His | His | His | His | His | Val | Gly | Thr | Val | Gly | Thr | Gly | Gly |
| 1 | | | 5 | | | | | 10 | | | | | 15 | |
| Gly | Ser | Gly | Gly | Ala | Ser | Thr | Ala | Leu | Lys | Thr | Ala | Gly | Arg | Arg | Asn |
| | | | 20 | | | | 25 | | | | | 30 | | | |
| Asp | Leu | His | Asp | Asp | Arg | Thr | Ala | Ser | Ala | His | Lys | Thr | Ser | Arg | Gln |
| | 35 | | | | | 40 | | | | | 45 | | | | |
| Lys | Arg | Arg | Ala | Glu | Tyr | Ala | Arg | Val | Gln | Glu | Leu | Tyr | Lys | Lys | Cys |
| 50 | | | | | 55 | | | | | 60 | | | | | |
| Arg | Ser | Arg | Ala | Ala | Ala | Glu | Val | Ile | Asp | Gly | Ala | Cys | Gly | Gly | Val |
| 65 | | | | 70 | | | | | 75 | | | | | 80 | |
| Gly | His | Ser | Leu | Glu | Glu | Met | Glu | Thr | Tyr | Trp | Arg | Pro | Ile | Leu | Glu |
| | | | | 85 | | | | | 90 | | | | | 95 | |
| Arg | Val | Ser | Asp | Ala | Pro | Gly | Pro | Thr | Pro | Glu | Ala | Leu | His | Ala | Leu |
| | | | | 100 | | | | | 105 | | | | | 110 | |
| Gly | Arg | Ala | Glu | Trp | His | Gly | Gly | Asn | Arg | Asp | Tyr | Thr | Gln | Leu | Trp |
| | | | 115 | | | | | 120 | | | | | 125 | | |
| Lys | Pro | Ile | Ser | Val | Glu | Glu | Ile | Lys | Ala | Ser | Arg | Phe | Asp | Trp | Arg |
| 130 | | | | | 135 | | | | | 140 | | | | | |
| Thr | Ser | Pro | Gly | Pro | Asp | Gly | Ile | Arg | Ser | Gly | Gln | Trp | Arg | Ala | Val |
| 145 | | | | | 150 | | | | | 155 | | | | | 160 |
| Pro | Val | His | Leu | Lys | Ala | Glu | Met | Phe | Asn | Ala | Trp | Met | Ala | Arg | Gly |
| | | | | 165 | | | | | 170 | | | | | 175 | |
| Glu | Ile | Pro | Glu | Ile | Leu | Arg | Gln | Cys | Arg | Thr | Val | Phe | Val | Pro | Lys |
| | | | 180 | | | | | 185 | | | | | 190 | | |
| Val | Glu | Arg | Pro | Gly | Gly | Pro | Gly | Glu | Tyr | Arg | Pro | Ile | Ser | Ile | Ala |
| | | 195 | | | | | 200 | | | | | 205 | | | |
| Ser | Ile | Pro | Leu | Arg | His | Phe | His | Ser | Ile | Leu | Ala | Arg | Arg | Leu | Leu |
| | 210 | | | | | 215 | | | | | 220 | | | | |
| Ala | Cys | Cys | Pro | Pro | Asp | Ala | Arg | Gln | Arg | Gly | Phe | Ile | Cys | Ala | Asp |
| 225 | | | | | 230 | | | | | 235 | | | | | 240 |
| Gly | Thr | Leu | Glu | Asn | Ser | Ala | Val | Leu | Asp | Ala | Val | Leu | Gly | Asp | Ser |
| | | | | 245 | | | | | 250 | | | | | 255 | |
| Arg | Lys | Lys | Leu | Arg | Glu | Cys | His | Val | Ala | Val | Leu | Asp | Phe | Ala | Lys |
| | | | 260 | | | | | 265 | | | | | 270 | | |
| Ala | Phe | Asp | Thr | Val | Ser | His | Glu | Ala | Leu | Val | Glu | Leu | Leu | Arg | Leu |
| | | 275 | | | | | 280 | | | | | 285 | | | |
| Arg | Gly | Met | Pro | Glu | Gln | Phe | Cys | Gly | Tyr | Ile | Ala | His | Leu | Tyr | Asp |
| 290 | | | | | 295 | | | | | 300 | | | | | |
| Thr | Ala | Ser | Thr | Thr | Leu | Ala | Val | Asn | Asn | Glu | Met | Ser | Ser | Pro | Val |
| 305 | | | | | 310 | | | | | 315 | | | | | 320 |
| Lys | Val | Gly | Arg | Gly | Val | Arg | Gln | Gly | Asp | Pro | Leu | Ser | Pro | Ile | Leu |
| | | | 325 | | | | | 330 | | | | | 335 | | |
| Phe | Asn | Val | Val | Met | Asp | Leu | Ile | Leu | Ala | Ser | Leu | Pro | Glu | Arg | Val |
| | | | 340 | | | | | 345 | | | | | 350 | | |
| Gly | Tyr | Arg | Leu | Glu | Met | Glu | Leu | Val | Ser | Ala | Leu | Ala | Tyr | Ala | Asp |
| | | 355 | | | | | 360 | | | | | 365 | | | |

-continued

```
Asp Leu Val Leu Leu Ala Gly Ser Lys Val Gly Met Gln Glu Ser Ile
370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495

Asn Ile Ser Asp Asp Arg Leu Arg Met Leu Asp Val Gln Ile Arg Lys
                500                 505                 510

Ala Val Gly Gln Trp Leu Arg Leu Pro Ala Asp Val Pro Lys Ala Tyr
            515                 520                 525

Tyr His Ala Val Gln Asp Gly Leu Ala Ile Pro Ser Val Arg
        530                 535                 540

Ala Thr Ile Pro Asp Leu Ile Val Arg Arg Phe Gly Gly Leu Asp Ser
545                 550                 555                 560

Ser Pro Trp Ser Val Ala Arg Ala Ala Lys Ser Asp Lys Ile Arg
                565                 570                 575

Lys Lys Leu Arg Trp Ala Trp Lys Gln Leu Arg Arg Phe Ser Arg Val
            580                 585                 590

Asp Ser Thr Thr Gln Arg Pro Ser Val Arg Leu Phe Trp Arg Glu His
        595                 600                 605

Leu His Ala Ser Val Asp Gly Arg Glu Leu Arg Glu Ser Thr Arg Thr
610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Gly Gly Glu Ser Ser Leu
                660                 665                 670

Thr Cys Arg Ala Gly Cys Lys Val Arg Glu Thr Thr Ala His Ile Leu
            675                 680                 685

Gln Gln Cys His Arg Thr His Gly Gly Arg Ile Leu Arg His Asn Lys
690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
                725                 730                 735

Ile Ile Ala Ser Arg Asp Gly Val Gly Val Ile Val Asp Val Gln Val
                740                 745                 750

Val Ser Gly Gln Arg Ser Leu Asp Glu Leu His Arg Glu Lys Arg Asn
            755                 760                 765

Lys Tyr Gly Asn His Gly Glu Leu Val Glu Leu Val Ala Gly Arg Leu
770                 775                 780

Gly Leu Pro Lys Ala Glu Cys Val Arg Ala Thr Ser Cys Thr Ile Ser
```

```
                785                 790                 795                 800
Trp Arg Gly Val Trp Ser Leu Thr Ser Tyr Lys Glu Leu Arg Ser Ile
                    805                 810                 815

Ile Gly Leu Arg Glu Pro Thr Leu Gln Ile Val Pro Ile Leu Ala Leu
                    820                 825                 830

Arg Gly Ser His Met Asn Trp Thr Arg Phe Asn Gln Met Thr Ser Val
                    835                 840                 845

Met Gly Gly Gly Val Gly Val Gly Thr Gly Gly Ser Gly Gly Gly
                    850                 855                 860

Thr Gly Gly Ser Ala Thr Val Lys Phe Lys Tyr Lys Gly Glu Glu
865                 870                 875                 880

Lys Glu Val Asp Ile Ser Lys Ile Lys Lys Val Trp Arg Val Gly Lys
                    885                 890                 895

Met Ile Ser Phe Thr Tyr Asp Glu Gly Gly Gly Lys Thr Gly Arg Gly
                    900                 905                 910

Ala Val Ser Glu Lys Asp Ala Pro Lys Glu Leu Leu Gln Met Leu Glu
                    915                 920                 925

Lys Gln Lys Lys
    930

<210> SEQ ID NO 20
<211> LENGTH: 1270
<212> TYPE: PRT
<213> ORGANISM: Artificial Sequence
<220> FEATURE:
<223> OTHER INFORMATION: Sso7d-Sso7d joined via a linker to the
      C-terminus of wild type R2 enzyme

<400> SEQUENCE: 20

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
        50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
                100                 105                 110

Thr Cys Gln Phe Cys Glu Arg Thr Phe Ser Thr Asn Arg Gly Leu Gly
            115                 120                 125

Val His Lys Arg Arg Ala His Pro Val Glu Thr Asn Thr Asp Ala Ala
        130                 135                 140

Pro Met Met Val Lys Arg Arg Trp His Gly Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
                180                 185                 190

Ile Lys Gly Gln Arg Arg Arg Glu Pro Tyr Arg Ala Leu Val Gln Ala
            195                 200                 205
```

-continued

His Leu Ala Arg Phe Gly Ser Gln Pro Gly Pro Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
                260                 265                 270

Gly Ala Gly Arg Arg Ala Cys Arg Ala Met Arg Pro Lys Thr Ala
                275                 280                 285

Gly Arg Arg Asn Asp Leu His Asp Asp Arg Thr Ala Ser Ala His Lys
290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
                340                 345                 350

Pro Ile Leu Glu Arg Val Ser Asp Ala Pro Gly Pro Thr Pro Glu Ala
                355                 360                 365

Leu His Ala Leu Gly Arg Ala Glu Trp His Gly Gly Asn Arg Asp Tyr
370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
                420                 425                 430

Met Ala Arg Gly Glu Ile Pro Glu Ile Leu Arg Gln Cys Arg Thr Val
                435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
                500                 505                 510

Leu Gly Asp Ser Arg Lys Lys Leu Arg Glu Cys His Val Ala Val Leu
                515                 520                 525

Asp Phe Ala Lys Ala Phe Asp Thr Val Ser His Glu Ala Leu Val Glu
530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
                580                 585                 590

Ser Pro Ile Leu Phe Asn Val Met Asp Leu Ile Leu Ala Ser Leu
                595                 600                 605

Pro Glu Arg Val Gly Tyr Arg Leu Glu Met Glu Leu Val Ser Ala Leu
610                 615                 620

Ala Tyr Ala Asp Asp Leu Val Leu Leu Ala Gly Ser Lys Val Gly Met

```
            625                 630                 635                 640
Gln Glu Ser Ile Ser Ala Val Asp Cys Val Gly Arg Gln Met Gly Leu
                    645                 650                 655

Arg Leu Asn Cys Arg Lys Ser Ala Val Leu Ser Met Ile Pro Asp Gly
                    660                 665                 670

His Arg Lys His His Tyr Leu Thr Glu Arg Thr Phe Asn Ile Gly
                675                 680                 685

Gly Lys Pro Leu Arg Gln Val Ser Cys Val Glu Arg Trp Arg Tyr Leu
            690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                    725                 730                 735

Arg Leu Glu Ile Leu Arg Ala His Leu Ile Pro Arg Phe Gln His Gly
                740                 745                 750

Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
            850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
                900                 905                 910

Ala Leu Pro Ser Arg Ile Arg Gly Ser Arg Gly Arg Gly Gly Gly
            915                 920                 925

Glu Ser Ser Leu Thr Cys Arg Ala Gly Cys Lys Val Arg Glu Thr Thr
            930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser  Arg Asp Gly Val Gly  Val Ile Val
            995                 1000                1005

Asp Val  Gln Val Val Ser Gly  Gln Arg Ser Leu Asp  Glu Leu His
        1010                1015                1020

Arg Glu  Lys Arg Asn Lys Tyr  Gly Asn His Gly Glu  Leu Val Glu
        1025                1030                1035

Leu Val  Ala Gly Arg Leu Gly  Leu Pro Lys Ala Glu  Cys Val Arg
        1040                1045                1050
```

-continued

```
Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Thr Gly Gly Gly
    1115                1120                1125

Ser Ala Thr Val Lys Phe Lys Tyr Lys Gly Glu Glu Lys Glu Val
    1130                1135                1140

Asp Ile Ser Lys Ile Lys Val Trp Arg Val Gly Lys Met Ile
    1145                1150                1155

Ser Phe Thr Tyr Asp Glu Gly Gly Gly Lys Thr Gly Arg Gly Ala
    1160                1165                1170

Val Ser Glu Lys Asp Ala Pro Lys Glu Leu Leu Gln Met Leu Glu
    1175                1180                1185

Lys Gln Lys Lys Val Gly Thr Gly Gly Gly Ser Gly Gly Gly Thr
    1190                1195                1200

Gly Gly Gly Ser Ala Thr Val Lys Phe Lys Tyr Lys Gly Glu Glu
    1205                1210                1215

Lys Glu Val Asp Ile Ser Lys Ile Lys Lys Val Trp Arg Val Gly
    1220                1225                1230

Lys Met Ile Ser Phe Thr Tyr Asp Glu Gly Gly Gly Lys Thr Gly
    1235                1240                1245

Arg Gly Ala Val Ser Glu Lys Asp Ala Pro Lys Glu Leu Leu Gln
    1250                1255                1260

Met Leu Glu Lys Gln Lys Lys
    1265                1270

<210> SEQ ID NO 21
<211> LENGTH: 985
<212> TYPE: PRT
<213> ORGANISM: Artificial Sequence
<220> FEATURE:
<223> OTHER INFORMATION: Sso7d-Sso7d joined via a linker to the
      C-terminus of deltaR2 enzyme

<400> SEQUENCE: 21

Lys Thr Ala Gly Arg Arg Asn Asp Leu His Asp Arg Thr Ala Ser
1               5                   10                  15

Ala His Lys Thr Ser Arg Gln Lys Arg Arg Ala Glu Tyr Ala Arg Val
                20                  25                  30

Gln Glu Leu Tyr Lys Lys Cys Arg Ser Arg Ala Ala Glu Val Ile
            35                  40                  45

Asp Gly Ala Cys Gly Gly Val Gly His Ser Leu Glu Glu Met Glu Thr
        50                  55                  60

Tyr Trp Arg Pro Ile Leu Glu Arg Val Ser Ala Pro Gly Pro Thr
65                  70                  75                  80

Pro Glu Ala Leu His Ala Leu Gly Arg Ala Glu Trp His Gly Gly Asn
                85                  90                  95

Arg Asp Tyr Thr Gln Leu Trp Lys Pro Ile Ser Val Glu Glu Ile Lys
                100                 105                 110

Ala Ser Arg Phe Asp Trp Arg Thr Ser Pro Gly Pro Asp Gly Ile Arg
```

```
                115                 120                 125
    Ser Gly Gln Trp Arg Ala Val Pro Val His Leu Lys Ala Glu Met Phe
        130                 135                 140
    Asn Ala Trp Met Ala Arg Gly Glu Ile Pro Glu Ile Leu Arg Gln Cys
    145                 150                 155                 160
    Arg Thr Val Phe Val Pro Lys Val Glu Arg Pro Gly Pro Gly Glu
                    165                 170                 175
    Tyr Arg Pro Ile Ser Ile Ala Ser Ile Pro Leu Arg His Phe His Ser
                    180                 185                 190
    Ile Leu Ala Arg Arg Leu Leu Ala Cys Cys Pro Pro Asp Ala Arg Gln
                    195                 200                 205
    Arg Gly Phe Ile Cys Ala Asp Gly Thr Leu Glu Asn Ser Ala Val Leu
                    210                 215                 220
    Asp Ala Val Leu Gly Asp Ser Arg Lys Lys Leu Arg Glu Cys His Val
    225                 230                 235                 240
    Ala Val Leu Asp Phe Ala Lys Ala Phe Asp Thr Val Ser His Glu Ala
                    245                 250                 255
    Leu Val Glu Leu Leu Arg Leu Arg Gly Met Pro Glu Gln Phe Cys Gly
                    260                 265                 270
    Tyr Ile Ala His Leu Tyr Asp Thr Ala Ser Thr Thr Leu Ala Val Asn
                    275                 280                 285
    Asn Glu Met Ser Ser Pro Val Lys Val Gly Arg Gly Val Arg Gln Gly
        290                 295                 300
    Asp Pro Leu Ser Pro Ile Leu Phe Asn Val Val Met Asp Leu Ile Leu
    305                 310                 315                 320
    Ala Ser Leu Pro Glu Arg Val Gly Tyr Arg Leu Glu Met Glu Leu Val
                    325                 330                 335
    Ser Ala Leu Ala Tyr Ala Asp Asp Leu Val Leu Ala Gly Ser Lys
                    340                 345                 350
    Val Gly Met Gln Glu Ser Ile Ser Ala Val Asp Cys Val Gly Arg Gln
                    355                 360                 365
    Met Gly Leu Arg Leu Asn Cys Arg Lys Ser Ala Val Leu Ser Met Ile
        370                 375                 380
    Pro Asp Gly His Arg Lys Lys His His Tyr Leu Thr Glu Arg Thr Phe
    385                 390                 395                 400
    Asn Ile Gly Gly Lys Pro Leu Arg Gln Val Ser Cys Val Glu Arg Trp
                    405                 410                 415
    Arg Tyr Leu Gly Val Asp Phe Glu Ala Ser Gly Cys Val Thr Leu Glu
                    420                 425                 430
    His Ser Ile Ser Ser Ala Leu Asn Asn Ile Ser Arg Ala Pro Leu Lys
                    435                 440                 445
    Pro Gln Gln Arg Leu Glu Ile Leu Arg Ala His Leu Ile Pro Arg Phe
        450                 455                 460
    Gln His Gly Phe Val Leu Gly Asn Ile Ser Asp Asp Arg Leu Arg Met
    465                 470                 475                 480
    Leu Asp Val Gln Ile Arg Lys Ala Val Gly Gln Trp Leu Arg Leu Pro
                    485                 490                 495
    Ala Asp Val Pro Lys Ala Tyr Tyr His Ala Ala Val Gln Asp Gly Gly
                    500                 505                 510
    Leu Ala Ile Pro Ser Val Arg Ala Thr Ile Pro Asp Leu Ile Val Arg
                    515                 520                 525
    Arg Phe Gly Gly Leu Asp Ser Ser Pro Trp Ser Val Ala Arg Ala Ala
        530                 535                 540
```

```
Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
        595                 600                 605

Arg Cys Ala Gln Ile Thr Gly Arg Asp Phe Val Gln Phe Val His Thr
    610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
                660                 665                 670

Arg Ile Leu Arg His Asn Lys Ile Val Ser Phe Val Ala Lys Ala Met
        675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
        755                 760                 765

Ala Thr Ser Cys Thr Ile Ser Trp Arg Gly Val Trp Ser Leu Thr Ser
770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
                805                 810                 815

Phe Asn Gln Met Thr Ser Val Met Gly Gly Val Gly Val Gly Thr
                820                 825                 830

Gly Gly Gly Ser Gly Gly Gly Thr Gly Gly Gly Ser Ala Thr Val Lys
            835                 840                 845

Phe Lys Tyr Lys Gly Glu Glu Lys Glu Val Asp Ile Ser Lys Ile Lys
        850                 855                 860

Lys Val Trp Arg Val Gly Lys Met Ile Ser Phe Thr Tyr Asp Glu Gly
865                 870                 875                 880

Gly Gly Lys Thr Gly Arg Gly Ala Val Ser Glu Lys Asp Ala Pro Lys
                885                 890                 895

Glu Leu Leu Gln Met Leu Glu Lys Gln Lys Val Gly Thr Gly Gly
                900                 905                 910

Gly Ser Gly Gly Gly Thr Gly Gly Gly Ser Ala Thr Val Lys Phe Lys
            915                 920                 925

Tyr Lys Gly Glu Glu Lys Glu Val Asp Ile Ser Lys Ile Lys Lys Val
        930                 935                 940

Trp Arg Val Gly Lys Met Ile Ser Phe Thr Tyr Asp Glu Gly Gly Gly
945                 950                 955                 960
```

-continued

```
Lys Thr Gly Arg Gly Ala Val Ser Glu Lys Asp Ala Pro Lys Glu Leu
                965                 970                 975

Leu Gln Met Leu Glu Lys Gln Lys Lys
        980                 985

<210> SEQ ID NO 22
<211> LENGTH: 1189
<212> TYPE: PRT
<213> ORGANISM: Artificial Sequence
<220> FEATURE:
<223> OTHER INFORMATION: Cren7 joined via a linker to the C-terminus of
      wild type R2 enzyme

<400> SEQUENCE: 22

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Ala Tyr Asp Pro Ser Ala Val
                245                 250                 255

Gly Gln Met Ser Pro Asp Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335
```

-continued

```
Cys Gly Gly Val Gly His Ser Leu Glu Glu Met Glu Thr Tyr Trp Arg
            340                 345                 350
Pro Ile Leu Glu Arg Val Ser Asp Ala Pro Gly Pro Thr Pro Glu Ala
            355                 360                 365
Leu His Ala Leu Gly Arg Ala Glu Trp His Gly Asn Arg Asp Tyr
370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
                405                 410                 415
Trp Arg Ala Val Pro Val His Leu Lys Ala Glu Met Phe Asn Ala Trp
            420                 425                 430
Met Ala Arg Gly Glu Ile Pro Glu Ile Leu Arg Gln Cys Arg Thr Val
            435                 440                 445
Phe Val Pro Lys Val Glu Arg Pro Gly Gly Pro Gly Glu Tyr Arg Pro
450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
            500                 505                 510
Leu Gly Asp Ser Arg Lys Lys Leu Arg Glu Cys His Val Ala Val Leu
            515                 520                 525
Asp Phe Ala Lys Ala Phe Asp Thr Val Ser His Glu Ala Leu Val Glu
            530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
            580                 585                 590
Ser Pro Ile Leu Phe Asn Val Val Met Asp Leu Ile Leu Ala Ser Leu
            595                 600                 605
Pro Glu Arg Val Gly Tyr Arg Leu Glu Met Glu Leu Val Ser Ala Leu
610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
            660                 665                 670
His Arg Lys Lys His His Tyr Leu Thr Glu Arg Thr Phe Asn Ile Gly
            675                 680                 685
Gly Lys Pro Leu Arg Gln Val Ser Cys Val Glu Arg Trp Arg Tyr Leu
            690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
            740                 745                 750
```

```
Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
        770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
                820                 825                 830

Asp Lys Ile Arg Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
                900                 905                 910

Ala Leu Pro Ser Arg Ile Arg Gly Ser Arg Gly Arg Gly Gly Gly
915                 920                 925

Glu Ser Ser Leu Thr Cys Arg Ala Gly Cys Lys Val Arg Glu Thr Thr
        930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
        995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Ala Ser Ser Gly Lys Lys Pro Val Lys Val Lys Thr Pro Ala
    1130                1135                1140

Gly Lys Glu Ala Glu Leu Val Pro Glu Lys Val Trp Ala Leu Ala
    1145                1150                1155

Pro Lys Gly Arg Lys Gly Val Lys Ile Gly Leu Phe Lys Asp Pro
```

-continued

```
            1160                1165                1170
Glu Thr Gly Lys Tyr Phe Arg His Lys Leu Pro Asp Asp Tyr Pro
    1175                1180                1185
Ile
```

<210> SEQ ID NO 23
<211> LENGTH: 929
<212> TYPE: PRT
<213> ORGANISM: Artificial Sequence
<220> FEATURE:
<223> OTHER INFORMATION: His Tag joined via a linker to Cren7 joined via
      a linker to the C-terminus of deltaR2 enzyme

<400> SEQUENCE: 23

```
Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
            20                  25                  30

Asp Leu His Asp Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
            180                 185                 190

Val Glu Arg Pro Gly Gly Pro Gly Glu Tyr Arg Pro Ile Ser Ile Ala
        195                 200                 205

Ser Ile Pro Leu Arg His Phe His Ser Ile Leu Ala Arg Arg Leu Leu
    210                 215                 220

Ala Cys Cys Pro Pro Asp Ala Arg Gln Arg Gly Phe Ile Cys Ala Asp
225                 230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
    290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
```

-continued

```
                 325                 330                 335
   Phe Asn Val Val Met Asp Leu Ile Leu Ala Ser Leu Pro Glu Arg Val
                 340                 345                 350
   Gly Tyr Arg Leu Glu Met Glu Leu Val Ser Ala Leu Tyr Ala Asp
                 355                 360                 365
   Asp Leu Val Leu Leu Ala Gly Ser Lys Val Gly Met Gln Glu Ser Ile
                 370                 375                 380
   Ser Ala Val Asp Cys Val Gly Arg Gln Met Gly Leu Arg Leu Asn Cys
   385                 390                 395                 400
   Arg Lys Ser Ala Val Leu Ser Met Ile Pro Asp Gly His Arg Lys Lys
                         405                 410                 415
   His His Tyr Leu Thr Glu Arg Thr Phe Asn Ile Gly Gly Lys Pro Leu
                         420                 425                 430
   Arg Gln Val Ser Cys Val Glu Arg Trp Arg Tyr Leu Gly Val Asp Phe
                         435                 440                 445
   Glu Ala Ser Gly Cys Val Thr Leu Glu His Ser Ile Ser Ser Ala Leu
                         450                 455                 460
   Asn Asn Ile Ser Arg Ala Pro Leu Lys Pro Gln Gln Arg Leu Glu Ile
   465                 470                 475                 480
   Leu Arg Ala His Leu Ile Pro Arg Phe Gln His Gly Phe Val Leu Gly
                         485                 490                 495
   Asn Ile Ser Asp Asp Arg Leu Arg Met Leu Asp Val Gln Ile Arg Lys
                         500                 505                 510
   Ala Val Gly Gln Trp Leu Arg Leu Pro Ala Asp Val Pro Lys Ala Tyr
                         515                 520                 525
   Tyr His Ala Ala Val Gln Asp Gly Gly Leu Ala Ile Pro Ser Val Arg
                         530                 535                 540
   Ala Thr Ile Pro Asp Leu Ile Val Arg Arg Phe Gly Gly Leu Asp Ser
   545                 550                 555                 560
   Ser Pro Trp Ser Val Ala Arg Ala Ala Lys Ser Asp Lys Ile Arg
                         565                 570                 575
   Lys Lys Leu Arg Trp Ala Trp Lys Gln Leu Arg Arg Phe Ser Arg Val
                         580                 585                 590
   Asp Ser Thr Thr Gln Arg Pro Ser Val Arg Leu Phe Trp Arg Glu His
                         595                 600                 605
   Leu His Ala Ser Val Asp Gly Arg Glu Leu Arg Glu Ser Thr Arg Thr
                         610                 615                 620
   Pro Thr Ser Thr Lys Trp Ile Arg Glu Arg Cys Ala Gln Ile Thr Gly
   625                 630                 635                 640
   Arg Asp Phe Val Gln Phe Val His Thr His Ile Asn Ala Leu Pro Ser
                         645                 650                 655
   Arg Ile Arg Gly Ser Arg Gly Arg Gly Gly Glu Ser Ser Leu
                         660                 665                 670
   Thr Cys Arg Ala Gly Cys Lys Val Arg Glu Thr Thr Ala His Ile Leu
                         675                 680                 685
   Gln Gln Cys His Arg Thr His Gly Gly Arg Ile Leu Arg His Asn Lys
                         690                 695                 700
   Ile Val Ser Phe Val Ala Lys Ala Met Glu Glu Asn Lys Trp Thr Val
   705                 710                 715                 720
   Glu Leu Glu Pro Arg Leu Arg Thr Ser Val Gly Leu Arg Lys Pro Asp
                         725                 730                 735
   Ile Ile Ala Ser Arg Asp Gly Val Gly Val Ile Val Asp Val Gln Val
                         740                 745                 750
```

Val Ser Gly Gln Arg Ser Leu Asp Glu Leu His Arg Glu Lys Arg Asn
          755                 760                 765

Lys Tyr Gly Asn His Gly Glu Leu Val Glu Leu Val Ala Gly Arg Leu
        770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
                820                 825                 830

Arg Gly Ser His Met Asn Trp Thr Arg Phe Asn Gln Met Thr Ser Val
        835                 840                 845

Met Gly Gly Gly Val Gly Val Gly Thr Gly Gly Ser Gly Gly Gly
    850                 855                 860

Thr Gly Gly Ser Ala Ser Ser Gly Lys Lys Pro Val Lys Val Lys
865                 870                 875                 880

Thr Pro Ala Gly Lys Glu Ala Glu Leu Val Pro Glu Lys Val Trp Ala
                885                 890                 895

Leu Ala Pro Lys Gly Arg Lys Gly Val Lys Ile Gly Leu Phe Lys Asp
            900                 905                 910

Pro Glu Thr Gly Lys Tyr Phe Arg His Lys Leu Pro Asp Asp Tyr Pro
        915                 920                 925

Ile

<210> SEQ ID NO 24
<211> LENGTH: 1264
<212> TYPE: PRT
<213> ORGANISM: Artificial Sequence
<220> FEATURE:
<223> OTHER INFORMATION: Cren7-Cren7 joined via a linker to the
      C-terminus of wild type R2 enzyme

<400> SEQUENCE: 24

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

-continued

```
Gly Asp Leu Phe Gly Ala Leu Pro Gly Phe Arg Thr Leu Glu Ala
            180                 185                 190
Ile Lys Gly Gln Arg Arg Glu Pro Tyr Arg Ala Leu Val Gln Ala
        195                 200                 205
His Leu Ala Arg Phe Gly Ser Gln Pro Gly Ser Ser Gly Gly Cys
    210                 215                 220
Ser Ala Glu Pro Asp Phe Arg Arg Ala Ser Gly Ala Glu Ala Gly
225                 230                 235                 240
Glu Glu Arg Cys Ala Glu Asp Ala Ala Tyr Asp Pro Ser Ala Val
                245                 250                 255
Gly Gln Met Ser Pro Asp Ala Ala Arg Val Leu Ser Glu Leu Leu Glu
            260                 265                 270
Gly Ala Gly Arg Arg Arg Ala Cys Arg Ala Met Arg Pro Lys Thr Ala
        275                 280                 285
Gly Arg Arg Asn Asp Leu His Asp Asp Arg Thr Ala Ser Ala His Lys
    290                 295                 300
Thr Ser Arg Gln Lys Arg Arg Ala Glu Tyr Ala Arg Val Gln Glu Leu
305                 310                 315                 320
Tyr Lys Lys Cys Arg Ser Arg Ala Ala Ala Glu Val Ile Asp Gly Ala
                325                 330                 335
Cys Gly Gly Val Gly His Ser Leu Glu Glu Met Glu Thr Tyr Trp Arg
            340                 345                 350
Pro Ile Leu Glu Arg Val Ser Asp Ala Pro Gly Pro Thr Pro Glu Ala
        355                 360                 365
Leu His Ala Leu Gly Arg Ala Glu Trp His Gly Gly Asn Arg Asp Tyr
    370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
                405                 410                 415
Trp Arg Ala Val Pro Val His Leu Lys Ala Glu Met Phe Asn Ala Trp
            420                 425                 430
Met Ala Arg Gly Glu Ile Pro Glu Ile Leu Arg Gln Cys Arg Thr Val
        435                 440                 445
Phe Val Pro Lys Val Glu Arg Pro Gly Gly Pro Gly Glu Tyr Arg Pro
    450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
            500                 505                 510
Leu Gly Asp Ser Arg Lys Lys Leu Arg Glu Cys His Val Ala Val Leu
        515                 520                 525
Asp Phe Ala Lys Ala Phe Asp Thr Val Ser His Glu Ala Leu Val Glu
    530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
            580                 585                 590
```

```
Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser  Arg Asp Gly Val Gly  Val Ile Val
        995                 1000                1005

Asp Val  Gln Val Val Ser Gly  Gln Arg Ser Leu Asp  Glu Leu His
```

-continued

```
                1010                1015                1020

Arg Glu Lys Arg Asn Lys Tyr Gly Asn His Gly Glu Leu Val Glu
        1025                1030                1035

Leu Val Ala Gly Arg Leu Gly Leu Pro Lys Ala Glu Cys Val Arg
        1040                1045                1050

Ala Thr Ser Cys Thr Ile Ser Trp Arg Gly Val Trp Ser Leu Thr
        1055                1060                1065

Ser Tyr Lys Glu Leu Arg Ser Ile Ile Gly Leu Arg Glu Pro Thr
        1070                1075                1080

Leu Gln Ile Val Pro Ile Leu Ala Leu Arg Gly Ser His Met Asn
        1085                1090                1095

Trp Thr Arg Phe Asn Gln Met Thr Ser Val Met Gly Gly Gly Val
        1100                1105                1110

Gly Val Gly Thr Gly Gly Gly Ser Gly Gly Gly Thr Gly Gly Gly
        1115                1120                1125

Ser Ala Ser Ser Gly Lys Lys Pro Val Lys Val Lys Thr Pro Ala
        1130                1135                1140

Gly Lys Glu Ala Glu Leu Val Pro Glu Lys Val Trp Ala Leu Ala
        1145                1150                1155

Pro Lys Gly Arg Lys Gly Val Lys Ile Gly Leu Phe Lys Asp Pro
        1160                1165                1170

Glu Thr Gly Lys Tyr Phe Arg His Lys Leu Pro Asp Asp Tyr Pro
        1175                1180                1185

Ile Val Gly Thr Gly Gly Ser Gly Gly Gly Thr Gly Gly Gly
        1190                1195                1200

Ser Ala Ser Ser Gly Lys Lys Pro Val Lys Val Lys Thr Pro Ala
        1205                1210                1215

Gly Lys Glu Ala Glu Leu Val Pro Glu Lys Val Trp Ala Leu Ala
        1220                1225                1230

Pro Lys Gly Arg Lys Gly Val Lys Ile Gly Leu Phe Lys Asp Pro
        1235                1240                1245

Glu Thr Gly Lys Tyr Phe Arg His Lys Leu Pro Asp Asp Tyr Pro
        1250                1255                1260

Ile
```

<210> SEQ ID NO 25
<211> LENGTH: 979
<212> TYPE: PRT
<213> ORGANISM: Artificial Sequence
<220> FEATURE:
<223> OTHER INFORMATION: Cren7-Cren7 joined via a linker to the
      C-terminus of deltaR2 enzyme

<400> SEQUENCE: 25

```
Lys Thr Ala Gly Arg Arg Asn Asp Leu His Asp Asp Arg Thr Ala Ser
1               5                   10                  15

Ala His Lys Thr Ser Arg Gln Lys Arg Ala Glu Tyr Ala Arg Val
            20                  25                  30

Gln Glu Leu Tyr Lys Lys Cys Arg Ser Arg Ala Ala Glu Val Ile
        35                  40                  45

Asp Gly Ala Cys Gly Gly Val Gly His Ser Leu Glu Glu Met Glu Thr
        50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Gly Asn
```

```
                       85                  90                  95
Arg Asp Tyr Thr Gln Leu Trp Lys Pro Ile Ser Val Glu Glu Ile Lys
                100                 105                 110

Ala Ser Arg Phe Asp Trp Arg Thr Ser Pro Gly Pro Asp Gly Ile Arg
                115                 120                 125

Ser Gly Gln Trp Arg Ala Val Pro Val His Leu Lys Ala Glu Met Phe
            130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Pro Gly Glu
                165                 170                 175

Tyr Arg Pro Ile Ser Ile Ala Ser Ile Pro Leu Arg His Phe His Ser
                180                 185                 190

Ile Leu Ala Arg Arg Leu Leu Ala Cys Cys Pro Pro Asp Ala Arg Gln
                195                 200                 205

Arg Gly Phe Ile Cys Ala Asp Gly Thr Leu Glu Asn Ser Ala Val Leu
            210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
                260                 265                 270

Tyr Ile Ala His Leu Tyr Asp Thr Ala Ser Thr Thr Leu Ala Val Asn
            275                 280                 285

Asn Glu Met Ser Ser Pro Val Lys Val Gly Arg Gly Val Arg Gln Gly
            290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Leu Val Leu Leu Ala Gly Ser Lys
            340                 345                 350

Val Gly Met Gln Glu Ser Ile Ser Ala Val Asp Cys Val Gly Arg Gln
            355                 360                 365

Met Gly Leu Arg Leu Asn Cys Arg Lys Ser Ala Val Leu Ser Met Ile
            370                 375                 380

Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
                405                 410                 415

Arg Tyr Leu Gly Val Asp Phe Glu Ala Ser Gly Cys Val Thr Leu Glu
            420                 425                 430

His Ser Ile Ser Ser Ala Leu Asn Asn Ile Ser Arg Ala Pro Leu Lys
            435                 440                 445

Pro Gln Gln Arg Leu Glu Ile Leu Arg Ala His Leu Ile Pro Arg Phe
            450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
            500                 505                 510
```

```
Leu Ala Ile Pro Ser Val Arg Ala Thr Ile Pro Asp Leu Ile Val Arg
            515                 520                 525

Arg Phe Gly Gly Leu Asp Ser Ser Pro Trp Ser Val Ala Arg Ala Ala
        530                 535                 540

Ala Lys Ser Asp Lys Ile Arg Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
            595                 600                 605

Arg Cys Ala Gln Ile Thr Gly Arg Asp Phe Val Gln Phe Val His Thr
            610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
            660                 665                 670

Arg Ile Leu Arg His Asn Lys Ile Val Ser Phe Val Ala Lys Ala Met
            675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
            755                 760                 765

Ala Thr Ser Cys Thr Ile Ser Trp Arg Gly Val Trp Ser Leu Thr Ser
            770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
                805                 810                 815

Phe Asn Gln Met Thr Ser Val Met Gly Gly Val Gly Val Gly Thr
            820                 825                 830

Gly Gly Gly Ser Gly Gly Gly Thr Gly Gly Gly Ser Ala Ser Ser Gly
                835                 840                 845

Lys Lys Pro Val Lys Val Lys Thr Pro Ala Gly Lys Glu Ala Glu Leu
            850                 855                 860

Val Pro Glu Lys Val Trp Ala Leu Ala Pro Lys Gly Arg Lys Gly Val
865                 870                 875                 880

Lys Ile Gly Leu Phe Lys Asp Pro Glu Thr Gly Lys Tyr Phe Arg His
                885                 890                 895

Lys Leu Pro Asp Asp Tyr Pro Ile Val Gly Thr Gly Gly Gly Ser Gly
                900                 905                 910

Gly Gly Thr Gly Gly Gly Ser Ala Ser Ser Gly Lys Lys Pro Val Lys
            915                 920                 925
```

```
Val Lys Thr Pro Ala Gly Lys Glu Ala Glu Leu Val Pro Glu Lys Val
    930                 935                 940

Trp Ala Leu Ala Pro Lys Gly Arg Lys Gly Val Lys Ile Gly Leu Phe
945                 950                 955                 960

Lys Asp Pro Glu Thr Gly Lys Tyr Phe Arg His Lys Leu Pro Asp Asp
                965                 970                 975

Tyr Pro Ile

<210> SEQ ID NO 26
<211> LENGTH: 1339
<212> TYPE: PRT
<213> ORGANISM: Artificial Sequence
<220> FEATURE:
<223> OTHER INFORMATION: Cren7-Cren7-Cren7 joined via a linker to the
      C-terminus of wild type R2 enzyme

<400> SEQUENCE: 26

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
            115                 120                 125

Val His Lys Arg Arg Ala His Pro Val Glu Thr Asn Thr Asp Ala Ala
    130                 135                 140

Pro Met Met Val Lys Arg Arg Trp His Gly Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300
```

Thr Ser Arg Gln Lys Arg Ala Glu Tyr Ala Val Gln Glu Leu
305                 310                 315                 320

Tyr Lys Lys Cys Arg Ser Arg Ala Ala Ala Glu Val Ile Asp Gly Ala
            325                 330                 335

Cys Gly Gly Val Gly His Ser Leu Glu Glu Met Glu Thr Tyr Trp Arg
                340                 345                 350

Pro Ile Leu Glu Arg Val Ser Asp Ala Pro Gly Pro Thr Pro Glu Ala
            355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
                420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
                500                 505                 510

Leu Gly Asp Ser Arg Lys Lys Leu Arg Glu Cys His Val Ala Val Leu
    515                 520                 525

Asp Phe Ala Lys Ala Phe Asp Thr Val Ser His Glu Ala Leu Val Glu
530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Met Asp Leu Ile Leu Ala Ser Leu
            595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
    675                 680                 685

Gly Lys Pro Leu Arg Gln Val Ser Cys Val Glu Arg Trp Arg Tyr Leu
            690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln

-continued

```
                725                 730                 735
Arg Leu Glu Ile Leu Arg Ala His Leu Ile Pro Arg Phe Gln His Gly
            740                 745                 750
Phe Val Leu Gly Asn Ile Ser Asp Asp Arg Leu Arg Met Leu Asp Val
            755                 760                 765
Gln Ile Arg Lys Ala Val Gly Gln Trp Leu Arg Leu Pro Ala Asp Val
    770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Ala Lys Ser
            820                 825                 830
Asp Lys Ile Arg Lys Leu Arg Trp Ala Trp Lys Gln Leu Arg Arg
            835                 840                 845
Phe Ser Arg Val Asp Ser Thr Thr Gln Arg Pro Ser Val Arg Leu Phe
    850                 855                 860
Trp Arg Glu His Leu His Ala Ser Val Asp Gly Arg Glu Leu Arg Glu
865                 870                 875                 880
Ser Thr Arg Thr Pro Thr Ser Thr Lys Trp Ile Arg Glu Arg Cys Ala
                885                 890                 895
Gln Ile Thr Gly Arg Asp Phe Val Gln Phe Val His Thr His Ile Asn
            900                 905                 910
Ala Leu Pro Ser Arg Ile Arg Gly Ser Arg Gly Arg Gly Gly Gly
            915                 920                 925
Glu Ser Ser Leu Thr Cys Arg Ala Gly Cys Lys Val Arg Glu Thr Thr
930                 935                 940
Ala His Ile Leu Gln Gln Cys His Arg Thr His Gly Gly Arg Ile Leu
945                 950                 955                 960
Arg His Asn Lys Ile Val Ser Phe Val Ala Lys Ala Met Glu Glu Asn
                965                 970                 975
Lys Trp Thr Val Glu Leu Glu Pro Arg Leu Arg Thr Ser Val Gly Leu
            980                 985                 990
Arg Lys Pro Asp Ile Ile Ala Ser  Arg Asp Gly Val Gly  Val Ile Val
            995                 1000                1005
Asp Val Gln Val Val Ser Gly  Gln Arg Ser Leu Asp  Glu Leu His
    1010                 1015                1020
Arg Glu Lys Arg Asn Lys Tyr  Gly Asn His Gly Glu  Leu Val Glu
    1025                 1030                1035
Leu Val Ala Gly Arg Leu Gly  Leu Pro Lys Ala Glu  Cys Val Arg
    1040                 1045                1050
Ala Thr Ser Cys Thr Ile Ser  Trp Arg Gly Val Trp  Ser Leu Thr
    1055                 1060                1065
Ser Tyr Lys Glu Leu Arg Ser  Ile Ile Gly Leu Arg  Glu Pro Thr
    1070                 1075                1080
Leu Gln Ile Val Pro Ile Leu  Ala Leu Arg Gly Ser  His Met Asn
    1085                 1090                1095
Trp Thr Arg Phe Asn Gln Met  Thr Ser Val Met Gly  Gly Gly Val
    1100                 1105                1110
Gly Val Gly Thr Gly Gly Gly  Ser Gly Gly Gly Thr  Gly Gly Gly
    1115                 1120                1125
Ser Ala Ser Ser Gly Lys Lys  Pro Val Lys Val Lys  Thr Pro Ala
    1130                 1135                1140
```

Gly Lys Glu Ala Glu Leu Val Pro Glu Lys Val Trp Ala Leu Ala
    1145                1150                1155

Pro Lys Gly Arg Lys Gly Val Lys Ile Gly Leu Phe Lys Asp Pro
    1160                1165                1170

Glu Thr Gly Lys Tyr Phe Arg His Lys Leu Pro Asp Asp Tyr Pro
    1175                1180                1185

Ile Val Gly Thr Gly Gly Gly Ser Gly Gly Gly Thr Gly Gly Gly
    1190                1195                1200

Ser Ala Ser Ser Gly Lys Lys Pro Val Lys Val Lys Thr Pro Ala
    1205                1210                1215

Gly Lys Glu Ala Glu Leu Val Pro Glu Lys Val Trp Ala Leu Ala
    1220                1225                1230

Pro Lys Gly Arg Lys Gly Val Lys Ile Gly Leu Phe Lys Asp Pro
    1235                1240                1245

Glu Thr Gly Lys Tyr Phe Arg His Lys Leu Pro Asp Asp Tyr Pro
    1250                1255                1260

Ile Val Gly Thr Gly Gly Gly Ser Gly Gly Gly Thr Gly Gly Gly
    1265                1270                1275

Ser Ala Ser Ser Gly Lys Lys Pro Val Lys Val Lys Thr Pro Ala
    1280                1285                1290

Gly Lys Glu Ala Glu Leu Val Pro Glu Lys Val Trp Ala Leu Ala
    1295                1300                1305

Pro Lys Gly Arg Lys Gly Val Lys Ile Gly Leu Phe Lys Asp Pro
    1310                1315                1320

Glu Thr Gly Lys Tyr Phe Arg His Lys Leu Pro Asp Asp Tyr Pro
    1325                1330                1335

Ile

<210> SEQ ID NO 27
<211> LENGTH: 1079
<212> TYPE: PRT
<213> ORGANISM: Artificial Sequence
<220> FEATURE:
<223> OTHER INFORMATION: His Tag joined via a linker to Cren7-Cren7-
      Cren7 joined via a linker to the C-terminus of deltaR2 enzyme

<400> SEQUENCE: 27

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
                20                  25                  30

Asp Leu His Asp Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
                100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

```
Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
            165                 170                 175

Glu Ile Pro Glu Ile Leu Arg Gln Cys Arg Thr Val Phe Val Pro Lys
        180                 185                 190

Val Glu Arg Pro Gly Pro Gly Glu Tyr Arg Pro Ile Ser Ile Ala
    195                 200                 205

Ser Ile Pro Leu Arg His Phe His Ser Ile Leu Ala Arg Arg Leu Leu
210                 215                 220

Ala Cys Cys Pro Pro Asp Ala Arg Gln Arg Gly Phe Ile Cys Ala Asp
225                 230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
                325                 330                 335

Phe Asn Val Val Met Asp Leu Ile Leu Ala Ser Leu Pro Glu Arg Val
            340                 345                 350

Gly Tyr Arg Leu Glu Met Glu Leu Val Ser Ala Leu Ala Tyr Ala Asp
        355                 360                 365

Asp Leu Val Leu Leu Ala Gly Ser Lys Val Gly Met Gln Glu Ser Ile
370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495

Asn Ile Ser Asp Asp Arg Leu Arg Met Leu Asp Val Gln Ile Arg Lys
            500                 505                 510

Ala Val Gly Gln Trp Leu Arg Leu Pro Ala Asp Val Pro Lys Ala Tyr
        515                 520                 525

Tyr His Ala Ala Val Gln Asp Gly Gly Leu Ala Ile Pro Ser Val Arg
530                 535                 540

Ala Thr Ile Pro Asp Leu Ile Val Arg Arg Phe Gly Gly Leu Asp Ser
545                 550                 555                 560
```

```
Ser Pro Trp Ser Val Ala Arg Ala Ala Ala Lys Ser Asp Lys Ile Arg
            565                 570                 575

Lys Lys Leu Arg Trp Ala Trp Lys Gln Leu Arg Arg Phe Ser Arg Val
            580                 585                 590

Asp Ser Thr Thr Gln Arg Pro Ser Val Arg Leu Phe Trp Arg Glu His
            595                 600                 605

Leu His Ala Ser Val Asp Gly Arg Glu Leu Arg Glu Ser Thr Arg Thr
            610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Arg Gly Gly Glu Ser Ser Leu
            660                 665                 670

Thr Cys Arg Ala Gly Cys Lys Val Arg Glu Thr Thr Ala His Ile Leu
            675                 680                 685

Gln Gln Cys His Arg Thr His Gly Gly Arg Ile Leu Arg His Asn Lys
            690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
                725                 730                 735

Ile Ile Ala Ser Arg Asp Gly Val Gly Val Ile Val Asp Val Gln Val
                740                 745                 750

Val Ser Gly Gln Arg Ser Leu Asp Glu Leu His Arg Glu Lys Arg Asn
            755                 760                 765

Lys Tyr Gly Asn His Gly Glu Leu Val Glu Leu Val Ala Gly Arg Leu
            770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
                820                 825                 830

Arg Gly Ser His Met Asn Trp Thr Arg Phe Asn Gln Met Thr Ser Val
            835                 840                 845

Met Gly Gly Gly Val Gly Val Gly Thr Gly Gly Gly Ser Gly Gly Gly
            850                 855                 860

Thr Gly Gly Gly Ser Ala Ser Ser Gly Lys Lys Pro Val Lys Val Lys
865                 870                 875                 880

Thr Pro Ala Gly Lys Glu Ala Glu Leu Val Pro Glu Lys Val Trp Ala
                885                 890                 895

Leu Ala Pro Lys Gly Arg Lys Gly Val Lys Ile Gly Leu Phe Lys Asp
                900                 905                 910

Pro Glu Thr Gly Lys Tyr Phe Arg His Lys Leu Pro Asp Asp Tyr Pro
            915                 920                 925

Ile Val Gly Thr Gly Gly Ser Gly Gly Gly Thr Gly Gly Gly Ser
            930                 935                 940

Ala Ser Ser Gly Lys Lys Pro Val Lys Val Lys Thr Pro Ala Gly Lys
945                 950                 955                 960

Glu Ala Glu Leu Val Pro Glu Lys Val Trp Ala Leu Ala Pro Lys Gly
                965                 970                 975

Arg Lys Gly Val Lys Ile Gly Leu Phe Lys Asp Pro Glu Thr Gly Lys
```

```
                    980             985                990
Tyr Phe Arg His Lys Leu Pro Asp Asp Tyr Pro Ile Val Gly Thr Gly
                995              1000               1005

Gly Gly Ser Gly Gly Gly Thr Gly Gly Gly Ser Ala Ser Ser Gly
        1010              1015              1020

Lys Lys Pro Val Lys Val Lys Thr Pro Ala Gly Lys Glu Ala Glu
        1025              1030              1035

Leu Val Pro Glu Lys Val Trp Ala Leu Ala Pro Lys Gly Arg Lys
        1040              1045              1050

Gly Val Lys Ile Gly Leu Phe Lys Asp Pro Glu Thr Gly Lys Tyr
        1055              1060              1065

Phe Arg His Lys Leu Pro Asp Asp Tyr Pro Ile
        1070              1075
```

<210> SEQ ID NO 28
<211> LENGTH: 1267
<212> TYPE: PRT
<213> ORGANISM: Artificial Sequence
<220> FEATURE:
<223> OTHER INFORMATION: Sso7d-Cren7 joined via a linker to the
      C-terminus of wild type R2 enzyme

<400> SEQUENCE: 28

```
Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
        50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Arg Glu Pro Tyr Arg Ala Leu Val Gln Ala
        195                 200                 205

His Leu Ala Arg Phe Gly Ser Gln Pro Gly Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255
```

-continued

```
Gly Gln Met Ser Pro Asp Ala Ala Arg Val Leu Ser Glu Leu Leu Glu
            260                 265                 270

Gly Ala Gly Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
        435                 440                 445

Phe Val Pro Lys Val Glu Arg Pro Gly Gly Pro Gly Glu Tyr Arg Pro
    450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
        515                 520                 525

Asp Phe Ala Lys Ala Phe Asp Thr Val Ser His Glu Ala Leu Val Glu
    530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
```

```
            675                 680                 685
Gly Lys Pro Leu Arg Gln Val Ser Cys Val Glu Arg Trp Arg Tyr Leu
    690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
            740                 745                 750
Phe Val Leu Gly Asn Ile Ser Asp Asp Arg Leu Arg Met Leu Asp Val
        755                 760                 765
Gln Ile Arg Lys Ala Val Gly Gln Trp Leu Arg Leu Pro Ala Asp Val
    770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Lys Ser
            820                 825                 830
Asp Lys Ile Arg Lys Lys Leu Arg Trp Ala Trp Lys Gln Leu Arg Arg
        835                 840                 845
Phe Ser Arg Val Asp Ser Thr Thr Gln Arg Pro Ser Val Arg Leu Phe
    850                 855                 860
Trp Arg Glu His Leu His Ala Ser Val Asp Gly Arg Glu Leu Arg Glu
865                 870                 875                 880
Ser Thr Arg Thr Pro Thr Ser Thr Lys Trp Ile Arg Glu Arg Cys Ala
                885                 890                 895
Gln Ile Thr Gly Arg Asp Phe Val Gln Phe Val His Thr His Ile Asn
            900                 905                 910
Ala Leu Pro Ser Arg Ile Arg Gly Ser Arg Gly Arg Gly Gly Gly
        915                 920                 925
Glu Ser Ser Leu Thr Cys Arg Ala Gly Cys Lys Val Arg Glu Thr Thr
    930                 935                 940
Ala His Ile Leu Gln Gln Cys His Arg Thr His Gly Gly Arg Ile Leu
945                 950                 955                 960
Arg His Asn Lys Ile Val Ser Phe Val Ala Lys Ala Met Glu Glu Asn
                965                 970                 975
Lys Trp Thr Val Glu Leu Glu Pro Arg Leu Arg Thr Ser Val Gly Leu
            980                 985                 990
Arg Lys Pro Asp Ile Ile Ala Ser Arg Asp Gly Val Gly Val Ile Val
        995                 1000                1005
Asp Val Gln Val Val Ser Gly Gln Arg Ser Leu Asp Glu Leu His
    1010                1015                1020
Arg Glu Lys Arg Asn Lys Tyr Gly Asn His Gly Glu Leu Val Glu
    1025                1030                1035
Leu Val Ala Gly Arg Leu Gly Leu Pro Lys Ala Glu Cys Val Arg
    1040                1045                1050
Ala Thr Ser Cys Thr Ile Ser Trp Arg Gly Val Trp Ser Leu Thr
    1055                1060                1065
Ser Tyr Lys Glu Leu Arg Ser Ile Ile Gly Leu Arg Glu Pro Thr
    1070                1075                1080
Leu Gln Ile Val Pro Ile Leu Ala Leu Arg Gly Ser His Met Asn
    1085                1090                1095
```

-continued

```
Trp Thr Arg Phe Asn Gln Met Thr Ser Val Met Gly Gly Gly Val
    1100                1105                1110

Gly Val Gly Thr Gly Gly Ser Gly Gly Gly Thr Gly Gly Gly
1115                1120                1125

Ser Ala Thr Val Lys Phe Lys Tyr Lys Gly Glu Glu Lys Glu Val
    1130                1135                1140

Asp Ile Ser Lys Ile Lys Lys Val Trp Arg Val Gly Lys Met Ile
    1145                1150                1155

Ser Phe Thr Tyr Asp Glu Gly Gly Gly Lys Thr Gly Arg Gly Ala
    1160                1165                1170

Val Ser Glu Lys Asp Ala Pro Lys Glu Leu Leu Gln Met Leu Glu
    1175                1180                1185

Lys Gln Lys Lys Val Gly Thr Gly Gly Gly Ser Gly Gly Gly Thr
    1190                1195                1200

Gly Gly Gly Ser Ala Ser Ser Gly Lys Lys Pro Val Lys Val Lys
    1205                1210                1215

Thr Pro Ala Gly Lys Glu Ala Glu Leu Val Pro Glu Lys Val Trp
    1220                1225                1230

Ala Leu Ala Pro Lys Gly Arg Lys Gly Val Lys Ile Gly Leu Phe
    1235                1240                1245

Lys Asp Pro Glu Thr Gly Lys Tyr Phe Arg His Lys Leu Pro Asp
    1250                1255                1260

Asp Tyr Pro Ile
    1265

<210> SEQ ID NO 29
<211> LENGTH: 1007
<212> TYPE: PRT
<213> ORGANISM: Artificial Sequence
<220> FEATURE:
<223> OTHER INFORMATION: His Tag joined via a linker to Sso7d-Cren7
      joined via a linker to the C-terminus of deltaR2 enzyme

<400> SEQUENCE: 29

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
                20                  25                  30

Asp Leu His Asp Asp Arg Thr Ala Ser Ala His Lys Thr Ser Arg Gln
            35                  40                  45

Lys Arg Arg Ala Glu Tyr Ala Arg Val Gln Glu Leu Tyr Lys Lys Cys
50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
```

```
                    165                 170                 175
Glu Ile Pro Glu Ile Leu Arg Gln Cys Arg Thr Val Phe Val Pro Lys
                180                 185                 190
Val Glu Arg Pro Gly Gly Pro Gly Glu Tyr Arg Pro Ile Ser Ile Ala
                195                 200                 205
Ser Ile Pro Leu Arg His Phe His Ser Ile Leu Ala Arg Arg Leu Leu
                210                 215                 220
Ala Cys Cys Pro Pro Asp Ala Arg Gln Arg Gly Phe Ile Cys Ala Asp
225                 230                 235                 240
Gly Thr Leu Glu Asn Ser Ala Val Leu Asp Ala Val Leu Gly Asp Ser
                245                 250                 255
Arg Lys Lys Leu Arg Glu Cys His Val Ala Val Leu Asp Phe Ala Lys
                260                 265                 270
Ala Phe Asp Thr Val Ser His Glu Ala Leu Val Glu Leu Leu Arg Leu
                275                 280                 285
Arg Gly Met Pro Glu Gln Phe Cys Gly Tyr Ile Ala His Leu Tyr Asp
                290                 295                 300
Thr Ala Ser Thr Thr Leu Ala Val Asn Asn Glu Met Ser Ser Pro Val
305                 310                 315                 320
Lys Val Gly Arg Gly Val Arg Gln Gly Asp Pro Leu Ser Pro Ile Leu
                325                 330                 335
Phe Asn Val Val Met Asp Leu Ile Leu Ala Ser Leu Pro Glu Arg Val
                340                 345                 350
Gly Tyr Arg Leu Glu Met Glu Leu Val Ser Ala Leu Ala Tyr Ala Asp
                355                 360                 365
Asp Leu Val Leu Leu Ala Gly Ser Lys Val Gly Met Gln Glu Ser Ile
                370                 375                 380
Ser Ala Val Asp Cys Val Gly Arg Gln Met Gly Leu Arg Leu Asn Cys
385                 390                 395                 400
Arg Lys Ser Ala Val Leu Ser Met Ile Pro Asp Gly His Arg Lys Lys
                405                 410                 415
His His Tyr Leu Thr Glu Arg Thr Phe Asn Ile Gly Gly Lys Pro Leu
                420                 425                 430
Arg Gln Val Ser Cys Val Glu Arg Trp Arg Tyr Leu Gly Val Asp Phe
                435                 440                 445
Glu Ala Ser Gly Cys Val Thr Leu Glu His Ser Ile Ser Ser Ala Leu
                450                 455                 460
Asn Asn Ile Ser Arg Ala Pro Leu Lys Pro Gln Gln Arg Leu Glu Ile
465                 470                 475                 480
Leu Arg Ala His Leu Ile Pro Arg Phe Gln His Gly Phe Val Leu Gly
                485                 490                 495
Asn Ile Ser Asp Asp Arg Leu Arg Met Leu Asp Val Gln Ile Arg Lys
                500                 505                 510
Ala Val Gly Gln Trp Leu Arg Leu Pro Ala Asp Val Pro Lys Ala Tyr
                515                 520                 525
Tyr His Ala Ala Val Gln Asp Gly Gly Leu Ala Ile Pro Ser Val Arg
                530                 535                 540
Ala Thr Ile Pro Asp Leu Ile Val Arg Arg Phe Gly Gly Leu Asp Ser
545                 550                 555                 560
Ser Pro Trp Ser Val Ala Arg Ala Ala Lys Ser Asp Lys Ile Arg
                565                 570                 575
Lys Lys Leu Arg Trp Ala Trp Lys Gln Leu Arg Arg Phe Ser Arg Val
                580                 585                 590
```

```
Asp Ser Thr Thr Gln Arg Pro Ser Val Arg Leu Phe Trp Arg Glu His
        595                 600                 605

Leu His Ala Ser Val Asp Gly Arg Glu Leu Arg Glu Ser Thr Arg Thr
    610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Arg Gly Gly Glu Ser Ser Leu
                660                 665                 670

Thr Cys Arg Ala Gly Cys Lys Val Arg Glu Thr Thr Ala His Ile Leu
        675                 680                 685

Gln Gln Cys His Arg Thr His Gly Gly Arg Ile Leu Arg His Asn Lys
    690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
                725                 730                 735

Ile Ile Ala Ser Arg Asp Gly Val Gly Val Ile Asp Val Gln Val
        740                 745                 750

Val Ser Gly Gln Arg Ser Leu Asp Glu Leu His Arg Glu Lys Arg Asn
    755                 760                 765

Lys Tyr Gly Asn His Gly Glu Leu Val Glu Leu Val Ala Gly Arg Leu
770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
        820                 825                 830

Arg Gly Ser His Met Asn Trp Thr Arg Phe Asn Gln Met Thr Ser Val
    835                 840                 845

Met Gly Gly Gly Val Gly Val Gly Thr Gly Gly Ser Gly Gly Gly
850                 855                 860

Thr Gly Gly Gly Ser Ala Thr Val Lys Phe Lys Tyr Lys Gly Glu Glu
865                 870                 875                 880

Lys Glu Val Asp Ile Ser Lys Ile Lys Lys Val Trp Arg Val Gly Lys
                885                 890                 895

Met Ile Ser Phe Thr Tyr Asp Glu Gly Gly Lys Thr Gly Arg Gly
        900                 905                 910

Ala Val Ser Glu Lys Asp Ala Pro Lys Glu Leu Leu Gln Met Leu Glu
    915                 920                 925

Lys Gln Lys Lys Val Gly Thr Gly Gly Ser Gly Gly Thr Gly
930                 935                 940

Gly Gly Ser Ala Ser Ser Gly Lys Lys Pro Val Lys Val Lys Thr Pro
945                 950                 955                 960

Ala Gly Lys Glu Ala Glu Leu Val Pro Glu Lys Val Trp Ala Leu Ala
                965                 970                 975

Pro Lys Gly Arg Lys Gly Val Lys Ile Gly Leu Phe Lys Asp Pro Glu
        980                 985                 990

Thr Gly Lys Tyr Phe Arg His Lys  Leu Pro Asp Asp Tyr  Pro Ile
    995                 1000                1005
```

<210> SEQ ID NO 30
<211> LENGTH: 1352
<212> TYPE: PRT
<213> ORGANISM: Artificial Sequence
<220> FEATURE:
<223> OTHER INFORMATION: Sso7d-Cren7-Cren7 joined via a linker to the
      C-terminus of wild type R2 enzyme

<400> SEQUENCE: 30

```
Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365
```

```
Leu His Ala Leu Gly Arg Ala Glu Trp His Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
            515                 520                 525

Asp Phe Ala Lys Ala Phe Asp Thr Val Ser His Glu Ala Leu Val Glu
530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
            595                 600                 605

Pro Glu Arg Val Gly Tyr Arg Leu Glu Met Glu Leu Val Ser Ala Leu
610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
                660                 665                 670

His Arg Lys His His Tyr Leu Thr Glu Arg Thr Phe Asn Ile Gly
            675                 680                 685

Gly Lys Pro Leu Arg Gln Val Ser Cys Val Glu Arg Trp Arg Tyr Leu
            690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
                740                 745                 750

Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
770                 775                 780
```

```
Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
            805                 810                 815

Gly Leu Asp Ser Ser Pro Trp Ser Val Ala Arg Ala Ala Lys Ser
            820                 825                 830

Asp Lys Ile Arg Lys Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
                900                 905                 910

Ala Leu Pro Ser Arg Ile Arg Gly Ser Arg Gly Arg Gly Gly
            915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Ala Thr Val Lys Phe Lys Tyr Lys Gly Glu Glu Lys Glu Val
    1130                1135                1140

Asp Ile Ser Lys Ile Lys Lys Val Trp Arg Val Gly Lys Met Ile
    1145                1150                1155

Ser Phe Thr Tyr Asp Glu Gly Gly Gly Lys Thr Gly Arg Gly Ala
    1160                1165                1170

Val Ser Glu Lys Asp Ala Pro Lys Glu Leu Leu Gln Met Leu Glu
    1175                1180                1185

Lys Gln Lys Lys Val Gly Thr Gly Gly Gly Ser Gly Gly Gly Thr
```

```
                        1190                1195                1200
Gly Gly Gly Ser Ala Ser Ser Gly Lys Lys Pro Val Lys Val Lys
            1205                1210                1215

Thr Pro Ala Gly Lys Glu Ala Glu Leu Val Pro Glu Lys Val Trp
    1220                1225                1230

Ala Leu Ala Pro Lys Gly Arg Lys Gly Val Lys Ile Gly Leu Phe
    1235                1240                1245

Lys Asp Pro Glu Thr Gly Lys Tyr Phe Arg His Lys Leu Pro Asp
    1250                1255                1260

Asp Tyr Pro Ile Val Gly Thr Gly Gly Ser Gly Gly Gly Gly Glu
    1265                1270                1275

Ala Ala Ala Lys Glu Ala Ala Lys Ser Gly Gly Gly Ser Ala
    1280                1285                1290

Ser Ser Gly Lys Lys Pro Val Lys Val Lys Thr Pro Ala Gly Lys
    1295                1300                1305

Glu Ala Glu Leu Val Pro Glu Lys Val Trp Ala Leu Ala Pro Lys
    1310                1315                1320

Gly Arg Lys Gly Val Lys Ile Gly Leu Phe Lys Asp Pro Glu Thr
    1325                1330                1335

Gly Lys Tyr Phe Arg His Lys Leu Pro Asp Asp Tyr Pro Ile
    1340                1345                1350

<210> SEQ ID NO 31
<211> LENGTH: 1092
<212> TYPE: PRT
<213> ORGANISM: Artificial Sequence
<220> FEATURE:
<223> OTHER INFORMATION: His Tag joined via a linker to Sso7d-Cren7-
      Cren7 joined via a linker to the C-terminus of deltaR2 enzyme

<400> SEQUENCE: 31

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
            20                  25                  30

Asp Leu His Asp Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
            180                 185                 190
```

```
Val Glu Arg Pro Gly Gly Pro Gly Glu Tyr Arg Pro Ile Ser Ile Ala
            195                 200                 205

Ser Ile Pro Leu Arg His Phe His Ser Ile Leu Ala Arg Arg Leu Leu
    210                 215                 220

Ala Cys Cys Pro Pro Asp Ala Arg Gln Arg Gly Phe Ile Cys Ala Asp
225                     230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
    290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
                325                 330                 335

Phe Asn Val Val Met Asp Leu Ile Leu Ala Ser Leu Pro Glu Arg Val
            340                 345                 350

Gly Tyr Arg Leu Glu Met Glu Leu Val Ser Ala Leu Ala Tyr Ala Asp
        355                 360                 365

Asp Leu Val Leu Leu Ala Gly Ser Lys Val Gly Met Gln Glu Ser Ile
    370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495

Asn Ile Ser Asp Asp Arg Leu Arg Met Leu Asp Val Gln Ile Arg Lys
            500                 505                 510

Ala Val Gly Gln Trp Leu Arg Leu Pro Ala Asp Val Pro Lys Ala Tyr
        515                 520                 525

Tyr His Ala Ala Val Gln Asp Gly Gly Leu Ala Ile Pro Ser Val Arg
    530                 535                 540

Ala Thr Ile Pro Asp Leu Ile Val Arg Arg Phe Gly Gly Leu Asp Ser
545                 550                 555                 560

Ser Pro Trp Ser Val Ala Arg Ala Ala Lys Ser Asp Lys Ile Arg
                565                 570                 575

Lys Lys Leu Arg Trp Ala Trp Lys Gln Leu Arg Arg Phe Ser Arg Val
            580                 585                 590

Asp Ser Thr Thr Gln Arg Pro Ser Val Arg Leu Phe Trp Arg Glu His
        595                 600                 605

Leu His Ala Ser Val Asp Gly Arg Glu Leu Arg Glu Ser Thr Arg Thr
```

```
                610             615             620
Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Gly Gly Gly Glu Ser Ser Leu
            660                 665                 670

Thr Cys Arg Ala Gly Cys Lys Val Arg Glu Thr Thr Ala His Ile Leu
            675                 680                 685

Gln Gln Cys His Arg Thr His Gly Gly Arg Ile Leu Arg His Asn Lys
690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
                725                 730                 735

Ile Ile Ala Ser Arg Asp Gly Val Gly Val Ile Val Asp Val Gln Val
                740                 745                 750

Val Ser Gly Gln Arg Ser Leu Asp Glu Leu His Arg Glu Lys Arg Asn
            755                 760                 765

Lys Tyr Gly Asn His Gly Glu Leu Val Glu Leu Val Ala Gly Arg Leu
770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
                820                 825                 830

Arg Gly Ser His Met Asn Trp Thr Arg Phe Asn Gln Met Thr Ser Val
            835                 840                 845

Met Gly Gly Gly Val Gly Val Gly Thr Gly Gly Gly Ser Gly Gly Gly
850                 855                 860

Thr Gly Gly Gly Ser Ala Thr Val Lys Phe Lys Tyr Lys Gly Glu Glu
865                 870                 875                 880

Lys Glu Val Asp Ile Ser Lys Ile Lys Lys Val Trp Arg Val Gly Lys
                885                 890                 895

Met Ile Ser Phe Thr Tyr Asp Glu Gly Gly Lys Thr Gly Arg Gly
                900                 905                 910

Ala Val Ser Glu Lys Asp Ala Pro Lys Glu Leu Leu Gln Met Leu Glu
            915                 920                 925

Lys Gln Lys Lys Val Gly Thr Gly Gly Gly Ser Gly Gly Gly Thr Gly
930                 935                 940

Gly Gly Ser Ala Ser Ser Gly Lys Lys Pro Lys Val Lys Thr Pro
945                 950                 955                 960

Ala Gly Lys Glu Ala Glu Leu Val Pro Glu Lys Val Trp Ala Leu Ala
                965                 970                 975

Pro Lys Gly Arg Lys Gly Val Lys Ile Gly Leu Phe Lys Asp Pro Glu
            980                 985                 990

Thr Gly Lys Tyr Phe Arg His Lys Leu Pro Asp Asp Tyr Pro Ile Val
            995                 1000                1005

Gly Thr Gly Gly Gly Ser Gly Gly Glu Ala Ala Ala Lys Glu
    1010                1015                1020

Ala Ala Ala Lys Ser Gly Gly Gly Ser Ala Ser Ser Gly Lys Lys
    1025                1030                1035
```

```
Pro Val Lys Val Lys Thr Pro Ala Gly Lys Glu Ala Glu Leu Val
    1040            1045                1050

Pro Glu Lys Val Trp Ala Leu Ala Pro Lys Gly Arg Lys Gly Val
    1055            1060                1065

Lys Ile Gly Leu Phe Lys Asp Pro Glu Thr Gly Lys Tyr Phe Arg
    1070            1075                1080

His Lys Leu Pro Asp Asp Tyr Pro Ile
    1085            1090

<210> SEQ ID NO 32
<211> LENGTH: 1267
<212> TYPE: PRT
<213> ORGANISM: Artificial Sequence
<220> FEATURE:
<223> OTHER INFORMATION: Cren7-Sso7d joined via a linker to the
      C-terminus of wild type R2 enzyme

<400> SEQUENCE: 32

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
```

-continued

```
                290                 295                 300
Thr Ser Arg Gln Lys Arg Arg Ala Glu Tyr Ala Arg Val Gln Glu Leu
305                 310                 315                 320
Tyr Lys Lys Cys Arg Ser Arg Ala Ala Ala Glu Val Ile Asp Gly Ala
                325                 330                 335
Cys Gly Gly Val Gly His Ser Leu Glu Glu Met Glu Thr Tyr Trp Arg
                340                 345                 350
Pro Ile Leu Glu Arg Val Ser Asp Ala Pro Gly Pro Thr Pro Glu Ala
                355                 360                 365
Leu His Ala Leu Gly Arg Ala Glu Trp His Gly Gly Asn Arg Asp Tyr
                370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
                405                 410                 415
Trp Arg Ala Val Pro Val His Leu Lys Ala Glu Met Phe Asn Ala Trp
                420                 425                 430
Met Ala Arg Gly Glu Ile Pro Glu Ile Leu Arg Gln Cys Arg Thr Val
                435                 440                 445
Phe Val Pro Lys Val Glu Arg Pro Gly Gly Pro Gly Glu Tyr Arg Pro
                450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
                500                 505                 510
Leu Gly Asp Ser Arg Lys Lys Leu Arg Glu Cys His Val Ala Val Leu
                515                 520                 525
Asp Phe Ala Lys Ala Phe Asp Thr Val Ser His Glu Ala Leu Val Glu
                530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
                580                 585                 590
Ser Pro Ile Leu Phe Asn Val Val Met Asp Leu Ile Leu Ala Ser Leu
                595                 600                 605
Pro Glu Arg Val Gly Tyr Arg Leu Glu Met Glu Leu Val Ser Ala Leu
                610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
                660                 665                 670
His Arg Lys Lys His Tyr Leu Thr Glu Arg Thr Phe Asn Ile Gly
                675                 680                 685
Gly Lys Pro Leu Arg Gln Val Ser Cys Val Arg Trp Arg Tyr Leu
                690                 695                 700
Gly Val Asp Phe Glu Ala Ser Gly Cys Val Thr Leu Glu His Ser Ile
705                 710                 715                 720
```

```
Ser Ser Ala Leu Asn Asn Ile Ser Arg Ala Pro Leu Lys Pro Gln Gln
            725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
            770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Ala Lys Ser
            820                 825                 830

Asp Lys Ile Arg Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
            850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
            915                 920                 925

Glu Ser Ser Leu Thr Cys Arg Ala Gly Cys Lys Val Arg Glu Thr Thr
            930                 935                 940

Ala His Ile Leu Gln Gln Cys His Arg Thr His Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125
```

```
Ser Ala Ser Ser Gly Lys Lys Pro Val Lys Val Lys Thr Pro Ala
    1130                1135                1140

Gly Lys Glu Ala Glu Leu Val Pro Glu Lys Val Trp Ala Leu Ala
    1145                1150                1155

Pro Lys Gly Arg Lys Gly Val Lys Ile Gly Leu Phe Lys Asp Pro
    1160                1165                1170

Glu Thr Gly Lys Tyr Phe Arg His Lys Leu Pro Asp Asp Tyr Pro
    1175                1180                1185

Ile Val Gly Thr Gly Gly Ser Gly Gly Gly Thr Gly Gly Gly
    1190                1195                1200

Ser Ala Thr Val Lys Phe Lys Tyr Lys Gly Glu Glu Lys Glu Val
    1205                1210                1215

Asp Ile Ser Lys Ile Lys Lys Val Trp Arg Val Gly Lys Met Ile
    1220                1225                1230

Ser Phe Thr Tyr Asp Glu Gly Gly Gly Lys Thr Gly Arg Gly Ala
    1235                1240                1245

Val Ser Glu Lys Asp Ala Pro Lys Glu Leu Leu Gln Met Leu Glu
    1250                1255                1260

Lys Gln Lys Lys
    1265

<210> SEQ ID NO 33
<211> LENGTH: 982
<212> TYPE: PRT
<213> ORGANISM: Artificial Sequence
<220> FEATURE:
<223> OTHER INFORMATION: Cren7-Sso7d joined via a linker to the
      C-terminus of deltaR2 enzyme

<400> SEQUENCE: 33

Lys Thr Ala Gly Arg Arg Asn Asp Leu His Asp Arg Thr Ala Ser
1               5                   10                  15

Ala His Lys Thr Ser Arg Gln Lys Arg Arg Ala Glu Tyr Ala Arg Val
                20                  25                  30

Gln Glu Leu Tyr Lys Lys Cys Arg Ser Arg Ala Ala Ala Glu Val Ile
                35                  40                  45

Asp Gly Ala Cys Gly Gly Val Gly His Ser Leu Glu Glu Met Glu Thr
    50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Asn
                    85                  90                  95

Arg Asp Tyr Thr Gln Leu Trp Lys Pro Ile Ser Val Glu Glu Ile Lys
                100                 105                 110

Ala Ser Arg Phe Asp Trp Arg Thr Ser Pro Gly Pro Asp Gly Ile Arg
            115                 120                 125

Ser Gly Gln Trp Arg Ala Val Pro Val His Leu Lys Ala Glu Met Phe
    130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
            180                 185                 190

Ile Leu Ala Arg Arg Leu Leu Ala Cys Cys Pro Pro Asp Ala Arg Gln
        195                 200                 205
```

```
Arg Gly Phe Ile Cys Ala Asp Gly Thr Leu Glu Asn Ser Ala Val Leu
        210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
            260                 265                 270

Tyr Ile Ala His Leu Tyr Asp Thr Ala Ser Thr Thr Leu Ala Val Asn
        275                 280                 285

Asn Glu Met Ser Ser Pro Val Lys Val Gly Arg Gly Val Arg Gln Gly
    290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Leu Val Leu Leu Ala Gly Ser Lys
            340                 345                 350

Val Gly Met Gln Glu Ser Ile Ser Ala Val Asp Cys Val Gly Arg Gln
        355                 360                 365

Met Gly Leu Arg Leu Asn Cys Arg Lys Ser Ala Val Leu Ser Met Ile
    370                 375                 380

Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
                405                 410                 415

Arg Tyr Leu Gly Val Asp Phe Glu Ala Ser Gly Cys Val Thr Leu Glu
            420                 425                 430

His Ser Ile Ser Ser Ala Leu Asn Asn Ile Ser Arg Ala Pro Leu Lys
        435                 440                 445

Pro Gln Gln Arg Leu Glu Ile Leu Arg Ala His Leu Ile Pro Arg Phe
    450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
            500                 505                 510

Leu Ala Ile Pro Ser Val Arg Ala Thr Ile Pro Asp Leu Ile Val Arg
        515                 520                 525

Arg Phe Gly Gly Leu Asp Ser Ser Pro Trp Ser Val Ala Arg Ala Ala
    530                 535                 540

Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Lys Trp Ile Arg Glu
        595                 600                 605

Arg Cys Ala Gln Ile Thr Gly Arg Asp Phe Val Gln Phe Val His Thr
    610                 615                 620
```

His Ile Asn Ala Leu Pro Ser Arg Ile Arg Ser Arg Gly Arg Arg
625                 630                 635                 640

Gly Gly Gly Glu Ser Ser Leu Thr Cys Arg Ala Gly Cys Lys Val Arg
            645                 650                 655

Glu Thr Thr Ala His Ile Leu Gln Gln Cys His Arg Thr His Gly Gly
        660                 665                 670

Arg Ile Leu Arg His Asn Lys Ile Val Ser Phe Val Ala Lys Ala Met
        675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Ser Gly Gln Arg Ser Leu Asp Glu
            725                 730                 735

Leu His Arg Glu Lys Arg Asn Lys Tyr Gly Asn His Gly Glu Leu Val
        740                 745                 750

Glu Leu Val Ala Gly Arg Leu Gly Leu Pro Lys Ala Glu Cys Val Arg
        755                 760                 765

Ala Thr Ser Cys Thr Ile Ser Trp Arg Gly Val Trp Ser Leu Thr Ser
770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
            805                 810                 815

Phe Asn Gln Met Thr Ser Val Met Gly Gly Val Gly Val Gly Thr
        820                 825                 830

Gly Gly Gly Ser Gly Gly Gly Thr Gly Gly Ser Ala Ser Ser Gly
        835                 840                 845

Lys Lys Pro Val Lys Val Lys Thr Pro Ala Gly Lys Glu Ala Glu Leu
850                 855                 860

Val Pro Glu Lys Val Trp Ala Leu Ala Pro Lys Gly Arg Lys Gly Val
865                 870                 875                 880

Lys Ile Gly Leu Phe Lys Asp Pro Glu Thr Gly Lys Tyr Phe Arg His
            885                 890                 895

Lys Leu Pro Asp Asp Tyr Pro Ile Val Gly Thr Gly Gly Ser Gly
        900                 905                 910

Gly Thr Gly Gly Ser Ala Thr Val Lys Phe Lys Tyr Lys Gly
        915                 920                 925

Glu Glu Lys Glu Val Asp Ile Ser Lys Ile Lys Lys Val Trp Arg Val
930                 935                 940

Gly Lys Met Ile Ser Phe Thr Tyr Asp Glu Gly Gly Lys Thr Gly
945                 950                 955                 960

Arg Gly Ala Val Ser Glu Lys Asp Ala Pro Lys Glu Leu Leu Gln Met
            965                 970                 975

Leu Glu Lys Gln Lys Lys
            980

<210> SEQ ID NO 34
<211> LENGTH: 1277
<212> TYPE: PRT
<213> ORGANISM: Artificial Sequence
<220> FEATURE:
<223> OTHER INFORMATION: SSB joined via a linker to the C-terminus of
      wild type R2 enzyme

<400> SEQUENCE: 34

```
Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Ile Asp Leu Leu
145                 150                 155                 160

Ala Arg Thr Glu Ala Arg Leu Leu Ala Glu Arg Gly Gln Cys Ser Gly
            165                 170                 175

Gly Asp Leu Phe Gly Ala Leu Pro Gly Phe Gly Arg Thr Leu Glu Ala
        180                 185                 190

Ile Lys Gly Gln Arg Arg Glu Pro Tyr Arg Ala Leu Val Gln Ala
    195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
            245                 250                 255

Gly Gln Met Ser Pro Asp Ala Ala Arg Val Leu Ser Glu Leu Leu Glu
        260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
            325                 330                 335

Cys Gly Gly Val Gly His Ser Leu Glu Glu Met Glu Thr Tyr Trp Arg
        340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
            405                 410                 415
```

```
Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
        435                 440                 445

Phe Val Pro Lys Val Glu Arg Pro Gly Gly Pro Gly Glu Tyr Arg Pro
    450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
        515                 520                 525

Asp Phe Ala Lys Ala Phe Asp Thr Val Ser His Glu Ala Leu Val Glu
    530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Ala Lys Ser
            820                 825                 830

Asp Lys Ile Arg Lys Lys Leu Arg Trp Ala Trp Lys Gln Leu Arg Arg
```

-continued

```
                835                 840                 845
Phe Ser Arg Val Asp Ser Thr Thr Gln Arg Pro Ser Val Arg Leu Phe
850                 855                 860
Trp Arg Glu His Leu His Ala Ser Val Asp Gly Arg Glu Leu Arg Glu
865                 870                 875                 880
Ser Thr Arg Thr Pro Thr Ser Thr Lys Trp Ile Arg Glu Arg Cys Ala
                885                 890                 895
Gln Ile Thr Gly Arg Asp Phe Val Gln Phe Val His Thr His Ile Asn
                900                 905                 910
Ala Leu Pro Ser Arg Ile Arg Gly Ser Arg Gly Arg Gly Gly Gly
                915                 920                 925
Glu Ser Ser Leu Thr Cys Arg Ala Gly Cys Lys Val Arg Glu Thr Thr
930                 935                 940
Ala His Ile Leu Gln Gln Cys His Arg Thr His Gly Gly Arg Ile Leu
945                 950                 955                 960
Arg His Asn Lys Ile Val Ser Phe Val Ala Lys Ala Met Glu Glu Asn
                965                 970                 975
Lys Trp Thr Val Glu Leu Glu Pro Arg Leu Arg Thr Ser Val Gly Leu
                980                 985                 990
Arg Lys Pro Asp Ile Ile Ala Ser Arg Asp Gly Val Gly Val Ile Val
                995                1000                1005
Asp Val Gln Val Val Ser Gly Gln Arg Ser Leu Asp Glu Leu His
1010                1015                1020
Arg Glu Lys Arg Asn Lys Tyr Gly Asn His Gly Glu Leu Val Glu
1025                1030                1035
Leu Val Ala Gly Arg Leu Gly Leu Pro Lys Ala Glu Cys Val Arg
1040                1045                1050
Ala Thr Ser Cys Thr Ile Ser Trp Arg Gly Val Trp Ser Leu Thr
1055                1060                1065
Ser Tyr Lys Glu Leu Arg Ser Ile Ile Gly Leu Arg Glu Pro Thr
1070                1075                1080
Leu Gln Ile Val Pro Ile Leu Ala Leu Arg Gly Ser His Met Asn
1085                1090                1095
Trp Thr Arg Phe Asn Gln Met Thr Ser Val Met Gly Gly Val
1100                1105                1110
Gly Val Gly Thr Gly Gly Ser Gly Gly Thr Gly Gly Gly
1115                1120                1125
Ser Met Glu Glu Lys Val Gly Asn Leu Lys Pro Asn Met Glu Ser
1130                1135                1140
Val Asn Val Thr Val Arg Val Leu Glu Ala Ser Glu Ala Arg Gln
1145                1150                1155
Ile Gln Thr Lys Asn Gly Val Arg Thr Ile Ser Glu Ala Ile Val
1160                1165                1170
Gly Asp Glu Thr Gly Arg Val Lys Leu Thr Leu Trp Gly Lys His
1175                1180                1185
Ala Gly Ser Ile Lys Glu Gly Gln Val Val Lys Ile Glu Asn Ala
1190                1195                1200
Trp Thr Thr Ala Phe Lys Gly Gln Val Gln Leu Asn Ala Gly Ser
1205                1210                1215
Lys Thr Lys Ile Ala Glu Ala Ser Glu Asp Gly Phe Pro Glu Ser
1220                1225                1230
Ser Gln Ile Pro Glu Asn Thr Pro Thr Ala Pro Gln Gln Met Arg
1235                1240                1245
```

```
Gly Gly Gly Arg Gly Phe Arg Gly Gly Gly Arg Arg Tyr Gly Arg
        1250                1255                1260

Arg Gly Gly Arg Arg Gln Glu Asn Glu Glu Gly Glu Glu Glu
        1265                1270                1275

<210> SEQ ID NO 35
<211> LENGTH: 1017
<212> TYPE: PRT
<213> ORGANISM: Artificial Sequence
<220> FEATURE:
<223> OTHER INFORMATION: His Tag joined via a linker to SSB joined via a
      linker to the C-terminus of deltaR2 enzyme

<400> SEQUENCE: 35

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
            20                  25                  30

Asp Leu His Asp Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
            180                 185                 190

Val Glu Arg Pro Gly Gly Pro Gly Glu Tyr Arg Pro Ile Ser Ile Ala
        195                 200                 205

Ser Ile Pro Leu Arg His Phe His Ser Ile Leu Ala Arg Arg Leu Leu
    210                 215                 220

Ala Cys Cys Pro Pro Asp Ala Arg Gln Arg Gly Phe Ile Cys Ala Asp
225                 230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
    290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
```

```
                325                 330                 335
Phe Asn Val Val Met Asp Leu Ile Leu Ala Ser Leu Pro Glu Arg Val
                340                 345                 350
Gly Tyr Arg Leu Glu Met Glu Leu Val Ser Ala Leu Ala Tyr Ala Asp
                355                 360                 365
Asp Leu Val Leu Leu Ala Gly Ser Lys Val Gly Met Gln Glu Ser Ile
                370                 375                 380
Ser Ala Val Asp Cys Val Gly Arg Gln Met Gly Leu Arg Leu Asn Cys
385                 390                 395                 400
Arg Lys Ser Ala Val Leu Ser Met Ile Pro Asp Gly His Arg Lys Lys
                405                 410                 415
His His Tyr Leu Thr Glu Arg Thr Phe Asn Ile Gly Gly Lys Pro Leu
                420                 425                 430
Arg Gln Val Ser Cys Val Glu Arg Trp Arg Tyr Leu Gly Val Asp Phe
                435                 440                 445
Glu Ala Ser Gly Cys Val Thr Leu Glu His Ser Ile Ser Ser Ala Leu
                450                 455                 460
Asn Asn Ile Ser Arg Ala Pro Leu Lys Pro Gln Gln Arg Leu Glu Ile
465                 470                 475                 480
Leu Arg Ala His Leu Ile Pro Arg Phe Gln His Gly Phe Val Leu Gly
                485                 490                 495
Asn Ile Ser Asp Asp Arg Leu Arg Met Leu Asp Val Gln Ile Arg Lys
                500                 505                 510
Ala Val Gly Gln Trp Leu Arg Leu Pro Ala Asp Val Pro Lys Ala Tyr
                515                 520                 525
Tyr His Ala Ala Val Gln Asp Gly Gly Leu Ala Ile Pro Ser Val Arg
                530                 535                 540
Ala Thr Ile Pro Asp Leu Ile Val Arg Arg Phe Gly Gly Leu Asp Ser
545                 550                 555                 560
Ser Pro Trp Ser Val Ala Arg Ala Ala Lys Ser Asp Lys Ile Arg
                565                 570                 575
Lys Lys Leu Arg Trp Ala Trp Lys Gln Leu Arg Arg Phe Ser Arg Val
                580                 585                 590
Asp Ser Thr Thr Gln Arg Pro Ser Val Arg Leu Phe Trp Arg Glu His
                595                 600                 605
Leu His Ala Ser Val Asp Gly Arg Glu Leu Arg Glu Ser Thr Arg Thr
                610                 615                 620
Pro Thr Ser Thr Lys Trp Ile Arg Glu Arg Cys Ala Gln Ile Thr Gly
625                 630                 635                 640
Arg Asp Phe Val Gln Phe Val His Thr His Ile Asn Ala Leu Pro Ser
                645                 650                 655
Arg Ile Arg Gly Ser Arg Gly Arg Gly Gly Glu Ser Ser Leu
                660                 665                 670
Thr Cys Arg Ala Gly Cys Lys Val Arg Glu Thr Thr Ala His Ile Leu
                675                 680                 685
Gln Gln Cys His Arg Thr His Gly Gly Arg Ile Leu Arg His Asn Lys
                690                 695                 700
Ile Val Ser Phe Val Ala Lys Ala Met Glu Glu Asn Lys Trp Thr Val
705                 710                 715                 720
Glu Leu Glu Pro Arg Leu Arg Thr Ser Val Gly Leu Arg Lys Pro Asp
                725                 730                 735
Ile Ile Ala Ser Arg Asp Gly Val Gly Val Ile Val Asp Val Gln Val
                740                 745                 750
```

```
Val Ser Gly Gln Arg Ser Leu Asp Glu Leu His Arg Glu Lys Arg Asn
        755                 760                 765

Lys Tyr Gly Asn His Gly Glu Leu Val Glu Leu Val Ala Gly Arg Leu
    770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
            820                 825                 830

Arg Gly Ser His Met Asn Trp Thr Arg Phe Asn Gln Met Thr Ser Val
        835                 840                 845

Met Gly Gly Gly Val Gly Val Gly Thr Gly Gly Ser Gly Gly Gly
    850                 855                 860

Thr Gly Gly Ser Met Glu Glu Lys Val Gly Asn Leu Lys Pro Asn
865                 870                 875                 880

Met Glu Ser Val Asn Val Thr Val Arg Val Leu Glu Ala Ser Glu Ala
                885                 890                 895

Arg Gln Ile Gln Thr Lys Asn Gly Val Arg Thr Ile Ser Glu Ala Ile
        900                 905                 910

Val Gly Asp Glu Thr Gly Arg Val Lys Leu Thr Leu Trp Gly Lys His
    915                 920                 925

Ala Gly Ser Ile Lys Glu Gly Gln Val Val Lys Ile Glu Asn Ala Trp
930                 935                 940

Thr Thr Ala Phe Lys Gly Val Gln Leu Asn Ala Gly Ser Lys Thr
945                 950                 955                 960

Lys Ile Ala Glu Ala Ser Glu Asp Gly Phe Pro Glu Ser Ser Gln Ile
                965                 970                 975

Pro Glu Asn Thr Pro Thr Ala Pro Gln Gln Met Arg Gly Gly Arg
        980                 985                 990

Gly Phe Arg Gly Gly Arg Arg  Tyr Gly Arg Arg Gly  Gly Arg Arg
        995                 1000                1005

Gln Glu  Asn Glu Glu Gly Glu  Glu Glu
    1010                1015

<210> SEQ ID NO 36
<211> LENGTH: 1440
<212> TYPE: PRT
<213> ORGANISM: Artificial Sequence
<220> FEATURE:
<223> OTHER INFORMATION: SSB-SSB joined via a linker to the C-terminus
      of wild type R2 enzyme

<400> SEQUENCE: 36

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
```

-continued

```
                    85                  90                  95
Arg Gly Ser Ala Gly Ala Asp Pro Val Gly Gln Asp Ala Pro Gly Trp
                100                 105                 110

Thr Cys Gln Phe Cys Glu Arg Thr Phe Ser Thr Asn Arg Gly Leu Gly
            115                 120                 125

Val His Lys Arg Arg Ala His Pro Val Glu Thr Asn Thr Asp Ala Ala
        130                 135                 140

Pro Met Met Val Lys Arg Arg Trp His Gly Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
        435                 440                 445

Phe Val Pro Lys Val Glu Arg Pro Gly Gly Pro Gly Glu Tyr Arg Pro
    450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510
```

```
Leu Gly Asp Ser Arg Lys Lys Leu Arg Glu Cys His Val Ala Val Leu
        515                 520                 525

Asp Phe Ala Lys Ala Phe Asp Thr Val Ser His Glu Ala Leu Val Glu
    530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
        595                 600                 605

Pro Glu Arg Val Gly Tyr Arg Leu Glu Met Glu Leu Val Ser Ala Leu
    610                 615                 620

Ala Tyr Ala Asp Asp Leu Val Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925
```

```
Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Asn
            965                 970                 975

Lys Trp Thr Val Glu Leu Glu Pro Arg Leu Arg Thr Ser Val Gly Leu
                980                 985                 990

Arg Lys Pro Asp Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Met Glu Glu Lys Val Gly Asn Leu Lys Pro Asn Met Glu Ser
    1130                1135                1140

Val Asn Val Thr Val Arg Val Leu Glu Ala Ser Glu Ala Arg Gln
    1145                1150                1155

Ile Gln Thr Lys Asn Gly Val Arg Thr Ile Ser Glu Ala Ile Val
    1160                1165                1170

Gly Asp Glu Thr Gly Arg Val Lys Leu Thr Leu Trp Gly Lys His
    1175                1180                1185

Ala Gly Ser Ile Lys Glu Gly Gln Val Val Lys Ile Glu Asn Ala
    1190                1195                1200

Trp Thr Thr Ala Phe Lys Gly Gln Val Gln Leu Asn Ala Gly Ser
    1205                1210                1215

Lys Thr Lys Ile Ala Glu Ala Ser Glu Asp Gly Phe Pro Glu Ser
    1220                1225                1230

Ser Gln Ile Pro Glu Asn Thr Pro Thr Ala Pro Gln Gln Met Arg
    1235                1240                1245

Gly Gly Gly Arg Gly Phe Arg Gly Gly Gly Arg Tyr Gly Arg
    1250                1255                1260

Arg Gly Gly Arg Arg Gln Glu Asn Glu Glu Gly Glu Glu Val
    1265                1270                1275

Gly Thr Gly Gly Gly Ser Gly Gly Thr Gly Gly Ser Met
    1280                1285                1290

Glu Glu Lys Val Gly Asn Leu Lys Pro Asn Met Glu Ser Val Asn
    1295                1300                1305

Val Thr Val Arg Val Leu Glu Ala Ser Glu Ala Arg Gln Ile Gln
    1310                1315                1320

Thr Lys Asn Gly Val Arg Thr Ile Ser Glu Ala Ile Val Gly Asp
```

```
            1325                1330                1335

Glu Thr Gly Arg Val Lys Leu Thr Leu Trp Gly Lys His Ala Gly
    1340                1345                1350

Ser Ile Lys Glu Gly Gln Val Val Lys Ile Glu Asn Ala Trp Thr
    1355                1360                1365

Thr Ala Phe Lys Gly Gln Val Gln Leu Asn Ala Gly Ser Lys Thr
    1370                1375                1380

Lys Ile Ala Glu Ala Ser Glu Asp Gly Phe Pro Glu Ser Ser Gln
    1385                1390                1395

Ile Pro Glu Asn Thr Pro Thr Ala Pro Gln Gln Met Arg Gly Gly
    1400                1405                1410

Gly Arg Gly Phe Arg Gly Gly Gly Arg Arg Tyr Gly Arg Arg Gly
    1415                1420                1425

Gly Arg Arg Gln Glu Asn Glu Glu Gly Glu Glu Glu
    1430                1435                1440

<210> SEQ ID NO 37
<211> LENGTH: 1180
<212> TYPE: PRT
<213> ORGANISM: Artificial Sequence
<220> FEATURE:
<223> OTHER INFORMATION: His Tag joined via a linker to SSB-SSB joined
      via a linker to the C-terminus of deltaR2 enzyme

<400> SEQUENCE: 37

Met Ala His His His His His His Val Gly Thr Val Gly Thr Gly
1               5                   10                  15

Gly Ser Gly Gly Ala Ser Thr Ala Leu Lys Thr Ala Gly Arg Arg Asn
                20                  25                  30

Asp Leu His Asp Asp Arg Thr Ala Ser Ala His Lys Thr Ser Arg Gln
            35                  40                  45

Lys Arg Arg Ala Glu Tyr Ala Arg Val Gln Glu Leu Tyr Lys Lys Cys
        50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
                100                 105                 110

Gly Arg Ala Glu Trp His Gly Gly Asn Arg Asp Tyr Thr Gln Leu Trp
            115                 120                 125

Lys Pro Ile Ser Val Glu Glu Ile Lys Ala Ser Arg Phe Asp Trp Arg
        130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
                180                 185                 190

Val Glu Arg Pro Gly Gly Pro Gly Glu Tyr Arg Pro Ile Ser Ile Ala
            195                 200                 205

Ser Ile Pro Leu Arg His Phe His Ser Ile Leu Ala Arg Arg Leu Leu
        210                 215                 220

Ala Cys Cys Pro Pro Asp Ala Arg Gln Arg Gly Phe Ile Cys Ala Asp
225                 230                 235                 240
```

```
Gly Thr Leu Glu Asn Ser Ala Val Leu Asp Ala Val Leu Gly Asp Ser
            245                 250                 255

Arg Lys Lys Leu Arg Glu Cys His Val Ala Val Leu Asp Phe Ala Lys
        260                 265                 270

Ala Phe Asp Thr Val Ser His Glu Ala Leu Val Glu Leu Leu Arg Leu
            275                 280                 285

Arg Gly Met Pro Glu Gln Phe Cys Gly Tyr Ile Ala His Leu Tyr Asp
        290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
                325                 330                 335

Phe Asn Val Val Met Asp Leu Ile Leu Ala Ser Leu Pro Glu Arg Val
                340                 345                 350

Gly Tyr Arg Leu Glu Met Glu Leu Val Ser Ala Leu Ala Tyr Ala Asp
            355                 360                 365

Asp Leu Val Leu Leu Ala Gly Ser Lys Val Gly Met Gln Glu Ser Ile
        370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495

Asn Ile Ser Asp Asp Arg Leu Arg Met Leu Asp Val Gln Ile Arg Lys
                500                 505                 510

Ala Val Gly Gln Trp Leu Arg Leu Pro Ala Asp Val Pro Lys Ala Tyr
            515                 520                 525

Tyr His Ala Ala Val Gln Asp Gly Gly Leu Ala Ile Pro Ser Val Arg
        530                 535                 540

Ala Thr Ile Pro Asp Leu Ile Val Arg Arg Phe Gly Gly Leu Asp Ser
545                 550                 555                 560

Ser Pro Trp Ser Val Ala Arg Ala Ala Lys Ser Asp Lys Ile Arg
                565                 570                 575

Lys Lys Leu Arg Trp Ala Trp Lys Gln Leu Arg Arg Phe Ser Arg Val
            580                 585                 590

Asp Ser Thr Thr Gln Arg Pro Ser Val Arg Leu Phe Trp Arg Glu His
        595                 600                 605

Leu His Ala Ser Val Asp Gly Arg Glu Leu Arg Glu Ser Thr Arg Thr
        610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Arg Gly Gly Gly Glu Ser Ser Leu
```

-continued

```
                660                 665                 670
Thr Cys Arg Ala Gly Cys Lys Val Arg Glu Thr Thr Ala His Ile Leu
            675                 680                 685
Gln Gln Cys His Arg Thr His Gly Gly Arg Ile Leu Arg His Asn Lys
            690                 695                 700
Ile Val Ser Phe Val Ala Lys Ala Met Glu Glu Asn Lys Trp Thr Val
705                 710                 715                 720
Glu Leu Glu Pro Arg Leu Arg Thr Ser Val Gly Leu Arg Lys Pro Asp
                725                 730                 735
Ile Ile Ala Ser Arg Asp Gly Val Gly Val Ile Val Asp Val Gln Val
            740                 745                 750
Val Ser Gly Gln Arg Ser Leu Asp Glu Leu His Arg Glu Lys Arg Asn
            755                 760                 765
Lys Tyr Gly Asn His Gly Glu Leu Val Glu Leu Val Ala Gly Arg Leu
            770                 775                 780
Gly Leu Pro Lys Ala Glu Cys Val Arg Ala Thr Ser Cys Thr Ile Ser
785                 790                 795                 800
Trp Arg Gly Val Trp Ser Leu Thr Ser Tyr Lys Glu Leu Arg Ser Ile
                805                 810                 815
Ile Gly Leu Arg Glu Pro Thr Leu Gln Ile Val Pro Ile Leu Ala Leu
            820                 825                 830
Arg Gly Ser His Met Asn Trp Thr Arg Phe Asn Gln Met Thr Ser Val
            835                 840                 845
Met Gly Gly Gly Val Gly Val Gly Thr Gly Gly Ser Gly Gly Gly
850                 855                 860
Thr Gly Gly Gly Ser Met Glu Glu Lys Val Gly Asn Leu Lys Pro Asn
865                 870                 875                 880
Met Glu Ser Val Asn Val Thr Val Arg Val Leu Glu Ala Ser Glu Ala
                885                 890                 895
Arg Gln Ile Gln Thr Lys Asn Gly Val Arg Thr Ile Ser Glu Ala Ile
            900                 905                 910
Val Gly Asp Glu Thr Gly Arg Val Lys Leu Thr Leu Trp Gly Lys His
            915                 920                 925
Ala Gly Ser Ile Lys Glu Gly Gln Val Val Lys Ile Glu Asn Ala Trp
            930                 935                 940
Thr Thr Ala Phe Lys Gly Gln Val Gln Leu Asn Ala Gly Ser Lys Thr
945                 950                 955                 960
Lys Ile Ala Glu Ala Ser Glu Asp Gly Phe Pro Glu Ser Ser Gln Ile
                965                 970                 975
Pro Glu Asn Thr Pro Thr Ala Pro Gln Gln Met Arg Gly Gly Gly Arg
            980                 985                 990
Gly Phe Arg Gly Gly Arg Arg  Tyr Gly Arg Arg  Gly Arg Arg
            995                 1000                1005
Gln Glu  Asn Glu Glu  Gly Glu  Glu Glu Val Gly Thr  Gly Gly Gly
            1010                1015                1020
Ser Gly  Gly Gly Thr Gly Gly  Gly Ser Met Glu Glu  Lys Val Gly
            1025                1030                1035
Asn Leu  Lys Pro Asn Met Glu  Ser Val Asn Val Thr  Val Arg Val
            1040                1045                1050
Leu Glu  Ala Ser Glu Ala Arg  Gln Ile Gln Thr Lys  Asn Gly Val
            1055                1060                1065
Arg Thr  Ile Ser Glu Ala Ile  Val Gly Asp Glu Thr  Gly Arg Val
            1070                1075                1080
```

Lys Leu Thr Leu Trp Gly Lys His Ala Gly Ser Ile Lys Glu Gly
    1085            1090            1095

Gln Val Val Lys Ile Glu Asn Ala Trp Thr Thr Ala Phe Lys Gly
    1100            1105            1110

Gln Val Gln Leu Asn Ala Gly Ser Lys Thr Lys Ile Ala Glu Ala
    1115            1120            1125

Ser Glu Asp Gly Phe Pro Glu Ser Ser Gln Ile Pro Glu Asn Thr
    1130            1135            1140

Pro Thr Ala Pro Gln Gln Met Arg Gly Gly Arg Gly Phe Arg
    1145            1150            1155

Gly Gly Gly Arg Arg Tyr Gly Arg Arg Gly Gly Arg Arg Gln Glu
    1160            1165            1170

Asn Glu Glu Gly Glu Glu Glu
    1175            1180

<210> SEQ ID NO 38
<211> LENGTH: 1603
<212> TYPE: PRT
<213> ORGANISM: Artificial Sequence
<220> FEATURE:
<223> OTHER INFORMATION: SSB-SSB-SSB joined via a linker to the
      C-terminus of wild type R2 enzyme

<400> SEQUENCE: 38

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Ala Tyr Asp Pro Ser Ala Val

-continued

```
                245                 250                 255
Gly Gln Met Ser Pro Asp Ala Ala Arg Val Leu Ser Glu Leu Leu Glu
            260                 265                 270

Gly Ala Gly Arg Arg Ala Cys Arg Ala Met Arg Pro Lys Thr Ala
            275                 280                 285

Gly Arg Arg Asn Asp Leu His Asp Asp Arg Thr Ala Ser Ala His Lys
            290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
                340                 345                 350

Pro Ile Leu Glu Arg Val Ser Asp Ala Pro Gly Pro Thr Pro Glu Ala
                355                 360                 365

Leu His Ala Leu Gly Arg Ala Glu Trp His Gly Gly Asn Arg Asp Tyr
            370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
                500                 505                 510

Leu Gly Asp Ser Arg Lys Lys Leu Arg Glu Cys His Val Ala Val Leu
            515                 520                 525

Asp Phe Ala Lys Ala Phe Asp Thr Val Ser His Glu Ala Leu Val Glu
            530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
                565                 570                 575

Ser Ser Pro Val Lys Val Gly Arg Gly Val Arg Gln Gly Asp Pro Leu
                580                 585                 590

Ser Pro Ile Leu Phe Asn Val Val Met Asp Leu Ile Leu Ala Ser Leu
                595                 600                 605

Pro Glu Arg Val Gly Tyr Arg Leu Glu Met Glu Leu Val Ser Ala Leu
            610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
                660                 665                 670
```

```
His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
        690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
        770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Ala Lys Ser
            820                 825                 830

Asp Lys Ile Arg Lys Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
        995                 1000                1005

Asp Val Gln Val Val Ser Gly Gln Arg Ser Leu Asp Glu Leu His
        1010                1015                1020

Arg Glu Lys Arg Asn Lys Tyr Gly Asn His Gly Glu Leu Val Glu
        1025                1030                1035

Leu Val Ala Gly Arg Leu Gly Leu Pro Lys Ala Glu Cys Val Arg
        1040                1045                1050

Ala Thr Ser Cys Thr Ile Ser Trp Arg Gly Val Trp Ser Leu Thr
        1055                1060                1065

Ser Tyr Lys Glu Leu Arg Ser Ile Ile Gly Leu Arg Glu Pro Thr
        1070                1075                1080
```

-continued

| | | | | | | | | | | | |
|---|---|---|---|---|---|---|---|---|---|---|---|
| Leu | Gln | Ile | Val | Pro | Ile | Leu | Ala | Leu | Arg | Gly | Ser | His | Met | Asn |
| | 1085 | | | | 1090 | | | | | 1095 | | | | |
| Trp | Thr | Arg | Phe | Asn | Gln | Met | Thr | Ser | Val | Met | Gly | Gly | Gly | Val |
| | 1100 | | | | | 1105 | | | | 1110 | | | | |
| Gly | Val | Gly | Thr | Gly | Gly | Gly | Ser | Gly | Gly | Gly | Thr | Gly | Gly | Gly |
| | 1115 | | | | 1120 | | | | | 1125 | | | | |
| Ser | Met | Glu | Glu | Lys | Val | Gly | Asn | Leu | Lys | Pro | Asn | Met | Glu | Ser |
| | 1130 | | | | 1135 | | | | | 1140 | | | | |
| Val | Asn | Val | Thr | Val | Arg | Val | Leu | Glu | Ala | Ser | Glu | Ala | Arg | Gln |
| | 1145 | | | | 1150 | | | | | 1155 | | | | |
| Ile | Gln | Thr | Lys | Asn | Gly | Val | Arg | Thr | Ile | Ser | Glu | Ala | Ile | Val |
| | 1160 | | | | 1165 | | | | | 1170 | | | | |
| Gly | Asp | Glu | Thr | Gly | Arg | Val | Lys | Leu | Thr | Leu | Trp | Gly | Lys | His |
| | 1175 | | | | 1180 | | | | | 1185 | | | | |
| Ala | Gly | Ser | Ile | Lys | Glu | Gly | Gln | Val | Val | Lys | Ile | Glu | Asn | Ala |
| | 1190 | | | | 1195 | | | | | 1200 | | | | |
| Trp | Thr | Thr | Ala | Phe | Lys | Gly | Gln | Val | Gln | Leu | Asn | Ala | Gly | Ser |
| | 1205 | | | | 1210 | | | | | 1215 | | | | |
| Lys | Thr | Lys | Ile | Ala | Glu | Ala | Ser | Glu | Asp | Gly | Phe | Pro | Glu | Ser |
| | 1220 | | | | 1225 | | | | | 1230 | | | | |
| Ser | Gln | Ile | Pro | Glu | Asn | Thr | Pro | Thr | Ala | Pro | Gln | Gln | Met | Arg |
| | 1235 | | | | 1240 | | | | | 1245 | | | | |
| Gly | Gly | Gly | Arg | Gly | Phe | Arg | Gly | Gly | Gly | Arg | Arg | Tyr | Gly | Arg |
| | 1250 | | | | 1255 | | | | | 1260 | | | | |
| Arg | Gly | Gly | Arg | Arg | Gln | Glu | Asn | Glu | Glu | Gly | Glu | Glu | Glu | Val |
| | 1265 | | | | 1270 | | | | | 1275 | | | | |
| Gly | Thr | Gly | Gly | Gly | Ser | Gly | Gly | Gly | Thr | Gly | Gly | Gly | Ser | Met |
| | 1280 | | | | 1285 | | | | | 1290 | | | | |
| Glu | Glu | Lys | Val | Gly | Asn | Leu | Lys | Pro | Asn | Met | Glu | Ser | Val | Asn |
| | 1295 | | | | 1300 | | | | | 1305 | | | | |
| Val | Thr | Val | Arg | Val | Leu | Glu | Ala | Ser | Glu | Ala | Arg | Gln | Ile | Gln |
| | 1310 | | | | 1315 | | | | | 1320 | | | | |
| Thr | Lys | Asn | Gly | Val | Arg | Thr | Ile | Ser | Glu | Ala | Ile | Val | Gly | Asp |
| | 1325 | | | | 1330 | | | | | 1335 | | | | |
| Glu | Thr | Gly | Arg | Val | Lys | Leu | Thr | Leu | Trp | Gly | Lys | His | Ala | Gly |
| | 1340 | | | | 1345 | | | | | 1350 | | | | |
| Ser | Ile | Lys | Glu | Gly | Gln | Val | Val | Lys | Ile | Glu | Asn | Ala | Trp | Thr |
| | 1355 | | | | 1360 | | | | | 1365 | | | | |
| Thr | Ala | Phe | Lys | Gly | Gln | Val | Gln | Leu | Asn | Ala | Gly | Ser | Lys | Thr |
| | 1370 | | | | 1375 | | | | | 1380 | | | | |
| Lys | Ile | Ala | Glu | Ala | Ser | Glu | Asp | Gly | Phe | Pro | Glu | Ser | Ser | Gln |
| | 1385 | | | | 1390 | | | | | 1395 | | | | |
| Ile | Pro | Glu | Asn | Thr | Pro | Thr | Ala | Pro | Gln | Gln | Met | Arg | Gly | Gly |
| | 1400 | | | | 1405 | | | | | 1410 | | | | |
| Gly | Arg | Gly | Phe | Arg | Gly | Gly | Arg | Arg | Tyr | Gly | Arg | Arg | Gly |
| | 1415 | | | | 1420 | | | | | 1425 | | | | |
| Gly | Arg | Arg | Gln | Glu | Asn | Glu | Glu | Gly | Glu | Glu | Glu | Val | Gly | Thr |
| | 1430 | | | | 1435 | | | | | 1440 | | | | |
| Gly | Gly | Gly | Ser | Gly | Gly | Gly | Thr | Gly | Gly | Gly | Ser | Met | Glu | Glu |
| | 1445 | | | | 1450 | | | | | 1455 | | | | |
| Lys | Val | Gly | Asn | Leu | Lys | Pro | Asn | Met | Glu | Ser | Val | Asn | Val | Thr |
| | 1460 | | | | 1465 | | | | | 1470 | | | | |
| Val | Arg | Val | Leu | Glu | Ala | Ser | Glu | Ala | Arg | Gln | Ile | Gln | Thr | Lys |

```
              1475                1480                1485

Asn Gly Val Arg Thr Ile Ser Glu Ala Ile Val Gly Asp Glu Thr
        1490                1495                1500

Gly Arg Val Lys Leu Thr Leu Trp Gly Lys His Ala Gly Ser Ile
        1505                1510                1515

Lys Glu Gly Gln Val Val Lys Ile Glu Asn Ala Trp Thr Thr Ala
        1520                1525                1530

Phe Lys Gly Gln Val Gln Leu Asn Ala Gly Ser Lys Thr Lys Ile
        1535                1540                1545

Ala Glu Ala Ser Glu Asp Gly Phe Pro Glu Ser Ser Gln Ile Pro
        1550                1555                1560

Glu Asn Thr Pro Thr Ala Pro Gln Gln Met Arg Gly Gly Gly Arg
        1565                1570                1575

Gly Phe Arg Gly Gly Gly Arg Arg Tyr Gly Arg Arg Gly Gly Arg
        1580                1585                1590

Arg Gln Glu Asn Glu Glu Gly Glu Glu Glu
        1595                1600
```

<210> SEQ ID NO 39
<211> LENGTH: 1318
<212> TYPE: PRT
<213> ORGANISM: Artificial Sequence
<220> FEATURE:
<223> OTHER INFORMATION: SSB-SSB-SSB joined via a linker to the
      C-terminus of deltaR2 enzyme

<400> SEQUENCE: 39

```
Lys Thr Ala Gly Arg Arg Asn Asp Leu His Asp Arg Thr Ala Ser
1               5                   10                  15

Ala His Lys Thr Ser Arg Gln Lys Arg Arg Ala Glu Tyr Ala Arg Val
            20                  25                  30

Gln Glu Leu Tyr Lys Lys Cys Arg Ser Arg Ala Ala Ala Glu Val Ile
            35                  40                  45

Asp Gly Ala Cys Gly Gly Val Gly His Ser Leu Glu Glu Met Glu Thr
        50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Asn
                85                  90                  95

Arg Asp Tyr Thr Gln Leu Trp Lys Pro Ile Ser Val Glu Glu Ile Lys
                100                 105                 110

Ala Ser Arg Phe Asp Trp Arg Thr Ser Pro Gly Pro Asp Gly Ile Arg
            115                 120                 125

Ser Gly Gln Trp Arg Ala Val Pro Val His Leu Lys Ala Glu Met Phe
        130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
                180                 185                 190

Ile Leu Ala Arg Arg Leu Leu Ala Cys Cys Pro Pro Asp Ala Arg Gln
            195                 200                 205

Arg Gly Phe Ile Cys Ala Asp Gly Thr Leu Glu Asn Ser Ala Val Leu
        210                 215                 220
```

```
Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
            245                 250                 255

Leu Val Glu Leu Leu Arg Leu Arg Gly Met Pro Glu Gln Phe Cys Gly
        260                 265                 270

Tyr Ile Ala His Leu Tyr Asp Thr Ala Ser Thr Thr Leu Ala Val Asn
    275                 280                 285

Asn Glu Met Ser Ser Pro Val Lys Val Gly Arg Gly Val Arg Gln Gly
290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
            325                 330                 335

Ser Ala Leu Ala Tyr Ala Asp Asp Leu Val Leu Leu Ala Gly Ser Lys
        340                 345                 350

Val Gly Met Gln Glu Ser Ile Ser Ala Val Asp Cys Val Gly Arg Gln
    355                 360                 365

Met Gly Leu Arg Leu Asn Cys Arg Lys Ser Ala Val Leu Ser Met Ile
370                 375                 380

Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
            405                 410                 415

Arg Tyr Leu Gly Val Asp Phe Glu Ala Ser Gly Cys Val Thr Leu Glu
        420                 425                 430

His Ser Ile Ser Ser Ala Leu Asn Asn Ile Ser Arg Ala Pro Leu Lys
    435                 440                 445

Pro Gln Gln Arg Leu Glu Ile Leu Arg Ala His Leu Ile Pro Arg Phe
450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
            485                 490                 495

Ala Asp Val Pro Lys Ala Tyr Tyr His Ala Ala Val Gln Asp Gly Gly
        500                 505                 510

Leu Ala Ile Pro Ser Val Arg Ala Thr Ile Pro Asp Leu Ile Val Arg
    515                 520                 525

Arg Phe Gly Gly Leu Asp Ser Ser Pro Trp Ser Val Ala Arg Ala Ala
530                 535                 540

Ala Lys Ser Asp Lys Ile Arg Lys Leu Arg Trp Ala Trp Lys Gln
545                 550                 555                 560

Leu Arg Arg Phe Ser Arg Val Asp Ser Thr Thr Gln Arg Pro Ser Val
            565                 570                 575

Arg Leu Phe Trp Arg Glu His Leu His Ala Ser Val Asp Gly Arg Glu
        580                 585                 590

Leu Arg Glu Ser Thr Arg Thr Pro Thr Ser Thr Lys Trp Ile Arg Glu
    595                 600                 605

Arg Cys Ala Gln Ile Thr Gly Arg Asp Phe Val Gln Phe Val His Thr
610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
```

-continued

```
              645                 650                 655
Glu Thr Thr Ala His Ile Leu Gln Gln Cys His Arg Thr His Gly Gly
              660                 665                 670
Arg Ile Leu Arg His Asn Lys Ile Val Ser Phe Val Ala Lys Ala Met
              675                 680                 685
Glu Glu Asn Lys Trp Thr Val Glu Leu Glu Pro Arg Leu Arg Thr Ser
              690                 695                 700
Val Gly Leu Arg Lys Pro Asp Ile Ile Ala Ser Arg Asp Gly Val Gly
 705                 710                 715                 720
Val Ile Val Asp Val Gln Val Val Ser Gly Gln Arg Ser Leu Asp Glu
              725                 730                 735
Leu His Arg Glu Lys Arg Asn Lys Tyr Gly Asn His Gly Glu Leu Val
              740                 745                 750
Glu Leu Val Ala Gly Arg Leu Gly Leu Pro Lys Ala Glu Cys Val Arg
              755                 760                 765
Ala Thr Ser Cys Thr Ile Ser Trp Arg Gly Val Trp Ser Leu Thr Ser
              770                 775                 780
Tyr Lys Glu Leu Arg Ser Ile Ile Gly Leu Arg Glu Pro Thr Leu Gln
 785                 790                 795                 800
Ile Val Pro Ile Leu Ala Leu Arg Gly Ser His Met Asn Trp Thr Arg
              805                 810                 815
Phe Asn Gln Met Thr Ser Val Met Gly Gly Val Gly Val Gly Thr
              820                 825                 830
Gly Gly Gly Ser Gly Gly Gly Thr Gly Gly Ser Met Glu Glu Lys
              835                 840                 845
Val Gly Asn Leu Lys Pro Asn Met Glu Ser Val Asn Val Thr Val Arg
 850                 855                 860
Val Leu Glu Ala Ser Glu Ala Arg Gln Ile Gln Thr Lys Asn Gly Val
 865                 870                 875                 880
Arg Thr Ile Ser Glu Ala Ile Val Gly Asp Glu Thr Gly Arg Val Lys
              885                 890                 895
Leu Thr Leu Trp Gly Lys His Ala Gly Ser Ile Lys Glu Gly Gln Val
              900                 905                 910
Val Lys Ile Glu Asn Ala Trp Thr Thr Ala Phe Lys Gly Gln Val Gln
              915                 920                 925
Leu Asn Ala Gly Ser Lys Thr Lys Ile Ala Glu Ala Ser Glu Asp Gly
              930                 935                 940
Phe Pro Glu Ser Ser Gln Ile Pro Glu Asn Thr Pro Thr Ala Pro Gln
 945                 950                 955                 960
Gln Met Arg Gly Gly Arg Gly Phe Arg Gly Gly Arg Arg Tyr
              965                 970                 975
Gly Arg Arg Gly Gly Arg Arg Gln Glu Asn Glu Gly Glu Glu
              980                 985                 990
Val Gly Thr Gly Gly Gly Ser Gly  Gly Gly Thr Gly  Gly Gly Ser Met
              995                 1000                1005
Glu Glu  Lys Val Gly Asn Leu  Lys Pro Asn Met Glu  Ser Val Asn
 1010                1015                1020
Val Thr  Val Arg Val Leu Glu  Ala Ser Glu Ala Arg  Gln Ile Gln
 1025                1030                1035
Thr Lys  Asn Gly Val Arg Thr  Ile Ser Glu Ala Ile  Val Gly Asp
 1040                1045                1050
Glu Thr  Gly Arg Val Lys Leu  Thr Leu Trp Gly Lys  His Ala Gly
 1055                1060                1065
```

```
Ser Ile Lys Glu Gly Gln Val Val Lys Ile Glu Asn Ala Trp Thr
    1070            1075               1080

Thr Ala Phe Lys Gly Gln Val Gln Leu Asn Ala Gly Ser Lys Thr
    1085            1090               1095

Lys Ile Ala Glu Ala Ser Glu Asp Gly Phe Pro Glu Ser Ser Gln
    1100            1105               1110

Ile Pro Glu Asn Thr Pro Thr Ala Pro Gln Gln Met Arg Gly Gly
    1115            1120               1125

Gly Arg Gly Phe Arg Gly Gly Arg Arg Tyr Gly Arg Arg Gly
    1130            1135               1140

Gly Arg Arg Gln Glu Asn Glu Glu Gly Glu Glu Val Gly Thr
    1145            1150               1155

Gly Gly Gly Ser Gly Gly Gly Thr Gly Gly Gly Ser Met Glu Glu
    1160            1165               1170

Lys Val Gly Asn Leu Lys Pro Asn Met Glu Ser Val Asn Val Thr
    1175            1180               1185

Val Arg Val Leu Glu Ala Ser Glu Ala Arg Gln Ile Gln Thr Lys
    1190            1195               1200

Asn Gly Val Arg Thr Ile Ser Glu Ala Ile Val Gly Asp Glu Thr
    1205            1210               1215

Gly Arg Val Lys Leu Thr Leu Trp Gly Lys His Ala Gly Ser Ile
    1220            1225               1230

Lys Glu Gly Gln Val Val Lys Ile Glu Asn Ala Trp Thr Thr Ala
    1235            1240               1245

Phe Lys Gly Gln Val Gln Leu Asn Ala Gly Ser Lys Thr Lys Ile
    1250            1255               1260

Ala Glu Ala Ser Glu Asp Gly Phe Pro Glu Ser Ser Gln Ile Pro
    1265            1270               1275

Glu Asn Thr Pro Thr Ala Pro Gln Gln Met Arg Gly Gly Gly Arg
    1280            1285               1290

Gly Phe Arg Gly Gly Gly Arg Arg Tyr Gly Arg Arg Gly Gly Arg
    1295            1300               1305

Arg Gln Glu Asn Glu Glu Gly Glu Glu Glu
    1310            1315

<210> SEQ ID NO 40
<211> LENGTH: 1352
<212> TYPE: PRT
<213> ORGANISM: Artificial Sequence
<220> FEATURE:
<223> OTHER INFORMATION: SSB-Cren7 joined via a linker to the C-terminus
      of wild type R2 enzyme

<400> SEQUENCE: 40

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
```

-continued

```
                85                  90                  95
Arg Gly Ser Ala Gly Ala Asp Pro Val Gly Gln Asp Ala Pro Gly Trp
            100                 105                 110
Thr Cys Gln Phe Cys Glu Arg Thr Phe Ser Thr Asn Arg Gly Leu Gly
            115                 120                 125
Val His Lys Arg Arg Ala His Pro Val Glu Thr Asn Thr Asp Ala Ala
            130                 135                 140
Pro Met Met Val Lys Arg Arg Trp His Gly Glu Glu Ile Asp Leu Leu
145                 150                 155                 160
Ala Arg Thr Glu Ala Arg Leu Leu Ala Glu Arg Gly Gln Cys Ser Gly
            165                 170                 175
Gly Asp Leu Phe Gly Ala Leu Pro Gly Phe Gly Arg Thr Leu Glu Ala
            180                 185                 190
Ile Lys Gly Gln Arg Arg Glu Pro Tyr Arg Ala Leu Val Gln Ala
            195                 200                 205
His Leu Ala Arg Phe Gly Ser Gln Pro Gly Pro Ser Ser Gly Gly Cys
            210                 215                 220
Ser Ala Glu Pro Asp Phe Arg Arg Ala Ser Gly Ala Glu Glu Ala Gly
225                 230                 235                 240
Glu Glu Arg Cys Ala Glu Asp Ala Ala Tyr Asp Pro Ser Ala Val
            245                 250                 255
Gly Gln Met Ser Pro Asp Ala Ala Arg Val Leu Ser Glu Leu Leu Glu
            260                 265                 270
Gly Ala Gly Arg Arg Arg Ala Cys Arg Ala Met Arg Pro Lys Thr Ala
            275                 280                 285
Gly Arg Arg Asn Asp Leu His Asp Arg Thr Ala Ser Ala His Lys
            290                 295                 300
Thr Ser Arg Gln Lys Arg Arg Ala Glu Tyr Ala Arg Val Gln Glu Leu
305                 310                 315                 320
Tyr Lys Lys Cys Arg Ser Arg Ala Ala Ala Glu Val Ile Asp Gly Ala
            325                 330                 335
Cys Gly Gly Val Gly His Ser Leu Glu Glu Met Glu Thr Tyr Trp Arg
            340                 345                 350
Pro Ile Leu Glu Arg Val Ser Asp Ala Pro Gly Pro Thr Pro Glu Ala
            355                 360                 365
Leu His Ala Leu Gly Arg Ala Glu Trp His Gly Asn Arg Asp Tyr
            370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
            405                 410                 415
Trp Arg Ala Val Pro Val His Leu Lys Ala Glu Met Phe Asn Ala Trp
            420                 425                 430
Met Ala Arg Gly Glu Ile Pro Glu Ile Leu Arg Gln Cys Arg Thr Val
            435                 440                 445
Phe Val Pro Lys Val Glu Arg Pro Gly Gly Pro Gly Glu Tyr Arg Pro
            450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
            485                 490                 495
Ile Cys Ala Asp Gly Thr Leu Glu Asn Ser Ala Val Leu Asp Ala Val
            500                 505                 510
```

-continued

```
Leu Gly Asp Ser Arg Lys Lys Leu Arg Glu Cys His Val Ala Val Leu
        515                 520                 525
Asp Phe Ala Lys Ala Phe Asp Thr Val Ser His Glu Ala Leu Val Glu
    530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
            580                 585                 590
Ser Pro Ile Leu Phe Asn Val Val Met Asp Leu Ile Leu Ala Ser Leu
        595                 600                 605
Pro Glu Arg Val Gly Tyr Arg Leu Glu Met Glu Leu Val Ser Ala Leu
    610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
            660                 665                 670
His Arg Lys Lys His His Tyr Leu Thr Glu Arg Thr Phe Asn Ile Gly
        675                 680                 685
Gly Lys Pro Leu Arg Gln Val Ser Cys Val Glu Arg Trp Arg Tyr Leu
    690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
            740                 745                 750
Phe Val Leu Gly Asn Ile Ser Asp Asp Arg Leu Arg Met Leu Asp Val
        755                 760                 765
Gln Ile Arg Lys Ala Val Gly Gln Trp Leu Arg Leu Pro Ala Asp Val
    770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Ala Lys Ser
            820                 825                 830
Asp Lys Ile Arg Lys Lys Leu Arg Trp Ala Trp Lys Gln Leu Arg Arg
        835                 840                 845
Phe Ser Arg Val Asp Ser Thr Thr Gln Arg Pro Ser Val Arg Leu Phe
    850                 855                 860
Trp Arg Glu His Leu His Ala Ser Val Asp Gly Arg Glu Leu Arg Glu
865                 870                 875                 880
Ser Thr Arg Thr Pro Thr Ser Thr Lys Trp Ile Arg Glu Arg Cys Ala
                885                 890                 895
Gln Ile Thr Gly Arg Asp Phe Val Gln Phe Val His Thr His Ile Asn
            900                 905                 910
Ala Leu Pro Ser Arg Ile Arg Gly Ser Arg Gly Arg Gly Gly Gly
        915                 920                 925
```

-continued

```
Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Asn
                965                 970                 975

Lys Trp Thr Val Glu Leu Glu Pro Arg Leu Arg Thr Ser Val Gly Leu
                980                 985                 990

Arg Lys Pro Asp Ile Ile Ala Ser Arg Asp Gly Val Gly Val Ile Val
            995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Met Glu Glu Lys Val Gly Asn Leu Lys Pro Asn Met Glu Ser
    1130                1135                1140

Val Asn Val Thr Val Arg Val Leu Glu Ala Ser Glu Ala Arg Gln
    1145                1150                1155

Ile Gln Thr Lys Asn Gly Val Arg Thr Ile Ser Glu Ala Ile Val
    1160                1165                1170

Gly Asp Glu Thr Gly Arg Val Lys Leu Thr Leu Trp Gly Lys His
    1175                1180                1185

Ala Gly Ser Ile Lys Glu Gly Gln Val Val Lys Ile Glu Asn Ala
    1190                1195                1200

Trp Thr Thr Ala Phe Lys Gly Gln Val Gln Leu Asn Ala Gly Ser
    1205                1210                1215

Lys Thr Lys Ile Ala Glu Ala Ser Glu Asp Gly Phe Pro Glu Ser
    1220                1225                1230

Ser Gln Ile Pro Glu Asn Thr Pro Thr Ala Pro Gln Gln Met Arg
    1235                1240                1245

Gly Gly Gly Arg Gly Phe Arg Gly Gly Gly Arg Tyr Gly Arg
    1250                1255                1260

Arg Gly Gly Arg Arg Gln Glu Asn Glu Glu Gly Glu Glu Val
    1265                1270                1275

Gly Thr Gly Gly Gly Ser Gly Gly Thr Gly Gly Ser Ala
    1280                1285                1290

Ser Ser Gly Lys Lys Pro Val Lys Val Lys Thr Pro Ala Gly Lys
    1295                1300                1305

Glu Ala Glu Leu Val Pro Glu Lys Val Trp Ala Leu Ala Pro Lys
    1310                1315                1320

Gly Arg Lys Gly Val Lys Ile Gly Leu Phe Lys Asp Pro Glu Thr
```

-continued

```
                    1325                1330                1335

Gly Lys Tyr Phe Arg His Lys Leu Pro Asp Asp Tyr Pro Ile
    1340                1345                1350

<210> SEQ ID NO 41
<211> LENGTH: 1092
<212> TYPE: PRT
<213> ORGANISM: Artificial Sequence
<220> FEATURE:
<223> OTHER INFORMATION: His Tag joined via a linker to SSB-Cren7 joined
      via a linker to the C-terminus of deltaR2 enzyme

<400> SEQUENCE: 41

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
                20                  25                  30

Asp Leu His Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80

Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
            180                 185                 190

Val Glu Arg Pro Gly Gly Pro Gly Glu Tyr Arg Pro Ile Ser Ile Ala
        195                 200                 205

Ser Ile Pro Leu Arg His Phe His Ser Ile Leu Ala Arg Arg Leu Leu
    210                 215                 220

Ala Cys Cys Pro Pro Asp Ala Arg Gln Arg Gly Phe Ile Cys Ala Asp
225                 230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
    290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
                325                 330                 335
```

```
Phe Asn Val Val Met Asp Leu Ile Leu Ala Ser Leu Pro Glu Arg Val
                340                 345                 350

Gly Tyr Arg Leu Glu Met Glu Leu Val Ser Ala Leu Ala Tyr Ala Asp
            355                 360                 365

Asp Leu Val Leu Leu Ala Gly Ser Lys Val Gly Met Gln Glu Ser Ile
        370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495

Asn Ile Ser Asp Asp Arg Leu Arg Met Leu Asp Val Gln Ile Arg Lys
            500                 505                 510

Ala Val Gly Gln Trp Leu Arg Leu Pro Ala Asp Val Pro Lys Ala Tyr
        515                 520                 525

Tyr His Ala Ala Val Gln Asp Gly Gly Leu Ala Ile Pro Ser Val Arg
            530                 535                 540

Ala Thr Ile Pro Asp Leu Ile Val Arg Arg Phe Gly Gly Leu Asp Ser
545                 550                 555                 560

Ser Pro Trp Ser Val Ala Arg Ala Ala Lys Ser Asp Lys Ile Arg
                565                 570                 575

Lys Lys Leu Arg Trp Ala Trp Lys Gln Leu Arg Arg Phe Ser Arg Val
            580                 585                 590

Asp Ser Thr Thr Gln Arg Pro Ser Val Arg Leu Phe Trp Arg Glu His
        595                 600                 605

Leu His Ala Ser Val Asp Gly Arg Glu Leu Arg Glu Ser Thr Arg Thr
610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
                645                 650                 655

Arg Ile Arg Gly Ser Arg Gly Arg Arg Gly Gly Glu Ser Ser Leu
            660                 665                 670

Thr Cys Arg Ala Gly Cys Lys Val Arg Glu Thr Thr Ala His Ile Leu
        675                 680                 685

Gln Gln Cys His Arg Thr His Gly Gly Arg Ile Leu Arg His Asn Lys
            690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
                725                 730                 735

Ile Ile Ala Ser Arg Asp Gly Val Gly Val Ile Val Asp Val Gln Val
            740                 745                 750

Val Ser Gly Gln Arg Ser Leu Asp Glu Leu His Arg Glu Lys Arg Asn
```

```
                    755                 760                 765
Lys Tyr Gly Asn His Gly Glu Leu Val Glu Leu Val Ala Gly Arg Leu
        770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
                805                 810                 815

Ile Gly Leu Arg Glu Pro Thr Leu Gln Ile Val Pro Ile Leu Ala Leu
        820                 825                 830

Arg Gly Ser His Met Asn Trp Thr Arg Phe Asn Gln Met Thr Ser Val
                835                 840                 845

Met Gly Gly Gly Val Gly Val Gly Thr Gly Gly Ser Gly Gly Gly
        850                 855                 860

Thr Gly Gly Gly Ser Met Glu Glu Lys Val Gly Asn Leu Lys Pro Asn
865                 870                 875                 880

Met Glu Ser Val Asn Val Thr Val Arg Val Leu Glu Ala Ser Glu Ala
                885                 890                 895

Arg Gln Ile Gln Thr Lys Asn Gly Val Arg Thr Ile Ser Glu Ala Ile
        900                 905                 910

Val Gly Asp Glu Thr Gly Arg Val Lys Leu Thr Leu Trp Gly Lys His
                915                 920                 925

Ala Gly Ser Ile Lys Glu Gly Gln Val Val Lys Ile Glu Asn Ala Trp
        930                 935                 940

Thr Thr Ala Phe Lys Gly Gln Val Gln Leu Asn Ala Gly Ser Lys Thr
945                 950                 955                 960

Lys Ile Ala Glu Ala Ser Glu Asp Gly Phe Pro Glu Ser Ser Gln Ile
                965                 970                 975

Pro Glu Asn Thr Pro Thr Ala Pro Gln Gln Met Arg Gly Gly Gly Arg
        980                 985                 990

Gly Phe Arg Gly Gly Gly Arg Tyr Gly Arg Gly Gly Arg Arg
            995                 1000                1005

Gln Glu Asn Glu Glu Gly Glu Glu Val Gly Thr Gly Gly Gly
    1010                1015                1020

Ser Gly Gly Gly Thr Gly Gly Gly Ser Ala Ser Ser Gly Lys Lys
    1025                1030                1035

Pro Val Lys Val Lys Thr Pro Ala Gly Lys Glu Ala Glu Leu Val
    1040                1045                1050

Pro Glu Lys Val Trp Ala Leu Ala Pro Lys Gly Arg Lys Gly Val
    1055                1060                1065

Lys Ile Gly Leu Phe Lys Asp Pro Glu Thr Gly Lys Tyr Phe Arg
    1070                1075                1080

His Lys Leu Pro Asp Asp Tyr Pro Ile
    1085                1090

<210> SEQ ID NO 42
<211> LENGTH: 1426
<212> TYPE: PRT
<213> ORGANISM: Artificial Sequence
<220> FEATURE:
<223> OTHER INFORMATION: SSB-Cren7-Cren7 joined via a linker to the
      C-terminus of wild type R2 enzyme

<400> SEQUENCE: 42

Met Met Ala Ser Thr Ala Leu Ser Leu Met Gly Arg Cys Asn Pro Asp
1               5                   10                  15
```

-continued

```
Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
        130                 135                 140

Pro Met Met Val Lys Arg Arg Trp His Gly Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
                245                 250                 255

Gly Gln Met Ser Pro Asp Ala Ala Arg Val Leu Ser Glu Leu Leu Glu
            260                 265                 270

Gly Ala Gly Arg Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
    290                 295                 300

Thr Ser Arg Gln Lys Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
        355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
                405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
```

-continued

```
            435                 440                 445
Phe Val Pro Lys Val Glu Arg Pro Gly Gly Pro Gly Glu Tyr Arg Pro
450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
                500                 505                 510
Leu Gly Asp Ser Arg Lys Lys Leu Arg Glu Cys His Val Ala Val Leu
                515                 520                 525
Asp Phe Ala Lys Ala Phe Asp Thr Val Ser His Glu Ala Leu Val Glu
                530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
                580                 585                 590
Ser Pro Ile Leu Phe Asn Val Met Asp Leu Ile Leu Ala Ser Leu
                595                 600                 605
Pro Glu Arg Val Gly Tyr Arg Leu Glu Met Glu Leu Val Ser Ala Leu
                610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
                660                 665                 670
His Arg Lys Lys His His Tyr Leu Thr Glu Arg Thr Phe Asn Ile Gly
                675                 680                 685
Gly Lys Pro Leu Arg Gln Val Ser Cys Val Glu Arg Trp Arg Tyr Leu
                690                 695                 700
Gly Val Asp Phe Glu Ala Ser Gly Cys Val Thr Leu Glu His Ser Ile
705                 710                 715                 720
Ser Ser Ala Leu Asn Asn Ile Ser Arg Ala Pro Leu Lys Pro Gln Gln
                725                 730                 735
Arg Leu Glu Ile Leu Arg Ala His Leu Ile Pro Arg Phe Gln His Gly
                740                 745                 750
Phe Val Leu Gly Asn Ile Ser Asp Asp Arg Leu Arg Met Leu Asp Val
                755                 760                 765
Gln Ile Arg Lys Ala Val Gly Gln Trp Leu Arg Leu Pro Ala Asp Val
                770                 775                 780
Pro Lys Ala Tyr Tyr His Ala Ala Val Gln Asp Gly Gly Leu Ala Ile
785                 790                 795                 800
Pro Ser Val Arg Ala Thr Ile Pro Asp Leu Ile Val Arg Arg Phe Gly
                805                 810                 815
Gly Leu Asp Ser Ser Pro Trp Ser Val Ala Arg Ala Ala Ala Lys Ser
                820                 825                 830
Asp Lys Ile Arg Lys Lys Leu Arg Trp Ala Trp Lys Gln Leu Arg Arg
                835                 840                 845
Phe Ser Arg Val Asp Ser Thr Thr Gln Arg Pro Ser Val Arg Leu Phe
                850                 855                 860
```

```
Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
            885                 890                 895

Gln Ile Thr Gly Arg Asp Phe Val Gln Phe Val His Thr His Ile Asn
        900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
        995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Met Glu Glu Lys Val Gly Asn Leu Lys Pro Asn Met Glu Ser
    1130                1135                1140

Val Asn Val Thr Val Arg Val Leu Glu Ala Ser Glu Ala Arg Gln
    1145                1150                1155

Ile Gln Thr Lys Asn Gly Val Arg Thr Ile Ser Glu Ala Ile Val
    1160                1165                1170

Gly Asp Glu Thr Gly Arg Val Lys Leu Thr Leu Trp Gly Lys His
    1175                1180                1185

Ala Gly Ser Ile Lys Glu Gly Gln Val Val Lys Ile Glu Asn Ala
    1190                1195                1200

Trp Thr Thr Ala Phe Lys Gly Gln Val Gln Leu Asn Ala Gly Ser
    1205                1210                1215

Lys Thr Lys Ile Ala Glu Ala Ser Glu Asp Gly Phe Pro Glu Ser
    1220                1225                1230

Ser Gln Ile Pro Glu Asn Thr Pro Thr Ala Pro Gln Gln Met Arg
    1235                1240                1245

Gly Gly Gly Arg Gly Phe Arg Gly Gly Gly Arg Arg Tyr Gly Arg
    1250                1255                1260
```

```
Arg Gly  Gly Arg Arg Gln  Glu Asn Glu Glu Gly  Glu Glu Val
    1265         1270                    1275

Gly Thr  Gly Gly Gly Ser  Gly Gly Thr Gly Gly  Gly Ser Ala
    1280         1285                    1290

Ser Ser  Gly Lys Lys Pro  Val Lys Val Lys Thr  Pro Ala Gly Lys
    1295         1300                    1305

Glu Ala  Glu Leu Val Pro  Glu Lys Val Trp Ala  Leu Ala Pro Lys
    1310         1315                    1320

Gly Arg  Lys Gly Val Lys  Ile Gly Leu Phe Lys  Asp Pro Glu Thr
    1325         1330                    1335

Gly Lys  Tyr Phe Arg His  Lys Leu Pro Asp Asp  Tyr Pro Ile Val
    1340         1345                    1350

Gly Thr  Gly Gly Gly Ser  Gly Gly Thr Gly Gly  Gly Ser Ala
    1355         1360                    1365

Ser Ser  Gly Lys Lys Pro  Val Lys Val Lys Thr  Pro Ala Gly Lys
    1370         1375                    1380

Glu Ala  Glu Leu Val Pro  Glu Lys Val Trp Ala  Leu Ala Pro Lys
    1385         1390                    1395

Gly Arg  Lys Gly Val Lys  Ile Gly Leu Phe Lys  Asp Pro Glu Thr
    1400         1405                    1410

Gly Lys  Tyr Phe Arg His  Lys Leu Pro Asp Asp  Tyr Pro
    1415         1420                    1425

<210> SEQ ID NO 43
<211> LENGTH: 1141
<212> TYPE: PRT
<213> ORGANISM: Artificial Sequence
<220> FEATURE:
<223> OTHER INFORMATION: SSB-Cren7-Cren7 joined via a linker to the
      C-terminus of deltaR2 enzyme

<400> SEQUENCE: 43

Lys Thr Ala Gly Arg Arg Asn Asp Leu His Asp Asp Arg Thr Ala Ser
1               5                   10                  15

Ala His Lys Thr Ser Arg Gln Lys Arg Arg Ala Glu Tyr Ala Arg Val
            20                  25                  30

Gln Glu Leu Tyr Lys Lys Cys Arg Ser Arg Ala Ala Ala Glu Val Ile
        35                  40                  45

Asp Gly Ala Cys Gly Gly Val Gly His Ser Leu Glu Glu Met Glu Thr
    50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Asn
                85                  90                  95

Arg Asp Tyr Thr Gln Leu Trp Lys Pro Ile Ser Val Glu Glu Ile Lys
            100                 105                 110

Ala Ser Arg Phe Asp Trp Arg Thr Ser Pro Gly Pro Asp Gly Ile Arg
        115                 120                 125

Ser Gly Gln Trp Arg Ala Val Pro Val His Leu Lys Ala Glu Met Phe
    130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
            180                 185                 190
```

```
Ile Leu Ala Arg Arg Leu Leu Ala Cys Cys Pro Pro Asp Ala Arg Gln
        195                 200                 205

Arg Gly Phe Ile Cys Ala Asp Gly Thr Leu Glu Asn Ser Ala Val Leu
    210                 215                 220

Asp Ala Val Leu Gly Asp Ser Arg Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Gln Phe Cys Gly
            260                 265                 270

Tyr Ile Ala His Leu Tyr Asp Thr Ala Ser Thr Thr Leu Ala Val Asn
        275                 280                 285

Asn Glu Met Ser Ser Pro Val Lys Val Gly Arg Gly Val Arg Gln Gly
    290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Leu Val Leu Leu Ala Gly Ser Lys
            340                 345                 350

Val Gly Met Gln Glu Ser Ile Ser Ala Val Asp Cys Val Gly Arg Gln
    355                 360                 365

Met Gly Leu Arg Leu Asn Cys Arg Lys Ser Ala Val Leu Ser Met Ile
    370                 375                 380

Pro Asp Gly His Arg Lys Lys His His Tyr Leu Thr Glu Arg Thr Phe
385                 390                 395                 400

Asn Ile Gly Gly Lys Pro Leu Arg Gln Val Ser Cys Val Glu Arg Trp
                405                 410                 415

Arg Tyr Leu Gly Val Asp Phe Glu Ala Ser Gly Cys Val Thr Leu Glu
            420                 425                 430

His Ser Ile Ser Ser Ala Leu Asn Asn Ile Ser Arg Ala Pro Leu Lys
        435                 440                 445

Pro Gln Gln Arg Leu Glu Ile Leu Arg Ala His Leu Ile Pro Arg Phe
    450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
            500                 505                 510

Leu Ala Ile Pro Ser Val Arg Ala Thr Ile Pro Asp Leu Ile Val Arg
        515                 520                 525

Arg Phe Gly Gly Leu Asp Ser Ser Pro Trp Ser Val Ala Arg Ala Ala
    530                 535                 540

Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
        595                 600                 605
```

-continued

Arg Cys Ala Gln Ile Thr Gly Arg Asp Phe Val Gln Phe Val His Thr
610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
            645                 650                 655

Glu Thr Thr Ala His Ile Leu Gln Gln Cys His Arg Thr His Gly Gly
            660                 665                 670

Arg Ile Leu Arg His Asn Lys Ile Val Ser Phe Val Ala Lys Ala Met
            675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Ser Gly Gln Arg Ser Leu Asp Glu
            725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
            755                 760                 765

Ala Thr Ser Cys Thr Ile Ser Trp Arg Gly Val Trp Ser Leu Thr Ser
770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
            805                 810                 815

Phe Asn Gln Met Thr Ser Val Met Gly Gly Val Gly Val Gly Thr
            820                 825                 830

Gly Gly Gly Ser Gly Gly Thr Gly Gly Gly Ser Met Glu Glu Lys
            835                 840                 845

Val Gly Asn Leu Lys Pro Asn Met Glu Ser Val Asn Val Thr Val Arg
850                 855                 860

Val Leu Glu Ala Ser Glu Ala Arg Gln Ile Gln Thr Lys Asn Gly Val
865                 870                 875                 880

Arg Thr Ile Ser Glu Ala Ile Val Gly Asp Glu Thr Gly Arg Val Lys
            885                 890                 895

Leu Thr Leu Trp Gly Lys His Ala Gly Ser Ile Lys Glu Gly Gln Val
            900                 905                 910

Val Lys Ile Glu Asn Ala Trp Thr Thr Ala Phe Lys Gly Gln Val Gln
            915                 920                 925

Leu Asn Ala Gly Ser Lys Thr Lys Ile Ala Glu Ala Ser Glu Asp Gly
930                 935                 940

Phe Pro Glu Ser Ser Gln Ile Pro Glu Asn Thr Pro Thr Ala Pro Gln
945                 950                 955                 960

Gln Met Arg Gly Gly Gly Arg Gly Phe Arg Gly Gly Arg Arg Tyr
            965                 970                 975

Gly Arg Arg Gly Gly Arg Arg Gln Glu Asn Glu Glu Gly Glu Glu Glu
            980                 985                 990

Val Gly Thr Gly Gly Gly Ser Gly Gly Gly Thr Gly Gly Gly Ser Ala
            995                 1000                1005

Ser Ser Gly Lys Lys Pro Val Lys Val Lys Thr Pro Ala Gly Lys
      1010                1015                1020

Glu Ala Glu Leu Val Pro Glu Lys Val Trp Ala Leu Ala Pro Lys

```
              1025                1030                1035

Gly Arg Lys Gly Val Lys Ile Gly Leu Phe Lys Asp Pro Glu Thr
            1040                1045                1050

Gly Lys Tyr Phe Arg His Lys Leu Pro Asp Asp Tyr Pro Ile Val
            1055                1060                1065

Gly Thr Gly Gly Gly Ser Gly Gly Thr Gly Gly Gly Ser Ala
            1070                1075                1080

Ser Ser Gly Lys Lys Pro Val Lys Val Lys Thr Pro Ala Gly Lys
            1085                1090                1095

Glu Ala Glu Leu Val Pro Glu Lys Val Trp Ala Leu Ala Pro Lys
            1100                1105                1110

Gly Arg Lys Gly Val Lys Ile Gly Leu Phe Lys Asp Pro Glu Thr
            1115                1120                1125

Gly Lys Tyr Phe Arg His Lys Leu Pro Asp Asp Tyr Pro
            1130                1135                1140

<210> SEQ ID NO 44
<211> LENGTH: 2254
<212> TYPE: PRT
<213> ORGANISM: Artificial Sequence
<220> FEATURE:
<223> OTHER INFORMATION: dimer of WT R2 enzyme

<400> SEQUENCE: 44

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
            20                  25                  30

Arg Gly Pro Ser Ser Leu Ala Gly Thr Phe Gly Trp Gly Leu Ala Ile
        35                  40                  45

Pro Ala Gly Glu Pro Cys Gly Arg Val Cys Ser Pro Ala Thr Val Gly
    50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
            100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
    130                 135                 140

Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
                165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Ala Tyr Asp Pro Ser Ala Val
```

```
                245                 250                 255
Gly Gln Met Ser Pro Asp Ala Ala Arg Val Leu Ser Glu Leu Leu Glu
            260                 265                 270
Gly Ala Gly Arg Arg Ala Cys Arg Ala Met Arg Pro Lys Thr Ala
            275                 280                 285
Gly Arg Arg Asn Asp Leu His Asp Asp Arg Thr Ala Ser Ala His Lys
        290                 295                 300
Thr Ser Arg Gln Lys Arg Arg Ala Glu Tyr Ala Arg Val Gln Glu Leu
305                 310                 315                 320
Tyr Lys Lys Cys Arg Ser Arg Ala Ala Ala Glu Val Ile Asp Gly Ala
                325                 330                 335
Cys Gly Gly Val Gly His Ser Leu Glu Glu Met Glu Thr Tyr Trp Arg
                340                 345                 350
Pro Ile Leu Glu Arg Val Ser Asp Ala Pro Gly Pro Thr Pro Glu Ala
                355                 360                 365
Leu His Ala Leu Gly Arg Ala Glu Trp His Gly Gly Asn Arg Asp Tyr
        370                 375                 380
Thr Gln Leu Trp Lys Pro Ile Ser Val Glu Glu Ile Lys Ala Ser Arg
385                 390                 395                 400
Phe Asp Trp Arg Thr Ser Pro Gly Pro Asp Gly Ile Arg Ser Gly Gln
                405                 410                 415
Trp Arg Ala Val Pro Val His Leu Lys Ala Glu Met Phe Asn Ala Trp
            420                 425                 430
Met Ala Arg Gly Glu Ile Pro Glu Ile Leu Arg Gln Cys Arg Thr Val
            435                 440                 445
Phe Val Pro Lys Val Glu Arg Pro Gly Gly Pro Gly Glu Tyr Arg Pro
        450                 455                 460
Ile Ser Ile Ala Ser Ile Pro Leu Arg His Phe His Ser Ile Leu Ala
465                 470                 475                 480
Arg Arg Leu Leu Ala Cys Cys Pro Pro Asp Ala Arg Gln Arg Gly Phe
                485                 490                 495
Ile Cys Ala Asp Gly Thr Leu Glu Asn Ser Ala Val Leu Asp Ala Val
                500                 505                 510
Leu Gly Asp Ser Arg Lys Lys Leu Arg Glu Cys His Val Ala Val Leu
            515                 520                 525
Asp Phe Ala Lys Ala Phe Asp Thr Val Ser His Glu Ala Leu Val Glu
            530                 535                 540
Leu Leu Arg Leu Arg Gly Met Pro Glu Gln Phe Cys Gly Tyr Ile Ala
545                 550                 555                 560
His Leu Tyr Asp Thr Ala Ser Thr Thr Leu Ala Val Asn Asn Glu Met
                565                 570                 575
Ser Ser Pro Val Lys Val Gly Arg Gly Val Arg Gln Gly Asp Pro Leu
                580                 585                 590
Ser Pro Ile Leu Phe Asn Val Val Met Asp Leu Ile Leu Ala Ser Leu
            595                 600                 605
Pro Glu Arg Val Gly Tyr Arg Leu Glu Met Glu Leu Val Ser Ala Leu
        610                 615                 620
Ala Tyr Ala Asp Asp Leu Val Leu Leu Ala Gly Ser Lys Val Gly Met
625                 630                 635                 640
Gln Glu Ser Ile Ser Ala Val Asp Cys Val Gly Arg Gln Met Gly Leu
                645                 650                 655
Arg Leu Asn Cys Arg Lys Ser Ala Val Leu Ser Met Ile Pro Asp Gly
                660                 665                 670
```

```
His Arg Lys Lys His His Tyr Leu Thr Glu Arg Thr Phe Asn Ile Gly
        675                 680                 685

Gly Lys Pro Leu Arg Gln Val Ser Cys Val Glu Arg Trp Arg Tyr Leu
    690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
        755                 760                 765

Gln Ile Arg Lys Ala Val Gly Gln Trp Leu Arg Leu Pro Ala Asp Val
    770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Lys Ser
            820                 825                 830

Asp Lys Ile Arg Lys Lys Leu Arg Trp Ala Trp Lys Gln Leu Arg Arg
        835                 840                 845

Phe Ser Arg Val Asp Ser Thr Thr Gln Arg Pro Ser Val Arg Leu Phe
    850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
        915                 920                 925

Glu Ser Ser Leu Thr Cys Arg Ala Gly Cys Lys Val Arg Glu Thr Thr
    930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990

Arg Lys Pro Asp Ile Ile Ala Ser Arg Asp Gly Val Gly Val Ile Val
        995                 1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080
```

-continued

| | | | | | | | | | | | | |
|---|---|---|---|---|---|---|---|---|---|---|---|---|
| Leu | Gln | Ile | Val | Pro | Ile | Leu | Ala | Leu | Arg | Gly | Ser | His | Met | Asn |
| | 1085 | | | | 1090 | | | | 1095 | | | |
| Trp | Thr | Arg | Phe | Asn | Gln | Met | Thr | Ser | Val | Met | Gly | Gly | Gly | Val |
| | 1100 | | | | 1105 | | | | 1110 | | | |
| Gly | Val | Gly | Thr | Gly | Gly | Gly | Ser | Gly | Gly | Gly | Glu | Ala | Ala | Ala |
| | 1115 | | | | 1120 | | | | 1125 | | | |
| Lys | Glu | Ala | Ala | Ala | Lys | Ser | Gly | Gly | Gly | Ser | Ala | Met | Met | Ala |
| | 1130 | | | | 1135 | | | | 1140 | | | |
| Ser | Thr | Ala | Leu | Ser | Leu | Met | Gly | Arg | Cys | Asn | Pro | Asp | Gly | Cys |
| | 1145 | | | | 1150 | | | | 1155 | | | |
| Thr | Arg | Gly | Lys | His | Val | Thr | Ala | Ala | Pro | Met | Asp | Gly | Pro | Arg |
| | 1160 | | | | 1165 | | | | 1170 | | | |
| Gly | Pro | Ser | Ser | Leu | Ala | Gly | Thr | Phe | Gly | Trp | Gly | Leu | Ala | Ile |
| | 1175 | | | | 1180 | | | | 1185 | | | |
| Pro | Ala | Gly | Glu | Pro | Cys | Gly | Arg | Val | Cys | Ser | Pro | Ala | Thr | Val |
| | 1190 | | | | 1195 | | | | 1200 | | | |
| Gly | Phe | Phe | Pro | Val | Ala | Lys | Lys | Ser | Asn | Lys | Glu | Asn | Arg | Pro |
| | 1205 | | | | 1210 | | | | 1215 | | | |
| Glu | Ala | Ser | Gly | Leu | Pro | Leu | Glu | Ser | Glu | Arg | Thr | Gly | Asp | Asn |
| | 1220 | | | | 1225 | | | | 1230 | | | |
| Pro | Thr | Val | Arg | Gly | Ser | Ala | Gly | Ala | Asp | Pro | Val | Gly | Gln | Asp |
| | 1235 | | | | 1240 | | | | 1245 | | | |
| Ala | Pro | Gly | Trp | Thr | Cys | Gln | Phe | Cys | Glu | Arg | Thr | Phe | Ser | Thr |
| | 1250 | | | | 1255 | | | | 1260 | | | |
| Asn | Arg | Gly | Leu | Gly | Val | His | Lys | Arg | Arg | Ala | His | Pro | Val | Glu |
| | 1265 | | | | 1270 | | | | 1275 | | | |
| Thr | Asn | Thr | Asp | Ala | Ala | Pro | Met | Met | Val | Lys | Arg | Arg | Trp | His |
| | 1280 | | | | 1285 | | | | 1290 | | | |
| Gly | Glu | Glu | Ile | Asp | Leu | Leu | Ala | Arg | Thr | Glu | Ala | Arg | Leu | Leu |
| | 1295 | | | | 1300 | | | | 1305 | | | |
| Ala | Glu | Arg | Gly | Gln | Cys | Ser | Gly | Gly | Asp | Leu | Phe | Gly | Ala | Leu |
| | 1310 | | | | 1315 | | | | 1320 | | | |
| Pro | Gly | Phe | Gly | Arg | Thr | Leu | Glu | Ala | Ile | Lys | Gly | Gln | Arg | Arg |
| | 1325 | | | | 1330 | | | | 1335 | | | |
| Arg | Glu | Pro | Tyr | Arg | Ala | Leu | Val | Gln | Ala | His | Leu | Ala | Arg | Phe |
| | 1340 | | | | 1345 | | | | 1350 | | | |
| Gly | Ser | Gln | Pro | Gly | Pro | Ser | Ser | Gly | Gly | Cys | Ser | Ala | Glu | Pro |
| | 1355 | | | | 1360 | | | | 1365 | | | |
| Asp | Phe | Arg | Arg | Ala | Ser | Gly | Ala | Glu | Glu | Ala | Gly | Glu | Glu | Arg |
| | 1370 | | | | 1375 | | | | 1380 | | | |
| Cys | Ala | Glu | Asp | Ala | Ala | Ala | Tyr | Asp | Pro | Ser | Ala | Val | Gly | Gln |
| | 1385 | | | | 1390 | | | | 1395 | | | |
| Met | Ser | Pro | Asp | Ala | Ala | Arg | Val | Leu | Ser | Glu | Leu | Leu | Glu | Gly |
| | 1400 | | | | 1405 | | | | 1410 | | | |
| Ala | Gly | Arg | Arg | Arg | Ala | Cys | Arg | Ala | Met | Arg | Pro | Lys | Thr | Ala |
| | 1415 | | | | 1420 | | | | 1425 | | | |
| Gly | Arg | Arg | Asn | Asp | Leu | His | Asp | Asp | Arg | Thr | Ala | Ser | Ala | His |
| | 1430 | | | | 1435 | | | | 1440 | | | |
| Lys | Thr | Ser | Arg | Gln | Lys | Arg | Arg | Ala | Glu | Tyr | Ala | Arg | Val | Gln |
| | 1445 | | | | 1450 | | | | 1455 | | | |
| Glu | Leu | Tyr | Lys | Lys | Cys | Arg | Ser | Arg | Ala | Ala | Ala | Glu | Val | Ile |
| | 1460 | | | | 1465 | | | | 1470 | | | |
| Asp | Gly | Ala | Cys | Gly | Gly | Val | Gly | His | Ser | Leu | Glu | Glu | Met | Glu |

```
              1475                1480               1485

Thr Tyr Trp Arg Pro Ile Leu Glu Arg Val Ser Asp Ala Pro Gly
         1490                1495               1500

Pro Thr Pro Glu Ala Leu His Ala Leu Gly Arg Ala Glu Trp His
         1505                1510               1515

Gly Gly Asn Arg Asp Tyr Thr Gln Leu Trp Lys Pro Ile Ser Val
         1520                1525               1530

Glu Glu Ile Lys Ala Ser Arg Phe Asp Trp Arg Thr Ser Pro Gly
         1535                1540               1545

Pro Asp Gly Ile Arg Ser Gly Gln Trp Arg Ala Val Pro Val His
         1550                1555               1560

Leu Lys Ala Glu Met Phe Asn Ala Trp Met Ala Arg Gly Glu Ile
         1565                1570               1575

Pro Glu Ile Leu Arg Gln Cys Arg Thr Val Phe Val Pro Lys Val
         1580                1585               1590

Glu Arg Pro Gly Gly Pro Gly Glu Tyr Arg Pro Ile Ser Ile Ala
         1595                1600               1605

Ser Ile Pro Leu Arg His Phe His Ser Ile Leu Ala Arg Arg Leu
         1610                1615               1620

Leu Ala Cys Cys Pro Pro Asp Ala Arg Gln Arg Gly Phe Ile Cys
         1625                1630               1635

Ala Asp Gly Thr Leu Glu Asn Ser Ala Val Leu Asp Ala Val Leu
         1640                1645               1650

Gly Asp Ser Arg Lys Lys Leu Arg Glu Cys His Val Ala Val Leu
         1655                1660               1665

Asp Phe Ala Lys Ala Phe Asp Thr Val Ser His Glu Ala Leu Val
         1670                1675               1680

Glu Leu Leu Arg Leu Arg Gly Met Pro Glu Gln Phe Cys Gly Tyr
         1685                1690               1695

Ile Ala His Leu Tyr Asp Thr Ala Ser Thr Thr Leu Ala Val Asn
         1700                1705               1710

Asn Glu Met Ser Ser Pro Val Lys Val Gly Arg Gly Val Arg Gln
         1715                1720               1725

Gly Asp Pro Leu Ser Pro Ile Leu Phe Asn Val Val Met Asp Leu
         1730                1735               1740

Ile Leu Ala Ser Leu Pro Glu Arg Val Gly Tyr Arg Leu Glu Met
         1745                1750               1755

Glu Leu Val Ser Ala Leu Ala Tyr Ala Asp Asp Leu Val Leu Leu
         1760                1765               1770

Ala Gly Ser Lys Val Gly Met Gln Glu Ser Ile Ser Ala Val Asp
         1775                1780               1785

Cys Val Gly Arg Gln Met Gly Leu Arg Leu Asn Cys Arg Lys Ser
         1790                1795               1800

Ala Val Leu Ser Met Ile Pro Asp Gly His Arg Lys Lys His His
         1805                1810               1815

Tyr Leu Thr Glu Arg Thr Phe Asn Ile Gly Gly Lys Pro Leu Arg
         1820                1825               1830

Gln Val Ser Cys Val Glu Arg Trp Arg Tyr Leu Gly Val Asp Phe
         1835                1840               1845

Glu Ala Ser Gly Cys Val Thr Leu Glu His Ser Ile Ser Ser Ala
         1850                1855               1860

Leu Asn Asn Ile Ser Arg Ala Pro Leu Lys Pro Gln Gln Arg Leu
         1865                1870               1875
```

-continued

Glu Ile Leu Arg Ala His Leu Ile Pro Arg Phe Gln His Gly Phe
    1880            1885                1890

Val Leu Gly Asn Ile Ser Asp Asp Arg Leu Arg Met Leu Asp Val
    1895            1900                1905

Gln Ile Arg Lys Ala Val Gly Gln Trp Leu Arg Leu Pro Ala Asp
    1910            1915                1920

Val Pro Lys Ala Tyr Tyr His Ala Ala Val Gln Asp Gly Gly Leu
    1925            1930                1935

Ala Ile Pro Ser Val Arg Ala Thr Ile Pro Asp Leu Ile Val Arg
    1940            1945                1950

Arg Phe Gly Gly Leu Asp Ser Ser Pro Trp Ser Val Ala Arg Ala
    1955            1960                1965

Ala Ala Lys Ser Asp Lys Ile Arg Lys Lys Leu Arg Trp Ala Trp
    1970            1975                1980

Lys Gln Leu Arg Arg Phe Ser Arg Val Asp Ser Thr Thr Gln Arg
    1985            1990                1995

Pro Ser Val Arg Leu Phe Trp Arg Glu His Leu His Ala Ser Val
    2000            2005                2010

Asp Gly Arg Glu Leu Arg Glu Ser Thr Arg Thr Pro Thr Ser Thr
    2015            2020                2025

Lys Trp Ile Arg Glu Arg Cys Ala Gln Ile Thr Gly Arg Asp Phe
    2030            2035                2040

Val Gln Phe Val His Thr His Ile Asn Ala Leu Pro Ser Arg Ile
    2045            2050                2055

Arg Gly Ser Arg Gly Arg Gly Gly Gly Glu Ser Ser Leu Thr
    2060            2065                2070

Cys Arg Ala Gly Cys Lys Val Arg Glu Thr Thr Ala His Ile Leu
    2075            2080                2085

Gln Gln Cys His Arg Thr His Gly Gly Arg Ile Leu Arg His Asn
    2090            2095                2100

Lys Ile Val Ser Phe Val Ala Lys Ala Met Glu Glu Asn Lys Trp
    2105            2110                2115

Thr Val Glu Leu Glu Pro Arg Leu Arg Thr Ser Val Gly Leu Arg
    2120            2125                2130

Lys Pro Asp Ile Ile Ala Ser Arg Asp Gly Val Gly Val Ile Val
    2135            2140                2145

Asp Val Gln Val Val Ser Gly Gln Arg Ser Leu Asp Glu Leu His
    2150            2155                2160

Arg Glu Lys Arg Asn Lys Tyr Gly Asn His Gly Glu Leu Val Glu
    2165            2170                2175

Leu Val Ala Gly Arg Leu Gly Leu Pro Lys Ala Glu Cys Val Arg
    2180            2185                2190

Ala Thr Ser Cys Thr Ile Ser Trp Arg Gly Val Trp Ser Leu Thr
    2195            2200                2205

Ser Tyr Lys Glu Leu Arg Ser Ile Ile Gly Leu Arg Glu Pro Thr
    2210            2215                2220

Leu Gln Ile Val Pro Ile Leu Ala Leu Arg Gly Ser His Met Asn
    2225            2230                2235

Trp Thr Arg Phe Asn Gln Met Thr Ser Val Met Gly Gly Gly Val
    2240            2245                2250

Gly

```
<210> SEQ ID NO 45
<211> LENGTH: 1684
<212> TYPE: PRT
<213> ORGANISM: Artificial Sequence
<220> FEATURE:
<223> OTHER INFORMATION: dimer of deltaR2 enzyme

<400> SEQUENCE: 45

Lys Thr Ala Gly Arg Arg Asn Asp Leu His Asp Asp Arg Thr Ala Ser
1               5                   10                  15

Ala His Lys Thr Ser Arg Gln Lys Arg Arg Ala Glu Tyr Ala Arg Val
            20                  25                  30

Gln Glu Leu Tyr Lys Lys Cys Arg Ser Arg Ala Ala Ala Glu Val Ile
        35                  40                  45

Asp Gly Ala Cys Gly Gly Val Gly His Ser Leu Glu Glu Met Glu Thr
    50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Gly Asn
                85                  90                  95

Arg Asp Tyr Thr Gln Leu Trp Lys Pro Ile Ser Val Glu Glu Ile Lys
            100                 105                 110

Ala Ser Arg Phe Asp Trp Arg Thr Ser Pro Gly Pro Asp Gly Ile Arg
        115                 120                 125

Ser Gly Gln Trp Arg Ala Val Pro Val His Leu Lys Ala Glu Met Phe
    130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
            180                 185                 190

Ile Leu Ala Arg Arg Leu Leu Ala Cys Cys Pro Pro Asp Ala Arg Gln
        195                 200                 205

Arg Gly Phe Ile Cys Ala Asp Gly Thr Leu Glu Asn Ser Ala Val Leu
    210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
            260                 265                 270

Tyr Ile Ala His Leu Tyr Asp Thr Ala Ser Thr Thr Leu Ala Val Asn
        275                 280                 285

Asn Glu Met Ser Ser Pro Val Lys Val Gly Arg Gly Val Arg Gln Gly
    290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335

Ser Ala Leu Ala Tyr Ala Asp Asp Val Leu Leu Ala Gly Ser Lys
            340                 345                 350

Val Gly Met Gln Glu Ser Ile Ser Ala Val Asp Cys Val Gly Arg Gln
        355                 360                 365

Met Gly Leu Arg Leu Asn Cys Arg Lys Ser Ala Val Leu Ser Met Ile
```

-continued

```
            370                 375                 380
Pro Asp Gly His Arg Lys His His Tyr Leu Thr Glu Arg Thr Phe
385                 390                 395                 400

Asn Ile Gly Gly Lys Pro Leu Arg Gln Val Ser Cys Val Glu Arg Trp
                    405                 410                 415

Arg Tyr Leu Gly Val Asp Phe Glu Ala Ser Gly Cys Val Thr Leu Glu
                420                 425                 430

His Ser Ile Ser Ser Ala Leu Asn Asn Ile Ser Arg Ala Pro Leu Lys
                435                 440                 445

Pro Gln Gln Arg Leu Glu Ile Leu Arg Ala His Leu Ile Pro Arg Phe
450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
                485                 490                 495

Ala Asp Val Pro Lys Ala Tyr Tyr His Ala Ala Val Gln Asp Gly Gly
                500                 505                 510

Leu Ala Ile Pro Ser Val Arg Ala Thr Ile Pro Asp Leu Ile Val Arg
                515                 520                 525

Arg Phe Gly Gly Leu Asp Ser Ser Pro Trp Ser Val Ala Arg Ala Ala
530                 535                 540

Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
                565                 570                 575

Arg Leu Phe Trp Arg Glu His Leu His Ala Ser Val Asp Gly Arg Glu
                580                 585                 590

Leu Arg Glu Ser Thr Arg Thr Pro Thr Ser Thr Lys Trp Ile Arg Glu
                595                 600                 605

Arg Cys Ala Gln Ile Thr Gly Arg Asp Phe Val Gln Phe Val His Thr
610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
                660                 665                 670

Arg Ile Leu Arg His Asn Lys Ile Val Ser Phe Val Ala Lys Ala Met
                675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
                740                 745                 750

Glu Leu Val Ala Gly Arg Leu Gly Leu Pro Lys Ala Glu Cys Val Arg
                755                 760                 765

Ala Thr Ser Cys Thr Ile Ser Trp Arg Gly Val Trp Ser Leu Thr Ser
                770                 775                 780

Tyr Lys Glu Leu Arg Ser Ile Ile Gly Leu Arg Glu Pro Thr Leu Gln
785                 790                 795                 800
```

```
Ile Val Pro Ile Leu Ala Leu Arg Gly Ser His Met Asn Trp Thr Arg
                805                 810                 815
Phe Asn Gln Met Thr Ser Val Met Gly Gly Val Gly Val Gly Thr
            820                 825                 830
Gly Gly Gly Ser Gly Gly Gly Glu Ala Ala Lys Glu Ala Ala Ala
            835                 840                 845
Lys Ser Gly Gly Gly Ser Ala Lys Thr Ala Gly Arg Arg Asn Asp Leu
    850                 855                 860
His Asp Asp Arg Thr Ala Ser Ala His Lys Thr Ser Arg Gln Lys Arg
865                 870                 875                 880
Arg Ala Glu Tyr Ala Arg Val Gln Glu Leu Tyr Lys Lys Cys Arg Ser
                885                 890                 895
Arg Ala Ala Ala Glu Val Ile Asp Gly Ala Cys Gly Gly Val Gly His
                900                 905                 910
Ser Leu Glu Glu Met Glu Thr Tyr Trp Arg Pro Ile Leu Glu Arg Val
                915                 920                 925
Ser Asp Ala Pro Gly Pro Thr Pro Glu Ala Leu His Ala Leu Gly Arg
                930                 935                 940
Ala Glu Trp His Gly Gly Asn Arg Asp Tyr Thr Gln Leu Trp Lys Pro
945                 950                 955                 960
Ile Ser Val Glu Glu Ile Lys Ala Ser Arg Phe Asp Trp Arg Thr Ser
                965                 970                 975
Pro Gly Pro Asp Gly Ile Arg Ser Gly Gln Trp Arg Ala Val Pro Val
                980                 985                 990
His Leu Lys Ala Glu Met Phe Asn Ala Trp Met Ala Arg Gly Glu Ile
                995                 1000                1005
Pro Glu Ile Leu Arg Gln Cys Arg Thr Val Phe Val Pro Lys Val
    1010                1015                1020
Glu Arg Pro Gly Gly Pro Gly Glu Tyr Arg Pro Ile Ser Ile Ala
    1025                1030                1035
Ser Ile Pro Leu Arg His Phe His Ser Ile Leu Ala Arg Arg Leu
    1040                1045                1050
Leu Ala Cys Cys Pro Pro Asp Ala Arg Gln Arg Gly Phe Ile Cys
    1055                1060                1065
Ala Asp Gly Thr Leu Glu Asn Ser Ala Val Leu Asp Ala Val Leu
    1070                1075                1080
Gly Asp Ser Arg Lys Lys Leu Arg Glu Cys His Val Ala Val Leu
    1085                1090                1095
Asp Phe Ala Lys Ala Phe Asp Thr Val Ser His Glu Ala Leu Val
    1100                1105                1110
Glu Leu Leu Arg Leu Arg Gly Met Pro Glu Gln Phe Cys Gly Tyr
    1115                1120                1125
Ile Ala His Leu Tyr Asp Thr Ala Ser Thr Thr Leu Ala Val Asn
    1130                1135                1140
Asn Glu Met Ser Ser Pro Val Lys Val Gly Arg Gly Val Arg Gln
    1145                1150                1155
Gly Asp Pro Leu Ser Pro Ile Leu Phe Asn Val Val Met Asp Leu
    1160                1165                1170
Ile Leu Ala Ser Leu Pro Glu Arg Val Gly Tyr Arg Leu Glu Met
    1175                1180                1185
Glu Leu Val Ser Ala Leu Ala Tyr Ala Asp Asp Leu Val Leu Leu
    1190                1195                1200
```

Ala Gly Ser Lys Val Gly Met Gln Glu Ser Ile Ser Ala Val Asp
1205                1210                1215

Cys Val Gly Arg Gln Met Gly Leu Arg Leu Asn Cys Arg Lys Ser
1220                1225                1230

Ala Val Leu Ser Met Ile Pro Asp Gly His Arg Lys Lys His His
1235                1240                1245

Tyr Leu Thr Glu Arg Thr Phe Asn Ile Gly Gly Lys Pro Leu Arg
1250                1255                1260

Gln Val Ser Cys Val Glu Arg Trp Arg Tyr Leu Gly Val Asp Phe
1265                1270                1275

Glu Ala Ser Gly Cys Val Thr Leu Glu His Ser Ile Ser Ser Ala
1280                1285                1290

Leu Asn Asn Ile Ser Arg Ala Pro Leu Lys Pro Gln Gln Arg Leu
1295                1300                1305

Glu Ile Leu Arg Ala His Leu Ile Pro Arg Phe Gln His Gly Phe
1310                1315                1320

Val Leu Gly Asn Ile Ser Asp Asp Arg Leu Arg Met Leu Asp Val
1325                1330                1335

Gln Ile Arg Lys Ala Val Gly Gln Trp Leu Arg Leu Pro Ala Asp
1340                1345                1350

Val Pro Lys Ala Tyr Tyr His Ala Ala Val Gln Asp Gly Gly Leu
1355                1360                1365

Ala Ile Pro Ser Val Arg Ala Thr Ile Pro Asp Leu Ile Val Arg
1370                1375                1380

Arg Phe Gly Gly Leu Asp Ser Ser Pro Trp Ser Val Ala Arg Ala
1385                1390                1395

Ala Ala Lys Ser Asp Lys Ile Arg Lys Lys Leu Arg Trp Ala Trp
1400                1405                1410

Lys Gln Leu Arg Arg Phe Ser Arg Val Asp Ser Thr Thr Gln Arg
1415                1420                1425

Pro Ser Val Arg Leu Phe Trp Arg Glu His Leu His Ala Ser Val
1430                1435                1440

Asp Gly Arg Glu Leu Arg Glu Ser Thr Arg Thr Pro Thr Ser Thr
1445                1450                1455

Lys Trp Ile Arg Glu Arg Cys Ala Gln Ile Thr Gly Arg Asp Phe
1460                1465                1470

Val Gln Phe Val His Thr His Ile Asn Ala Leu Pro Ser Arg Ile
1475                1480                1485

Arg Gly Ser Arg Gly Arg Arg Gly Gly Gly Glu Ser Ser Leu Thr
1490                1495                1500

Cys Arg Ala Gly Cys Lys Val Arg Glu Thr Thr Ala His Ile Leu
1505                1510                1515

Gln Gln Cys His Arg Thr His Gly Gly Arg Ile Leu Arg His Asn
1520                1525                1530

Lys Ile Val Ser Phe Val Ala Lys Ala Met Glu Glu Asn Lys Trp
1535                1540                1545

Thr Val Glu Leu Glu Pro Arg Leu Arg Thr Ser Val Gly Leu Arg
1550                1555                1560

Lys Pro Asp Ile Ile Ala Ser Arg Asp Gly Val Gly Val Ile Val
1565                1570                1575

Asp Val Gln Val Val Ser Gly Gln Arg Ser Leu Asp Glu Leu His
1580                1585                1590

Arg Glu Lys Arg Asn Lys Tyr Gly Asn His Gly Glu Leu Val Glu

-continued

```
          1595                1600                1605
Leu Val Ala Gly Arg Leu Gly Leu Pro Lys Ala Glu Cys Val Arg
    1610                1615                1620

Ala Thr Ser Cys Thr Ile Ser Trp Arg Gly Val Trp Ser Leu Thr
    1625                1630                1635

Ser Tyr Lys Glu Leu Arg Ser Ile Ile Gly Leu Arg Glu Pro Thr
    1640                1645                1650

Leu Gln Ile Val Pro Ile Leu Ala Leu Arg Gly Ser His Met Asn
    1655                1660                1665

Trp Thr Arg Phe Asn Gln Met Thr Ser Val Met Gly Gly Gly Val
    1670                1675                1680

Gly

<210> SEQ ID NO 46
<211> LENGTH: 117
<212> TYPE: PRT
<213> ORGANISM: Artificial Sequence
<220> FEATURE:
<223> OTHER INFORMATION: C-terminal truncated SSB

<400> SEQUENCE: 46

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Arg Arg Arg
        115

<210> SEQ ID NO 47
<211> LENGTH: 1121
<212> TYPE: PRT
<213> ORGANISM: Artificial Sequence
<220> FEATURE:
<223> OTHER INFORMATION: His Tag joined via a linker to a dimer of
      truncated SSB joined via a linker to the C-terminus of deltaR2
      enzyme

<400> SEQUENCE: 47

Met Ala His His His His His His Val Gly Thr Val Gly Thr Gly Gly
1               5                   10                  15

Gly Ser Gly Gly Ala Ser Thr Ala Leu Lys Thr Ala Gly Arg Arg Asn
            20                  25                  30

Asp Leu His Asp Asp Arg Thr Ala Ser Ala His Lys Thr Ser Arg Gln
        35                  40                  45

Lys Arg Arg Ala Glu Tyr Ala Arg Val Gln Glu Leu Tyr Lys Lys Cys
    50                  55                  60

Arg Ser Arg Ala Ala Ala Glu Val Ile Asp Gly Ala Cys Gly Gly Val
65                  70                  75                  80
```

-continued

```
Gly His Ser Leu Glu Glu Met Glu Thr Tyr Trp Arg Pro Ile Leu Glu
                85                  90                  95

Arg Val Ser Asp Ala Pro Gly Pro Thr Pro Glu Ala Leu His Ala Leu
            100                 105                 110

Gly Arg Ala Glu Trp His Gly Gly Asn Arg Asp Tyr Thr Gln Leu Trp
        115                 120                 125

Lys Pro Ile Ser Val Glu Glu Ile Lys Ala Ser Arg Phe Asp Trp Arg
    130                 135                 140

Thr Ser Pro Gly Pro Asp Gly Ile Arg Ser Gly Gln Trp Arg Ala Val
145                 150                 155                 160

Pro Val His Leu Lys Ala Glu Met Phe Asn Ala Trp Met Ala Arg Gly
                165                 170                 175

Glu Ile Pro Glu Ile Leu Arg Gln Cys Arg Thr Val Phe Val Pro Lys
            180                 185                 190

Val Glu Arg Pro Gly Gly Pro Gly Glu Tyr Arg Pro Ile Ser Ile Ala
        195                 200                 205

Ser Ile Pro Leu Arg His Phe His Ser Ile Leu Ala Arg Arg Leu Leu
    210                 215                 220

Ala Cys Cys Pro Pro Asp Ala Arg Gln Arg Gly Phe Ile Cys Ala Asp
225                 230                 235                 240

Gly Thr Leu Glu Asn Ser Ala Val Leu Asp Ala Val Leu Gly Asp Ser
                245                 250                 255

Arg Lys Lys Leu Arg Glu Cys His Val Ala Val Leu Asp Phe Ala Lys
            260                 265                 270

Ala Phe Asp Thr Val Ser His Glu Ala Leu Val Glu Leu Leu Arg Leu
        275                 280                 285

Arg Gly Met Pro Glu Gln Phe Cys Gly Tyr Ile Ala His Leu Tyr Asp
    290                 295                 300

Thr Ala Ser Thr Thr Leu Ala Val Asn Asn Glu Met Ser Ser Pro Val
305                 310                 315                 320

Lys Val Gly Arg Gly Val Arg Gln Gly Asp Pro Leu Ser Pro Ile Leu
                325                 330                 335

Phe Asn Val Val Met Asp Leu Ile Leu Ala Ser Leu Pro Glu Arg Val
            340                 345                 350

Gly Tyr Arg Leu Glu Met Glu Leu Val Ser Ala Leu Ala Tyr Ala Asp
        355                 360                 365

Asp Leu Val Leu Leu Ala Gly Ser Lys Val Gly Met Gln Glu Ser Ile
    370                 375                 380

Ser Ala Val Asp Cys Val Gly Arg Gln Met Gly Leu Arg Leu Asn Cys
385                 390                 395                 400

Arg Lys Ser Ala Val Leu Ser Met Ile Pro Asp Gly His Arg Lys Lys
                405                 410                 415

His His Tyr Leu Thr Glu Arg Thr Phe Asn Ile Gly Gly Lys Pro Leu
            420                 425                 430

Arg Gln Val Ser Cys Val Glu Arg Trp Arg Tyr Leu Gly Val Asp Phe
        435                 440                 445

Glu Ala Ser Gly Cys Val Thr Leu Glu His Ser Ile Ser Ser Ala Leu
    450                 455                 460

Asn Asn Ile Ser Arg Ala Pro Leu Lys Pro Gln Gln Arg Leu Glu Ile
465                 470                 475                 480

Leu Arg Ala His Leu Ile Pro Arg Phe Gln His Gly Phe Val Leu Gly
                485                 490                 495
```

```
Asn Ile Ser Asp Asp Arg Leu Arg Met Leu Asp Val Gln Ile Arg Lys
            500                 505                 510

Ala Val Gly Gln Trp Leu Arg Leu Pro Ala Asp Val Pro Lys Ala Tyr
        515                 520                 525

Tyr His Ala Ala Val Gln Asp Gly Gly Leu Ala Ile Pro Ser Val Arg
        530                 535                 540

Ala Thr Ile Pro Asp Leu Ile Val Arg Arg Phe Gly Gly Leu Asp Ser
545                 550                 555                 560

Ser Pro Trp Ser Val Ala Arg Ala Ala Lys Ser Asp Lys Ile Arg
            565                 570                 575

Lys Lys Leu Arg Trp Ala Trp Lys Gln Leu Arg Arg Phe Ser Arg Val
        580                 585                 590

Asp Ser Thr Thr Gln Arg Pro Ser Val Arg Leu Phe Trp Arg Glu His
            595                 600                 605

Leu His Ala Ser Val Asp Gly Arg Glu Leu Arg Glu Ser Thr Arg Thr
        610                 615                 620

Pro Thr Ser Thr Lys Trp Ile Arg Glu Arg Cys Ala Gln Ile Thr Gly
625                 630                 635                 640

Arg Asp Phe Val Gln Phe Val His Thr His Ile Asn Ala Leu Pro Ser
            645                 650                 655

Arg Ile Arg Gly Ser Arg Gly Arg Gly Gly Glu Ser Ser Leu
            660                 665                 670

Thr Cys Arg Ala Gly Cys Lys Val Arg Glu Thr Thr Ala His Ile Leu
        675                 680                 685

Gln Gln Cys His Arg Thr His Gly Gly Arg Ile Leu Arg His Asn Lys
        690                 695                 700

Ile Val Ser Phe Val Ala Lys Ala Met Glu Glu Asn Lys Trp Thr Val
705                 710                 715                 720

Glu Leu Glu Pro Arg Leu Arg Thr Ser Val Gly Leu Arg Lys Pro Asp
            725                 730                 735

Ile Ile Ala Ser Arg Asp Gly Val Gly Val Ile Asp Val Gln Val
            740                 745                 750

Val Ser Gly Gln Arg Ser Leu Asp Glu Leu His Arg Glu Lys Arg Asn
        755                 760                 765

Lys Tyr Gly Asn His Gly Glu Leu Val Glu Leu Val Ala Gly Arg Leu
        770                 775                 780

Gly Leu Pro Lys Ala Glu Cys Val Arg Ala Thr Ser Cys Thr Ile Ser
785                 790                 795                 800

Trp Arg Gly Val Trp Ser Leu Thr Ser Tyr Lys Glu Leu Arg Ser Ile
            805                 810                 815

Ile Gly Leu Arg Glu Pro Thr Leu Gln Ile Val Pro Ile Leu Ala Leu
            820                 825                 830

Arg Gly Ser His Met Asn Trp Thr Arg Phe Asn Gln Met Thr Ser Val
        835                 840                 845

Met Gly Gly Gly Val Gly Val Thr Gly Gly Ser Gly Gly Gly
        850                 855                 860

Thr Gly Gly Ser Met Glu Glu Lys Val Gly Asn Leu Lys Pro Asn
865                 870                 875                 880

Met Glu Ser Val Asn Val Thr Val Arg Val Leu Glu Ala Ser Glu Ala
            885                 890                 895

Arg Gln Ile Gln Thr Lys Asn Gly Val Arg Thr Ile Ser Glu Ala Ile
        900                 905                 910

Val Gly Asp Glu Thr Gly Arg Val Lys Leu Thr Leu Trp Gly Lys His
```

```
                915                 920                 925
Ala Gly Ser Ile Lys Glu Gly Gln Val Val Lys Ile Glu Asn Ala Trp
    930                 935                 940
Thr Thr Ala Phe Lys Gly Gln Val Gln Leu Asn Ala Gly Ser Lys Thr
945                 950                 955                 960
Lys Ile Ala Glu Ala Ser Glu Asp Gly Phe Pro Glu Ser Ser Gln Ile
                965                 970                 975
Pro Glu Asn Thr Pro Thr Ala Arg Arg Arg Gly Gly Gly Val Gly Thr
            980                 985                 990
Gly Gly Gly Ser Gly Gly Gly Thr Gly Gly Gly Ser Met Glu Glu Lys
        995                1000                1005
Val Gly Asn Leu Lys Pro Asn Met Glu Ser Val Asn Val Thr Val
    1010                1015                1020
Arg Val Leu Glu Ala Ser Glu Ala Arg Gln Ile Gln Thr Lys Asn
    1025                1030                1035
Gly Val Arg Thr Ile Ser Glu Ala Ile Val Gly Asp Glu Thr Gly
    1040                1045                1050
Arg Val Lys Leu Thr Leu Trp Gly Lys His Ala Gly Ser Ile Lys
    1055                1060                1065
Glu Gly Gln Val Val Lys Ile Glu Asn Ala Trp Thr Thr Ala Phe
    1070                1075                1080
Lys Gly Gln Val Gln Leu Asn Ala Gly Ser Lys Thr Lys Ile Ala
    1085                1090                1095
Glu Ala Ser Glu Asp Gly Phe Pro Glu Ser Ser Gln Ile Pro Glu
    1100                1105                1110
Asn Thr Pro Thr Ala Arg Arg Arg
    1115                1120

<210> SEQ ID NO 48
<211> LENGTH: 13
<212> TYPE: PRT
<213> ORGANISM: Artificial Sequence
<220> FEATURE:
<223> OTHER INFORMATION: Spytag

<400> SEQUENCE: 48

Ala His Ile Val Met Val Asp Ala Tyr Lys Pro Thr Lys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: SpyTag002

<400> SEQUENCE: 49

Val Pro Thr Ile Val Met Val Asp Ala Tyr Lys Arg Tyr Lys
1               5                   10

<210> SEQ ID NO 50
<211> LENGTH: 16
<212> TYPE: PRT
<213> ORGANISM: Artificial Sequence
<220> FEATURE:
<223> OTHER INFORMATION: Isopeptag

<400> SEQUENCE: 50

Thr Asp Lys Asp Met Thr Ile Thr Phe Thr Asn Lys Lys Asp Ala Glu
1               5                   10                  15
```

<210> SEQ ID NO 51
<211> LENGTH: 115
<212> TYPE: PRT
<213> ORGANISM: Artificial Sequence
<220> FEATURE:
<223> OTHER INFORMATION: SpyCatcher

<400> SEQUENCE: 51

Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Glu
        35                  40                  45

Leu Arg Ser Ser Gly Lys Thr Ile Ser Thr Trp Ile Ser Asp Gly Gln
    50                  55                  60

Val Lys Asp Phe Tyr Leu Tyr Pro Gly Lys Tyr Thr Phe Val Glu Thr
65                  70                  75                  80

Ala Ala Pro Asp Gly Tyr Glu Val Ala Thr Ala Ile Thr Phe Thr Val
                85                  90                  95

Asn Glu Gln Gly Gln Val Thr Val Asn Gly Lys Ala Thr Lys Gly Asp
            100                 105                 110

Ala His Ile
        115

<210> SEQ ID NO 52
<211> LENGTH: 119
<212> TYPE: PRT
<213> ORGANISM: Artificial Sequence
<220> FEATURE:
<223> OTHER INFORMATION: SpyCatcher002

<400> SEQUENCE: 52

Ala Met Val Thr Thr Leu Ser Gly Leu Ser Gly Glu Gln Gly Pro Ser
1               5                   10                  15

Gly Asp Met Thr Thr Glu Glu Asp Ser Ala Thr His Ile Lys Phe Ser
            20                  25                  30

Lys Arg Asp Glu Asp Gly Arg Glu Leu Ala Gly Ala Thr Met Glu Leu
        35                  40                  45

Arg Asp Ser Ser Gly Lys Thr Ile Ser Thr Trp Ser Asp Gly His Val
    50                  55                  60

Lys Asp Phe Tyr Leu Tyr Pro Gly Lys Tyr Thr Phe Val Glu Thr Ala
65                  70                  75                  80

Ala Pro Asp Gly Tyr Glu Val Ala Thr Ala Ile Thr Phe Thr Val Asn
                85                  90                  95

Glu Gln Gly Gln Val Thr Val Asn Gly Glu Ala Thr Lys Gly Asp Ala
            100                 105                 110

His Thr Gly Ser Ser Gly Ser
        115

<210> SEQ ID NO 53
<211> LENGTH: 83
<212> TYPE: PRT
<213> ORGANISM: Artificial Sequence
<220> FEATURE:
<223> OTHER INFORMATION: SpyCatcher short

<400> SEQUENCE: 53

```
Gly Asp Ser Ala Thr His Ile Lys Phe Ser Lys Arg Asp Glu Asp Gly
1               5                   10                  15

Lys Glu Leu Ala Gly Ala Thr Met Glu Leu Arg Asp Ser Ser Gly Lys
            20                  25                  30

Thr Ile Ser Thr Trp Ile Ser Asp Gly Gln Val Lys Asp Phe Tyr Leu
        35                  40                  45

Tyr Pro Lys Tyr Thr Phe Val Glu Thr Ala Ala Pro Asp Gly Tyr Glu
50                  55                  60

Val Ala Thr Ala Ile Thr Phe Thr Val Asn Glu Gln Gly Gln Val Thr
65                  70                  75                  80

Val Asn Gly

<210> SEQ ID NO 54
<211> LENGTH: 282
<212> TYPE: PRT
<213> ORGANISM: Artificial Sequence
<220> FEATURE:
<223> OTHER INFORMATION: Split Spy0128

<400> SEQUENCE: 54

Ala Thr Thr Val His Gly Glu Thr Val Val Asn Gly Ala Lys Leu Thr
1               5                   10                  15

Val Thr Lys Asn Leu Asp Leu Val Asn Ser Asn Ala Leu Ile Pro Asn
            20                  25                  30

Thr Asp Phe Thr Phe Lys Ile Glu Pro Asp Thr Thr Val Asn Glu Asp
        35                  40                  45

Gly Asn Lys Phe Lys Gly Val Ala Leu Asn Thr Pro Met Thr Lys Val
    50                  55                  60

Thr Tyr Thr Asn Ser Asp Lys Gly Gly Ser Asn Thr Lys Thr Ala Glu
65                  70                  75                  80

Phe Asp Phe Ser Glu Val Thr Phe Glu Lys Pro Gly Val Tyr Tyr Tyr
                85                  90                  95

Lys Val Thr Glu Glu Lys Ile Asp Lys Val Pro Gly Val Ser Tyr Asp
            100                 105                 110

Thr Thr Ser Tyr Thr Val Gln Val His Val Leu Trp Asn Glu Glu Gln
        115                 120                 125

Gln Lys Pro Val Ala Thr Tyr Ile Val Gly Tyr Lys Glu Gly Ser Lys
    130                 135                 140

Val Pro Ile Gln Phe Lys Asn Ser Leu Asp Ser Thr Thr Leu Thr Val
145                 150                 155                 160

Lys Lys Lys Val Ser Gly Thr Gly Gly Asp Arg Ser Lys Asp Phe Asn
                165                 170                 175

Phe Gly Leu Thr Leu Lys Ala Asn Gln Tyr Tyr Lys Ala Ser Glu Lys
            180                 185                 190

Val Met Ile Glu Lys Thr Thr Lys Gly Gly Gln Ala Pro Val Gln Thr
        195                 200                 205

Glu Ala Ser Ile Asp Gln Leu Tyr His Phe Thr Leu Lys Asp Gly Glu
    210                 215                 220

Ser Ile Lys Val Thr Asn Leu Pro Val Gly Val Asp Tyr Val Val Thr
225                 230                 235                 240

Glu Asp Asp Tyr Lys Ser Glu Lys Tyr Thr Thr Asn Val Glu Val Ser
                245                 250                 255

Pro Gln Asp Gly Ala Val Lys Asn Ile Ala Gly Asn Ser Thr Glu Gln
            260                 265                 270

Glu Thr Ser Thr Asp Lys Asp Met Thr Ile
```

```
                    275                 280

<210> SEQ ID NO 55
<211> LENGTH: 10
<212> TYPE: PRT
<213> ORGANISM: Artificial Sequence
<220> FEATURE:
<223> OTHER INFORMATION: K-Tag

<400> SEQUENCE: 55

Ala Thr His Ile Lys Phe Ser Lys Arg Asp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: SnoopTag

<400> SEQUENCE: 56

Lys Leu Gly Asp Ile Glu Phe Ile Lys Val Asn Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: SdyTag

<400> SEQUENCE: 57

Asp Pro Ile Val Met Ile Asp Asn Asp Lys Pro Ile Thr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: SnoopTagJr

<400> SEQUENCE: 58

Lys Leu Gly Ser Ile Glu Phe Ile Lys Val Asn Lys
1               5                   10

<210> SEQ ID NO 59
<211> LENGTH: 112
<212> TYPE: PRT
<213> ORGANISM: Artificial Sequence
<220> FEATURE:
<223> OTHER INFORMATION: SnoopCatcher

<400> SEQUENCE: 59

Lys Pro Leu Arg Gly Ala Val Phe Ser Leu Gln Lys Gln His Pro Asp
1               5                   10                  15

Tyr Pro Asp Ile Tyr Gly Ala Ile Asp Gln Asn Gly Thr Tyr Gln Asn
            20                  25                  30

Val Arg Thr Gly Glu Asp Gly Lys Leu Thr Phe Lys Asn Leu Ser Asp
        35                  40                  45

Gly Lys Tyr Arg Leu Phe Glu Asn Ser Glu Pro Ala Gly Tyr Lys Pro
    50                  55                  60

Val Gln Asn Lys Pro Ile Val Ala Phe Gln Ile Val Asn Gly Glu Val
65                  70                  75                  80
```

```
Arg Asp Val Thr Ser Ile Val Pro Gln Asp Ile Pro Ala Thr Tyr Glu
             85                  90                  95

Phe Thr Asn Gly Lys His Tyr Ile Thr Asn Glu Pro Ile Pro Pro Lys
        100                 105                 110

<210> SEQ ID NO 60
<211> LENGTH: 104
<212> TYPE: PRT
<213> ORGANISM: Artificial Sequence
<220> FEATURE:
<223> OTHER INFORMATION: SdyCatcherDANG short

<400> SEQUENCE: 60

Gly Arg Gly Ser Ser Gly Leu Ser Gly Glu Thr Gly Gln Ser Gly Asn
1               5                   10                  15

Thr Thr Ile Glu Glu Asp Ser Thr Thr His Val Lys Phe Ser Lys Arg
            20                  25                  30

Asp Ala Asn Gly Lys Glu Leu Ala Gly Ala Met Ile Glu Leu Arg Asn
        35                  40                  45

Leu Ser Gly Gln Thr Ile Gln Ser Trp Ile Ser Asp Gly Thr Val Lys
    50                  55                  60

Val Phe Tyr Leu Met Pro Gly Thr Tyr Gln Phe Val Glu Thr Ala Ala
65                  70                  75                  80

Pro Glu Gly Tyr Glu Leu Ala Ala Pro Ile Thr Phe Thr Ile Asp Glu
                85                  90                  95

Lys Gly Gln Ile Trp Val Asp Ser
            100

<210> SEQ ID NO 61
<211> LENGTH: 23
<212> TYPE: PRT
<213> ORGANISM: Artificial Sequence
<220> FEATURE:
<223> OTHER INFORMATION: DogTag

<400> SEQUENCE: 61

Asp Ile Pro Ala Thr Tyr Glu Phe Thr Asn Gly Lys His Tyr Ile Thr
1               5                   10                  15

Asn Glu Pro Ile Pro Pro Lys
            20

<210> SEQ ID NO 62
<211> LENGTH: 6
<212> TYPE: PRT
<213> ORGANISM: Artificial Sequence
<220> FEATURE:
<223> OTHER INFORMATION: sortase A recognition domain

<400> SEQUENCE: 62

Leu Pro Thr Gly Ala Ala
1               5

<210> SEQ ID NO 63
<211> LENGTH: 6
<212> TYPE: PRT
<213> ORGANISM: Artificial Sequence
<220> FEATURE:
<223> OTHER INFORMATION: sortase A recognition domain

<400> SEQUENCE: 63

Leu Pro Thr Gly Gly Gly
1               5
```

```
<210> SEQ ID NO 64
<211> LENGTH: 6
<212> TYPE: PRT
<213> ORGANISM: Artificial Sequence
<220> FEATURE:
<223> OTHER INFORMATION: sortase A recognition domain

<400> SEQUENCE: 64

Leu Pro Lys Thr Gly Gly
1               5

<210> SEQ ID NO 65
<211> LENGTH: 5
<212> TYPE: PRT
<213> ORGANISM: Artificial Sequence
<220> FEATURE:
<223> OTHER INFORMATION: sortase A recognition domain

<400> SEQUENCE: 65

Leu Pro Glu Thr Gly
1               5

<210> SEQ ID NO 66
<211> LENGTH: 5
<212> TYPE: PRT
<213> ORGANISM: Artificial Sequence
<220> FEATURE:
<223> OTHER INFORMATION: sortase A recognition domain
<220> FEATURE:
<221> NAME/KEY: MISC_FEATURE
<222> LOCATION: (3)..(3)
<223> OTHER INFORMATION: any amino acid

<400> SEQUENCE: 66

Leu Pro Xaa Thr Gly
1               5

<210> SEQ ID NO 67
<211> LENGTH: 6
<212> TYPE: PRT
<213> ORGANISM: Artificial Sequence
<220> FEATURE:
<223> OTHER INFORMATION: sortase A recognition domain
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: PEPTIDE
<222> LOCATION: (6)..(6)
<223> OTHER INFORMATION: peptide comprising any amino acids of length 1,
     2, 3, 4, 5, 6, 7, 8, 9, or 10 amino acids

<400> SEQUENCE: 67

Leu Pro Xaa Thr Gly Xaa
1               5

<210> SEQ ID NO 68
<211> LENGTH: 5
<212> TYPE: PRT
<213> ORGANISM: Artificial Sequence
<220> FEATURE:
<223> OTHER INFORMATION: sortase B recognition domain
<220> FEATURE:
<221> NAME/KEY: MISC_FEATURE
<222> LOCATION: (3)..(3)
<223> OTHER INFORMATION: Q or L
<220> FEATURE:
<221> NAME/KEY: MISC_FEATURE
<222> LOCATION: (5)..(5)
```

<223> OTHER INFORMATION: N or G

<400> SEQUENCE: 68

Asn Pro Xaa Thr Xaa
1               5

<210> SEQ ID NO 69
<211> LENGTH: 882
<212> TYPE: PRT
<213> ORGANISM: Artificial Sequence
<220> FEATURE:
<223> OTHER INFORMATION: deltaR2 enzyme-linker-SpyTag-linker-His Tag

<400> SEQUENCE: 69

```
Lys Thr Ala Gly Arg Asn Asp Leu His Asp Asp Arg Thr Ala Ser
1               5                   10                  15

Ala His Lys Thr Ser Arg Gln Lys Arg Ala Glu Tyr Ala Arg Val
                20                  25                  30

Gln Glu Leu Tyr Lys Lys Cys Arg Ser Arg Ala Ala Glu Val Ile
                35                  40                  45

Asp Gly Ala Cys Gly Gly Val Gly His Ser Leu Glu Glu Met Glu Thr
            50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Gly Asn
                85                  90                  95

Arg Asp Tyr Thr Gln Leu Trp Lys Pro Ile Ser Val Glu Glu Ile Lys
                100                 105                 110

Ala Ser Arg Phe Asp Trp Arg Thr Ser Pro Gly Pro Asp Gly Ile Arg
                115                 120                 125

Ser Gly Gln Trp Arg Ala Val Pro Val His Leu Lys Ala Glu Met Phe
            130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
                180                 185                 190

Ile Leu Ala Arg Arg Leu Leu Ala Cys Cys Pro Pro Asp Ala Arg Gln
            195                 200                 205

Arg Gly Phe Ile Cys Ala Asp Gly Thr Leu Glu Asn Ser Ala Val Leu
            210                 215                 220

Asp Ala Val Leu Gly Asp Ser Arg Lys Lys Leu Arg Glu Cys His Val
225                 230                 235                 240

Ala Val Leu Asp Phe Ala Lys Ala Phe Asp Thr Val Ser His Glu Ala
                245                 250                 255

Leu Val Glu Leu Leu Arg Leu Arg Gly Met Pro Glu Gln Phe Cys Gly
                260                 265                 270

Tyr Ile Ala His Leu Tyr Asp Thr Ala Ser Thr Thr Leu Ala Val Asn
            275                 280                 285

Asn Glu Met Ser Ser Pro Val Lys Val Gly Arg Gly Val Arg Gln Gly
            290                 295                 300

Asp Pro Leu Ser Pro Ile Leu Phe Asn Val Val Met Asp Leu Ile Leu
305                 310                 315                 320

Ala Ser Leu Pro Glu Arg Val Gly Tyr Arg Leu Glu Met Glu Leu Val
                325                 330                 335
```

```
Ser Ala Leu Ala Tyr Ala Asp Asp Leu Val Leu Ala Gly Ser Lys
            340                 345                 350

Val Gly Met Gln Glu Ser Ile Ser Ala Val Asp Cys Val Gly Arg Gln
            355                 360                 365

Met Gly Leu Arg Leu Asn Cys Arg Lys Ser Ala Val Leu Ser Met Ile
    370                 375                 380

Pro Asp Gly His Arg Lys His His Tyr Leu Thr Glu Arg Thr Phe
385                 390                 395                 400

Asn Ile Gly Gly Lys Pro Leu Arg Gln Val Ser Cys Val Glu Arg Trp
                405                 410                 415

Arg Tyr Leu Gly Val Asp Phe Glu Ala Ser Gly Cys Val Thr Leu Glu
            420                 425                 430

His Ser Ile Ser Ser Ala Leu Asn Asn Ile Ser Arg Ala Pro Leu Lys
        435                 440                 445

Pro Gln Gln Arg Leu Glu Ile Leu Arg Ala His Leu Ile Pro Arg Phe
450                 455                 460

Gln His Gly Phe Val Leu Gly Asn Ile Ser Asp Asp Arg Leu Arg Met
465                 470                 475                 480

Leu Asp Val Gln Ile Arg Lys Ala Val Gly Gln Trp Leu Arg Leu Pro
            485                 490                 495

Ala Asp Val Pro Lys Ala Tyr Tyr His Ala Ala Val Gln Asp Gly Gly
                500                 505                 510

Leu Ala Ile Pro Ser Val Arg Ala Thr Ile Pro Asp Leu Ile Val Arg
        515                 520                 525

Arg Phe Gly Gly Leu Asp Ser Ser Pro Trp Ser Val Ala Arg Ala Ala
    530                 535                 540

Ala Lys Ser Asp Lys Ile Arg Lys Lys Leu Arg Trp Ala Trp Lys Gln
545                 550                 555                 560

Leu Arg Arg Phe Ser Arg Val Asp Ser Thr Thr Gln Arg Pro Ser Val
            565                 570                 575

Arg Leu Phe Trp Arg Glu His Leu His Ala Ser Val Asp Gly Arg Glu
            580                 585                 590

Leu Arg Glu Ser Thr Arg Thr Pro Thr Ser Thr Lys Trp Ile Arg Glu
        595                 600                 605

Arg Cys Ala Gln Ile Thr Gly Arg Asp Phe Val Gln Phe Val His Thr
    610                 615                 620

His Ile Asn Ala Leu Pro Ser Arg Ile Arg Gly Ser Arg Gly Arg Arg
625                 630                 635                 640

Gly Gly Gly Glu Ser Ser Leu Thr Cys Arg Ala Gly Cys Lys Val Arg
                645                 650                 655

Glu Thr Thr Ala His Ile Leu Gln Gln Cys His Arg Thr His Gly Gly
            660                 665                 670

Arg Ile Leu Arg His Asn Lys Ile Val Ser Phe Val Ala Lys Ala Met
    675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
            705                 710                 715                 720

Val Ile Val Asp Val Gln Val Val Ser Gly Gln Arg Ser Leu Asp Glu
                725                 730                 735

Leu His Arg Glu Lys Arg Asn Lys Tyr Gly Asn His Gly Glu Leu Val
        740                 745                 750
```

```
Glu Leu Val Ala Gly Arg Leu Gly Leu Pro Lys Ala Glu Cys Val Arg
            755                 760                 765

Ala Thr Ser Cys Thr Ile Ser Trp Arg Gly Val Trp Ser Leu Thr Ser
770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
                805                 810                 815

Phe Asn Gln Met Thr Ser Val Met Gly Gly Val Gly Val Gly Thr
                820                 825                 830

Gly Gly Gly Ser Gly Gly Gly Thr Gly Gly Gly Ser Ala His Ile Val
            835                 840                 845

Met Val Asp Ala Tyr Lys Pro Thr Lys Lys Gly Val Gly Thr Val Gly
            850                 855                 860

Thr Gly Gly Gly Ser Gly Gly Ala Ser Thr Ala Leu His His His His
865                 870                 875                 880

His His
```

<210> SEQ ID NO 70
<211> LENGTH: 996
<212> TYPE: PRT
<213> ORGANISM: Artificial Sequence
<220> FEATURE:
<223> OTHER INFORMATION: deltaR2 enzyme-linker-SpyCatcher-linker-His Tag

<400> SEQUENCE: 70

```
Lys Thr Ala Gly Arg Arg Asn Asp Leu His Asp Arg Thr Ala Ser
1               5                   10                  15

Ala His Lys Thr Ser Arg Gln Lys Arg Arg Ala Glu Tyr Ala Arg Val
                20                  25                  30

Gln Glu Leu Tyr Lys Lys Cys Arg Ser Arg Ala Ala Ala Glu Val Ile
            35                  40                  45

Asp Gly Ala Cys Gly Gly Val Gly His Ser Leu Glu Glu Met Glu Thr
50                  55                  60

Tyr Trp Arg Pro Ile Leu Glu Arg Val Ser Asp Ala Pro Gly Pro Thr
65                  70                  75                  80

Pro Glu Ala Leu His Ala Leu Gly Arg Ala Glu Trp His Gly Gly Asn
                85                  90                  95

Arg Asp Tyr Thr Gln Leu Trp Lys Pro Ile Ser Val Glu Glu Ile Lys
            100                 105                 110

Ala Ser Arg Phe Asp Trp Arg Thr Ser Pro Gly Pro Asp Gly Ile Arg
        115                 120                 125

Ser Gly Gln Trp Arg Ala Val Pro Val His Leu Lys Ala Glu Met Phe
130                 135                 140

Asn Ala Trp Met Ala Arg Gly Glu Ile Pro Glu Ile Leu Arg Gln Cys
145                 150                 155                 160

Arg Thr Val Phe Val Pro Lys Val Glu Arg Pro Gly Gly Pro Gly Glu
                165                 170                 175

Tyr Arg Pro Ile Ser Ile Ala Ser Ile Pro Leu Arg His Phe His Ser
            180                 185                 190

Ile Leu Ala Arg Arg Leu Leu Ala Cys Cys Pro Pro Asp Ala Arg Gln
        195                 200                 205

Arg Gly Phe Ile Cys Ala Asp Gly Thr Leu Glu Asn Ser Ala Val Leu
210                 215                 220

Asp Ala Val Leu Gly Asp Ser Arg Lys Lys Leu Arg Glu Cys His Val
```

-continued

```
            225                 230                 235                 240
        Ala Val Leu Asp Phe Ala Lys Ala Phe Asp Thr Val Ser His Glu Ala
                        245                 250                 255
        Leu Val Glu Leu Leu Arg Leu Arg Gly Met Pro Glu Gln Phe Cys Gly
                        260                 265                 270
        Tyr Ile Ala His Leu Tyr Asp Thr Ala Ser Thr Thr Leu Ala Val Asn
                        275                 280                 285
        Asn Glu Met Ser Ser Pro Val Lys Val Gly Arg Gly Val Arg Gln Gly
                        290                 295                 300
        Asp Pro Leu Ser Pro Ile Leu Phe Asn Val Val Met Asp Leu Ile Leu
        305                 310                 315                 320
        Ala Ser Leu Pro Glu Arg Val Gly Tyr Arg Leu Glu Met Glu Leu Val
                        325                 330                 335
        Ser Ala Leu Ala Tyr Ala Asp Asp Leu Val Leu Leu Ala Gly Ser Lys
                        340                 345                 350
        Val Gly Met Gln Glu Ser Ile Ser Ala Val Asp Cys Val Gly Arg Gln
                        355                 360                 365
        Met Gly Leu Arg Leu Asn Cys Arg Lys Ser Ala Val Leu Ser Met Ile
            370                 375                 380
        Pro Asp Gly His Arg Lys Lys His His Tyr Leu Thr Glu Arg Thr Phe
        385                 390                 395                 400
        Asn Ile Gly Gly Lys Pro Leu Arg Gln Val Ser Cys Val Glu Arg Trp
                        405                 410                 415
        Arg Tyr Leu Gly Val Asp Phe Glu Ala Ser Gly Cys Val Thr Leu Glu
                        420                 425                 430
        His Ser Ile Ser Ser Ala Leu Asn Asn Ile Ser Arg Ala Pro Leu Lys
                        435                 440                 445
        Pro Gln Gln Arg Leu Glu Ile Leu Arg Ala His Leu Ile Pro Arg Phe
            450                 455                 460
        Gln His Gly Phe Val Leu Gly Asn Ile Ser Asp Asp Arg Leu Arg Met
        465                 470                 475                 480
        Leu Asp Val Gln Ile Arg Lys Ala Val Gly Gln Trp Leu Arg Leu Pro
                        485                 490                 495
        Ala Asp Val Pro Lys Ala Tyr Tyr His Ala Ala Val Gln Asp Gly Gly
                        500                 505                 510
        Leu Ala Ile Pro Ser Val Arg Ala Thr Ile Pro Asp Leu Ile Val Arg
                        515                 520                 525
        Arg Phe Gly Gly Leu Asp Ser Ser Pro Trp Ser Val Ala Arg Ala Ala
            530                 535                 540
        Ala Lys Ser Asp Lys Ile Arg Lys Lys Leu Arg Trp Ala Trp Lys Gln
        545                 550                 555                 560
        Leu Arg Arg Phe Ser Arg Val Asp Ser Thr Thr Gln Arg Pro Ser Val
                        565                 570                 575
        Arg Leu Phe Trp Arg Glu His Leu His Ala Ser Val Asp Gly Arg Glu
                        580                 585                 590
        Leu Arg Glu Ser Thr Arg Thr Pro Thr Ser Thr Lys Trp Ile Arg Glu
                        595                 600                 605
        Arg Cys Ala Gln Ile Thr Gly Arg Asp Phe Val Gln Phe Val His Thr
                        610                 615                 620
        His Ile Asn Ala Leu Pro Ser Arg Ile Arg Gly Ser Arg Gly Arg Arg
        625                 630                 635                 640
        Gly Gly Gly Glu Ser Ser Leu Thr Cys Arg Ala Gly Cys Lys Val Arg
                        645                 650                 655
```

Glu Thr Thr Ala His Ile Leu Gln Gln Cys His Arg Thr His Gly Gly
                    660                 665                 670

Arg Ile Leu Arg His Asn Lys Ile Val Ser Phe Val Ala Lys Ala Met
            675                 680                 685

Glu Glu Asn Lys Trp Thr Val Glu Leu Glu Pro Arg Leu Arg Thr Ser
690                 695                 700

Val Gly Leu Arg Lys Pro Asp Ile Ile Ala Ser Arg Asp Gly Val Gly
705                 710                 715                 720

Val Ile Val Asp Val Gln Val Ser Gly Gln Arg Ser Leu Asp Glu
                725                 730                 735

Leu His Arg Glu Lys Arg Asn Lys Tyr Gly Asn His Gly Glu Leu Val
            740                 745                 750

Glu Leu Val Ala Gly Arg Leu Gly Leu Pro Lys Ala Glu Cys Val Arg
            755                 760                 765

Ala Thr Ser Cys Thr Ile Ser Trp Arg Gly Val Trp Ser Leu Thr Ser
            770                 775                 780

Tyr Lys Glu Leu Arg Ser Ile Ile Gly Leu Arg Glu Pro Thr Leu Gln
785                 790                 795                 800

Ile Val Pro Ile Leu Ala Leu Arg Gly Ser His Met Asn Trp Thr Arg
                805                 810                 815

Phe Asn Gln Met Thr Ser Val Met Gly Gly Val Gly Val Gly Thr
            820                 825                 830

Gly Gly Gly Ser Gly Gly Gly Thr Gly Gly Gly Ser Asp Tyr Asp Ile
            835                 840                 845

Pro Thr Thr Glu Asn Leu Tyr Phe Gln Gly Ala Met Val Asp Thr Leu
            850                 855                 860

Ser Gly Leu Ser Ser Glu Gln Gly Gln Ser Gly Asp Met Thr Ile Glu
865                 870                 875                 880

Glu Asp Ser Ala Thr His Ile Lys Phe Ser Lys Arg Asp Glu Asp Gly
                885                 890                 895

Lys Glu Leu Ala Gly Ala Thr Met Glu Leu Arg Asp Ser Ser Gly Lys
            900                 905                 910

Thr Ile Ser Thr Trp Ile Ser Asp Gly Gln Val Lys Asp Phe Tyr Leu
            915                 920                 925

Tyr Pro Gly Lys Tyr Thr Phe Val Glu Thr Ala Ala Pro Asp Gly Tyr
930                 935                 940

Glu Val Ala Thr Ala Ile Thr Phe Thr Val Asn Glu Gln Gly Gln Val
945                 950                 955                 960

Thr Val Asn Gly Lys Ala Thr Lys Gly Asp Ala His Ile Val Gly Thr
                965                 970                 975

Val Gly Thr Gly Gly Gly Ser Gly Gly Ala Ser Thr Ala Leu His His
            980                 985                 990

His His His His
        995

<210> SEQ ID NO 71
<211> LENGTH: 116
<212> TYPE: PRT
<213> ORGANISM: Artificial Sequence
<220> FEATURE:
<223> OTHER INFORMATION: Sso7d-linker-SpyTag-linker-His Tag

<400> SEQUENCE: 71

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
            35                  40                  45

Asp Ala Pro Lys Glu Leu Leu Gln Met Leu Glu Lys Gln Lys Lys Val
        50                  55                  60

Gly Thr Gly Gly Gly Ser Gly Gly Gly Thr Gly Gly Gly Ser Ala His
65                  70                  75                  80

Ile Val Met Val Asp Ala Tyr Lys Pro Thr Lys Lys Gly Val Gly Thr
                85                  90                  95

Val Gly Thr Gly Gly Gly Ser Gly Gly Ala Ser Thr Ala Leu His His
            100                 105                 110

His His His His
        115

<210> SEQ ID NO 72
<211> LENGTH: 230
<212> TYPE: PRT
<213> ORGANISM: Artificial Sequence
<220> FEATURE:
<223> OTHER INFORMATION: Sso7d-linker-SpyCatcher-linker-His Tag

<400> SEQUENCE: 72

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
            35                  40                  45

Asp Ala Pro Lys Glu Leu Leu Gln Met Leu Glu Lys Gln Lys Lys Val
        50                  55                  60

Gly Thr Gly Gly Gly Ser Gly Gly Gly Thr Gly Gly Gly Ser Asp Tyr
65                  70                  75                  80

Asp Ile Pro Thr Thr Glu Asn Leu Tyr Phe Gln Gly Ala Met Val Asp
                85                  90                  95

Thr Leu Ser Gly Leu Ser Ser Glu Gln Gly Gln Ser Gly Asp Met Thr
            100                 105                 110

Ile Glu Glu Asp Ser Ala Thr His Ile Lys Phe Ser Lys Arg Asp Glu
            115                 120                 125

Asp Gly Lys Glu Leu Ala Gly Ala Thr Met Glu Leu Arg Asp Ser Ser
        130                 135                 140

Gly Lys Thr Ile Ser Thr Trp Ile Ser Asp Gly Gln Val Lys Asp Phe
145                 150                 155                 160

Tyr Leu Tyr Pro Gly Lys Tyr Thr Phe Val Glu Thr Ala Ala Pro Asp
                165                 170                 175

Gly Tyr Glu Val Ala Thr Ala Ile Thr Phe Thr Val Asn Glu Gln Gly
            180                 185                 190

Gln Val Thr Val Asn Gly Lys Ala Thr Lys Gly Asp Ala His Ile Val
        195                 200                 205

Gly Thr Val Gly Thr Gly Gly Gly Ser Gly Gly Ala Ser Thr Ala Leu
    210                 215                 220

His His His His His His
225                 230

<210> SEQ ID NO 73

```
<211> LENGTH: 114
<212> TYPE: PRT
<213> ORGANISM: Artificial Sequence
<220> FEATURE:
<223> OTHER INFORMATION: Cren7-linker-SpyTag-linker-His Tag

<400> SEQUENCE: 73

Ser Ser Gly Lys Lys Pro Val Lys Val Lys Thr Pro Ala Gly Lys Glu
1               5                   10                  15

Ala Glu Leu Val Pro Glu Lys Val Trp Ala Leu Ala Pro Lys Gly Arg
            20                  25                  30

Lys Gly Val Lys Ile Gly Leu Phe Lys Asp Pro Glu Thr Gly Lys Tyr
        35                  40                  45

Phe Arg His Lys Leu Pro Asp Asp Tyr Pro Ile Val Gly Thr Val Gly
    50                  55                  60

Thr Gly Gly Gly Ser Glu Ala Ala Ala Lys Gly Gly Ala His Ile Val
65                  70                  75                  80

Met Val Asp Ala Tyr Lys Pro Thr Lys Lys Gly Val Gly Thr Val Gly
                85                  90                  95

Thr Gly Gly Gly Ser Gly Gly Ala Ser Thr Ala Leu His His His His
                100                 105                 110

His His

<210> SEQ ID NO 74
<211> LENGTH: 226
<212> TYPE: PRT
<213> ORGANISM: Artificial Sequence
<220> FEATURE:
<223> OTHER INFORMATION: Cren7-linker-SpyCatcher-linker-His Tag

<400> SEQUENCE: 74

Ser Ser Gly Lys Lys Pro Val Lys Val Lys Thr Pro Ala Gly Lys Glu
1               5                   10                  15

Ala Glu Leu Val Pro Glu Lys Val Trp Ala Leu Ala Pro Lys Gly Arg
            20                  25                  30

Lys Gly Val Lys Ile Gly Leu Phe Lys Asp Pro Glu Thr Gly Lys Tyr
        35                  40                  45

Phe Arg His Lys Leu Pro Asp Asp Tyr Pro Ile Val Gly Thr Gly Gly
    50                  55                  60

Gly Ser Gly Gly Thr Gly Gly Ser Asp Tyr Asp Ile Pro Thr
65                  70                  75                  80

Thr Glu Asn Leu Tyr Phe Gln Gly Ala Met Val Asp Thr Leu Ser Gly
                85                  90                  95

Leu Ser Ser Glu Gln Gly Gln Ser Gly Asp Met Thr Ile Glu Glu Asp
                100                 105                 110

Ser Ala Thr His Ile Lys Phe Ser Lys Arg Asp Glu Asp Gly Lys Glu
            115                 120                 125

Leu Ala Gly Ala Thr Met Glu Leu Arg Asp Ser Ser Gly Lys Thr Ile
        130                 135                 140

Ser Thr Trp Ile Ser Asp Gly Gln Val Lys Asp Phe Tyr Leu Tyr Pro
145                 150                 155                 160

Gly Lys Tyr Thr Phe Val Glu Thr Ala Ala Pro Asp Gly Tyr Glu Val
                165                 170                 175

Ala Thr Ala Ile Thr Phe Thr Val Asn Glu Gln Gly Gln Val Thr Val
            180                 185                 190

Asn Gly Lys Ala Thr Lys Gly Asp Ala His Ile Val Gly Thr Val Gly
        195                 200                 205
```

```
Thr Gly Gly Gly Ser Gly Gly Ala Ser Thr Ala Leu His His His
    210             215                 220
His His
225
```

<210> SEQ ID NO 75
<211> LENGTH: 202
<212> TYPE: PRT
<213> ORGANISM: Artificial Sequence
<220> FEATURE:
<223> OTHER INFORMATION: SSB-linker-SpyTag-linker-His Tag

<400> SEQUENCE: 75

```
Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140

Gly Glu Glu Gly Thr Val Gly Thr Gly Gly Gly Ser Glu Ala Ala
145                 150                 155                 160

Ala Lys Gly Gly Ala His Ile Val Met Val Asp Ala Tyr Lys Pro Thr
                165                 170                 175

Lys Lys Gly Val Gly Thr Val Gly Thr Gly Gly Ser Gly Gly Ala
            180                 185                 190

Ser Thr Ala Leu His His His His His His
        195                 200
```

<210> SEQ ID NO 76
<211> LENGTH: 321
<212> TYPE: PRT
<213> ORGANISM: Artificial Sequence
<220> FEATURE:
<223> OTHER INFORMATION: SSB-linker-SpyCatcher-linker-His Tag

<400> SEQUENCE: 76

```
Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
```

```
                65                  70                  75                  80
Gly Gln Val Gln Leu Asn Ala Gly Ser Lys Thr Lys Ile Ala Glu Ala
                    85                  90                  95

Ser Glu Asp Gly Phe Pro Glu Ser Ser Gln Ile Pro Glu Asn Thr Pro
                    100                 105                 110

Thr Ala Pro Gln Gln Met Arg Gly Gly Arg Gly Phe Arg Gly Gly
                    115                 120                 125

Gly Arg Arg Tyr Gly Arg Arg Gly Gly Arg Gln Glu Asn Glu Glu
            130                 135                 140

Gly Glu Glu Glu Gly Thr Val Gly Thr Gly Gly Ser Glu Ala Ala
145                 150                 155                 160

Ala Lys Gly Gly Ala Ser Thr Ala Leu Asp Tyr Asp Ile Pro Thr Thr
                    165                 170                 175

Glu Asn Leu Tyr Phe Gln Gly Ala Met Val Asp Thr Leu Ser Gly Leu
                    180                 185                 190

Ser Ser Glu Gln Gly Gln Ser Gly Asp Met Thr Ile Glu Glu Asp Ser
                    195                 200                 205

Ala Thr His Ile Lys Phe Ser Lys Arg Asp Glu Asp Gly Lys Glu Leu
                    210                 215                 220

Ala Gly Ala Thr Met Glu Leu Arg Asp Ser Ser Gly Lys Thr Ile Ser
225                 230                 235                 240

Thr Trp Ile Ser Asp Gly Gln Val Lys Asp Phe Tyr Leu Tyr Pro Gly
                    245                 250                 255

Lys Tyr Thr Phe Val Glu Thr Ala Ala Pro Asp Gly Tyr Glu Val Ala
                    260                 265                 270

Thr Ala Ile Thr Phe Thr Val Asn Glu Gln Gly Gln Val Thr Val Asn
                    275                 280                 285

Gly Lys Ala Thr Lys Gly Asp Ala His Ile Val Gly Thr Val Gly Thr
                    290                 295                 300

Gly Gly Gly Ser Gly Gly Ala Ser Thr Ala Leu His His His His
305                 310                 315                 320

His

<210> SEQ ID NO 77
<211> LENGTH: 884
<212> TYPE: PRT
<213> ORGANISM: Artificial Sequence
<220> FEATURE:
<223> OTHER INFORMATION: His Tag-linker-SpyTag-linker-deltaR2 enzyme

<400> SEQUENCE: 77

His His His His His His Val Gly Thr Val Gly Thr Gly Gly Ser
1                   5                   10                  15

Gly Gly Ala Ser Thr Ala Leu Ala His Ile Val Met Val Asp Ala Tyr
                    20                  25                  30

Lys Pro Thr Lys Lys Gly Val Gly Thr Val Gly Thr Gly Gly Ser
            35                  40                  45

Gly Gly Ala Ser Thr Ala Leu Lys Thr Ala Gly Arg Arg Asn Asp Leu
        50                  55                  60

His Asp Asp Arg Thr Ala Ser Ala His Lys Thr Ser Arg Gln Lys Arg
65                  70                  75                  80

Arg Ala Glu Tyr Ala Arg Val Gln Glu Leu Tyr Lys Lys Cys Arg Ser
                    85                  90                  95

Arg Ala Ala Ala Glu Val Ile Asp Gly Ala Cys Gly Gly Val Gly His
                    100                 105                 110
```

```
Ser Leu Glu Glu Met Glu Thr Tyr Trp Arg Pro Ile Leu Glu Arg Val
    115                 120                 125

Ser Asp Ala Pro Gly Pro Thr Pro Glu Ala Leu His Ala Leu Gly Arg
130                 135                 140

Ala Glu Trp His Gly Gly Asn Arg Asp Tyr Thr Gln Leu Trp Lys Pro
145                 150                 155                 160

Ile Ser Val Glu Glu Ile Lys Ala Ser Arg Phe Asp Trp Arg Thr Ser
                165                 170                 175

Pro Gly Pro Asp Gly Ile Arg Ser Gly Gln Trp Arg Ala Val Pro Val
                180                 185                 190

His Leu Lys Ala Glu Met Phe Asn Ala Trp Met Ala Arg Gly Glu Ile
            195                 200                 205

Pro Glu Ile Leu Arg Gln Cys Arg Thr Val Phe Val Pro Lys Val Glu
        210                 215                 220

Arg Pro Gly Gly Pro Gly Glu Tyr Arg Pro Ile Ser Ile Ala Ser Ile
225                 230                 235                 240

Pro Leu Arg His Phe His Ser Ile Leu Ala Arg Arg Leu Leu Ala Cys
                245                 250                 255

Cys Pro Pro Asp Ala Arg Gln Arg Gly Phe Ile Cys Ala Asp Gly Thr
                260                 265                 270

Leu Glu Asn Ser Ala Val Leu Asp Ala Val Leu Gly Asp Ser Arg Lys
            275                 280                 285

Lys Leu Arg Glu Cys His Val Ala Val Leu Asp Phe Ala Lys Ala Phe
        290                 295                 300

Asp Thr Val Ser His Glu Ala Leu Val Glu Leu Arg Leu Arg Gly
305                 310                 315                 320

Met Pro Glu Gln Phe Cys Gly Tyr Ile Ala His Leu Tyr Asp Thr Ala
                325                 330                 335

Ser Thr Thr Leu Ala Val Asn Asn Glu Met Ser Ser Pro Val Lys Val
            340                 345                 350

Gly Arg Gly Val Arg Gln Gly Asp Pro Leu Ser Pro Ile Leu Phe Asn
        355                 360                 365

Val Val Met Asp Leu Ile Leu Ala Ser Leu Pro Glu Arg Val Gly Tyr
370                 375                 380

Arg Leu Glu Met Glu Leu Val Ser Ala Leu Ala Tyr Ala Asp Asp Leu
385                 390                 395                 400

Val Leu Leu Ala Gly Ser Lys Val Gly Met Gln Glu Ser Ile Ser Ala
                405                 410                 415

Val Asp Cys Val Gly Arg Gln Met Gly Leu Arg Leu Asn Cys Arg Lys
                420                 425                 430

Ser Ala Val Leu Ser Met Ile Pro Asp Gly His Arg Lys Lys His His
            435                 440                 445

Tyr Leu Thr Glu Arg Thr Phe Asn Ile Gly Gly Lys Pro Leu Arg Gln
        450                 455                 460

Val Ser Cys Val Glu Arg Trp Arg Tyr Leu Gly Val Asp Phe Glu Ala
465                 470                 475                 480

Ser Gly Cys Val Thr Leu Glu His Ser Ile Ser Ser Ala Leu Asn Asn
                485                 490                 495

Ile Ser Arg Ala Pro Leu Lys Pro Gln Gln Arg Leu Glu Ile Leu Arg
                500                 505                 510

Ala His Leu Ile Pro Arg Phe Gln His Gly Phe Val Leu Gly Asn Ile
            515                 520                 525
```

```
Ser Asp Asp Arg Leu Arg Met Leu Asp Val Gln Ile Arg Lys Ala Val
    530                 535                 540
Gly Gln Trp Leu Arg Leu Pro Ala Asp Val Pro Lys Ala Tyr Tyr His
545                 550                 555                 560
Ala Ala Val Gln Asp Gly Gly Leu Ala Ile Pro Ser Val Arg Ala Thr
                565                 570                 575
Ile Pro Asp Leu Ile Val Arg Arg Phe Gly Gly Leu Asp Ser Ser Pro
                580                 585                 590
Trp Ser Val Ala Arg Ala Ala Lys Ser Asp Lys Ile Arg Lys Lys
            595                 600                 605
Leu Arg Trp Ala Trp Lys Gln Leu Arg Arg Phe Ser Arg Val Asp Ser
610                 615                 620
Thr Thr Gln Arg Pro Ser Val Arg Leu Phe Trp Arg Glu His Leu His
625                 630                 635                 640
Ala Ser Val Asp Gly Arg Glu Leu Arg Glu Ser Arg Thr Pro Thr
                645                 650                 655
Ser Thr Lys Trp Ile Arg Glu Arg Cys Ala Gln Ile Thr Gly Arg Asp
                660                 665                 670
Phe Val Gln Phe Val His Thr His Ile Asn Ala Leu Pro Ser Arg Ile
            675                 680                 685
Arg Gly Ser Arg Gly Arg Gly Gly Glu Ser Ser Leu Thr Cys
690                 695                 700
Arg Ala Gly Cys Lys Val Arg Glu Thr Thr Ala His Ile Leu Gln Gln
705                 710                 715                 720
Cys His Arg Thr His Gly Gly Arg Ile Leu Arg His Asn Lys Ile Val
                725                 730                 735
Ser Phe Val Ala Lys Ala Met Glu Glu Asn Lys Trp Thr Val Glu Leu
                740                 745                 750
Glu Pro Arg Leu Arg Thr Ser Val Gly Leu Arg Lys Pro Asp Ile Ile
            755                 760                 765
Ala Ser Arg Asp Gly Val Gly Val Ile Val Asp Val Gln Val Val Ser
            770                 775                 780
Gly Gln Arg Ser Leu Asp Glu Leu His Arg Glu Lys Arg Asn Lys Tyr
785                 790                 795                 800
Gly Asn His Gly Glu Leu Val Glu Leu Val Ala Gly Arg Leu Gly Leu
                805                 810                 815
Pro Lys Ala Glu Cys Val Arg Ala Thr Ser Cys Thr Ile Ser Trp Arg
                820                 825                 830
Gly Val Trp Ser Leu Thr Ser Tyr Lys Glu Leu Arg Ser Ile Ile Gly
            835                 840                 845
Leu Arg Glu Pro Thr Leu Gln Ile Val Pro Ile Leu Ala Leu Arg Gly
850                 855                 860
Ser His Met Asn Trp Thr Arg Phe Asn Gln Met Thr Ser Val Met Gly
865                 870                 875                 880
Gly Gly Val Gly

<210> SEQ ID NO 78
<211> LENGTH: 998
<212> TYPE: PRT
<213> ORGANISM: Artificial Sequence
<220> FEATURE:
<223> OTHER INFORMATION: His Tag-linker-SpyCatcher-linker-deltaR2 enzyme

<400> SEQUENCE: 78

His His His His His His Val Gly Thr Val Gly Thr Gly Gly Gly Ser
```

-continued

```
1               5                   10                  15
Gly Gly Ala Ser Thr Ala Leu Asp Tyr Asp Ile Pro Thr Thr Glu Asn
            20                  25                  30

Leu Tyr Phe Gln Gly Ala Met Val Asp Thr Leu Ser Gly Leu Ser Ser
            35                  40                  45

Glu Gln Gly Gln Ser Gly Asp Met Thr Ile Glu Glu Asp Ser Ala Thr
    50                  55                  60

His Ile Lys Phe Ser Lys Arg Asp Glu Asp Gly Lys Glu Leu Ala Gly
65                  70                  75                  80

Ala Thr Met Glu Leu Arg Asp Ser Ser Gly Lys Thr Ile Ser Thr Trp
                85                  90                  95

Ile Ser Asp Gly Gln Val Lys Asp Phe Tyr Leu Tyr Pro Gly Lys Tyr
            100                 105                 110

Thr Phe Val Glu Thr Ala Ala Pro Asp Gly Tyr Glu Val Ala Thr Ala
            115                 120                 125

Ile Thr Phe Thr Val Asn Glu Gln Gly Gln Val Thr Val Asn Gly Lys
            130                 135                 140

Ala Thr Lys Gly Asp Ala His Ile Val Gly Thr Val Gly Thr Gly Gly
145                 150                 155                 160

Gly Ser Gly Gly Ala Ser Thr Ala Leu Lys Thr Ala Gly Arg Arg Asn
                165                 170                 175

Asp Leu His Asp Asp Arg Thr Ala Ser Ala His Lys Thr Ser Arg Gln
            180                 185                 190

Lys Arg Arg Ala Glu Tyr Ala Arg Val Gln Glu Leu Tyr Lys Lys Cys
            195                 200                 205

Arg Ser Arg Ala Ala Ala Glu Val Ile Asp Gly Ala Cys Gly Gly Val
    210                 215                 220

Gly His Ser Leu Glu Glu Met Glu Thr Tyr Trp Arg Pro Ile Leu Glu
225                 230                 235                 240

Arg Val Ser Asp Ala Pro Gly Pro Thr Pro Glu Ala Leu His Ala Leu
                245                 250                 255

Gly Arg Ala Glu Trp His Gly Gly Asn Arg Asp Tyr Thr Gln Leu Trp
            260                 265                 270

Lys Pro Ile Ser Val Glu Glu Ile Lys Ala Ser Arg Phe Asp Trp Arg
            275                 280                 285

Thr Ser Pro Gly Pro Asp Gly Ile Arg Ser Gly Gln Trp Arg Ala Val
    290                 295                 300

Pro Val His Leu Lys Ala Glu Met Phe Asn Ala Trp Met Ala Arg Gly
305                 310                 315                 320

Glu Ile Pro Glu Ile Leu Arg Gln Cys Arg Thr Val Phe Val Pro Lys
                325                 330                 335

Val Glu Arg Pro Gly Gly Pro Gly Glu Tyr Arg Pro Ile Ser Ile Ala
            340                 345                 350

Ser Ile Pro Leu Arg His Phe His Ser Ile Leu Ala Arg Arg Leu Leu
            355                 360                 365

Ala Cys Cys Pro Pro Asp Ala Arg Gln Arg Gly Phe Ile Cys Ala Asp
    370                 375                 380

Gly Thr Leu Glu Asn Ser Ala Val Leu Asp Ala Val Leu Gly Asp Ser
385                 390                 395                 400

Arg Lys Lys Leu Arg Glu Cys His Val Ala Val Leu Asp Phe Ala Lys
                405                 410                 415

Ala Phe Asp Thr Val Ser His Glu Ala Leu Val Glu Leu Leu Arg Leu
            420                 425                 430
```

```
Arg Gly Met Pro Glu Gln Phe Cys Gly Tyr Ile Ala His Leu Tyr Asp
            435                 440                 445

Thr Ala Ser Thr Thr Leu Ala Val Asn Asn Glu Met Ser Ser Pro Val
    450                 455                 460

Lys Val Gly Arg Gly Val Arg Gln Gly Asp Pro Leu Ser Pro Ile Leu
465                 470                 475                 480

Phe Asn Val Val Met Asp Leu Ile Leu Ala Ser Leu Pro Glu Arg Val
                485                 490                 495

Gly Tyr Arg Leu Glu Met Glu Leu Val Ser Ala Leu Ala Tyr Ala Asp
            500                 505                 510

Asp Leu Val Leu Leu Ala Gly Ser Lys Val Gly Met Gln Glu Ser Ile
            515                 520                 525

Ser Ala Val Asp Cys Val Gly Arg Gln Met Gly Leu Arg Leu Asn Cys
        530                 535                 540

Arg Lys Ser Ala Val Leu Ser Met Ile Pro Asp Gly His Arg Lys Lys
545                 550                 555                 560

His His Tyr Leu Thr Glu Arg Thr Phe Asn Ile Gly Gly Lys Pro Leu
                565                 570                 575

Arg Gln Val Ser Cys Val Glu Arg Trp Arg Tyr Leu Gly Val Asp Phe
            580                 585                 590

Glu Ala Ser Gly Cys Val Thr Leu Glu His Ser Ile Ser Ser Ala Leu
            595                 600                 605

Asn Asn Ile Ser Arg Ala Pro Leu Lys Pro Gln Gln Arg Leu Glu Ile
        610                 615                 620

Leu Arg Ala His Leu Ile Pro Arg Phe Gln His Gly Phe Val Leu Gly
625                 630                 635                 640

Asn Ile Ser Asp Asp Arg Leu Arg Met Leu Asp Val Gln Ile Arg Lys
                645                 650                 655

Ala Val Gly Gln Trp Leu Arg Leu Pro Ala Asp Val Pro Lys Ala Tyr
            660                 665                 670

Tyr His Ala Ala Val Gln Asp Gly Gly Leu Ala Ile Pro Ser Val Arg
        675                 680                 685

Ala Thr Ile Pro Asp Leu Ile Val Arg Arg Phe Gly Gly Leu Asp Ser
        690                 695                 700

Ser Pro Trp Ser Val Ala Arg Ala Ala Ala Lys Ser Asp Lys Ile Arg
705                 710                 715                 720

Lys Lys Leu Arg Trp Ala Trp Lys Gln Leu Arg Arg Phe Ser Arg Val
                725                 730                 735

Asp Ser Thr Thr Gln Arg Pro Ser Val Arg Leu Phe Trp Arg Glu His
            740                 745                 750

Leu His Ala Ser Val Asp Gly Arg Glu Leu Arg Glu Ser Thr Arg Thr
            755                 760                 765

Pro Thr Ser Thr Lys Trp Ile Arg Glu Arg Cys Ala Gln Ile Thr Gly
    770                 775                 780

Arg Asp Phe Val Gln Phe Val His Thr His Ile Asn Ala Leu Pro Ser
785                 790                 795                 800

Arg Ile Arg Gly Ser Arg Gly Arg Gly Gly Glu Ser Ser Leu
                805                 810                 815

Thr Cys Arg Ala Gly Cys Lys Val Arg Glu Thr Thr Ala His Ile Leu
        820                 825                 830

Gln Gln Cys His Arg Thr His Gly Gly Arg Ile Leu Arg His Asn Lys
            835                 840                 845
```

Ile Val Ser Phe Val Ala Lys Ala Met Glu Glu Asn Lys Trp Thr Val
850                 855                 860

Glu Leu Glu Pro Arg Leu Arg Thr Ser Val Gly Leu Arg Lys Pro Asp
865                 870                 875                 880

Ile Ile Ala Ser Arg Asp Gly Val Gly Val Ile Val Asp Val Gln Val
            885                 890                 895

Val Ser Gly Gln Arg Ser Leu Asp Glu Leu His Arg Glu Lys Arg Asn
            900                 905                 910

Lys Tyr Gly Asn His Gly Glu Leu Val Glu Leu Val Ala Gly Arg Leu
            915                 920                 925

Gly Leu Pro Lys Ala Glu Cys Val Arg Ala Thr Ser Cys Thr Ile Ser
930                 935                 940

Trp Arg Gly Val Trp Ser Leu Thr Ser Tyr Lys Glu Leu Arg Ser Ile
945                 950                 955                 960

Ile Gly Leu Arg Glu Pro Thr Leu Gln Ile Val Pro Ile Leu Ala Leu
            965                 970                 975

Arg Gly Ser His Met Asn Trp Thr Arg Phe Asn Gln Met Thr Ser Val
            980                 985                 990

Met Gly Gly Gly Val Gly
        995

<210> SEQ ID NO 79
<211> LENGTH: 118
<212> TYPE: PRT
<213> ORGANISM: Artificial Sequence
<220> FEATURE:
<223> OTHER INFORMATION: His Tag-linker-SpyTag-linker-Sso7d

<400> SEQUENCE: 79

His His His His His His Val Gly Thr Val Gly Thr Gly Gly Gly Ser
1               5                   10                  15

Gly Gly Ala Ser Thr Ala Leu Ala His Ile Val Met Val Asp Ala Tyr
            20                  25                  30

Lys Pro Thr Lys Lys Gly Val Gly Thr Val Gly Thr Gly Gly Gly Ser
        35                  40                  45

Gly Gly Ala Ser Thr Ala Leu Ala Thr Val Lys Phe Lys Tyr Lys Gly
    50                  55                  60

Glu Glu Lys Glu Val Asp Ile Ser Lys Ile Lys Lys Val Trp Arg Val
65                  70                  75                  80

Gly Lys Met Ile Ser Phe Thr Tyr Asp Glu Gly Gly Gly Lys Thr Gly
                85                  90                  95

Arg Gly Ala Val Ser Glu Lys Asp Ala Pro Lys Glu Leu Leu Gln Met
            100                 105                 110

Leu Glu Lys Gln Lys Lys
        115

<210> SEQ ID NO 80
<211> LENGTH: 232
<212> TYPE: PRT
<213> ORGANISM: Artificial Sequence
<220> FEATURE:
<223> OTHER INFORMATION: His Tag-linker-SpyCatcher-linker-Sso7d

<400> SEQUENCE: 80

His His His His His His Val Gly Thr Val Gly Thr Gly Gly Gly Ser
1               5                   10                  15

Gly Gly Ala Ser Thr Ala Leu Asp Tyr Asp Ile Pro Thr Thr Glu Asn
            20                  25                  30

```
Leu Tyr Phe Gln Gly Ala Met Val Asp Thr Leu Ser Gly Leu Ser Ser
            35                  40                  45

Glu Gln Gly Gln Ser Gly Asp Met Thr Ile Glu Asp Ser Ala Thr
 50                  55                  60

His Ile Lys Phe Ser Lys Arg Asp Glu Asp Gly Lys Glu Leu Ala Gly
 65                  70                  75                  80

Ala Thr Met Glu Leu Arg Asp Ser Ser Gly Lys Thr Ile Ser Thr Trp
                85                  90                  95

Ile Ser Asp Gly Gln Val Lys Asp Phe Tyr Leu Tyr Pro Gly Lys Tyr
                100                 105                 110

Thr Phe Val Glu Thr Ala Ala Pro Asp Gly Tyr Glu Val Ala Thr Ala
                115                 120                 125

Ile Thr Phe Thr Val Asn Glu Gln Gly Gln Val Thr Val Asn Gly Lys
130                 135                 140

Ala Thr Lys Gly Asp Ala His Ile Val Gly Thr Val Gly Thr Gly Gly
145                 150                 155                 160

Gly Ser Gly Gly Ala Ser Thr Ala Leu Ala Thr Val Lys Phe Lys Tyr
                165                 170                 175

Lys Gly Glu Glu Lys Glu Val Asp Ile Ser Lys Ile Lys Lys Val Trp
                180                 185                 190

Arg Val Gly Lys Met Ile Ser Phe Thr Tyr Asp Glu Gly Gly Gly Lys
                195                 200                 205

Thr Gly Arg Gly Ala Val Ser Glu Lys Asp Ala Pro Lys Glu Leu Leu
210                 215                 220

Gln Met Leu Glu Lys Gln Lys Lys
225                 230

<210> SEQ ID NO 81
<211> LENGTH: 114
<212> TYPE: PRT
<213> ORGANISM: Artificial Sequence
<220> FEATURE:
<223> OTHER INFORMATION: His Tag-linker-SpyTag-linker-Cren7

<400> SEQUENCE: 81

His His His His His Val Gly Thr Val Gly Thr Gly Gly Gly Ser
 1               5                  10                  15

Gly Gly Ala Ser Thr Ala Leu Ala His Ile Val Met Val Asp Ala Tyr
                20                  25                  30

Lys Pro Thr Lys Lys Gly Val Gly Thr Val Gly Thr Gly Gly Gly Ser
                35                  40                  45

Gly Gly Ala Ser Thr Ala Leu Ser Ser Gly Lys Lys Pro Val Lys Val
 50                  55                  60

Lys Thr Pro Ala Gly Lys Glu Ala Glu Leu Val Pro Glu Lys Val Trp
 65                  70                  75                  80

Ala Leu Ala Pro Lys Gly Arg Lys Gly Val Lys Ile Gly Leu Phe Lys
                85                  90                  95

Asp Pro Glu Thr Gly Lys Tyr Phe Arg His Lys Leu Pro Asp Asp Tyr
                100                 105                 110

Pro Ile

<210> SEQ ID NO 82
<211> LENGTH: 228
<212> TYPE: PRT
<213> ORGANISM: Artificial Sequence
<220> FEATURE:
```

<223> OTHER INFORMATION: His Tag-linker-SpyCatcher-linker-Cren7

<400> SEQUENCE: 82

```
His His His His His Val Gly Thr Val Gly Thr Gly Gly Gly Ser
1               5                   10                  15

Gly Gly Ala Ser Thr Ala Leu Asp Tyr Asp Ile Pro Thr Thr Glu Asn
            20                  25                  30

Leu Tyr Phe Gln Gly Ala Met Val Asp Thr Leu Ser Gly Leu Ser Ser
        35                  40                  45

Glu Gln Gly Gln Ser Gly Asp Met Thr Ile Glu Asp Ser Ala Thr
50                  55                  60

His Ile Lys Phe Ser Lys Arg Asp Glu Asp Gly Lys Glu Leu Ala Gly
65                  70                  75                  80

Ala Thr Met Glu Leu Arg Asp Ser Ser Gly Lys Thr Ile Ser Thr Trp
                85                  90                  95

Ile Ser Asp Gly Gln Val Lys Asp Phe Tyr Leu Tyr Pro Gly Lys Tyr
            100                 105                 110

Thr Phe Val Glu Thr Ala Ala Pro Asp Gly Tyr Glu Val Ala Thr Ala
        115                 120                 125

Ile Thr Phe Thr Val Asn Glu Gln Gly Gln Val Thr Val Asn Gly Lys
    130                 135                 140

Ala Thr Lys Gly Asp Ala His Ile Val Gly Thr Val Gly Thr Gly Gly
145                 150                 155                 160

Gly Ser Gly Gly Ala Ser Thr Ala Leu Ser Ser Gly Lys Lys Pro Val
                165                 170                 175

Lys Val Lys Thr Pro Ala Gly Lys Glu Ala Glu Leu Val Pro Glu Lys
            180                 185                 190

Val Trp Ala Leu Ala Pro Lys Gly Arg Lys Gly Val Lys Ile Gly Leu
        195                 200                 205

Phe Lys Asp Pro Glu Thr Gly Lys Tyr Phe Arg His Lys Leu Pro Asp
    210                 215                 220

Asp Tyr Pro Ile
225
```

<210> SEQ ID NO 83
<211> LENGTH: 203
<212> TYPE: PRT
<213> ORGANISM: Artificial Sequence
<220> FEATURE:
<223> OTHER INFORMATION: His Tag-linker-SpyTag-linker-SSB

<400> SEQUENCE: 83

```
His His His His His Val Gly Thr Val Gly Thr Gly Gly Gly Ser
1               5                   10                  15

Gly Gly Ala Ser Thr Ala Leu Ala His Ile Val Met Val Asp Ala Tyr
            20                  25                  30

Lys Pro Thr Lys Lys Gly Val Gly Thr Val Gly Thr Gly Gly Gly Ser
        35                  40                  45

Gly Gly Ala Ser Thr Ala Leu Met Glu Glu Lys Val Gly Asn Leu Lys
50                  55                  60

Pro Asn Met Glu Ser Val Asn Val Thr Val Arg Val Leu Glu Ala Ser
65                  70                  75                  80

Glu Ala Arg Gln Ile Gln Thr Lys Asn Gly Val Arg Thr Ile Ser Glu
                85                  90                  95

Ala Ile Val Gly Asp Glu Thr Gly Arg Val Lys Leu Thr Leu Trp Gly
            100                 105                 110
```

Lys His Ala Gly Ser Ile Lys Glu Gly Gln Val Val Lys Ile Glu Asn
              115                 120                 125

Ala Trp Thr Thr Ala Phe Lys Gly Gln Val Gln Leu Asn Ala Gly Ser
    130                 135                 140

Lys Thr Lys Ile Ala Glu Ala Ser Glu Asp Gly Phe Pro Glu Ser Ser
145                 150                 155                 160

Gln Ile Pro Glu Asn Thr Pro Thr Ala Pro Gln Gln Met Arg Gly Gly
                165                 170                 175

Gly Arg Gly Phe Arg Gly Gly Arg Arg Tyr Gly Arg Arg Gly Gly
            180                 185                 190

Arg Arg Gln Glu Asn Glu Glu Gly Glu Glu
            195                 200

<210> SEQ ID NO 84
<211> LENGTH: 315
<212> TYPE: PRT
<213> ORGANISM: Artificial Sequence
<220> FEATURE:
<223> OTHER INFORMATION: His Tag-linker-SpyCatcher-linker-SSB

<400> SEQUENCE: 84

His His His His His Val Gly Thr Val Gly Thr Gly Gly Gly Ser
1               5                   10                  15

Gly Gly Ala Ser Thr Ala Leu Asp Tyr Asp Ile Pro Thr Thr Glu Asn
                20                  25                  30

Leu Tyr Phe Gln Gly Ala Met Val Asp Thr Leu Ser Gly Leu Ser Ser
            35                  40                  45

Glu Gln Gly Gln Ser Gly Asp Met Thr Ile Glu Glu Asp Ser Ala Thr
50                  55                  60

His Ile Lys Phe Ser Lys Arg Asp Glu Asp Gly Lys Glu Leu Ala Gly
65                  70                  75                  80

Ala Thr Met Glu Leu Arg Asp Ser Ser Gly Lys Thr Ile Ser Thr Trp
                85                  90                  95

Ile Ser Asp Gly Gln Val Lys Asp Phe Tyr Leu Tyr Pro Gly Lys Tyr
            100                 105                 110

Thr Phe Val Glu Thr Ala Ala Pro Asp Gly Tyr Glu Val Ala Thr Ala
        115                 120                 125

Ile Thr Phe Thr Val Asn Glu Gln Gly Gln Val Thr Val Asn Gly Lys
    130                 135                 140

Ala Thr Lys Gly Asp Ala His Ile Val Gly Thr Gly Gly Ser Gly
145                 150                 155                 160

Gly Gly Thr Gly Gly Ser Met Glu Glu Lys Val Gly Asn Leu Lys
                165                 170                 175

Pro Asn Met Glu Ser Val Asn Val Thr Val Arg Val Leu Glu Ala Ser
                180                 185                 190

Glu Ala Arg Gln Ile Gln Thr Lys Asn Gly Val Arg Thr Ile Ser Glu
            195                 200                 205

Ala Ile Val Gly Asp Glu Thr Gly Arg Val Lys Leu Thr Leu Trp Gly
        210                 215                 220

Lys His Ala Gly Ser Ile Lys Glu Gly Gln Val Val Lys Ile Glu Asn
225                 230                 235                 240

Ala Trp Thr Thr Ala Phe Lys Gly Gln Val Gln Leu Asn Ala Gly Ser
                245                 250                 255

Lys Thr Lys Ile Ala Glu Ala Ser Glu Asp Gly Phe Pro Glu Ser Ser
            260                 265                 270

```
Gln Ile Pro Glu Asn Thr Pro Thr Ala Pro Gln Gln Met Arg Gly Gly
        275                 280                 285

Gly Arg Gly Phe Arg Gly Gly Gly Arg Arg Tyr Gly Arg Gly Gly
    290                 295                 300

Arg Arg Gln Glu Asn Glu Glu Gly Glu Glu Glu
305                 310                 315

<210> SEQ ID NO 85
<211> LENGTH: 15
<212> TYPE: PRT
<213> ORGANISM: Artificial Sequence
<220> FEATURE:
<223> OTHER INFORMATION: AviTag

<400> SEQUENCE: 85

Gly Leu Asn Asp Ile Phe Glu Ala Gln Lys Ile Glu Trp His Glu
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: BioTag

<400> SEQUENCE: 86

Ala Leu Asn Asp Ile Phe Glu Ala Gln Lys Ile Glu Trp His Ala
1               5                   10                  15

<210> SEQ ID NO 87
<211> LENGTH: 23
<212> TYPE: PRT
<213> ORGANISM: Artificial Sequence
<220> FEATURE:
<223> OTHER INFORMATION: Biotin ligase recognition peptide

<400> SEQUENCE: 87

Met Ala Gly Gly Leu Asn Asp Ile Phe Glu Ala Gln Lys Ile Glu Trp
1               5                   10                  15

His Glu Asp Thr Gly Gly Ser
            20

<210> SEQ ID NO 88
<211> LENGTH: 15
<212> TYPE: PRT
<213> ORGANISM: Artificial Sequence
<220> FEATURE:
<223> OTHER INFORMATION: BirA Substrate Peptide

<400> SEQUENCE: 88

Leu His His Ile Leu Asp Ala Gln Lys Met Val Trp Asn His Arg
1               5                   10                  15

<210> SEQ ID NO 89
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
```

<223> OTHER INFORMATION: any amino acid other than L, V, I, W, F, or Y

<400> SEQUENCE: 89

```
Leu Xaa Xaa Ile Phe Glu Ala Gln Lys Ile Glu Trp Arg
1               5                   10
```

<210> SEQ ID NO 90
<211> LENGTH: 882
<212> TYPE: PRT
<213> ORGANISM: Artificial Sequence
<220> FEATURE:
<223> OTHER INFORMATION: His Tag-linker-deltaR2 enzyme-linker-AviTag

<400> SEQUENCE: 90

```
His His His His His His Val Gly Thr Val Gly Thr Gly Gly Gly Ser
1               5                   10                  15

Gly Gly Ala Ser Thr Ala Leu Lys Thr Ala Gly Arg Arg Asn Asp Leu
            20                  25                  30

His Asp Asp Arg Thr Ala Ser Ala His Lys Thr Ser Arg Gln Lys Arg
        35                  40                  45

Arg Ala Glu Tyr Ala Arg Val Gln Glu Leu Tyr Lys Lys Cys Arg Ser
    50                  55                  60

Arg Ala Ala Ala Glu Val Ile Asp Gly Ala Cys Gly Gly Val Gly His
65                  70                  75                  80

Ser Leu Glu Glu Met Glu Thr Tyr Trp Arg Pro Ile Leu Glu Arg Val
                85                  90                  95

Ser Asp Ala Pro Gly Pro Thr Pro Glu Ala Leu His Ala Leu Gly Arg
            100                 105                 110

Ala Glu Trp His Gly Gly Asn Arg Asp Tyr Thr Gln Leu Trp Lys Pro
        115                 120                 125

Ile Ser Val Glu Glu Ile Lys Ala Ser Arg Phe Asp Trp Arg Thr Ser
    130                 135                 140

Pro Gly Pro Asp Gly Ile Arg Ser Gly Gln Trp Arg Ala Val Pro Val
145                 150                 155                 160

His Leu Lys Ala Glu Met Phe Asn Ala Trp Met Ala Arg Gly Glu Ile
                165                 170                 175

Pro Glu Ile Leu Arg Gln Cys Arg Thr Val Phe Val Pro Lys Val Glu
            180                 185                 190

Arg Pro Gly Gly Pro Gly Glu Tyr Arg Pro Ile Ser Ile Ala Ser Ile
        195                 200                 205

Pro Leu Arg His Phe His Ser Ile Leu Ala Arg Arg Leu Leu Ala Cys
    210                 215                 220

Cys Pro Pro Asp Ala Arg Gln Arg Gly Phe Ile Cys Ala Asp Gly Thr
225                 230                 235                 240

Leu Glu Asn Ser Ala Val Leu Asp Ala Val Leu Gly Asp Ser Arg Lys
                245                 250                 255

Lys Leu Arg Glu Cys His Val Ala Val Leu Asp Phe Ala Lys Ala Phe
            260                 265                 270

Asp Thr Val Ser His Glu Ala Leu Val Glu Leu Leu Arg Leu Arg Gly
        275                 280                 285

Met Pro Glu Gln Phe Cys Gly Tyr Ile Ala His Leu Tyr Asp Thr Ala
    290                 295                 300

Ser Thr Thr Leu Ala Val Asn Asn Glu Met Ser Ser Pro Val Lys Val
305                 310                 315                 320

Gly Arg Gly Val Arg Gln Gly Asp Pro Leu Ser Pro Ile Leu Phe Asn
                325                 330                 335
```

-continued

Val Val Met Asp Leu Ile Leu Ala Ser Leu Pro Glu Arg Val Gly Tyr
            340                 345                 350

Arg Leu Glu Met Glu Leu Val Ser Ala Leu Ala Tyr Ala Asp Asp Leu
            355                 360                 365

Val Leu Leu Ala Gly Ser Lys Val Gly Met Gln Glu Ser Ile Ser Ala
    370                 375                 380

Val Asp Cys Val Gly Arg Gln Met Gly Leu Arg Leu Asn Cys Arg Lys
385                 390                 395                 400

Ser Ala Val Leu Ser Met Ile Pro Asp Gly His Arg Lys Lys His His
                405                 410                 415

Tyr Leu Thr Glu Arg Thr Phe Asn Ile Gly Gly Lys Pro Leu Arg Gln
            420                 425                 430

Val Ser Cys Val Glu Arg Trp Arg Tyr Leu Gly Val Asp Phe Glu Ala
            435                 440                 445

Ser Gly Cys Val Thr Leu Glu His Ser Ile Ser Ser Ala Leu Asn Asn
    450                 455                 460

Ile Ser Arg Ala Pro Leu Lys Pro Gln Gln Arg Leu Glu Ile Leu Arg
465                 470                 475                 480

Ala His Leu Ile Pro Arg Phe Gln His Gly Phe Val Leu Gly Asn Ile
                485                 490                 495

Ser Asp Asp Arg Leu Arg Met Leu Asp Val Gln Ile Arg Lys Ala Val
            500                 505                 510

Gly Gln Trp Leu Arg Leu Pro Ala Asp Val Pro Lys Ala Tyr Tyr His
            515                 520                 525

Ala Ala Val Gln Asp Gly Gly Leu Ala Ile Pro Ser Val Arg Ala Thr
    530                 535                 540

Ile Pro Asp Leu Ile Val Arg Arg Phe Gly Gly Leu Asp Ser Ser Pro
545                 550                 555                 560

Trp Ser Val Ala Arg Ala Ala Lys Ser Asp Lys Ile Arg Lys Lys
                565                 570                 575

Leu Arg Trp Ala Trp Lys Gln Leu Arg Arg Phe Ser Arg Val Asp Ser
            580                 585                 590

Thr Thr Gln Arg Pro Ser Val Arg Leu Phe Trp Arg Glu His Leu His
            595                 600                 605

Ala Ser Val Asp Gly Arg Glu Leu Arg Glu Ser Thr Arg Thr Pro Thr
    610                 615                 620

Ser Thr Lys Trp Ile Arg Glu Arg Cys Ala Gln Ile Thr Gly Arg Asp
625                 630                 635                 640

Phe Val Gln Phe Val His Thr His Ile Asn Ala Leu Pro Ser Arg Ile
                645                 650                 655

Arg Gly Ser Arg Gly Arg Gly Gly Gly Glu Ser Ser Leu Thr Cys
            660                 665                 670

Arg Ala Gly Cys Lys Val Arg Glu Thr Thr Ala His Ile Leu Gln Gln
    675                 680                 685

Cys His Arg Thr His Gly Gly Arg Ile Leu Arg His Asn Lys Ile Val
            690                 695                 700

Ser Phe Val Ala Lys Ala Met Glu Glu Asn Lys Trp Thr Val Glu Leu
705                 710                 715                 720

Glu Pro Arg Leu Arg Thr Ser Val Gly Leu Arg Lys Pro Asp Ile Ile
                725                 730                 735

Ala Ser Arg Asp Gly Val Gly Val Ile Val Asp Val Gln Val Val Ser
            740                 745                 750

-continued

```
Gly Gln Arg Ser Leu Asp Glu Leu His Arg Glu Lys Arg Asn Lys Tyr
            755                 760                 765

Gly Asn His Gly Glu Leu Val Glu Leu Val Ala Gly Arg Leu Gly Leu
        770                 775                 780

Pro Lys Ala Glu Cys Val Arg Ala Thr Ser Cys Thr Ile Ser Trp Arg
785                 790                 795                 800

Gly Val Trp Ser Leu Thr Ser Tyr Lys Glu Leu Arg Ser Ile Ile Gly
                805                 810                 815

Leu Arg Glu Pro Thr Leu Gln Ile Val Pro Ile Leu Ala Leu Arg Gly
            820                 825                 830

Ser His Met Asn Trp Thr Arg Phe Asn Gln Met Thr Ser Val Met Gly
        835                 840                 845

Gly Gly Val Gly Val Gly Thr Gly Gly Ser Gly Gly Gly Thr Gly
    850                 855                 860

Gly Gly Ser Gly Leu Asn Asp Ile Phe Glu Ala Gln Lys Ile Glu Trp
865                 870                 875                 880

His Glu
```

<210> SEQ ID NO 91
<211> LENGTH: 116
<212> TYPE: PRT
<213> ORGANISM: Artificial Sequence
<220> FEATURE:
<223> OTHER INFORMATION: His Tag-linker-Sso7d-linker-AviTag

<400> SEQUENCE: 91

```
His His His His His His Val Gly Thr Val Gly Thr Gly Gly Gly Ser
1               5                   10                  15

Gly Gly Ala Ser Thr Ala Leu Ala Thr Val Lys Phe Lys Tyr Lys Gly
            20                  25                  30

Glu Glu Lys Glu Val Asp Ile Ser Lys Ile Lys Lys Val Trp Arg Val
        35                  40                  45

Gly Lys Met Ile Ser Phe Thr Tyr Asp Glu Gly Gly Lys Thr Gly
    50                  55                  60

Arg Gly Ala Val Ser Glu Lys Asp Ala Pro Lys Glu Leu Leu Gln Met
65                  70                  75                  80

Leu Glu Lys Gln Lys Lys Val Gly Thr Gly Gly Ser Gly Gly Gly
                85                  90                  95

Thr Gly Gly Gly Ser Gly Leu Asn Asp Ile Phe Glu Ala Gln Lys Ile
            100                 105                 110

Glu Trp His Glu
        115
```

<210> SEQ ID NO 92
<211> LENGTH: 114
<212> TYPE: PRT
<213> ORGANISM: Artificial Sequence
<220> FEATURE:
<223> OTHER INFORMATION: His Tag-linker-Cren7-linker-AviTag

<400> SEQUENCE: 92

```
His His His His His His Val Gly Thr Val Gly Thr Gly Gly Gly Ser
1               5                   10                  15

Gly Gly Ala Ser Thr Ala Leu Ser Ser Gly Lys Lys Pro Val Lys Val
            20                  25                  30

Lys Thr Pro Ala Gly Lys Glu Ala Glu Leu Val Pro Glu Lys Val Trp
        35                  40                  45
```

```
Ala Leu Ala Pro Lys Gly Arg Lys Gly Val Lys Ile Gly Leu Phe Lys
        50                  55                  60
Asp Pro Glu Thr Gly Lys Tyr Phe Arg His Lys Leu Pro Asp Asp Tyr
 65                  70                  75                  80
Pro Ile Val Gly Thr Val Gly Thr Gly Gly Ser Glu Ala Ala Ala
                85                  90                  95
Lys Gly Gly Gly Leu Asn Asp Ile Phe Glu Ala Gln Lys Ile Glu Trp
                100                 105                 110
His Glu
```

<210> SEQ ID NO 93
<211> LENGTH: 202
<212> TYPE: PRT
<213> ORGANISM: Artificial Sequence
<220> FEATURE:
<223> OTHER INFORMATION: His Tag-linker-SSB-linker-AviTag

<400> SEQUENCE: 93

```
His His His His His His Val Gly Thr Val Gly Thr Gly Gly Gly Ser
 1               5                  10                  15
Gly Gly Ala Ser Thr Ala Leu Met Glu Glu Lys Val Gly Asn Leu Lys
                20                  25                  30
Pro Asn Met Glu Ser Val Asn Val Thr Val Arg Val Leu Glu Ala Ser
                35                  40                  45
Glu Ala Arg Gln Ile Gln Thr Lys Asn Gly Val Arg Thr Ile Ser Glu
        50                  55                  60
Ala Ile Val Gly Asp Glu Thr Gly Arg Val Lys Leu Thr Leu Trp Gly
 65                  70                  75                  80
Lys His Ala Gly Ser Ile Lys Glu Gly Gln Val Val Lys Ile Glu Asn
                85                  90                  95
Ala Trp Thr Thr Ala Phe Lys Gly Gln Val Gln Leu Asn Ala Gly Ser
                100                 105                 110
Lys Thr Lys Ile Ala Glu Ala Ser Glu Asp Gly Phe Pro Glu Ser Ser
        115                 120                 125
Gln Ile Pro Glu Asn Thr Pro Thr Ala Pro Gln Met Arg Gly Gly
        130                 135                 140
Gly Arg Gly Phe Arg Gly Gly Arg Arg Tyr Gly Arg Arg Gly Gly
145                 150                 155                 160
Arg Arg Gln Glu Asn Glu Glu Gly Glu Glu Gly Thr Val Gly Thr
                165                 170                 175
Gly Gly Gly Ser Glu Ala Ala Ala Lys Gly Gly Gly Leu Asn Asp Ile
                180                 185                 190
Phe Glu Ala Gln Lys Ile Glu Trp His Glu
        195                 200
```

<210> SEQ ID NO 94
<211> LENGTH: 884
<212> TYPE: PRT
<213> ORGANISM: Artificial Sequence
<220> FEATURE:
<223> OTHER INFORMATION: His Tag-linker-AviTag-linker-deltaR2 enzyme

<400> SEQUENCE: 94

```
His His His His His His Val Gly Thr Val Gly Thr Gly Gly Gly Ser
 1               5                  10                  15
Gly Gly Ala Ser Thr Ala Leu Gly Leu Asn Asp Ile Phe Glu Ala Gln
                20                  25                  30
```

-continued

```
Lys Ile Glu Trp His Glu Val Thr Val Thr Gly Gly Ser
         35                  40              45

Gly Gly Ala Ser Thr Ala Leu Lys Thr Ala Gly Arg Arg Asn Asp Leu
 50                  55                  60

His Asp Asp Arg Thr Ala Ser Ala His Lys Thr Ser Arg Gln Lys Arg
 65                  70                  75                  80

Arg Ala Glu Tyr Ala Arg Val Gln Glu Leu Tyr Lys Lys Cys Arg Ser
                 85                  90                  95

Arg Ala Ala Ala Glu Val Ile Asp Gly Ala Cys Gly Gly Val Gly His
                100                 105                 110

Ser Leu Glu Glu Met Glu Thr Tyr Trp Arg Pro Ile Leu Glu Arg Val
            115                 120                 125

Ser Asp Ala Pro Gly Pro Thr Pro Glu Ala Leu His Ala Leu Gly Arg
130                 135                 140

Ala Glu Trp His Gly Gly Asn Arg Asp Tyr Thr Gln Leu Trp Lys Pro
145                 150                 155                 160

Ile Ser Val Glu Glu Ile Lys Ala Ser Arg Phe Asp Trp Arg Thr Ser
                165                 170                 175

Pro Gly Pro Asp Gly Ile Arg Ser Gly Gln Trp Arg Ala Val Pro Val
            180                 185                 190

His Leu Lys Ala Glu Met Phe Asn Ala Trp Met Ala Arg Gly Glu Ile
            195                 200                 205

Pro Glu Ile Leu Arg Gln Cys Arg Thr Val Phe Val Pro Lys Val Glu
210                 215                 220

Arg Pro Gly Gly Pro Gly Glu Tyr Arg Pro Ile Ser Ile Ala Ser Ile
225                 230                 235                 240

Pro Leu Arg His Phe His Ser Ile Leu Ala Arg Arg Leu Leu Ala Cys
                245                 250                 255

Cys Pro Pro Asp Ala Arg Gln Arg Gly Phe Ile Cys Ala Asp Gly Thr
            260                 265                 270

Leu Glu Asn Ser Ala Val Leu Asp Ala Val Leu Gly Asp Ser Arg Lys
            275                 280                 285

Lys Leu Arg Glu Cys His Val Ala Val Leu Asp Phe Ala Lys Ala Phe
290                 295                 300

Asp Thr Val Ser His Glu Ala Leu Val Glu Leu Leu Arg Leu Arg Gly
305                 310                 315                 320

Met Pro Glu Gln Phe Cys Gly Tyr Ile Ala His Leu Tyr Asp Thr Ala
                325                 330                 335

Ser Thr Thr Leu Ala Val Asn Asn Glu Met Ser Ser Pro Val Lys Val
            340                 345                 350

Gly Arg Gly Val Arg Gln Gly Asp Pro Leu Ser Pro Ile Leu Phe Asn
            355                 360                 365

Val Val Met Asp Leu Ile Leu Ala Ser Leu Pro Glu Arg Val Gly Tyr
370                 375                 380

Arg Leu Glu Met Glu Leu Val Ser Ala Leu Ala Tyr Ala Asp Asp Leu
385                 390                 395                 400

Val Leu Leu Ala Gly Ser Lys Val Gly Met Gln Glu Ser Ile Ser Ala
                405                 410                 415

Val Asp Cys Val Gly Arg Gln Met Gly Leu Arg Leu Asn Cys Arg Lys
            420                 425                 430

Ser Ala Val Leu Ser Met Ile Pro Asp Gly His Arg Lys Lys His His
            435                 440                 445

Tyr Leu Thr Glu Arg Thr Phe Asn Ile Gly Gly Lys Pro Leu Arg Gln
```

```
                450             455             460
Val Ser Cys Val Glu Arg Trp Arg Tyr Leu Gly Val Asp Phe Glu Ala
465             470             475             480

Ser Gly Cys Val Thr Leu Glu His Ser Ile Ser Ala Leu Asn Asn
                485             490             495

Ile Ser Arg Ala Pro Leu Lys Pro Gln Gln Arg Leu Glu Ile Leu Arg
                500             505             510

Ala His Leu Ile Pro Arg Phe Gln His Gly Phe Val Leu Gly Asn Ile
        515             520             525

Ser Asp Asp Arg Leu Arg Met Leu Asp Val Gln Ile Arg Lys Ala Val
        530             535             540

Gly Gln Trp Leu Arg Leu Pro Ala Asp Val Pro Lys Ala Tyr Tyr His
545             550             555             560

Ala Ala Val Gln Asp Gly Gly Leu Ala Ile Pro Ser Val Arg Ala Thr
                565             570             575

Ile Pro Asp Leu Ile Val Arg Arg Phe Gly Gly Leu Asp Ser Ser Pro
                580             585             590

Trp Ser Val Ala Arg Ala Ala Lys Ser Asp Lys Ile Arg Lys Lys
        595             600             605

Leu Arg Trp Ala Trp Lys Gln Leu Arg Arg Phe Ser Arg Val Asp Ser
        610             615             620

Thr Thr Gln Arg Pro Ser Val Arg Leu Phe Trp Arg Glu His Leu His
625             630             635             640

Ala Ser Val Asp Gly Arg Glu Leu Arg Glu Ser Thr Arg Thr Pro Thr
                645             650             655

Ser Thr Lys Trp Ile Arg Glu Arg Cys Ala Gln Ile Thr Gly Arg Asp
                660             665             670

Phe Val Gln Phe Val His Thr His Ile Asn Ala Leu Pro Ser Arg Ile
        675             680             685

Arg Gly Ser Arg Gly Arg Gly Gly Glu Ser Ser Leu Thr Cys
        690             695             700

Arg Ala Gly Cys Lys Val Arg Glu Thr Thr Ala His Ile Leu Gln Gln
705             710             715             720

Cys His Arg Thr His Gly Gly Arg Ile Leu Arg His Asn Lys Ile Val
                725             730             735

Ser Phe Val Ala Lys Ala Met Glu Glu Asn Lys Trp Thr Val Glu Leu
                740             745             750

Glu Pro Arg Leu Arg Thr Ser Val Gly Leu Arg Lys Pro Asp Ile Ile
        755             760             765

Ala Ser Arg Asp Gly Val Gly Val Ile Val Asp Val Gln Val Val Ser
770             775             780

Gly Gln Arg Ser Leu Asp Glu Leu His Arg Glu Lys Arg Asn Lys Tyr
785             790             795             800

Gly Asn His Gly Glu Leu Val Glu Leu Val Ala Gly Arg Leu Gly Leu
                805             810             815

Pro Lys Ala Glu Cys Val Arg Ala Thr Ser Cys Thr Ile Ser Trp Arg
                820             825             830

Gly Val Trp Ser Leu Thr Ser Tyr Lys Glu Leu Arg Ser Ile Ile Gly
                835             840             845

Leu Arg Glu Pro Thr Leu Gln Ile Val Pro Ile Leu Ala Leu Arg Gly
        850             855             860

Ser His Met Asn Trp Thr Arg Phe Asn Gln Met Thr Ser Val Met Gly
865             870             875             880
```

Gly Gly Val Gly

<210> SEQ ID NO 95
<211> LENGTH: 118
<212> TYPE: PRT
<213> ORGANISM: Artificial Sequence
<220> FEATURE:
<223> OTHER INFORMATION: His Tag-linker-AviTag-linker-Sso7d

<400> SEQUENCE: 95

His His His His His His Val Gly Thr Val Gly Thr Gly Gly Gly Ser
1               5                   10                  15

Gly Gly Ala Ser Thr Ala Leu Gly Leu Asn Asp Ile Phe Glu Ala Gln
            20                  25                  30

Lys Ile Glu Trp His Glu Val Gly Thr Val Gly Thr Gly Gly Gly Ser
        35                  40                  45

Gly Gly Ala Ser Thr Ala Leu Ala Thr Val Lys Phe Lys Tyr Lys Gly
    50                  55                  60

Glu Glu Lys Glu Val Asp Ile Ser Lys Ile Lys Lys Val Trp Arg Val
65                  70                  75                  80

Gly Lys Met Ile Ser Phe Thr Tyr Asp Glu Gly Gly Lys Thr Gly
                85                  90                  95

Arg Gly Ala Val Ser Glu Lys Asp Ala Pro Lys Glu Leu Leu Gln Met
                100                 105                 110

Leu Glu Lys Gln Lys Lys
        115

<210> SEQ ID NO 96
<211> LENGTH: 114
<212> TYPE: PRT
<213> ORGANISM: Artificial Sequence
<220> FEATURE:
<223> OTHER INFORMATION: His Tag-linker-AviTag-linker-Cren7

<400> SEQUENCE: 96

His His His His His His Val Gly Thr Val Gly Thr Gly Gly Gly Ser
1               5                   10                  15

Gly Gly Ala Ser Thr Ala Leu Gly Leu Asn Asp Ile Phe Glu Ala Gln
            20                  25                  30

Lys Ile Glu Trp His Glu Val Gly Thr Val Gly Thr Gly Gly Gly Ser
        35                  40                  45

Gly Gly Ala Ser Thr Ala Leu Ser Ser Gly Lys Lys Pro Val Lys Val
    50                  55                  60

Lys Thr Pro Ala Gly Lys Glu Ala Glu Leu Val Pro Glu Lys Val Trp
65                  70                  75                  80

Ala Leu Ala Pro Lys Gly Arg Lys Gly Val Lys Ile Gly Leu Phe Lys
                85                  90                  95

Asp Pro Glu Thr Gly Lys Tyr Phe Arg His Lys Leu Pro Asp Asp Tyr
                100                 105                 110

Pro Ile

<210> SEQ ID NO 97
<211> LENGTH: 203
<212> TYPE: PRT
<213> ORGANISM: Artificial Sequence
<220> FEATURE:
<223> OTHER INFORMATION: His Tag-linker-AviTag-linker-SSB

<400> SEQUENCE: 97

His His His His His Val Gly Thr Val Gly Thr Gly Gly Gly Ser
1               5                   10                  15

Gly Gly Ala Ser Thr Ala Leu Gly Leu Asn Asp Ile Phe Glu Ala Gln
                20                  25                  30

Lys Ile Glu Trp His Glu Val Gly Thr Val Gly Thr Gly Gly Gly Ser
            35                  40                  45

Gly Gly Ala Ser Thr Ala Leu Met Glu Glu Lys Val Gly Asn Leu Lys
        50                  55                  60

Pro Asn Met Glu Ser Val Asn Val Thr Val Arg Val Leu Glu Ala Ser
65                  70                  75                  80

Glu Ala Arg Gln Ile Gln Thr Lys Asn Gly Val Arg Thr Ile Ser Glu
                85                  90                  95

Ala Ile Val Gly Asp Glu Thr Gly Arg Val Lys Leu Thr Leu Trp Gly
                100                 105                 110

Lys His Ala Gly Ser Ile Lys Glu Gly Gln Val Val Lys Ile Glu Asn
        115                 120                 125

Ala Trp Thr Thr Ala Phe Lys Gly Gln Val Gln Leu Asn Ala Gly Ser
130                 135                 140

Lys Thr Lys Ile Ala Glu Ala Ser Glu Asp Gly Phe Pro Glu Ser Ser
145                 150                 155                 160

Gln Ile Pro Glu Asn Thr Pro Thr Ala Pro Gln Gln Met Arg Gly Gly
                165                 170                 175

Gly Arg Gly Phe Arg Gly Gly Arg Arg Tyr Gly Arg Arg Gly Gly
                180                 185                 190

Arg Arg Gln Glu Asn Glu Glu Gly Glu Glu
                195                 200

<210> SEQ ID NO 98
<211> LENGTH: 1316
<212> TYPE: PRT
<213> ORGANISM: Artificial Sequence
<220> FEATURE:
<223> OTHER INFORMATION: His Tag joined via a linker to a dimer of
      truncated SSB joined via a linker to the C-terminus of wild type
      R2 enzyme

<400> SEQUENCE: 98

Met Met Ala Ser Thr Ala Leu Ser Leu Met Gly Arg Cys Asn Pro Asp
1               5                   10                  15

Gly Cys Thr Arg Gly Lys His Val Thr Ala Ala Pro Met Asp Gly Pro
                20                  25                  30

Arg Gly Pro Ser Ser Leu Ala Gly Thr Phe Gly Trp Gly Leu Ala Ile
            35                  40                  45

Pro Ala Gly Glu Pro Cys Gly Arg Val Cys Ser Pro Ala Thr Val Gly
        50                  55                  60

Phe Phe Pro Val Ala Lys Lys Ser Asn Lys Glu Asn Arg Pro Glu Ala
65                  70                  75                  80

Ser Gly Leu Pro Leu Glu Ser Glu Arg Thr Gly Asp Asn Pro Thr Val
                85                  90                  95

Arg Gly Ser Ala Gly Ala Asp Pro Val Gly Gln Asp Ala Pro Gly Trp
                100                 105                 110

Thr Cys Gln Phe Cys Glu Arg Thr Phe Ser Thr Asn Arg Gly Leu Gly
        115                 120                 125

Val His Lys Arg Arg Ala His Pro Val Glu Thr Asn Thr Asp Ala Ala
130                 135                 140

```
Pro Met Met Val Lys Arg Arg Trp His Gly Glu Glu Ile Asp Leu Leu
145                 150                 155                 160

Ala Arg Thr Glu Ala Arg Leu Leu Ala Glu Arg Gly Gln Cys Ser Gly
            165                 170                 175

Gly Asp Leu Phe Gly Ala Leu Pro Gly Phe Gly Arg Thr Leu Glu Ala
            180                 185                 190

Ile Lys Gly Gln Arg Arg Glu Pro Tyr Arg Ala Leu Val Gln Ala
        195                 200                 205

His Leu Ala Arg Phe Gly Ser Gln Pro Gly Pro Ser Gly Gly Cys
    210                 215                 220

Ser Ala Glu Pro Asp Phe Arg Arg Ala Ser Gly Ala Glu Glu Ala Gly
225                 230                 235                 240

Glu Glu Arg Cys Ala Glu Asp Ala Ala Tyr Asp Pro Ser Ala Val
            245                 250                 255

Gly Gln Met Ser Pro Asp Ala Ala Arg Val Leu Ser Glu Leu Leu Glu
            260                 265                 270

Gly Ala Gly Arg Arg Ala Cys Arg Ala Met Arg Pro Lys Thr Ala
        275                 280                 285

Gly Arg Arg Asn Asp Leu His Asp Asp Arg Thr Ala Ser Ala His Lys
        290                 295                 300

Thr Ser Arg Gln Lys Arg Arg Ala Glu Tyr Ala Arg Val Gln Glu Leu
305                 310                 315                 320

Tyr Lys Lys Cys Arg Ser Arg Ala Ala Ala Glu Val Ile Asp Gly Ala
                325                 330                 335

Cys Gly Gly Val Gly His Ser Leu Glu Glu Met Glu Thr Tyr Trp Arg
            340                 345                 350

Pro Ile Leu Glu Arg Val Ser Asp Ala Pro Gly Pro Thr Pro Glu Ala
            355                 360                 365

Leu His Ala Leu Gly Arg Ala Glu Trp His Gly Gly Asn Arg Asp Tyr
    370                 375                 380

Thr Gln Leu Trp Lys Pro Ile Ser Val Glu Glu Ile Lys Ala Ser Arg
385                 390                 395                 400

Phe Asp Trp Arg Thr Ser Pro Gly Pro Asp Gly Ile Arg Ser Gly Gln
            405                 410                 415

Trp Arg Ala Val Pro Val His Leu Lys Ala Glu Met Phe Asn Ala Trp
            420                 425                 430

Met Ala Arg Gly Glu Ile Pro Glu Ile Leu Arg Gln Cys Arg Thr Val
            435                 440                 445

Phe Val Pro Lys Val Glu Arg Pro Gly Gly Pro Gly Glu Tyr Arg Pro
450                 455                 460

Ile Ser Ile Ala Ser Ile Pro Leu Arg His Phe His Ser Ile Leu Ala
465                 470                 475                 480

Arg Arg Leu Leu Ala Cys Cys Pro Pro Asp Ala Arg Gln Arg Gly Phe
                485                 490                 495

Ile Cys Ala Asp Gly Thr Leu Glu Asn Ser Ala Val Leu Asp Ala Val
            500                 505                 510

Leu Gly Asp Ser Arg Lys Lys Leu Arg Glu Cys His Val Ala Val Leu
        515                 520                 525

Asp Phe Ala Lys Ala Phe Asp Thr Val Ser His Glu Ala Leu Val Glu
    530                 535                 540

Leu Leu Arg Leu Arg Gly Met Pro Glu Gln Phe Cys Gly Tyr Ile Ala
545                 550                 555                 560

His Leu Tyr Asp Thr Ala Ser Thr Thr Leu Ala Val Asn Asn Glu Met
```

```
                565                 570                 575
Ser Ser Pro Val Lys Val Gly Arg Gly Val Arg Gln Gly Asp Pro Leu
            580                 585                 590

Ser Pro Ile Leu Phe Asn Val Val Met Asp Leu Ile Leu Ala Ser Leu
            595                 600                 605

Pro Glu Arg Val Gly Tyr Arg Leu Glu Met Glu Leu Val Ser Ala Leu
            610                 615                 620

Ala Tyr Ala Asp Asp Leu Val Leu Leu Ala Gly Ser Lys Val Gly Met
625                 630                 635                 640

Gln Glu Ser Ile Ser Ala Val Asp Cys Val Gly Arg Gln Met Gly Leu
                645                 650                 655

Arg Leu Asn Cys Arg Lys Ser Ala Val Leu Ser Met Ile Pro Asp Gly
            660                 665                 670

His Arg Lys Lys His His Tyr Leu Thr Glu Arg Thr Phe Asn Ile Gly
            675                 680                 685

Gly Lys Pro Leu Arg Gln Val Ser Cys Val Glu Arg Trp Arg Tyr Leu
            690                 695                 700

Gly Val Asp Phe Glu Ala Ser Gly Cys Val Thr Leu Glu His Ser Ile
705                 710                 715                 720

Ser Ser Ala Leu Asn Asn Ile Ser Arg Ala Pro Leu Lys Pro Gln Gln
                725                 730                 735

Arg Leu Glu Ile Leu Arg Ala His Leu Ile Pro Arg Phe Gln His Gly
            740                 745                 750

Phe Val Leu Gly Asn Ile Ser Asp Asp Arg Leu Arg Met Leu Asp Val
            755                 760                 765

Gln Ile Arg Lys Ala Val Gly Gln Trp Leu Arg Leu Pro Ala Asp Val
            770                 775                 780

Pro Lys Ala Tyr Tyr His Ala Ala Val Gln Asp Gly Gly Leu Ala Ile
785                 790                 795                 800

Pro Ser Val Arg Ala Thr Ile Pro Asp Leu Ile Val Arg Arg Phe Gly
                805                 810                 815

Gly Leu Asp Ser Ser Pro Trp Ser Val Ala Arg Ala Ala Ala Lys Ser
            820                 825                 830

Asp Lys Ile Arg Lys Leu Arg Trp Ala Trp Lys Gln Leu Arg Arg
            835                 840                 845

Phe Ser Arg Val Asp Ser Thr Thr Gln Arg Pro Ser Val Arg Leu Phe
            850                 855                 860

Trp Arg Glu His Leu His Ala Ser Val Asp Gly Arg Glu Leu Arg Glu
865                 870                 875                 880

Ser Thr Arg Thr Pro Thr Ser Thr Lys Trp Ile Arg Glu Arg Cys Ala
                885                 890                 895

Gln Ile Thr Gly Arg Asp Phe Val Gln Phe Val His Thr His Ile Asn
            900                 905                 910

Ala Leu Pro Ser Arg Ile Arg Gly Ser Arg Gly Arg Gly Gly Gly
            915                 920                 925

Glu Ser Ser Leu Thr Cys Arg Ala Gly Cys Lys Val Arg Glu Thr Thr
            930                 935                 940

Ala His Ile Leu Gln Gln Cys His Arg Thr His Gly Gly Arg Ile Leu
945                 950                 955                 960

Arg His Asn Lys Ile Val Ser Phe Val Ala Lys Ala Met Glu Glu Asn
                965                 970                 975

Lys Trp Thr Val Glu Leu Glu Pro Arg Leu Arg Thr Ser Val Gly Leu
            980                 985                 990
```

Arg Lys Pro Asp Ile Ile Ala Ser Arg Asp Gly Val Gly Val Ile Val
        995                1000                1005

Asp Val Gln Val Val Ser Gly Gln Arg Ser Leu Asp Glu Leu His
    1010                1015                1020

Arg Glu Lys Arg Asn Lys Tyr Gly Asn His Gly Glu Leu Val Glu
    1025                1030                1035

Leu Val Ala Gly Arg Leu Gly Leu Pro Lys Ala Glu Cys Val Arg
    1040                1045                1050

Ala Thr Ser Cys Thr Ile Ser Trp Arg Gly Val Trp Ser Leu Thr
    1055                1060                1065

Ser Tyr Lys Glu Leu Arg Ser Ile Ile Gly Leu Arg Glu Pro Thr
    1070                1075                1080

Leu Gln Ile Val Pro Ile Leu Ala Leu Arg Gly Ser His Met Asn
    1085                1090                1095

Trp Thr Arg Phe Asn Gln Met Thr Ser Val Met Gly Gly Gly Val
    1100                1105                1110

Gly Val Gly Thr Gly Gly Gly Ser Gly Gly Gly Thr Gly Gly Gly
    1115                1120                1125

Ser Met Glu Glu Lys Val Gly Asn Leu Lys Pro Asn Met Glu Ser
    1130                1135                1140

Val Asn Val Thr Val Arg Val Leu Glu Ala Ser Glu Ala Arg Gln
    1145                1150                1155

Ile Gln Thr Lys Asn Gly Val Arg Thr Ile Ser Glu Ala Ile Val
    1160                1165                1170

Gly Asp Glu Thr Gly Arg Val Lys Leu Thr Leu Trp Gly Lys His
    1175                1180                1185

Ala Gly Ser Ile Lys Glu Gly Gln Val Val Lys Ile Glu Asn Ala
    1190                1195                1200

Trp Thr Thr Ala Phe Lys Gly Gln Val Gln Leu Asn Ala Gly Ser
    1205                1210                1215

Lys Thr Lys Ile Ala Glu Ala Ser Glu Asp Gly Phe Pro Glu Ser
    1220                1225                1230

Ser Gln Ile Pro Glu Asn Thr Pro Thr Ala Arg Arg Arg Gly Gly
    1235                1240                1245

Gly Val Gly Thr Gly Gly Gly Ser Gly Gly Gly Thr Gly Gly Gly
    1250                1255                1260

Ser Met Glu Glu Lys Val Gly Asn Leu Lys Pro Asn Met Glu Ser
    1265                1270                1275

Val Asn Val Thr Val Arg Val Leu Glu Ala Ser Glu Ala Arg Gln
    1280                1285                1290

Ile Gln Thr Lys Asn Gly Val Arg Thr Ile Ser Glu Ala Ile Val
    1295                1300                1305

Gly Asp Glu Thr Gly Arg Val Lys
    1310                1315

<210> SEQ ID NO 99
<211> LENGTH: 1381
<212> TYPE: PRT
<213> ORGANISM: Artificial Sequence
<220> FEATURE:
<223> OTHER INFORMATION: His Tag joined via a linker to a dimer of
      truncated SSB joined via a linker to the N-terminus of wild type
      R2 enzyme

<400> SEQUENCE: 99

-continued

```
Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
            35                  40                  45

Gly Arg Val Lys Leu Thr Leu Trp Gly Lys His Ala Gly Ser Ile Lys
50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
            85                  90                  95

Ser Glu Asp Gly Phe Pro Glu Ser Ser Gln Ile Pro Glu Asn Thr Pro
            100                 105                 110

Thr Ala Arg Arg Arg Gly Gly Val Gly Thr Gly Gly Ser Gly
            115                 120                 125

Gly Gly Thr Gly Gly Gly Ser Met Glu Glu Lys Val Gly Asn Leu Lys
            130                 135                 140

Pro Asn Met Glu Ser Val Asn Val Thr Val Arg Val Leu Glu Ala Ser
145                 150                 155                 160

Glu Ala Arg Gln Ile Gln Thr Lys Asn Gly Val Arg Thr Ile Ser Glu
            165                 170                 175

Ala Ile Val Gly Asp Glu Thr Gly Arg Val Lys Leu Thr Leu Trp Gly
            180                 185                 190

Lys His Ala Gly Ser Ile Lys Glu Gly Gln Val Val Lys Ile Glu Asn
            195                 200                 205

Ala Trp Thr Thr Ala Phe Lys Gly Gln Val Gln Leu Asn Ala Gly Ser
210                 215                 220

Lys Thr Lys Ile Ala Glu Ala Ser Glu Asp Gly Phe Pro Glu Ser Ser
225                 230                 235                 240

Gln Ile Pro Glu Asn Thr Pro Thr Ala Arg Arg Val Gly Thr Gly
            245                 250                 255

Gly Gly Ser Gly Gly Gly Thr Gly Gly Gly Ser Met Met Ala Ser Thr
            260                 265                 270

Ala Leu Ser Leu Met Gly Arg Cys Asn Pro Asp Gly Cys Thr Arg Gly
            275                 280                 285

Lys His Val Thr Ala Ala Pro Met Asp Gly Pro Arg Gly Pro Ser Ser
            290                 295                 300

Leu Ala Gly Thr Phe Gly Trp Gly Leu Ala Ile Pro Ala Gly Glu Pro
305                 310                 315                 320

Cys Gly Arg Val Cys Ser Pro Ala Thr Val Gly Phe Phe Pro Val Ala
            325                 330                 335

Lys Lys Ser Asn Lys Glu Asn Arg Pro Glu Ala Ser Gly Leu Pro Leu
            340                 345                 350

Glu Ser Glu Arg Thr Gly Asp Asn Pro Thr Val Arg Gly Ser Ala Gly
            355                 360                 365

Ala Asp Pro Val Gly Gln Asp Ala Pro Gly Trp Thr Cys Gln Phe Cys
370                 375                 380

Glu Arg Thr Phe Ser Thr Asn Arg Gly Leu Gly Val His Lys Arg Arg
385                 390                 395                 400

Ala His Pro Val Glu Thr Asn Thr Asp Ala Ala Pro Met Met Val Lys
            405                 410                 415

Arg Arg Trp His Gly Glu Glu Ile Asp Leu Leu Ala Arg Thr Glu Ala
```

```
                420             425             430
Arg Leu Leu Ala Glu Arg Gly Gln Cys Ser Gly Gly Asp Leu Phe Gly
            435             440             445

Ala Leu Pro Gly Phe Gly Arg Thr Leu Glu Ala Ile Lys Gly Gln Arg
        450             455             460

Arg Arg Glu Pro Tyr Arg Ala Leu Val Gln Ala His Leu Ala Arg Phe
465             470             475             480

Gly Ser Gln Pro Gly Pro Ser Ser Gly Gly Cys Ser Ala Glu Pro Asp
            485             490             495

Phe Arg Arg Ala Ser Gly Ala Glu Glu Ala Gly Glu Glu Arg Cys Ala
        500             505             510

Glu Asp Ala Ala Ala Tyr Asp Pro Ser Ala Val Gly Gln Met Ser Pro
        515             520             525

Asp Ala Ala Arg Val Leu Ser Glu Leu Leu Glu Gly Ala Gly Arg Arg
        530             535             540

Arg Ala Cys Arg Ala Met Arg Pro Lys Thr Ala Gly Arg Arg Asn Asp
545             550             555             560

Leu His Asp Asp Arg Thr Ala Ser Ala His Lys Thr Ser Arg Gln Lys
            565             570             575

Arg Arg Ala Glu Tyr Ala Arg Val Gln Glu Leu Tyr Lys Lys Cys Arg
        580             585             590

Ser Arg Ala Ala Ala Glu Val Ile Asp Gly Ala Cys Gly Gly Val Gly
        595             600             605

His Ser Leu Glu Glu Met Glu Thr Tyr Trp Arg Pro Ile Leu Glu Arg
    610             615             620

Val Ser Asp Ala Pro Gly Pro Thr Pro Glu Ala Leu His Ala Leu Gly
625             630             635             640

Arg Ala Glu Trp His Gly Gly Asn Arg Asp Tyr Thr Gln Leu Trp Lys
            645             650             655

Pro Ile Ser Val Glu Glu Ile Lys Ala Ser Arg Phe Asp Trp Arg Thr
        660             665             670

Ser Pro Gly Pro Asp Gly Ile Arg Ser Gly Gln Trp Arg Ala Val Pro
    675             680             685

Val His Leu Lys Ala Glu Met Phe Asn Ala Trp Met Ala Arg Gly Glu
    690             695             700

Ile Pro Glu Ile Leu Arg Gln Cys Arg Thr Val Phe Val Pro Lys Val
705             710             715             720

Glu Arg Pro Gly Gly Pro Gly Glu Tyr Arg Pro Ile Ser Ile Ala Ser
            725             730             735

Ile Pro Leu Arg His Phe His Ser Ile Leu Ala Arg Arg Leu Leu Ala
            740             745             750

Cys Cys Pro Pro Asp Ala Arg Gln Arg Gly Phe Ile Cys Ala Asp Gly
        755             760             765

Thr Leu Glu Asn Ser Ala Val Leu Asp Ala Val Leu Gly Asp Ser Arg
        770             775             780

Lys Lys Leu Arg Glu Cys His Val Ala Val Leu Asp Phe Ala Lys Ala
785             790             795             800

Phe Asp Thr Val Ser His Glu Ala Leu Val Glu Leu Leu Arg Leu Arg
            805             810             815

Gly Met Pro Glu Gln Phe Cys Gly Tyr Ile Ala His Leu Tyr Asp Thr
        820             825             830

Ala Ser Thr Thr Leu Ala Val Asn Asn Glu Met Ser Ser Pro Val Lys
        835             840             845
```

-continued

```
Val Gly Arg Gly Val Arg Gln Gly Asp Pro Leu Ser Pro Ile Leu Phe
    850             855                 860
Asn Val Val Met Asp Leu Ile Leu Ala Ser Leu Pro Glu Arg Val Gly
865             870                 875                 880
Tyr Arg Leu Glu Met Glu Leu Val Ser Ala Leu Ala Tyr Ala Asp Asp
                885                 890                 895
Leu Val Leu Leu Ala Gly Ser Lys Val Gly Met Gln Glu Ser Ile Ser
            900                 905                 910
Ala Val Asp Cys Val Gly Arg Gln Met Gly Leu Arg Leu Asn Cys Arg
            915                 920                 925
Lys Ser Ala Val Leu Ser Met Ile Pro Asp Gly His Arg Lys Lys His
        930                 935                 940
His Tyr Leu Thr Glu Arg Thr Phe Asn Ile Gly Gly Lys Pro Leu Arg
945                 950                 955                 960
Gln Val Ser Cys Val Glu Arg Trp Arg Tyr Leu Gly Val Asp Phe Glu
                965                 970                 975
Ala Ser Gly Cys Val Thr Leu Glu His Ser Ile Ser Ser Ala Leu Asn
            980                 985                 990
Asn Ile Ser Arg Ala Pro Leu Lys  Pro Gln Gln Arg Leu  Glu Ile Leu
        995                 1000                1005
Arg Ala  His Leu Ile Pro Arg  Phe Gln His Gly Phe  Val Leu Gly
        1010                1015                1020
Asn Ile  Ser Asp Asp Arg Leu  Arg Met Leu Asp Val  Gln Ile Arg
        1025                1030                1035
Lys Ala  Val Gly Gln Trp Leu  Arg Leu Pro Ala Asp  Val Pro Lys
        1040                1045                1050
Ala Tyr  Tyr His Ala Ala Val  Gln Asp Gly Gly Leu  Ala Ile Pro
        1055                1060                1065
Ser Val  Arg Ala Thr Ile Pro  Asp Leu Ile Val Arg  Arg Phe Gly
        1070                1075                1080
Gly Leu  Asp Ser Ser Pro Trp  Ser Val Ala Arg Ala  Ala Ala Lys
        1085                1090                1095
Ser Asp  Lys Ile Arg Lys Lys  Leu Arg Trp Ala Trp  Lys Gln Leu
        1100                1105                1110
Arg Arg  Phe Ser Arg Val Asp  Ser Thr Thr Gln Arg  Pro Ser Val
        1115                1120                1125
Arg Leu  Phe Trp Arg Glu His  Leu His Ala Ser Val  Asp Gly Arg
        1130                1135                1140
Glu Leu  Arg Glu Ser Thr Arg  Thr Pro Thr Ser Thr  Lys Trp Ile
        1145                1150                1155
Arg Glu  Arg Cys Ala Gln Ile  Thr Gly Arg Asp Phe  Val Gln Phe
        1160                1165                1170
Val His  Thr His Ile Asn Ala  Leu Pro Ser Arg Ile  Arg Gly Ser
        1175                1180                1185
Arg Gly  Arg Arg Gly Gly Gly  Glu Ser Ser Leu Thr  Cys Arg Ala
        1190                1195                1200
Gly Cys  Lys Val Arg Glu Thr  Thr Ala His Ile Leu  Gln Gln Cys
        1205                1210                1215
His Arg  Thr His Gly Gly Arg  Ile Leu Arg His Asn  Lys Ile Val
        1220                1225                1230
Ser Phe  Val Ala Lys Ala Met  Glu Glu Asn Lys Trp  Thr Val Glu
        1235                1240                1245
```

-continued

```
Leu Glu Pro Arg Leu Arg Thr Ser Val Gly Leu Arg Lys Pro Asp
    1250                1255                1260

Ile Ile Ala Ser Arg Asp Gly Val Gly Val Ile Val Asp Val Gln
    1265                1270                1275

Val Val Ser Gly Gln Arg Ser Leu Asp Glu Leu His Arg Glu Lys
    1280                1285                1290

Arg Asn Lys Tyr Gly Asn His Gly Glu Leu Val Glu Leu Val Ala
    1295                1300                1305

Gly Arg Leu Gly Leu Pro Lys Ala Glu Cys Val Arg Ala Thr Ser
    1310                1315                1320

Cys Thr Ile Ser Trp Arg Gly Val Trp Ser Leu Thr Ser Tyr Lys
    1325                1330                1335

Glu Leu Arg Ser Ile Ile Gly Leu Arg Glu Pro Thr Leu Gln Ile
    1340                1345                1350

Val Pro Ile Leu Ala Leu Arg Gly Ser His Met Asn Trp Thr Arg
    1355                1360                1365

Phe Asn Gln Met Thr Ser Val Met Gly Gly Val Gly
    1370                1375                1380

<210> SEQ ID NO 100
<211> LENGTH: 1096
<212> TYPE: PRT
<213> ORGANISM: Artificial Sequence
<220> FEATURE:
<223> OTHER INFORMATION: His Tag joined via a linker to a dimer of
      truncated SSB joined via a linker to the N-terminus of deltaR2
      enzyme

<400> SEQUENCE: 100

Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
                20                  25                  30

Lys Asn Gly Val Arg Thr Ile Ser Glu Ala Ile Val Gly Asp Glu Thr
            35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Gln Ile Pro Glu Asn Thr Pro
            100                 105                 110

Thr Ala Arg Arg Arg Gly Gly Gly Val Gly Thr Gly Gly Gly Ser Gly
            115                 120                 125

Gly Gly Thr Gly Gly Gly Ser Met Glu Glu Lys Val Gly Asn Leu Lys
    130                 135                 140

Pro Asn Met Glu Ser Val Asn Val Thr Val Arg Val Leu Glu Ala Ser
145                 150                 155                 160

Glu Ala Arg Gln Ile Gln Thr Lys Asn Gly Val Arg Thr Ile Ser Glu
                165                 170                 175

Ala Ile Val Gly Asp Glu Thr Gly Arg Val Lys Leu Thr Leu Trp Gly
            180                 185                 190

Lys His Ala Gly Ser Ile Lys Glu Gly Gln Val Val Lys Ile Glu Asn
        195                 200                 205

Ala Trp Thr Thr Ala Phe Lys Gly Gln Val Gln Leu Asn Ala Gly Ser
```

```
              210                 215                 220
Lys Thr Lys Ile Ala Glu Ala Ser Glu Asp Gly Phe Pro Glu Ser Ser
225                 230                 235                 240

Gln Ile Pro Glu Asn Thr Pro Thr Ala Arg Arg Val Gly Thr Gly
                245                 250                 255

Gly Gly Ser Gly Gly Thr Gly Gly Ser Lys Thr Ala Gly Arg
            260                 265                 270

Arg Asn Asp Leu His Asp Asp Arg Thr Ala Ser Ala His Lys Thr Ser
            275                 280                 285

Arg Gln Lys Arg Arg Ala Glu Tyr Ala Arg Val Gln Glu Leu Tyr Lys
            290                 295                 300

Lys Cys Arg Ser Arg Ala Ala Ala Glu Val Ile Asp Gly Ala Cys Gly
305                 310                 315                 320

Gly Val Gly His Ser Leu Glu Glu Met Glu Thr Tyr Trp Arg Pro Ile
                325                 330                 335

Leu Glu Arg Val Ser Asp Ala Pro Gly Pro Thr Pro Glu Ala Leu His
                340                 345                 350

Ala Leu Gly Arg Ala Glu Trp His Gly Gly Asn Arg Asp Tyr Thr Gln
                355                 360                 365

Leu Trp Lys Pro Ile Ser Val Glu Ile Lys Ala Ser Arg Phe Asp
370                 375                 380

Trp Arg Thr Ser Pro Gly Pro Asp Gly Ile Arg Ser Gly Gln Trp Arg
385                 390                 395                 400

Ala Val Pro Val His Leu Lys Ala Glu Met Phe Asn Ala Trp Met Ala
                405                 410                 415

Arg Gly Glu Ile Pro Glu Ile Leu Arg Gln Cys Arg Thr Val Phe Val
                420                 425                 430

Pro Lys Val Glu Arg Pro Gly Gly Pro Gly Glu Tyr Arg Pro Ile Ser
                435                 440                 445

Ile Ala Ser Ile Pro Leu Arg His Phe His Ser Ile Leu Ala Arg Arg
450                 455                 460

Leu Leu Ala Cys Cys Pro Pro Asp Ala Arg Gln Arg Gly Phe Ile Cys
465                 470                 475                 480

Ala Asp Gly Thr Leu Glu Asn Ser Ala Val Leu Asp Ala Val Leu Gly
                485                 490                 495

Asp Ser Arg Lys Lys Leu Arg Glu Cys His Val Ala Val Leu Asp Phe
                500                 505                 510

Ala Lys Ala Phe Asp Thr Val Ser His Glu Ala Leu Val Glu Leu Leu
            515                 520                 525

Arg Leu Arg Gly Met Pro Glu Gln Phe Cys Gly Tyr Ile Ala His Leu
530                 535                 540

Tyr Asp Thr Ala Ser Thr Thr Leu Ala Val Asn Asn Glu Met Ser Ser
545                 550                 555                 560

Pro Val Lys Val Gly Arg Gly Val Arg Gln Gly Asp Pro Leu Ser Pro
                565                 570                 575

Ile Leu Phe Asn Val Val Met Asp Leu Ile Leu Ala Ser Leu Pro Glu
                580                 585                 590

Arg Val Gly Tyr Arg Leu Glu Met Glu Leu Val Ser Ala Leu Ala Tyr
                595                 600                 605

Ala Asp Asp Leu Val Leu Leu Ala Gly Ser Lys Val Gly Met Gln Glu
            610                 615                 620

Ser Ile Ser Ala Val Asp Cys Val Gly Arg Gln Met Gly Leu Arg Leu
625                 630                 635                 640
```

-continued

```
Asn Cys Arg Lys Ser Ala Val Leu Ser Met Ile Pro Asp Gly His Arg
            645                 650                 655
Lys Lys His His Tyr Leu Thr Glu Arg Thr Phe Asn Ile Gly Gly Lys
        660                 665                 670
Pro Leu Arg Gln Val Ser Cys Val Glu Arg Trp Arg Tyr Leu Gly Val
    675                 680                 685
Asp Phe Glu Ala Ser Gly Cys Val Thr Leu Glu His Ser Ile Ser Ser
690                 695                 700
Ala Leu Asn Asn Ile Ser Arg Ala Pro Leu Lys Pro Gln Gln Arg Leu
705                 710                 715                 720
Glu Ile Leu Arg Ala His Leu Ile Pro Arg Phe Gln His Gly Phe Val
                725                 730                 735
Leu Gly Asn Ile Ser Asp Asp Arg Leu Arg Met Leu Asp Val Gln Ile
            740                 745                 750
Arg Lys Ala Val Gly Gln Trp Leu Arg Leu Pro Ala Asp Val Pro Lys
        755                 760                 765
Ala Tyr Tyr His Ala Ala Val Gln Asp Gly Gly Leu Ala Ile Pro Ser
    770                 775                 780
Val Arg Ala Thr Ile Pro Asp Leu Ile Val Arg Arg Phe Gly Gly Leu
785                 790                 795                 800
Asp Ser Ser Pro Trp Ser Val Ala Arg Ala Ala Lys Ser Asp Lys
                805                 810                 815
Ile Arg Lys Lys Leu Arg Trp Ala Trp Lys Gln Leu Arg Arg Phe Ser
            820                 825                 830
Arg Val Asp Ser Thr Thr Gln Arg Pro Ser Val Arg Leu Phe Trp Arg
        835                 840                 845
Glu His Leu His Ala Ser Val Asp Gly Arg Glu Leu Arg Glu Ser Thr
    850                 855                 860
Arg Thr Pro Thr Ser Thr Lys Trp Ile Arg Glu Arg Cys Ala Gln Ile
865                 870                 875                 880
Thr Gly Arg Asp Phe Val Gln Phe Val His Thr His Ile Asn Ala Leu
                885                 890                 895
Pro Ser Arg Ile Arg Gly Ser Arg Gly Arg Arg Gly Gly Glu Ser
            900                 905                 910
Ser Leu Thr Cys Arg Ala Gly Cys Lys Val Arg Glu Thr Thr Ala His
        915                 920                 925
Ile Leu Gln Gln Cys His Arg Thr His Gly Gly Arg Ile Leu Arg His
    930                 935                 940
Asn Lys Ile Val Ser Phe Val Ala Lys Ala Met Glu Glu Asn Lys Trp
945                 950                 955                 960
Thr Val Glu Leu Glu Pro Arg Leu Arg Thr Ser Val Gly Leu Arg Lys
                965                 970                 975
Pro Asp Ile Ile Ala Ser Arg Asp Gly Val Gly Val Ile Val Asp Val
            980                 985                 990
Gln Val Val Ser Gly Gln Arg Ser Leu Asp Glu Leu His Arg Glu Lys
        995                 1000                1005
Arg Asn Lys Tyr Gly Asn His Gly Glu Leu Val Glu Leu Val Ala
    1010                1015                1020
Gly Arg Leu Gly Leu Pro Lys Ala Glu Cys Val Arg Ala Thr Ser
    1025                1030                1035
Cys Thr Ile Ser Trp Arg Gly Val Trp Ser Leu Thr Ser Tyr Lys
    1040                1045                1050
```

```
Glu Leu Arg Ser Ile Ile Gly Leu Arg Glu Pro Thr Leu Gln Ile
    1055                1060                1065

Val Pro Ile Leu Ala Leu Arg Gly Ser His Met Asn Trp Thr Arg
    1070                1075                1080

Phe Asn Gln Met Thr Ser Val Met Gly Gly Gly Val Gly
    1085                1090                1095

<210> SEQ ID NO 101
<211> LENGTH: 17
<212> TYPE: PRT
<213> ORGANISM: Artificial Sequence
<220> FEATURE:
<223> OTHER INFORMATION: Synthetic

<400> SEQUENCE: 101

Val Gly Thr Val Gly Thr Gly Gly Gly Ser Gly Gly Ala Ser Thr Ala
1               5                   10                  15

Leu

<210> SEQ ID NO 102
<211> LENGTH: 22
<212> TYPE: PRT
<213> ORGANISM: Artificial Sequence
<220> FEATURE:
<223> OTHER INFORMATION: Synthetic

<400> SEQUENCE: 102

Val Gly Thr Val Gly Thr Gly Gly Gly Ser Glu Ala Ala Ala Lys Gly
1               5                   10                  15

Gly Ala Ser Thr Ala Leu
            20

<210> SEQ ID NO 103
<211> LENGTH: 19
<212> TYPE: PRT
<213> ORGANISM: Artificial Sequence
<220> FEATURE:
<223> OTHER INFORMATION: Synthetic

<400> SEQUENCE: 103

Val Gly Thr Gly Gly Gly Ser Glu Ala Ala Ala Lys Gly Gly Ala Ser
1               5                   10                  15

Thr Ala Leu

<210> SEQ ID NO 104
<211> LENGTH: 25
<212> TYPE: PRT
<213> ORGANISM: Artificial Sequence
<220> FEATURE:
<223> OTHER INFORMATION: Synthetic

<400> SEQUENCE: 104

Val Gly Thr Gly Gly Gly Ser Gly Gly Gly Glu Ala Ala Ala Lys Glu
1               5                   10                  15

Ala Ala Ala Lys Ser Gly Gly Gly Ser
            20                  25

<210> SEQ ID NO 105
<211> LENGTH: 26
<212> TYPE: PRT
<213> ORGANISM: Artificial Sequence
<220> FEATURE:
<223> OTHER INFORMATION: Synthetic
```

```
<400> SEQUENCE: 105

Val Gly Thr Gly Gly Gly Ser Gly Gly Gly Glu Ala Ala Ala Lys Glu
1               5                   10                  15

Ala Ala Ala Lys Ser Gly Gly Gly Ser Ala
            20                  25

<210> SEQ ID NO 106
<211> LENGTH: 15
<212> TYPE: PRT
<213> ORGANISM: Artificial Sequence
<220> FEATURE:
<223> OTHER INFORMATION: Synthetic

<400> SEQUENCE: 106

Val Gly Thr Gly Gly Gly Ser Gly Gly Gly Thr Gly Gly Gly Ser
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic

<400> SEQUENCE: 107

Val Gly Thr Gly Gly Gly Ser Gly Gly Gly Thr Gly Gly Gly Ser Ala
1               5                   10                  15

<210> SEQ ID NO 108
<211> LENGTH: 4
<212> TYPE: PRT
<213> ORGANISM: Artificial Sequence
<220> FEATURE:
<223> OTHER INFORMATION: Synthetic

<400> SEQUENCE: 108

Gly Gly Gly Ser
1

<210> SEQ ID NO 109
<211> LENGTH: 5
<212> TYPE: PRT
<213> ORGANISM: Artificial Sequence
<220> FEATURE:
<223> OTHER INFORMATION: Synthetic

<400> SEQUENCE: 109

Gly Gly Gly Gly Ser
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic

<400> SEQUENCE: 110

Glu Ala Ala Ala Lys
1               5

<210> SEQ ID NO 111
<211> LENGTH: 522
<212> TYPE: DNA
<213> ORGANISM: Artificial Sequence
<220> FEATURE:
```

<223> OTHER INFORMATION: Synthetic

<400> SEQUENCE: 111

```
tggacattaa ttagggctga aagccctaac ttaatggacg ggaggtatcc caataggagg    60
tttcctccta tggttttcaa aacaatcacc atcatgctat taatgatatt aaaatcccaa   120
ctataccaaa gaatatccca attatccata aaactgtaac taagtgaggc tctctcattg   180
gtttatactt caatataagc cttggtaggg atagatagcc acctatatag tatagcttcc   240
catcttcttt gagagttgtt ggtttatgct catccctact cataacccca gcacttagat   300
attttaaaga ggcatctatc acataaggca tcattataac taaaaatggg atatattcct   360
tataaactac tgctaagaca gctaagaaag ctccaattgg tagagttcca acatctcctg   420
gaaaaacctt tgctggatat ttgttaaata tcaatagccc taaataggat gcagagaata   480
tcaaagcgga aaaatccaa aaaaaaaaaa aaaaaaaaa aa                         522
```

<210> SEQ ID NO 112
<211> LENGTH: 1061
<212> TYPE: DNA
<213> ORGANISM: Artificial Sequence
<220> FEATURE:
<223> OTHER INFORMATION: Synthetic

<400> SEQUENCE: 112

```
tccagattac ttccatttcc gcccaagctg ctcacagtat acgggcgtcg gcatccagac    60
cgtcggctga tcgtggtttt actaggctag actagcgtac gagcactatg gtcagtaatt   120
cctggaggaa taggtaccaa gaaaaaaacg aacctttggg ttccagagct gtacggtcgc   180
actgaactcg gataggtctc agaaaaacga aatataggct tacggtaggt ccgaatggca   240
caaagcttgt tccgttagct ggcataagat tccatgccta gatgtgatac acgtttctgg   300
aaactgcctc gtcatgcgac tgttccccgg ggtcagggcc gctggtattt gctgtaaaga   360
ggggcgttga gtccgtccga cttcactgcc cctttcagc cttttgggtc ctgtatccca   420
attctcagag gtcccgccgt acgctgagga ccacctgaaa cgggcatcgt cgctcttcgt   480
tgttcgtcga cttctagtgt ggagacgaat tgccagaatt attaactgcg cagttagggc   540
agcgtctgag gaagtttgct gcggtttcgc cttgaccgcg ggaaggagac ataacgatag   600
cgactctgtc tcaggggatc tgcatatgtt tgcagcatac tttaggtggg ccttggcttc   660
cttccgcagt caaaaccgcg caattatccc cgtcctgatt tactggactc gcaacgtggg   720
tccatcagtt gtccgtatac caagacgtct aagggcggtg tacacccttt tgagcaatga   780
ttgcacaacc tgcgatcacc ttatacagaa ttatcaatca agctccccga ggagcggact   840
tgtaaggacc gccgctttcg ctcgggtctg cgggttatag cttttcagtc tcgacgggct   900
agcacacatc tggttgacta ggcgcatagt cgccattcac agatttgctc ggcaatcagt   960
actggtaggc gttagacccc gtgactcgtg gctgaacggc cgtacaactc gacagccggt  1020
gcttgcgttt tacccttaaa aaaaaaaaaa aaaaaaaaa a                        1061
```

<210> SEQ ID NO 113
<211> LENGTH: 33
<212> TYPE: DNA
<213> ORGANISM: Artificial Sequence
<220> FEATURE:
<223> OTHER INFORMATION: Synthetic

<400> SEQUENCE: 113

```
acactctttc cctacacgac gctcttccga tct                                 33
```

```
<210> SEQ ID NO 114
<211> LENGTH: 34
<212> TYPE: DNA
<213> ORGANISM: Artificial Sequence
<220> FEATURE:
<223> OTHER INFORMATION: Synthetic

<400> SEQUENCE: 114
gtgactggag ttcagacgtg tgctcttccg atct                              34

<210> SEQ ID NO 115
<211> LENGTH: 23
<212> TYPE: DNA
<213> ORGANISM: Artificial Sequence
<220> FEATURE:
<223> OTHER INFORMATION: Synthetic

<400> SEQUENCE: 115
acactctttc cctacacgac gct                                          23

<210> SEQ ID NO 116
<211> LENGTH: 24
<212> TYPE: DNA
<213> ORGANISM: Artificial Sequence
<220> FEATURE:
<223> OTHER INFORMATION: Synthetic

<400> SEQUENCE: 116
ctgagaccta tccgagttca gtgc                                         24

<210> SEQ ID NO 117
<211> LENGTH: 32
<212> TYPE: DNA
<213> ORGANISM: Artificial Sequence
<220> FEATURE:
<223> OTHER INFORMATION: Synthetic

<400> SEQUENCE: 117
gtggctatct atccctacca aggcttatat tg                                32

<210> SEQ ID NO 118
<211> LENGTH: 4
<212> TYPE: PRT
<213> ORGANISM: Artificial Sequence
<220> FEATURE:
<223> OTHER INFORMATION: Synthetic

<400> SEQUENCE: 118

Gly Ser Gly Ser
1

<210> SEQ ID NO 119
<211> LENGTH: 19
<212> TYPE: PRT
<213> ORGANISM: Artificial Sequence
<220> FEATURE:
<223> OTHER INFORMATION: Synthetic

<400> SEQUENCE: 119

Gly Gly Gly Gly Ser Gly Gly Gly Ser Gly Ala Gly Ser Gly Gly
1               5                   10                  15

Gly Gly Ser

<210> SEQ ID NO 120
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 120

Gly Gly Gly Gly Gly Ser Gly Gly Gly Gly Ser
1               5                   10

<210> SEQ ID NO 121
<211> LENGTH: 6
<212> TYPE: PRT
<213> ORGANISM: Artificial Sequence
<220> FEATURE:
<223> OTHER INFORMATION: Synthetic

<400> SEQUENCE: 121

Gly Gly Gly Gly Ser Gly
1               5

<210> SEQ ID NO 122
<211> LENGTH: 4
<212> TYPE: PRT
<213> ORGANISM: Artificial Sequence
<220> FEATURE:
<223> OTHER INFORMATION: Synthetic

<400> SEQUENCE: 122

Gly Ser Gly Gly
1

<210> SEQ ID NO 123
<211> LENGTH: 5
<212> TYPE: PRT
<213> ORGANISM: Artificial Sequence
<220> FEATURE:
<223> OTHER INFORMATION: Synthetic

<400> SEQUENCE: 123

Gly Ser Gly Gly Gly
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Asp Tyr Lys Asp Asp Asp Asp Lys
1               5
```